US008092998B2

(12) United States Patent
Stuhlmüller et al.

(10) Patent No.: US 8,092,998 B2
(45) Date of Patent: Jan. 10, 2012

(54) BIOMARKERS PREDICTIVE OF THE RESPONSIVENESS TO TNFα INHIBITORS IN AUTOIMMUNE DISORDERS

(75) Inventors: Bruno Stuhlmüller, Berlin (DE); Gerd-Reudiger Burmester, Berlin (DE)

(73) Assignee: Abbott Laboratories, Abbott Park, IL (US)

(*) Notice: Subject to any disclaimer, the term of this patent is extended or adjusted under 35 U.S.C. 154(b) by 5 days.

(21) Appl. No.: 12/130,373

(22) Filed: May 30, 2008

(65) Prior Publication Data

US 2009/0017472 A1    Jan. 15, 2009

Related U.S. Application Data

(60) Provisional application No. 60/932,888, filed on May 31, 2007.

(51) Int. Cl.
*C12Q 1/68* (2006.01)
*G01N 33/53* (2006.01)
(52) U.S. Cl. .......................................... 435/6.1; 435/7.1
(58) Field of Classification Search .................. None
See application file for complete search history.

(56) References Cited

U.S. PATENT DOCUMENTS

| | | | |
|---|---|---|---|
| 6,090,382 A | 7/2000 | Salfeld et al. | |
| 6,258,562 B1 | 7/2001 | Salfeld et al. | |
| 6,506,607 B1 | 1/2003 | Shyjan | |
| 6,509,015 B1 | 1/2003 | Salfeld et al. | |
| 6,607,879 B1 | 8/2003 | Cocks et al. | |
| 7,223,394 B2 | 5/2007 | Salfeld et al. | |
| 7,541,031 B2 | 6/2009 | Salfeld et al. | |
| 7,588,761 B2 | 9/2009 | Salfeld et al. | |
| 2003/0012786 A1 | 1/2003 | Teoh et al. | |
| 2003/0161828 A1 | 8/2003 | Abdelghany et al. | |
| 2003/0206898 A1 | 11/2003 | Fischkoff et al. | |
| 2003/0219438 A1 | 11/2003 | Salfeld et al. | |
| 2003/0235585 A1 | 12/2003 | Fischkoff | |
| 2004/0009172 A1 | 1/2004 | Fischkoff et al. | |
| 2004/0033228 A1 | 2/2004 | Krause et al. | |
| 2004/0126372 A1 | 7/2004 | Banerjee et al. | |
| 2004/0126373 A1 | 7/2004 | Banerjee et al. | |
| 2004/0131614 A1 | 7/2004 | Banerjee et al. | |
| 2004/0136989 A1 | 7/2004 | Banerjee et al. | |
| 2004/0136990 A1 | 7/2004 | Banerjee et al. | |
| 2004/0136991 A1 | 7/2004 | Banerjee et al. | |
| 2004/0151722 A1 | 8/2004 | Banerjee et al. | |
| 2004/0166111 A1 | 8/2004 | Kaymakcalan et al. | |
| 2004/0219142 A1 | 11/2004 | Banerjee et al. | |
| 2006/0009385 A1 | 1/2006 | Hoffman et al. | |
| 2006/0083741 A1 | 4/2006 | Hoffman et al. | |
| 2006/0149042 A1 | 7/2006 | Konstantinov | |
| 2006/0153846 A1 | 7/2006 | Krause et al. | |
| 2006/0216707 A1* | 9/2006 | Stuhlmuller et al. | ........... 435/6 |
| 2006/0269479 A1 | 11/2006 | Colton et al. | |
| 2007/0041905 A1 | 2/2007 | Hoffman et al. | |
| 2007/0071747 A1 | 3/2007 | Hoffman et al. | |
| 2007/0081996 A1 | 4/2007 | Hoffman et al. | |
| 2007/0172475 A1 | 7/2007 | Matheus et al. | |
| 2007/0172897 A1 | 7/2007 | Maksymowych et al. | |
| 2007/0184045 A1 | 8/2007 | Doctor et al. | |
| 2007/0202051 A1 | 8/2007 | Schusching | |
| 2007/0202104 A1 | 8/2007 | Banerjee et al. | |
| 2007/0237831 A1 | 10/2007 | Sung et al. | |
| 2007/0269463 A1 | 11/2007 | Donavan | |
| 2007/0292442 A1 | 12/2007 | Wan et al. | |
| 2008/0118496 A1 | 5/2008 | Medich et al. | |
| 2008/0131374 A1 | 6/2008 | Medich et al. | |
| 2008/0166348 A1 | 7/2008 | Kupper et al. | |
| 2008/0193466 A1 | 8/2008 | Banerjee et al. | |
| 2008/0227136 A1 | 9/2008 | Pla et al. | |
| 2008/0311043 A1 | 12/2008 | Hoffman et al. | |
| 2009/0028794 A1 | 1/2009 | Medich et al. | |
| 2009/0110679 A1 | 4/2009 | Li et al. | |
| 2009/0123378 A1 | 5/2009 | Wong et al. | |
| 2009/0148513 A1 | 6/2009 | Fraunhofer et al. | |

(Continued)

FOREIGN PATENT DOCUMENTS

EP        1795610 A1 *    6/2007

(Continued)

OTHER PUBLICATIONS

Asli, Bouchra et al., "Inhibition of Tumor Necrosis Factor α and Ankylosing Spondyiltis," *N. Engl. J. Med.*, vol. 348(4):359-361 (2003).
Boeger, C.A. et al., "Treatment of ankylosing spondylitis with infliximab," *Ann. Rheum. Dis.*, vol. 60(12):1159-1160 (2001).
Brandt, Jan et al., "Successful Short Term Treatment of Severe Undifferentiated Spondyloarthropathy with the Anti-Tumor Necrosis Factor-α Monoclonal Antibody lnfliximab," *The Journal of Rheumatology*, vol. 29(1):118-122 (2002).
Brandt, Jan et al., "Successful Treatment of Active Ankylosing Spondylitis with the Anti-tumor Necrosis Factor α Monoclonal Antibody lnfliximab," *Arthritis & Rheumatism*, vol. 43(6):1346-1352 (2000).
Braun, J. et al., "Anti-TNFα: a new dimension in the pharmacotherapy of the spondyloarthropathies!?," *Ann. Rheum. Dis.*, vol. 59(6):404-407 (2000).

(Continued)

*Primary Examiner* — James Martinell
(74) *Attorney, Agent, or Firm* — McCarter & English, LLP; Cristin Howley Cowles; Deborah L. Nagle

(57) ABSTRACT

The invention provides methods for predicting responsiveness to TNFα inhibitors in a subject suffering from an autoimmune disorder, such as rheumatoid arthritis. The methods involve assaying for expression of one or more biomarkers in the subject that are predictive of responsiveness to TNFα inhibitors. A preferred biomarker of the invention is CD11c. The methods can further comprise selecting a treatment regimen with a TNFα inhibitor in an autoimmune disorder subject based upon expression of the biomarker(s) in the subject. The methods can further comprise administering a TNFα inhibitor to the subject according to the selected treatment regimen. Kits that include means for measuring expression of one or more biomarkers that are predictive of responsiveness to TNFα inhibitors for an autoimmune disorder are also provided. Methods of preparing and using databases, and computer program products therefore, for selecting an autoimmune disorder subject for treatment with a TNFα inhibitor are also provided.

42 Claims, 3 Drawing Sheets

U.S. PATENT DOCUMENTS

| | | | |
|---|---|---|---|
| 2009/0155205 | A1 | 6/2009 | Salfeld et al. |
| 2009/0280065 | A1 | 11/2009 | Willian et al. |
| 2010/0034823 | A1 | 2/2010 | Borhani et al. |
| 2010/0040604 | A1 | 2/2010 | Salfeld et al. |
| 2010/0160894 | A1 | 6/2010 | Julian et al. |

FOREIGN PATENT DOCUMENTS

| | | |
|---|---|---|
| WO | WO9729131 | 8/1997 |
| WO | WO-2004/016809 A1 * | 2/2004 |
| WO | WO 2006092530 | 9/2006 |
| WO | WO 2008028044 | 3/2008 |

OTHER PUBLICATIONS

Braun, J. et al., "Anti-tumour necrosis factor α therapy for ankylosing spondylitis: international experience," *Ann. Rheum. Dis.*, vol. 61(Suppl. III):iii51-iii60 (2002).

Braun, J. et al., "Biologic therapies in the spondyloarthritis: new opportunities, new challenges," *Curr. Opin. Rheumatol.*, vol. 15:394-407 (2003).

Braun, J. et al., "International ASAS consensus statement for the use of anti-tumour necrosis factor agents in patients with ankylosing spondylitis," *Ann. Rheum. Dis.*, vol. 62:817-824 (2003).

Braun, Jürgen et al., "New treatment options in spondyloarthropathies: increasing evidence for significant efficacy of anti-tumor necrosis factor therapy," *Current Opinion in Rheumatology*, vol. 13:245-249 (2001).

Braun, Juergen et al., "Novel approaches in the treatment of ankylosing spondylitis and other spondyloarthritides," *Expert Opin. Investig. Drugs*, vol. 12(7):1097-1109 (2003).

Braun, J. et al., "Persistent clinical response to the anti-TNFα antibody infliximab in patients with ankylosing spondylitis over 3 years," *Rheumatology*, vol. 44:670-676 (2005).

Braun, Juergen et al., "Therapy of ankylosing spondylitis and other spondyloarthritides: established medical treatment, anti-TNF-α therapy and other novel approaches," *Arthritis Res.*, vol. 4:307-321 (2002).

Braun, J. et al., "Treatment of active ankylosing spondylitis with infliximab: a randomised controlled multicentre trial," *Lancet*, vol. 359:1187-1193 (2002).

Breban, M. et al., "Efficacy of infliximab in refractory ankylosing spondylitis: results of a six-month open-label study," *Rheumatology*, vol. 41:1280-1285 (2002).

Briot, K. et al., "Body weight, body composition, and bone turnover changes in patients with spondyloarthropathy receiving anti-tumour necrosis factor α treatment," *Ann. Rheum. Dis.*, vol. 64:1137-1140 (2005).

Casset, Florence et al., "A peptide mimetic of an anti-CD4 monoclonal antibody by rational design," *Biochemical and Biophysical Research Communications*, vol. 307:198-205 (2003).

Cherouvim, E.P. et al., "Infliximab Therapy for Patients With Active and Refractory Spondyloarthropathies at the Dose of 3 mg/kg," *J. Clin. Rheumatol.*, vol. 10:162-168 (2004).

Choi, Kang-Seuk et al., "Monoclonal antibody-based competitive ELISA for simultaneous detection of rinderpest virus and peste des petits ruminants virus antibodies," *Veterinary Microbiology*, vol. 96:1-16 (2003).

Davis, J.C. Jr. et al., "New therapies for ankylosing spondylitis: etanercept, thalidomide, adn pamidronate," *Rheum. Dis. Clin. North Am.*, vol. 29(3):481-494 (2003).

Dayer, Jean-Michel et al., "Anti-TNF-α Therapy for Ankylosing Spondylitis, a Specific or Nonspecific Treatment?" *N. Engl. J. Med.*, vol. 346(18):1399-1400 (2002).

De Keyser, Filip et al., "Anti-TNF-alpha therapy in ankylosing spondylitis," *Cytokine*, vol. 33:294-298 (2006).

den Broeder, A.A. et al., "Long term anti-tumour necrosis factor α monotherapy in rheumatoid arthritis: effect on radiological course and prognostic value of markers of cartilage turnover and endothelial activation," *Ann. Rheum. Dis.*, vol. 61:311-318 (2002).

Dernis, E. et al., "Infliximab in spondylarthropathy—Influence on bone density," *Clin. Exp. Rheumatol.*, vol. 20(Suppl. 28):S185-S186 (2002).

Emery, Paul et al., "Changes in PRO-MMP-1 in Relation to Standard Measures of Disease Activity Over a 6 Months Treatment Period with Adalimumab (D2E7) in Rheumatoid Arthritis," *Arthritis Rheum.*, vol. 44(Suppl.):S215, No. 976 (2001).

Furst, D. et al., "TNF Blockade by the Fully Human Monoclonal Antibody Adalimumab (D2E7) in the Armada Trial Results in Decrease in Serum Matrix Metalloproteinase (MMP) Levels Along with Impressive Clinical Improvement in Refractory RA Patients," *Arthritis Rheum.*, vol. 44(9 Suppl.):S215, No. 975 (2001).

Garnero, Patrick et al., "Association of Baseline Levels of Urinary Glucosyl-Galactosyl-Pyridinoline and Type II Collagen C-Telopeptide With Progression of Joint Destruction in Patients With Early Rheumatoid Arthritis," *Arthritis & Rheumatism*, vol. 46(1):21-30 (2002).

Gorman, Jennifer D. et al., "Treatment of Ankylosing Spondylitis by Inhibition of Tumor Necrosis Factor α," *The New England Journal of Medicine*, vol. 346(18):1349-1356 (2002).

Hawley, Peter et al., "Evaluation of an ELISA Assay for the Simultaneous Detection of HIV-1 Antibodies and Hepatitis B Surface Antigen," *VII International Conference on Aids*, Abstracts vol. II, p. 345, No. W.C.3196 (1991).

Horneff, G. et al., "TNF-α antagonists for the treatment of juvenile-onset spondyloarthritides," *Clin. Exp. Rheumatol.*, vol. 20(Suppl. 28):S137-S142 (2002).

Kaiser, M.J. et al., "Efficacy of infliximab (Remicade®) in the treatment of spondyloarthropathies. Two case reports," *Joint Bone Spine*, vol. 68:525-527 (2001).

Keyszer, G. et al., "Circulating levels of matrix metalloproteinases MMP-3 and MMP-1, tissue inhibitor of metalloproteinases 1 (TIMP-1), and MMP-1/TIMP-1 complex in rheumatoid disease. Correlation with clinical activity of rheumatoid arthritis versus other surrogate markers," *J. Rheumatol.*, vol. 26(2):251-258 (1999).

MacCallum, Robert M. et al., "Antibody-antigen Interactions: Contact Analysis and Binding Site Topography," *J. Mol. Biol.*, vol. 262:732-745 (1996).

Maini R et al., "Infliximab (chimeric anti-tumour necrosis factor alpha monoclonal antibody) versus placebo in rheumatoid arthritis patients receiving concomitant methotrexate: a randomised phase III trial," *The Lancet*, vol. 354:1932-39 (1999).

Maksymowych, Walter P. et al., "Canadian Rheumatology Association Consensus on the Use of Anti-Tumor Necrosis Factor-α Directed Therapies in the Treatment of Spondyloarthritis," *The Journal of Rheumatology*, vol. 30(6):1356-1363 (2003).

Maksymowych, Walter P. et al., "Etanercept Exerts Beneficial Effects on Articular Cartilage Biomarkers of Degradation and Turnover in Patients with Ankylosing Spondylitis," *J. Rheumatol.*, vol. 32:1911-1917 (2005).

Maksymowych, Walter P. et al., "Infliximab in Ankylosing Spondylitis: A Prospective Observational Inception Cohort Analysis of Efficacy and Safety," *J. Rheumatol.*, vol. 29:959-965 (2002).

Marzo-Ortega, Helena et al., "Inhibition of Tumor Necrosis Factor α and Ankylosing Spondylitis," *The New England Journal of Medicine*, vol. 348(4):359-360; author reply 360-361 (2003).

Ogilvie, A.L.J. et al., "Treatment of psoriatic arthritis with antitumor necrosis factor-α antibody clears skin lesions of psoriasis resistant to treatment with mexotrexate," *British Journal of Dermatology*, vol. 144:587-589 (2001).

Paul, William E., Fundamental Immunology, Third Edition, pp. 292-295 (1993).

Pham, T. et al., "Initiation of biological agents in patients with ankylosing spondylitis: results of a Delphi study by the ASAS Group," *Ann. Rheum. Dis.*, vol. 62:812-816 (2003).

Reimold, Andreas M., "New Indications for Treatment of Chronic Inflammation by TNF-α Blockade," *The American Journal of the Medical Sciences*, vol. 325(2):75-92 (2003).

Ribbens, C. et al., "Increased matrix metalloproteinase-3 serum levels in rheumatic diseases: relationship with synovitis and steroid treatment," *Ann. Rheum. Dis.*, vol. 61:161-166 (2002).

Rudikoff, Stuart et al., "Single amino acid substitution altering antigen-binding specificity," *Proc. Natl. Acad. Sci. USA*, vol. 79:1979-1983 (1982).

Schnarr, S. et al., "Anti-tumour necrosis factor (TNF)-α therapy in undifferentiated sponsyloarthropathy," *Clin. Res. Rheumatol.*, vol. 20(Suppl. 28):S126-S129 (2002).

Sieper, J. et al., "New treatment options in ankylosing spondylitis: a role for anti-TNFα therapy," *Ann. Rheum. Dis.*, vol. 60:iii58-iii61 (2001).

Smith, David Lloyd et al., "Ibuprofen in psoriatic arthritis," *Arthritis Rheum.*, vol. 23(8):961-962 (2005).

Stokes, David G. et al., "Potential of Tumor Necrosis Factor Neutralization Strategies in Rheumatologic Disorders Other Than Rheumatoid Arthritis," *Semin. Arthritis Rheum.*, vol. 33:1-18 (2003).

Stone, Millicent et al., "Clinical and Imaging Correlates of Response to Treatment with Infliximab in Patients with Ankylosing Spondylitis," *J. Rheumatol.*, vol. 28:1605-1614 (2001).

Van den Bosch, Filip et al., "Crohn's disease associated with spondyloarthropathy: effect of TNF-α blockade with infliximab on articular symptoms," *The Lancet*, vol. 356:1821-1822 (2000).

Yang, Chunhua et al., "Serum Levels of Matrix Metalloproteinase 3 and Macrophage Colony-Stimulating Factor 1 Correlate With Disease Activity in Ankylosing Spondylitis," *Arthritis & Rheumatism*, vol. 51(5):691-699 (2004).

Zou, J.X. et al., "Immunological basis for the use of TNFα-blocking agents in ankylosing spondylitis and immunological changes during treatment," *Clin. Exp. Rheumatol.*, vol. 20(Suppl. 28):S34-S37 (2002).

European Search Report for Application No. 06849865.8, dated Oct. 29, 2008.

International Search Report for Application No. PCT/US06/42564, dated Nov. 14, 2008.

International Search Report for Application No. PCT/US08/06912, dated Nov. 13, 2008.

Database Geo (online) "Expression profiling in RA disease pre and post anti-TNF treatment," NCBI; Apr. 16, 2007.

Lequerre et al., "Gene profiling in white blood cells predicts infliximab responsiveness in rheumatoid arthritis," *Arthritis Reseach & Therapy* 8(4):R105 (2006).

Lindberg et al., "Effect of Infliximab on mRNA expression profiles in synovial tissue of rheumatoid arthritis patients," *Arthritis Research & Therapyl* 8(6):R179 (2006).

Bobbio-Pallavicini et al., "High IgA rheumatoid factor levels are associate with poor clinical response to tumour necrosis factor alpha inhibitors in rheumatoid arthritis," *Ann Rheum Dis* 66(3):302-307 (2007).

Lequerre et al., "Autoantibodies, metalloproteinases and bone markers in rheumatoid arthritis patents are unable to predict their responses to infliximab," *Rheumatol.* 46(3):446-453 (2007).

Balanescu et al., "Early and late effect of infliximab on circulating dendritic cells phenotype in rheumatoid arthritis patients," *International J of Clinical Pharmacy Researchl* 25(1):9-18 (2005).

Hernandez et al., "influence of anti-TNF therapy on monocye gene expression in rheumatoid arthritis" Annals of the Rheaumatic Diseases, and Annual European Congress of Rheumatology 62(Suppl. 1):180 (2003).

\* cited by examiner

US 8,092,998 B2

BIOMARKERS PREDICTIVE OF THE RESPONSIVENESS TO TNFα INHIBITORS IN AUTOIMMUNE DISORDERS

RELATED APPLICATIONS

This application claims the benefit of priority to U.S. provisional patent application No. 60/932,888 filed on May 31, 2007 The contents of the above-mentioned priority application is hereby incorporated by reference in its entirety

BACKGROUND OF THE INVENTION

Autoimmune disorders are a significant and widespread medical problem. For example, rheumatoid arthritis (RA) is an autoimmune disease affecting more than two million people in the United States. RA causes chronic inflammation of the joints and typically is a progressive illness that has the potential to cause joint destruction and functional disability. The cause of rheumatoid arthritis is unknown, although genetic predisposition, infectious agents and environmental factors have all been implicated in the etiology of the disease. In active RA, symptoms can include fatigue, lack of appetite, low grade fever, muscle and joint aches and stiffness. Also during disease flare ups, joints frequently become red, swollen, painful and tender, due to inflammation of the synovium. Furthermore, since RA is a systemic disease, inflammation can affect organs and areas of the body other than the joints, including glands of the eyes and mouth, the lung lining, the pericardium, and blood vessels.

Traditional treatments for the management of RA and other autoimmune disorders include fast acting "first line drugs" and slower acting "second line drugs." The first line drugs reduce pain and inflammation. Example of such first line drugs include aspirin, naproxen, ibuprofen etodolac and other nonsteroidal anti-inflammatory drugs (NSAIDs), as well as corticosteroids, given orally or injected directly into tissues and joints. The second line drugs promote disease remission and prevent progressive joint destruction and are also referred to as disease-modifying anti-rheumatic drugs or DMARDs. Examples of second line drugs include gold, hydrochloroquine, azulfidine and immunosuppressive agents, such as methotrexate, azathioprine, cyclophosphamide, chlorambucil and cyclosporine. Many of these drugs, however, can have detrimental side-effects. Thus, additional therapies for rheumatoid arthritis and other autoimmune disorders have been sought.

More recently, biological therapies have been applied to the treatment of autoimmune disorders such as rheumatoid arthritis. For example, three TNFα inhibitors, REMICADE™ (infliximab), a chimeric anti-TNFα mAb, ENBREL™ (etanercept), a TNFR-Ig Fc fusion protein, and HUMIRA™ (adalimumab), a human anti-TNFα mAb, have been approved by the FDA for treatment of rheumatoid arthritis. While such biologic therapies have demonstrated success in the treatment of rheumatoid arthritis and other autoimmune disorders, not all subjects treated respond, or respond well, to a TNFα inhibitor. The use of TNFα inhibitors such as TNFα inhibitors typically is more expensive than traditional treatments and usually requires administration by injection, which, at least for certain agents, may require that the patient visit a medical office on a frequent basis. Thus, it would be very helpful to predict in advance of treatment whether a rheumatoid arthritis patient is likely to be responsive to treatment with a TNFα inhibitor. Accordingly, ways for predicting responsiveness to a TNFα inhibitor in patients having autoimmune disorders, such as rheumatoid arthritis patients, are of particular interest.

SUMMARY OF THE INVENTION

This invention provides methods and compositions for predicting responsiveness to a TNFα inhibitor in a subject having an autoimmune disorder, such as rheumatoid arthritis, based on the discovery that the expression patterns of particular biomarkers in the subject correlate with responsiveness to a TNFα inhibitor. Using microarray analysis of monocytes from representative rheumatoid arthritis (RA) patients treated with an anti-TNFα monoclonal antibody, 82 differentially expressed genes predictive of responsiveness to TNFα inhibitor treatment were identified by pairwise comparisons between future RA responders and future RA non-responders to anti-TNFα therapy. Furthermore, hierarchical clustering and TaqMan®-PCR of RA responders/non-responders pre-treatment identified one gene of particular interest, CD11c, which was fully predictive of future response to anti-TNFα treatment.

Accordingly, in one aspect, the invention pertains to a method for predicting responsiveness to a TNFα inhibitor in a subject having an autoimmune disorder (e.g., rheumatoid arthritis). The method comprises: (i) assaying the subject for expression of one or more biomarkers predictive of responsiveness to a TNFα inhibitor in an autoimmune disorder, and (ii) predicting responsiveness of the subject to the TNFα inhibitor based on expression of the one or more biomarkers in the subject, wherein the one or more biomarkers is encoded by a nucleic acid molecule comprising a nucleotide sequence selected from the group consisting of SEQ ID NO: 1-82 (corresponding to the sequences set forth in Table 9)

Within SEQ ID NOs: 1-82, certain genes were found to be upregulated in RA responders to TNFα inhibitors. Accordingly, in one embodiment, the one or more biomarkers is encoded by a nucleic acid molecule comprising a nucleotide sequence selected from the group consisting of SEQ ID NOs: 6, 7, 10, 15-17, 19, 22, 24, 27, 31, 34-39, 43-47, 49, 51, 54, 55, 57, 59, 61, 62, 64, 70, 75, 79 and 82 (corresponding to sequences from Table 9 that are increased in ≧80% of responders vs. non-responders). More preferably, the one or more biomarkers is encoded by a nucleic acid molecule comprising a nucleotide sequence selected from the group consisting of SEQ ID NOs: 31, 37, 44, 47, 62 and 70 (corresponding to sequences from Table 9 that are increased in ≧90% of responders vs. non-responders). Even more preferably, the one or more biomarkers is encoded by a nucleic acid molecule comprising the nucleotide sequence of SEQ ID NO: 44. (corresponding to CD11c, from Table 9, which is increased in 100% of responders vs. non-responders). In each of these embodiments, increased expression of the one or more biomarkers is predictive of responsiveness of the subject to a TNFα inhibitor.

Within SEQ ID NOs: 1-82, certain genes were found to be downregulated in RA responders to TNFα inhibitors. Accordingly, in one embodiment, the one or more biomarkers is encoded by a nucleic acid molecule comprising a nucleotide sequence selected from the group consisting of SEQ ID NOs: 1-5, 8, 9, 11-14, 18, 20, 21, 23, 25, 26, 28-30, 32, 33, 40-42, 48, 50, 52, 53, 56, 58, 60, 63, 65-69, 71-74, 76-78, 80 and 81. (corresponding to sequences from Table 9 that are decreased in ≧80% of responders vs. non-responders). More preferably, the one or more biomarkers is encoded by a nucleic acid molecule comprising a nucleotide sequence selected from the group consisting of SEQ ID NOs: 11, 29, 65, 73 and 74 (corresponding to sequences from Table 9 that are decreased in ≧90% of responders vs. non-responders). Even more preferably, the one or more biomarkers is encoded by a nucleic acid molecule comprising the nucleotide sequence of SEQ ID NO: 11 or SEQ ID NO: 74 (corresponding to sequences from Table 9 that are decreased in 100% of responders vs. non-responders). In each of these embodiments, decreased expression of the one or more biomarkers is predictive of responsiveness of the subject to a TNFα inhibitor.

In another aspect, the invention provides a method for predicting responsiveness to a TNFα inhibitor in a subject having an autoimmune disorder, the method comprising: (i) assaying the subject for expression of one or more biomarkers predictive of responsiveness to a TNFα inhibitor in an autoimmune disorder, and (ii) predicting responsiveness of the subject to the TNFα inhibitor based on expression of the one or more biomarkers in the subject, wherein the one or more biomarkers is selected from the group consisting of Aquaporin 3 (Genbank Accession No. NM_004925); Similar to ribosomal protein S24, clone MGC:8595 (Genbank Accession No. NM_033022); Transmembrane emp24 domain trafficking protein 2 (Genbank Accession No. NM_006815; Superoxide dismutase 1, soluble (amyotrophic lateral sclerosis 1 (Genbank Accession No. NM_000454); Calmodulin 1 (phosphorylase kinase, delta) (Genbank Accession No. NM_006888); Guanine nucleotide binding protein (G protein), beta polypeptide 1 (Genbank Accession No. NM_002074); Prothymosin, alpha (gene sequence 28) (Genbank Accession No. NM_002823); *Homo sapiens* isocitrate dehydrogenase 1 (NADP+) soluble (IDH1) (Genbank Accession No. NM_005896); Tumor protein D52 (Genbank Accession Nos. NM_001025252, NM_001025253, NM_005079); Early growth response 1 (Genbank Accession No. NM_001964); *Homo sapiens* predicted osteoblast protein (GS3786) (Genbank Accession Nos. NM_014888, NM_001040020); Cytochrome c oxidase subunit VIIb (Genbank Accession No. NM_001866); CUG triplet repeat, RNA binding protein 2 (Genbank Accession No. NM_001025077, NM_001025076, NM_006561); Ubiquinol-cytochrome c reductase hinge protein (Genbank Accession No. NM_006004); Homos *sapiens* leptin receptor gene-related protein (HS0BRGRP) (Genbank Accession No. NM_017526); Wiskott-Aldrich syndrome protein interacting protein (Genbank Accession Nos. NM_001077269, NM_003387); CD97 antigen (Genbank Accession Nos. NM_001025160, NM_001784, NM_078481); Glutamate-cysteine ligase, catalytic subunit (Genbank Accession No. NM_001498); Crystallin, zeta (quinone reductase) (Genbank Accession No. NM_001889); Rap guanine nucleotide exchange factor (GEF) 2 (Genbank Accession No. NM_014247); Ataxin 1 (Genbank Accession No. NM_000332); Adaptor-related protein complex 1, sigma 2 subunit (Genbank Accession No. NM_003916); Ectonucleotide pyrophosphatase/phosphodiesterase 4 (Genbank Accession No. NM_014936); Desmocollin 2 (Genbank Accession Nos. NM_024422, NM_004949); MAL, T-cell differentiation protein (Genbank Accession Nos. NM_002371, NM_022438, NM_022439, NM_022440); Glucosamine (UDP-N-acetyl)-2-epimerase/N-acetylmannosamine kinase (Genbank Accession No. NM_005476); Chemokine (C-C motif) ligand 3 (Genbank Accession Nos. NM_001001437, NM_021006); Carboxypeptidase A3 (Genbank Accession No. NM_001870); Charcot-Leyden crystal protein (Genbank Accession No. NM_001828); NADH dehydrogenase (ubiquinone) 1 beta subcomplex, 1, 7 kDa (Genbank Accession No. NM_004545); Interleukin 8 receptor, beta (Genbank Accession No. NM_001557); Platelet factor 4 variant 1 (Genbank Accession No. NM_002620); Poly(A) binding protein interacting protein 1 (Genbank Accession No. NM_006451); ATP-binding cassette, sub-family C (CFTR/MRP), member 3 (Genbank Accession No. NM_003786); Actinin, alpha 1 (Genbank Accession No. NM_001102); NAD kinase (Genbank Accession No. NM_023018); Platelet/endothelial cell adhesion molecule (CD31 antigen) (Genbank Accession No. NM_000442); Esterase D/formylglutathione hydrolase (Genbank Accession No. NM_001984); Chromosome 20 open reading frame 111 (Genbank Accession No. NM_016470); Sterol-C4-methyl oxidase-like (Genbank Accession Nos. NM_001017369, NM_006745); PIM-1 oncogene (Genbank Accession No. NM_002648); GATA binding protein 2 (Genbank Accession No. NM_032638); Cathepsin Z (Genbank Accession No. NM_001336); Integrin alpha-X (antigen CD11c) (Genbank Accession No. NM_000887); Lectin, galactoside-binding, soluble, 8 (galectin 8) (Genbank Accession Nos. NM_006499, NM_201545); CD86 antigen (CD28 antigen ligand 2, B7-2 antigen) (Genbank Accession Nos. NM_006889, NM_175862); Interleukin 8 (Genbank Accession No. NM_000584); Fc fragment of IgE, high affinity I, receptor for alpha polypeptide (Genbank Accession No. NM_002001); Actin, gamma 1 (Genbank Accession No. NM_001614); KIAA0746 protein (Genbank Accession No. NM_015187); Glucosamine (N-acetyl)-6-sulfatase (Sanfilippo disease IIID) (Genbank Accession No. NM_002076); Transcription factor 4 (Genbank Accession Nos. BF592782, CR612521); Major histocompatibility complex, class II, DQ alpha 1 (Genbank Accession Nos. NM_002122, NM_020056); Cell division cycle 2-like 6 (CDK8-like) (Genbank Accession No. NM_015076); Major histocompatibility complex, class II, DQ beta 1 (Genbank Accession No. XM_942240); Phospholipase C-like 2 (Genbank Accession No. NM_015184); Coagulation factor II (thrombin) receptor-like 1 (Genbank Accession No. NM_005242); TM2 domain containing 1 (Genbank Accession No. NM_032027); Splicing factor 3b, subunit 1, 155 kDa (Genbank Accession No. NM_012433); SUB1 homolog (*S. cerevisiae*) (Genbank Accession No. NM_006713); MRNA; cDNA DKFZp56400862 (Genbank Accession No. AI278204); Amyloid beta (A4) precursor protein (peptidase nexin-II, Alzheimer disease) (Genbank Accession Nos. NM_201413, NM_000484, NM_201414); Cytochrome b-5 (Genbank Accession Nos. NM_001914, NM_148923); Cold autoinflammatory syndrome 1 (Genbank Accession No. NM_183395); Neugrin, neurite outgrowth associated (Genbank Accession Nos. NM_016645, NM_001033088); Ribosomal protein S26, 40S ribosomal protein (Genbank Accession No. XM_941927); CCR4-NOT transcription complex, subunit 6 (Genbank Accession No. NM_015455); Ubiquinol-cytochrome c reductase complex (7.2 kD) (Genbank Accession Nos. NM_013387, NM_001003684); Hepatocellular carcinoma-associated antigen 112 (Genbank Accession No. NM_018487); Kruppel-like factor 11 (Genbank Accession No. XM_001129527); GGA binding partner (Genbank Accession No. NM_018318); Cornichon homolog 4 (Drosophila) (Genbank Accession No. NM_014184); Hypothetical protein FLJ21616 (Genbank Accession No. NM_024567); *Homo sapiens* hypothetical protein FLJ10134 (Genbank Accession No. NM_018004); Nuclear prelamin A recognition factor (Genbank Accession Nos. NM_012336, NM_001038618); Erythroblast membrane-associated protein (Genbank Accession Nos. NM_018538, NM_001017922); LR8 protein (Genbank Accession No. NM_014020); Likely ortholog of mouse limb-bud and heart gene (LBH) (Genbank Accession No. NM_030915); Calmin (calponin-like, transmembrane) (Genbank Accession No. NM_024734); Chromosome 14 open reading frame 156 (Genbank Accession No. NM_031210); Guanine nucleotide binding protein (G protein) alpha 12 (Genbank Accession No. NM_007353); and SRY (sex determining region Y)-box 18 (Genbank Accession No. NR_003287) (corresponding to biomarkers listed in Table 9).

Within the above-listed biomarkers, certain genes were found to be upregulated in RA responders to TNFα inhibitors. Accordingly, in one embodiment, the one or more biomarkers is selected from the group consisting of Guanine nucleotide binding protein (G protein), beta polypeptide 1; Prothymosin, alpha (gene sequence 28); Early growth response 1; *Homo sapiens* leptin receptor gene-related protein (HS0BRGRP); Wiskott-Aldrich syndrome protein interacting protein; CD97 antigen; Crystallin, zeta (quinone reductase); Adaptor-related protein complex 1, sigma 2 subunit; Desmocollin 2; Chemokine (C-C motif) ligand 3; Interleukin 8 receptor, beta; ATP-binding cassette, sub-family C (CFTR/MRP), member 3; Actinin, alpha 1; NAD kinase; Platelet/endothelial cell adhesion molecule (CD31 antigen); Esterase D/formylglutathione hydrolase; Chromosome 20 open reading frame 111; Cathepsin Z; Integrin alpha-X (antigen CD 11c); Lectin, galactoside-binding, soluble, 8 (galectin 8); CD86 antigen (CD28 antigen ligand 2, B7-2 antigen); Interleukin 8; Actin, gamma 1; Glucosamine (N-acetyl)-6-sulfatase (Sanfilippo disease IIID); Cell division cycle 2-like 6 (CDK8-like); Major histocompatibility complex, class II, DQ beta 1; Coagulation factor II (thrombin) receptor-like 1; Splicing factor 3b, subunit 1, 155 kDa; MRNA; cDNA DKFZp56400862; Amyloid beta (A4) precursor protein (peptidase nexin-II, Alzheimer disease); Cold autoinflammatory syndrome 1; Kruppel-like factor 11; Nuclear prelamin A recognition factor; Calmin (calponin-like, transmembrane); and SRY (sex determining region Y)-box 18 (corresponding to biomarkers from Table 9 that are increased in >80% of responders vs. non-responders). More preferably, the one or more biomarkers is selected from the group consisting of Interleukin 8 receptor, beta; Platelet/endothelial cell adhesion molecule (CD31 antigen); Integrin alpha-X (antigen CD11c); Interleukin 8; Amyloid beta (A4) precursor protein (peptidase nexin-II, Alzheimer disease); and Kruppel-like factor 11 (corresponding to biomarkers from Table 9 that are increased in >90% of responders vs. non-responders). Even more preferably, the one or more biomarkers is Integrin alpha-X (antigen CD11c) (corresponding to a biomarker from Table 9 that is increased in 100% of responders vs. non-responders). In each of these embodiments, increased expression of the one or more biomarkers is predictive of responsiveness of the subject to a TNF.alpha. inhibitor.

Within the above-listed biomarkers, certain genes were found to be downregulated in RA responders to TNFα inhibitors. Accordingly, in one embodiment, the one or more biomarkers is selected from the group consisting of Aquaporin 3; Similar to ribosomal protein S24, clone MGC:8595; Transmembrane emp24 domain trafficking protein 2; Superoxide dismutase 1, soluble (amyotrophic lateral sclerosis 1; Calmodulin 1 (phosphorylase kinase, delta); *Homo sapiens* isocitrate dehydrogenase 1 (NADP+) soluble (IDH1); Tumor protein D52; *Homo sapiens* predicted osteoblast protein (GS3786); Cytochrome c oxidase subunit VIIb; CUG triplet repeat, RNA binding protein 2; Ubiquinol-cytochrome c reductase hinge protein; Glutamate-cysteine ligase, catalytic subunit; Rap guanine nucleotide exchange factor (GEF)2; Ataxin 1; Ectonucleotide pyrophosphatase/phosphodiesterase 4; MAL, T-cell differentiation protein; Glucosamine (UDP-N-acetyl)-2-epimerase/N-acetylmannosamine kinase; Carboxypeptidase A3; Charcot-Leyden crystal protein; NADH dehydrogenase (ubiquinone) 1 beta subcomplex, 1, 7 kDa; Platelet factor 4 variant 1; Poly(A) binding protein interacting protein 1; Sterol-C4-methyl oxidase-like; PIM-1 oncogene; GATA binding protein 2; Fc fragment of IgE, high affinity I, receptor for; alpha polypeptide; KIAA0746 protein; Transcription factor 4; Major histocompatibility complex, class II, DQ alpha 1; Phospholipase C-like 2; TM2 domain containing 1; SUB1 homolog (*S. cerevisiae*); Cytochrome b-5; Neugrin, neurite outgrowth associated; Ribosomal protein S26, 40S ribosomal protein; CCR4-NOT transcription complex, subunit 6; Ubiquinol-cytochrome c reductase complex (7.2 kD); Hepatocellular carcinoma-associated antigen 112; GGA binding partner; Cornichon homolog 4 (Drosophila); Hypothetical protein FLJ21616; *Homo sapiens* hypothetical protein FLJ10134; Erythroblast membrane-associated protein; LR8 protein; Likely ortholog of mouse limb-bud and heart gene (LBH); Chromosome 14 open reading frame 156; and Guanine nucleotide binding protein (G protein) alpha 12 (corresponding to biomarkers from Table 9 that are decreased in ≧80% of responders vs. non-responders). More preferably, the one or more biomarkers is selected from the group consisting of *Homo sapiens* predicted osteoblast protein (GS3786); Charcot-Leyden crystal protein; Neugrin, neurite outgrowth associated; Hypothetical protein FLJ21616; and *Homo sapiens* hypothetical protein FLJ10134 (corresponding to biomarkers from Table 9 that are decreased in ≧90% of responders vs. non-responders). Even more preferably, the one or more biomarkers is *Homo sapiens* predicted osteoblast protein (GS3786) or *Homo sapiens* hypothetical protein FLJ10134 (corresponding to biomarkers from Table 9 that are decreased in 100% of responders vs. non-responders). In each of these embodiments, decreased expression of the one or more biomarkers is predictive of responsiveness of the subject to a TNFα inhibitor.

In yet another aspect, the invention provides a method for predicting responsiveness to a TNFα inhibitor in a subject having an autoimmune disorder, the method comprising: (i) assaying the subject for increased expression of a biomarker, which biomarker is CD11c, and (ii) predicting responsiveness of the subject to the TNFα inhibitor based on increased expression of CD11c in the subject.

In yet another aspect, the invention provides a method for predicting responsiveness to a TNFα inhibitor, which TNFα inhibitor is adalimumab, in a subject having an autoimmune disorder, the method comprising: (i) assaying the subject for expression of one or more biomarkers predictive of responsiveness to adalimumab in an autoimmune disorder, and (ii) predicting responsiveness of the subject to adalimumab based on expression of the one or more biomarkers in the subject. Preferably, the one or more biomarkers is encoded by a nucleic acid molecule comprising a nucleotide sequence selected from the group consisting of SEQ ID NO: 1-82 (corresponding to biomarkers set forth in Table 9).

In one embodiment of the methods of the invention, a sample from the subject is assayed for expression of mRNA encoding the one or more biomarkers. In another embodiment of the methods of the invention, a sample from the subject is assayed for protein expression of the one or more biomarkers.

In one embodiment, the methods of the invention further comprise selecting a treatment regimen with the TNFα inhibitor based upon expression of the one or more biomarkers in the subject. In another embodiment, the methods of the invention further comprise administering the TNFα inhibitor to the subject according to the treatment regimen such that autoimmune disorder is inhibited in the subject.

A preferred TNFα inhibitor of the invention is an anti-tumor necrosis factor-alpha (TNFα) antibody, or antigen-binding portion thereof. The anti-TNFα antibody, or antigen-binding portion thereof, can be, for example, a humanized antibody, a chimeric antibody or a multivalent antibody. For example, the anti-TNFα antibody, or antigen-binding portion thereof, can be infliximab or golimumab. In another embodiment, the anti-TNFα antibody, or antigen-binding portion thereof, is a human antibody. For example, the anti-TNFα antibody, or antigen-binding portion thereof, can be an isolated human antibody that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less. In another embodiment, the anti-TNFα antibody, or antigen-binding portion thereof, is an isolated human antibody with the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 305, or modified from SEQ ID NO: 305 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 306, or modified from SEQ ID NO: 306 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In another embodiment, the anti-TNFα antibody, or antigen-binding portion thereof, is an isolated human antibody with a light chain variable region (LCVR) comprising the amino acid sequence of SEQ ID NO: 303 and a heavy chain variable region (HCVR) comprising the amino acid sequence of SEQ ID NO: 304. In yet another embodiment, the anti-TNFα antibody, or antigen-binding portion thereof, is adalimumab. Yet another example of a TNFα inhibitor is etanercept.

Preferably, in the methods of the invention, the subject is a human.

In another aspect, the invention pertains to a kit for predicting responsiveness to a TNFα inhibitor in a subject having an autoimmune disorder (e.g., rheumatoid arthritis). The kit comprises:

a) means for isolating monocytes;

b) means for measuring expression in the subject of one or more biomarkers predictive of responsiveness to a TNFα inhibitor in an autoimmune disorder;

c) means for measuring expression of at least one housekeeping gene; and d) instructions for use of the kit to predicting responsiveness to a TNFα inhibitor in a subject having an autoimmune disorder, wherein the one or more biomarkers is encoded by a nucleic acid molecule comprising a nucleotide sequence selected from the group consisting of SEQ ID NO: 1-82.

In one embodiment of the kit, the one or more biomarkers is encoded by a nucleic acid molecule comprising a nucleotide sequence selected from the group consisting of SEQ ID NOs: 6, 7, 10, 15-17, 19, 22, 24, 27, 31, 34-39, 43-47, 49, 51, 54, 55, 57, 59, 61, 62, 64, 70, 75, 79 and 82, more preferably the one or more biomarkers is encoded by a nucleic acid molecule comprising a nucleotide sequence selected from the group consisting of SEQ ID NOs: 31, 37, 44, 47, 62 and 70, even more preferably the one or more biomarkers is encoded by a nucleic acid molecule comprising the nucleotide sequence of SEQ ID NO: 44 (CD11c). In each of these embodiments, the instructions for use of the kit instruct that increased expression of the one or more biomarkers is predictive of responsiveness of the subject to a TNFα inhibitor.

In another embodiment of the kit, the one or more biomarkers is encoded by a nucleic acid molecule comprising a nucleotide sequence selected from the group consisting of SEQ ID NOs: 1-5, 8, 9, 11-14, 18, 20, 21, 23, 25, 26, 28-30, 32, 33, 40-42, 48, 50, 52, 53, 56, 58, 60, 63, 65-69, 71-74, 76-78, 80 and 81, more preferably the one or more biomarkers is encoded by a nucleic acid molecule comprising a nucleotide sequence selected from the group consisting of SEQ ID NOs: 11, 29, 65, 73 and 74, even more preferably the one or more biomarkers is encoded by a nucleic acid molecule comprising the nucleotide sequence of SEQ ID NO: 11 or SEQ ID NO: 74. In each of these embodiments, the instructions for use of the kit instruct that decreased expression of the one or more biomarkers is predictive of responsiveness of the subject to a TNFα inhibitor.

In one embodiment of the kit, the means for measuring expression in the subject of one or more biomarkers predictive of responsiveness to a TNFα inhibitor in an autoimmune disorder comprises a nucleic acid preparation sufficient to detect expression of mRNA encoding the biomarker in a sample from the subject. In another embodiment of the kit, the means for measuring expression in the subject of one or more biomarkers predictive of responsiveness to a TNFα inhibitor in an autoimmune disorder comprises an antibody preparation sufficient to detect protein expression of the biomarker in a sample from the subject. The kit can further comprise a TNFα inhibitor for treating the autoimmune disorder in the subject.

In another aspect, the invention pertains to methods of monitoring an autoimmune disorder (e.g., RA) in a subject having the autoimmune disorder (e.g., RA). These methods are based, at least in part, on microarray analysis of monocytes from representative rheumatoid arthritis (RA) patients treated with an anti-TNFα monoclonal antibody, including (i) hierarchical clustering with the genes resulting from a simultaneous comparison between RA versus ND and RA responders pre- versus post-anti-TNFα therapy, (ii) prediction analysis of microarrays (PAM); and (iii) hierarchical clustering based on the comparison between RA responders and non-responders post-treatment.

Accordingly, in another aspect, the invention provides a method of monitoring an autoimmune disorder in a subject having the autoimmune disorder, the method comprising: assaying the subject for expression of one or more biomarkers, wherein the one or more biomarkers is encoded by a nucleic acid molecule comprising a nucleotide sequence selected from the group consisting of SEQ ID NO: 83-133 (corresponding to biomarkers set forth in Table 3), thereby monitoring the autoimmune disorder in the subject.

In another aspect, the invention provides a method of monitoring an autoimmune disorder in a subject having the autoimmune disorder, the method comprising: assaying the subject for expression of one or more biomarkers, wherein the one or more biomarkers is encoded by a nucleic acid molecule comprising a nucleotide sequence selected from the group consisting of SEQ ID NO: 134-177, 110, 112, 118, 123 and 131 (corresponding to biomarkers set forth in Table 4), thereby monitoring the autoimmune disorder in the subject. In one embodiment, preferably the one or more biomarkers is encoded by a nucleic acid molecule comprising a nucleotide sequence selected from the group consisting of SEQ ID NO: 134-150, 112, 118 and 131 (upregulated biomarkers from Table 4), wherein expression of the one or more biomarkers is increased in the subject. In another embodiment, the one or more biomarkers is encoded by a nucleic acid molecule comprising a nucleotide sequence selected from the group consisting of SEQ ID NO: 151-177, 110 and 123 (downregulated biomarkers from Table 4), wherein expression of the one or more biomarkers is decreased in the subject.

In another aspect, the invention provides a method of monitoring an autoimmune disorder in a subject having the autoimmune disorder, the method comprising: assaying the subject for expression of one or more biomarkers, wherein the one or more biomarkers is encoded by a nucleic acid molecule comprising a nucleotide sequence selected from the group consisting of SEQ ID NO: 178-292, 91 and 97 (corresponding to biomarkers set forth in Table 5), thereby monitoring the autoimmune disorder in the subject. In one embodiment, the one or more biomarkers is encoded by a nucleic acid molecule comprising a nucleotide sequence selected from the group consisting of SEQ ID NO: 178-185; 187-200, 202, 203, 205-207; 211, 213, 214, 216, 220, 221, 226, 228, 229, 231, 232, 234, 235, 238-247, 249, 250, 253, 262-265, 268-282 and 285-288 (upregulated biomarkers from Table 5), wherein expression of the one or more biomarkers is increased in the subject. In another embodiment, the one or more biomarkers is encoded by a nucleic acid molecule comprising a nucleotide sequence selected from the group consisting of SEQ ID NO: 186, 201, 204, 208, 209, 91, 210, 212, 97, 215, 217-219, 222-225, 227, 230, 233, 236, 237, 248, 251, 252, 254-261, 266, 267, 283, 284 and 289-292 (downregulated biomarkers from Table 5), wherein expression of the one or more biomarkers is decreased in the subject.

In another aspect, the invention provides a method of monitoring an autoimmune disorder in a subject having the autoimmune disorder, the method comprising: assaying the subject for expression of one or more biomarkers, wherein the one or more biomarkers is encoded by a nucleic acid molecule comprising a nucleotide sequence selected from the group consisting of SEQ ID NO: 87, 97, 101, 293, 92, 272, 93, 107, 108, 121 and 123 (corresponding to pre-treatment biomarkers set forth in Table 6), and wherein the subject is monitored prior to treatment with a TNFα inhibitor, thereby monitoring the autoimmune disorder in the subject.

In another aspect, the invention provides a method of monitoring an autoimmune disorder in a subject having the autoimmune disorder the method comprising: assaying the subject for expression of one or more biomarkers, wherein the one or more biomarkers is encoded by a nucleic acid molecule comprising a nucleotide sequence selected from the group consisting of SEQ ID NO: 290, 209, 98, 112, 116, 121, 130, 155, 92, 289, 216 and 131 (corresponding to post-treatment biomarkers set forth in Table 6), and wherein the subject is monitored after treatment with a TNFα inhibitor, thereby monitoring the autoimmune disorder in the subject.

In yet another aspect, the invention provides a method of monitoring an autoimmune disorder in a subject having the autoimmune disorder, the method comprising: assaying the subject for expression of one or more biomarkers, wherein the one or more biomarkers is encoded by a nucleic acid molecule comprising a nucleotide sequence selected from the group consisting of SEQ ID NO: 97, 102, 29, 294, 295, 91, 131, 290, 100, 134, 296, 297, 298, 299, 136, 174 and 300 (corresponding to biomarkers set forth in Table 7), thereby monitoring the autoimmune disorder in the subject.

In yet another aspect, the invention pertains to a method of building a database for use in selecting a subject having an autoimmune disorder (e.g., RA) for treatment with a TNFα inhibitor. The method comprises: receiving, in a computer system, biomarker expression patterns from a plurality of subjects having an autoimmune disorder; and storing the biomarker expression pattern from each subject such that the biomarker expression pattern is associated with an identifier of the subject, wherein the biomarker expression pattern reports expression in the subject of one or more biomarkers encoded by a nucleic acid molecule comprising a nucleotide sequence selected from the group consisting of SEQ ID NO: 1-82. The identifier of the subject can be, for example, a numerical identifier coded to an identity of the subject. In a preferred embodiment, the method further comprises receiving, in the computer system, one or more treatment regimens for treatment of the autoimmune disorder in a subject such that the treatment regimen is associated with the biomarker expression pattern of the subject and the identifier of the subject.

The invention also pertains to a computer program product containing executable instructions that when executed cause a processor to perform operations comprising: receiving, in a computer system, a biomarker expression pattern of a subject at one or more biomarkers predictive of responsiveness to a TNFα inhibitor in an autoimmune disorder; and storing the biomarker expression pattern such that the biomarker expression pattern is associated with an identifier of the subject, wherein the biomarker expression pattern reports expression in the subject of one or more biomarkers encoded by a nucleic acid molecule comprising a nucleotide sequence selected from the group consisting of SEQ ID NO: 1-82. The computer program can further cause the processor to perform an operation comprising: receiving, in the computer system, a treatment regimen for treatment of the autoimmune disorder in the subject such that the treatment regimen is associated with the biomarker expression pattern of the subject and the identifier of the subject.

In yet another aspect, the invention pertains to a method of selecting an autoimmune disorder subject for treatment with a TNFα inhibitor, the method comprising: (i) identifying, in a database comprising a plurality of autoimmune disorder subjects, a subject whose database entry is associated with a biomarker expression pattern that is predictive of responsiveness to treatment with a TNFα inhibitor, and (ii) selecting the subject for treatment with a TNFα inhibitor, wherein the biomarker expression pattern reports expression in the subject of one or more biomarkers encoded by a nucleic acid molecule comprising a nucleotide sequence selected from the group consisting of SEQ ID NO: 1-82. The method can further comprise selecting a treatment regimen by identifying, in the database, a treatment regimen that has been associated with the biomarker expression pattern of the subject and with an identifier of the subject.

The invention also pertains to a computer program product containing executable instructions that when executed cause a processor to perform operations comprising: (i) identifying, in a database including a plurality of autoimmune disorder subjects associated with biomarker expression patterns, a subject that is associated with a biomarker expression pattern that is predictive of responsiveness to treatment with a TNFα inhibitor; and (ii) outputting the identified subject as a subject to be treated with a TNFα inhibitor; wherein the biomarker expression pattern reports expression in the subject of one or more biomarkers encoded by a nucleic acid molecule comprising a nucleotide sequence selected from the group consisting of SEQ ID NO: 1-82. In one embodiment, the computer program further causes the processor to perform an operation comprising outputting a treatment regimen that is associated with the subject to be treated with the TNFα inhibitor.

DETAILED DESCRIPTION OF THE INVENTION

Figure 1:
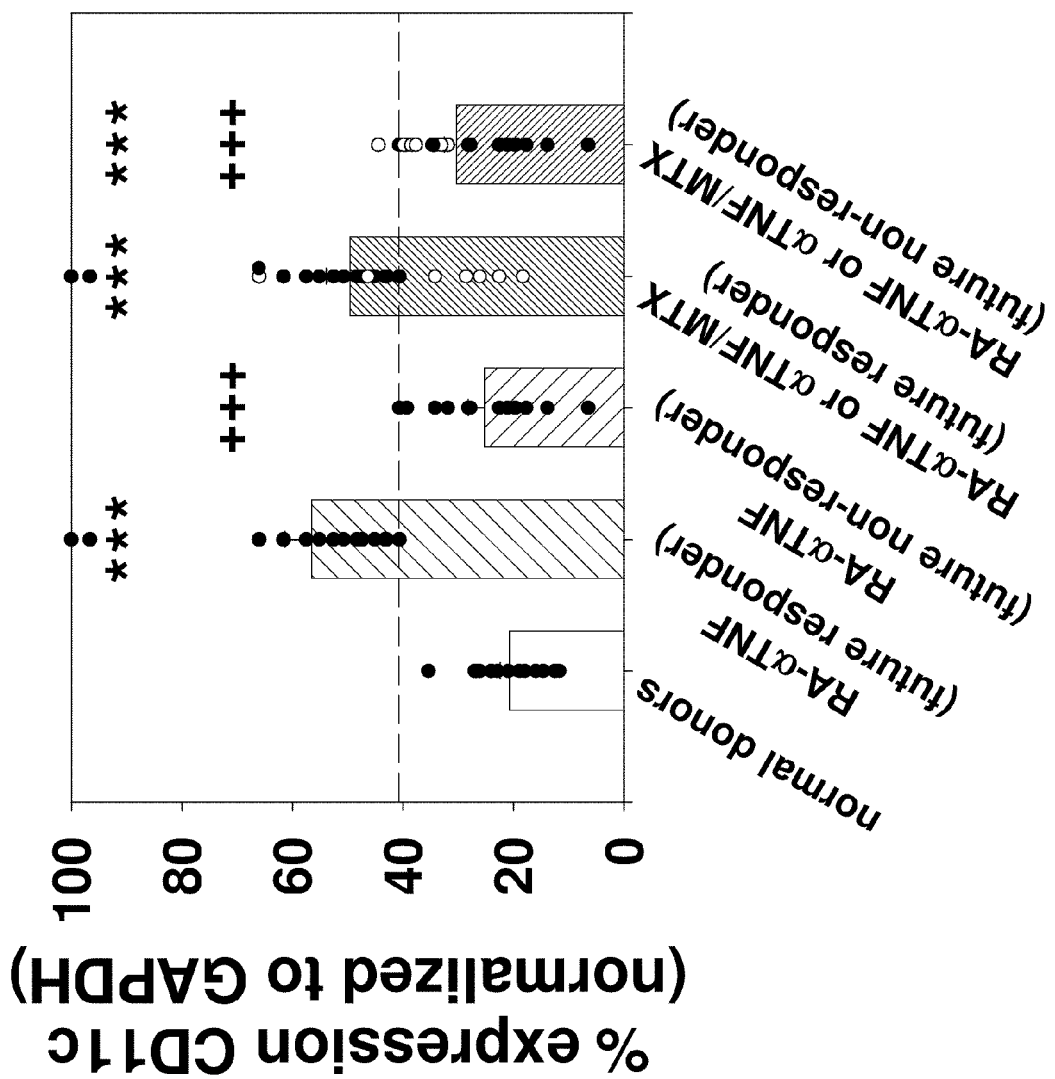
FIG. 1 is a bar graph showing the results of experiments validating the predictive gene CD11c by quantitative real-time PCR. mRNA expression was compared in monocytes from normal donors (n=16), as well as future responders and future non-responders to therapy with anti-TNFα (RA-αTNF; filled circles •; 15 responders and 12 non-responders) or to combination therapy with anti-TNFα/methotrexate (RA-αTNF/MTX; empty circles ○; 7 responders and 9 non-responders) The expression of CD11c is expressed as the means±standard error of the mean normalized to that of the house keeping gene glycerol-aldehyd-3-phosphate dehydrogenase (GAPDH; % expression). Except for 1 RA patient with a borderline ACR response of 30 and a CD11c mRNA level directly at the distinction threshold (who was therefore classified as a false negative), the threshold level (40%) almost fully distinguished future responders from nonresponders (100% specificity, 94% sensitivity, and 96% power). The threshold level to distinguish future responders from non-responders is indicated by a broken line ( - - - ); * $P\leq0.05$, ** $P\leq0.01$ as compared to normal donors; +++$P\leq0.005$ as compared to future responders to anti-TNFα therapy.

This invention provides methods for predicting responsiveness to a TNFα inhibitor in a subject suffering from an autoimmune disorder, and methods for selecting a treatment regimen with a TNFα inhibitor, based on expression of particular biomarkers in the subject to be treated. The invention is based, at least in part, on the observation that altered expression of particular biomarkers in a subject suffering from rheumatoid arthritis is associated with increased or decreased responsiveness to therapy with a TNFα inhibitor. Microarray analysis, hierarchical clustering and TaqMan®-PCR analysis were used to examine normal donors (NA) and rheumatoid arthritis (RA) patients, who were categorized as being responsive to treatment with an anti-TNFα antibody (RA responders) or nonresponsive to treatment with an anti-TNFα antibody (RA nonresponders). A panel of 82 genes were identified whose expression was altered (upregulated or downregulated) in patients identified as either future RA responders or future RA nonresponders, demonstrating the ability of these genes to act as biomarkers for predicting responsiveness to TNFα inhibitor treatment. In particular, one gene, encoding the antigen CD11c, was identified as fully predicting the future response to anti-TNFα treatment. Accordingly, the expression pattern of one or more biomarkers can be assessed in RA subjects for which TNFα inhibitor therapy is being considered, or subjects suffering from other autoimmune disorders amenable to TNFα inhibitor therapy, to thereby predict responsiveness of the subject to such therapy and/or to aid in the selection of an appropriate treatment regimen.

Furthermore, additional patterns of biomarker expression were identified by (i) hierarchical clustering with the genes resulting from a simultaneous comparison between RA versus ND and RA responders pre- versus post-anti-TNFα therapy; (ii) prediction analysis of microarrays; and (iii) hierarchical clustering based on the comparison between RA responders and non-responders post-treatment. Accordingly, the biomarker expression patterns described herein also can be using in monitoring an autoimmune disorder in a subject, e.g., monitoring the responsiveness of the subject to a particular therapy or assisting in the diagnosis or prognosis of the autoimmune disorder (e.g., RA) in the subject.

In order that the present invention may be more readily understood, certain terms are first defined. Additional definitions are set forth throughout the detailed description.

The term "predicting responsiveness to a TNFα inhibitor", as used herein, is intended to refer to an ability to assess the likelihood that treatment of a subject with a TNFα inhibitor will or will not be effective in (e.g., provide a measurable benefit to) the subject. In particular, such an ability to assess the likelihood that treatment will or will not be effective typically is exercised before treatment with the TNFα inhibitor is begun in the subject. However, it is also possible that such an ability to assess the likelihood that treatment will or will not be effective can be exercised after treatment has begun but before an indicator of effectiveness (e.g., an indicator of measurable benefit) has been observed in the subject.

The term "TNFα inhibitor" as used herein is intended to encompass agents including proteins, antibodies, antibody fragments, fusion proteins (e.g., Ig fusion proteins or Fc fusion proteins), multivalent binding proteins (e.g., DVD Ig), small molecule TNFα antagonists and similar naturally- or nonnaturally-occurring molecules, and/or recombinant and/or engineered forms thereof, that, directly or indirectly, inhibits TNFα activity, such as by inhibiting interaction of TNFα with a cell surface receptor for TNFα, inhibiting TNFα protein production, inhibiting TNFα gene expression, inhibiting TNFα secretion from cells, inhibiting TNFα receptor signaling or any other means resulting in decreased TNFα activity in a subject. The term "TNFα inhibitor" also includes agents which interfere with TNFα activity. Examples of TNFα inhibitors include etanercept (ENBREL™, Amgen), infliximab (REMICADE™, Johnson and Johnson), human anti-TNF monoclonal antibody adalimumab (D2E7/HUMIRA™, Abbott Laboratories), CDP 571 (Celltech), and CDP 870 (Celltech), as well as other compounds which inhibit TNFα activity, such that when administered to a subject suffering from or at risk of suffering from a disorder in which TNFα activity is detrimental (e.g., RA), the disorder is treated. The term also includes each of the anti-TNFα human antibodies and antibody portions described herein as well as those described in U.S. Pat. Nos. 6,090,382; 6,258,562; 6,509,015, and in U.S. patent application Ser. No. 09/801,185 (U.S. Publication No. 20030092059) and Ser. No. 10/302,356 (U.S. Publication No. 20030219438), each incorporated by reference herein.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" is also intended to encompass dual-specific antibodies and bispecific antibodies. The term "dual-specific antibody", as used herein, refers to full-length antibodies that can bind two different antigens (or epitopes) in each of its two binding arms (a pair of HC/LC) (see e.g., PCT publication WO 02/02773). Accordingly a dual-specific binding protein has two identical antigen binding arms, with identical specificity and identical CDR sequences, and is bi-valent for each antigen it binds to. The term "bispecific antibody", as used herein, refers to full-length antibodies that are generated by quadroma technology (see Milstein, C. and A. C. Cuello (1983) *Nature*, 305:537-40), by chemical conjugation of two different mAbs (see Staerz, U. D., et al. (1985) *Nature* 314: 628-31), or by knob-into-hole or similar approaches which introduces mutations in the Fc region (see Holliger, P., T. Prospero, and G. Winter (1993) *Proc. Natl. Acad. Sci. USA* 90:6444-8), resulting in multiple different immunogloblin species of which only one is the functional bispecific antibody. By molecular function, a bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen binding arms (in both specificity and CDR sequences), and is mono-valent for each antigen it binds to. Thus, when used herein, a "bispecific" antibody of the invention has one binding arm that is specific for an epitope of TNFα and a second binding arm that is specific for a different antigen or epitope.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')₂ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The terms "monoclonal antibody" or "monoclonal antibody composition" as used herein refer to a preparation of antibody molecules of single molecular composition. A monoclonal antibody composition displays a single binding specificity and affinity for a particular epitope.

The terms "chimeric antibody" or "chimeric monoclonal antibody" are intended to refer to antibodies in which the variable region sequences are derived from one species and the constant region sequences are derived from another species, such as an antibody in which the variable region sequences are derived from a mouse antibody and the constant region sequences are derived from a human antibody. Such "chimeric antibodies" can be prepared by standard recombinant technology well established in the art. For example, a nucleic acid encoding a $V_H$ region from a mouse antibody can be operatively linked to a nucleic acid encoding the heavy chain constant regions from a human antibody and, likewise, a nucleic acid encoding a $V_L$ region from a mouse antibody can be operatively linked to a nucleic acid encoding the light chain constant region from a human antibody.

The terms "humanized antibody" or "humanized monoclonal antibody" are intended to refer to antibodies in which CDR sequences derived from the germline of a non-human mammalian species, such as a mouse, have been grafted onto human framework sequences. Additional framework region modifications may be made within the human framework sequences. Such "humanized antibodies" can be prepared by standard recombinant technology well established in the art. For example, nucleic acids encoding the CDR1, CD2 and CDR3 regions from a $V_H$ region of a mouse antibody can be operatively linked to nucleic acids encoding the FR1, FR2, FR3 and FR4 regions of a human $V_H$ region, and the entire "CDR-grafted" $V_H$ region can be operatively linked to nucleic acid encoding the heavy chain constant regions from a human antibody. Likewise, nucleic acids encoding the CDR1, CD2 and CDR3 regions from a $V_L$ region of a mouse antibody can be operatively linked to nucleic acids encoding the FR1, FR2, FR3 and FR4 regions of a human $V_L$ region, and the entire "CDR-grafted" $V_L$ region can be operatively linked to nucleic acid encoding the light chain constant region from a human antibody.

The term "human antibody", as used herein, is intended to refer to antibodies having variable regions in which both the framework and CDR regions are derived from human germline immunoglobulin sequences. Furthermore, if the antibody contains a constant region, the constant region also is derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human germline immunoglobulin sequences. Human monoclonal antibodies can be produced by a hybridoma which includes a B cell obtained from a transgenic nonhuman animal, e.g., a transgenic mouse, having a genome comprising a human heavy chain transgene and a light chain transgene fused to an immortalized cell. The term "human monoclonal antibody", as used herein, also includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. Such recombinant human antibodies, however, can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The terms "Ig fusion protein" and "Fc fusion protein" are intended to refer to a recombinant, composite protein comprising a polypeptide of interest operatively linked to a constant region portion of immunoglobulin, typically the hinge, $CH_2$ and $CH_3$ domains of heavy chain constant region, more typically the human IgG1 hinge, $CH_2$ and $CH_3$ domains. The polypeptide of interest operatively linked to the Fc portion can be, for example, a full-length protein or only a portion of a full-length protein, such as one or more extracellular domains of a protein, e.g., one or more extracellular domains of a cell-surface protein. Such "Ig fusion proteins" can be prepared by standard recombinant technology well established in the art. For example, a nucleic acid encoding the polypeptide of interest can be operatively linked to a nucleic acid encoding the hinge, $CH_2$ and $CH_3$ domains of a heavy chain constant region.

The term "multivalent binding protein", as a form of TNFα inhibitor, is used in this specification to denote a binding protein comprising two or more antigen binding sites. Examples of multivalent binding proteins include dual variable domain (DVD) binding proteins. The multivalent binding protein is preferably engineered to have three or more antigen binding sites, and is generally not a naturally occurring antibody. A multivalent binding protein also can be a "multispecific binding protein." The term "multi specific binding protein" refers to a binding protein capable of binding two or more related or unrelated targets (wherein, with respect to this specification at least one of the targets is TNFα). Dual variable domain (DVD) binding proteins, as used herein, are binding proteins that comprise two or more antigen binding sites and are tetravalent or multivalent binding proteins. Such DVDs may be monospecific, i.e., capable of binding one antigen (e.g., TNFα) or multispecific, i.e., capable of binding two or more antigens (e.g., TNFα and one or more other antigens). DVD binding proteins comprising two heavy chain DVD polypeptides and two light chain DVD polypeptides are referred to as "DVD Ig." Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in US. Publication No. 20070071675, the entire contents of which are specifically incorporated herein by reference.

As used herein, the term "biomarker" is intended to encompass a substance that is used as an indicator of a biologic state and includes genes (and nucleotide sequences of such genes), mRNAs (and nucleotide sequences of such mRNAs) and proteins (and amino acid sequences of such proteins). A "biomarker expression pattern" is intended to refer to a quantitative or qualitative summary of the expression of one or more biomarkers in a subject, such as in comparison to a standard or a control.

The terms "increased" or "increased expression" and "decreased" or "decreased expression", with respect to the expression pattern of a biomarker(s), are used herein as meaning that the level of expression is increased or decreased relative to a constant basal level of expression of a household, or housekeeping, gene, whose expression level does not significantly vary under different conditions. A nonlimiting example of such a household, or housekeeping, gene is GAPDH. Other suitable household, or housekeeping, gene are well-established in the art.

As used herein, the term "CD11c" refers to a protein having a full-length amino acid sequence as set forth at Genbank Accession No. NP_000878 (also shown as SEQ ID NO: 302) and encoded by a full-length nucleotide sequence as set forth at Genbank Accession No. NM_000887 (also shown as SEQ ID NO: 301). CD11c is also known in the art as CD11C, CD11c antigen, Integrin alpha X, complement component 3 receptor 4 subunit, ITGAX, LeuM5, Integrin alpha X precursor, Leukocyte adhesion glycoprotein p150,p95 alpha chain, and Leukocyte adhesion receptor p150 subunit, which terms may be used interchangeably herein to refer to CD11c.

As used herein, the term "Affymetrix ID" refers to a numerical identifier that corresponds to a sequence entry in an Affymetrix database, which entry includes the sequence as well as additional information relating to the sequence and corresponding protein. The sequence entries, and additional information in the entries, for each Affymetrix ID are publicly available (e.g., by entering the Affymetrix ID number into the Affymetrix database search engine, e.g., at https://www.affymetrix.com/analysis/netaffx/index.affx). All sequence entries (such as Genbank Accession numbers), and additional information provided for each entry, corresponding to each of the Affymetrix ID numbers disclosed herein are hereby specifically incorporated by reference in their entirety.

As used herein, the term "subject" includes humans, and non-human animals amenable to TNFα inhibitor therapy, e.g., preferably mammals, such as non-human primates, sheep, dogs, cats, horses and cows.

As used herein, the term "autoimmune disorder subject" or "AD subject" is intended to refer to a subject (e.g., human patient) suffering from an autoimmune disorder.

As used herein, the term "rheumatoid arthritis subject" or "RA subject" is intended to refer to a subject (e.g., human patient) suffering from rheumatoid arthritis.

As used herein, the term "treatment regimen" is intended to refer to one or more parameters selected for the treatment of a subject, e.g., with a TNFα inhibitor, which parameters can include, but are not necessarily limited to, the type of agent chosen for administration, the dosage, the formulation, the route of administration and the frequency of administration.

Various aspects of the invention are described in further detail in the following subsections.

Prediction of Responsiveness to a TNFα Inhibitor for Autoimmune Disorders

In one aspect, the invention pertains to a method for predicting responsiveness to a TNFα inhibitor in a subject having an autoimmune disorder, such as rheumatoid arthritis. Typically, the method comprises (i) assaying the subject for the expression of one or more biomarkers predictive of responsiveness to a TNFα inhibitor in an autoimmune disorder, and (ii) predicting responsiveness of the subject to the TNFα inhibitor based on expression of the one or more biomarkers in the subject. As used herein, the term "one or more biomarkers" is intended to mean that at least one biomarker in a disclosed list of biomarkers is assayed and, in various embodiments, more than one biomarker set forth in the list may be assayed, such as two, three, four, five, ten, twenty, thirty, forty, fifty, more than fifty, or all the biomarkers in the list may be assayed.

Predicting responsiveness of the subject to the TNFα inhibitor "based on expression of the one or more biomarkers in the subject" typically involves comparing the level, or pattern, of expression of the one or more biomarkers in the subject to a known standard or control (which known standard or control may be derived from, for example, a normal subject, a pre-established TNFα inhibitor responder or a pre-established TNFα inhibitor non-responder). In a preferred embodiment, the level of expression of the biomarker(s) is measured in parallel with measurement of the level of expression of one or more "housekeeping" genes, such as GAPDH, whose expression level is not altered by the autoimmune disorder. The level of expression of the biomarker(s) is determined to be "increased" or "decreased" relative to a constant basal level of expression of the housekeeping gene. Examples of suitable housekeeping genes, such as GAPDH, that can be used for comparison purposes are well known in the art.

Preferably, the one or more biomarkers is encoded by a nucleic acid molecule comprising a nucleotide sequence selected from the group consisting of SEQ ID NO: 1-82 (corresponding to sequences of the biomarkers set forth in Table 9). Thus, at least one of the biomarkers encoded by a nucleic acid molecule comprising a nucleotide sequence selected from the group consisting of SEQ ID NO: 1-82 is assayed and, in various embodiments, for example, two, three, four, five, ten, twenty, thirty, forty, fifty, more than fifty, or all the biomarkers in the list may be assayed.

In a preferred embodiment, the one or more biomarkers is encoded by a nucleic acid molecule comprising a nucleotide sequence selected from the group consisting of SEQ ID NOs: 6, 7, 10, 15-17, 19, 22, 24, 27, 31, 34-39, 43-47, 49, 51, 54, 55, 57, 59, 61, 62, 64, 70, 75, 79 and 82 (corresponding to sequences from Table 9 that are increased in ≧80% of responders vs. non-responders). More preferably, the one or more biomarkers is encoded by a nucleic acid molecule comprising a nucleotide sequence selected from the group consisting of SEQ ID NOs: 31, 37, 44, 47, 62 and 70 (corresponding to sequences from Table 9 that are increased in ≧90% of responders vs. non-responders). Even more preferably, at least one of the biomarkers to be assayed is encoded by a nucleic acid molecule comprising the nucleotide sequence of SEQ ID NO: 44 (corresponding to the biomarker CD11c, which, as set forth in Table 9, is increased in 100% of responders vs. non-responders). In each of these embodiments, increased expression of the one or more biomarkers is predictive of responsiveness of the subject to a TNFα inhibitor (e.g., increased expression relative to a standard or control level of expression, which standard or control level of expression can be based, for example, on the level of expression in previously established TNFα inhibitor non-responder RA subjects).

In another preferred embodiment, the one or more biomarkers is encoded by a nucleic acid molecule comprising a nucleotide sequence selected from the group consisting of SEQ ID NOs: 1-5, 8, 9, 11-14, 18, 20, 21, 23, 25, 26, 28-30, 32, 33, 40-42, 48, 50, 52, 53, 56, 58, 60, 63, 65-69, 71-74, 76-78, 80 and 81 (corresponding to sequences from Table 9 that are decreased in ≧80% of responders vs. non-responders). More preferably, the one or more biomarkers is encoded by a nucleic acid molecule comprising a nucleotide sequence selected from the group consisting of SEQ ID NOs: 11, 29, 65, 73 and 74 (corresponding to sequences from Table 9 that are decreased in ≧90% of responders vs. non-responders). Even more preferably, the one or more biomarkers is encoded by a nucleic acid molecule comprising the nucleotide sequence of SEQ ID NO: 11 or SEQ ID NO: 74 (corresponding to sequences from Table 9 that are decreased in 100% of responders vs. non-responders). In each of these embodiments, decreased expression of the one or more biomarkers is predictive of responsiveness of the subject to a TNFα inhibitor (e.g., decreased expression relative to a standard or control level of expression, which standard or control level of expression can be based, for example, on the level of expression in previously established TNFα inhibitor non-responder RA subjects).

In another aspect, the invention provides a method for predicting responsiveness to a TNFα inhibitor in a subject having an autoimmune disorder, the method comprising: (i) assaying the subject for expression of one or more biomarkers predictive of responsiveness to a TNFα inhibitor in the autoimmune disorder, and (ii) predicting responsiveness of the subject to the TNFα inhibitor based on expression of the one or more biomarkers in the subject, wherein the one or more biomarkers is selected from the group consisting of Aquaporin 3 (Genbank Accession No. NM_004925); Similar to ribosomal protein S24, clone MGC:8595 (Genbank Accession No. NM_033022); Transmembrane emp24 domain trafficking protein 2 (Genbank Accession No. NM_006815; Superoxide dismutase 1, soluble (amyotrophic lateral sclerosis 1 (Genbank Accession No. NM_000454); Calmodulin 1 (phosphorylase kinase, delta) (Genbank Accession No. NM_006888); Guanine nucleotide binding protein (G protein), beta polypeptide 1 (Genbank Accession No. NM_002074); Prothymosin, alpha (gene sequence 28) (Genbank Accession No. NM_002823); *Homo sapiens* isocitrate dehydrogenase 1 (NADP+) soluble (IDH1) (Genbank Accession No. NM_005896); Tumor protein D52 (Genbank Accession Nos. NM_001025252, NM_001025253, NM_005079); Early growth response 1 (Genbank Accession No. NM_001964); *Homo sapiens* predicted osteoblast protein (GS3786) (Genbank Accession Nos. NM_014888, NM_001040020); Cytochrome c oxidase subunit VIIb (Genbank Accession No. NM_001866); CUG triplet repeat, RNA binding protein 2 (Genbank Accession No. NM_001025077, NM_001025076, NM_006561); Ubiquinol-cytochrome c reductase hinge protein (Genbank Accession No. NM_006004); Homos *sapiens* leptin receptor gene-related protein (HS0BRGRP) (Genbank Accession No. NM_017526); Wiskott-Aldrich syndrome protein interacting protein (Genbank Accession Nos. NM_001077269, NM_003387); CD97 antigen (Genbank Accession Nos. NM_001025160, NM_001784, NM_078481); Glutamate-cysteine ligase, catalytic subunit (Genbank Accession No. NM_001498); Crystallin, zeta (quinone reductase) (Genbank Accession No. NM_001889); Rap guanine nucleotide exchange factor (GEF) 2 (Genbank Accession No. NM_014247); Ataxin 1 (Genbank Accession No. NM_000332); Adaptor-related protein complex 1, sigma 2 subunit (Genbank Accession No. NM_003916); Ectonucleotide pyrophosphatase/phosphodiesterase 4 (Genbank Accession No. NM_014936); Desmocollin 2 (Genbank Accession Nos. NM_024422, NM_004949); MAL, T-cell differentiation protein (Genbank Accession Nos. NM_002371, NM_022438, NM_022439, NM_022440); Glucosamine (UDP-N-acetyl)-2-epimerase/N-acetylmannosamine kinase (Genbank Accession No. NM_005476); Chemokine (C-C motif) ligand 3 (Genbank Accession Nos. NM_001001437, NM_021006); Carboxypeptidase A3 (Genbank Accession No. NM_001870); Charcot-Leyden crystal protein (Genbank Accession No. NM_001828); NADH dehydrogenase (ubiquinone) 1 beta subcomplex, 1, 7 kDa (Genbank Accession No. NM_004545); Interleukin 8 receptor, beta (Genbank Accession No. NM_001557); Platelet factor 4 variant 1 (Genbank Accession No. NM_002620); Poly(A) binding protein interacting protein 1 (Genbank Accession No. NM_006451); ATP-binding cassette, sub-family C (CFTR/MRP), member 3 (Genbank Accession No. NM_003786); Actinin, alpha 1 (Genbank Accession No. NM_001102); NAD kinase (Genbank Accession No. NM_023018); Platelet/endothelial cell adhesion molecule (CD31 antigen) (Genbank Accession No. NM_000442); Esterase D/formylglutathione hydrolase (Genbank Accession No. NM_001984); Chromosome 20 open reading frame 111 (Genbank Accession No. NM_016470); Sterol-C4-methyl oxidase-like (Genbank Accession Nos. NM_001017369, NM_006745); PIM-1 oncogene (Genbank Accession No. NM_002648); GATA binding protein 2 (Genbank Accession No. NM_032638); Cathepsin Z (Genbank Accession No. NM_001336); Integrin alpha-X (antigen CD11c) (Genbank Accession No. NM_000887); Lectin, galactoside-binding, soluble, 8 (galectin 8) (Genbank Accession Nos. NM_006499, NM_201545); CD86 antigen (CD28 antigen ligand 2, B7-2 antigen) (Genbank Accession Nos. NM_006889, NM_175862); Interleukin 8 (Genbank Accession No. NM_000584); Fc fragment of IgE, high affinity I, receptor for alpha polypeptide (Genbank Accession No. NM_002001); Actin, gamma 1 (Genbank Accession No. NM_001614); KIAA0746 protein (Genbank Accession No. NM_015187); Glucosamine (N-acetyl)-6-sulfatase (Sanfilippo disease IIID) (Genbank Accession No. NM_002076); Transcription factor 4 (Genbank Accession Nos. BF592782, CR612521); Major histocompatibility complex, class II, DQ alpha 1 (Genbank Accession Nos. NM_002122, NM_020056); Cell division cycle 2-like 6 (CDK8-like) (Genbank Accession No. NM_015076); Major histocompatibility complex, class II, DQ beta 1 (Genbank Accession No. XM_942240); Phospholipase C-like 2 (Genbank Accession No. NM_015184); Coagulation factor II (thrombin) receptor-like 1 (Genbank Accession No. NM_005242); TM2 domain containing 1 (Genbank Accession No. NM_032027); Splicing factor 3b, subunit 1, 155 kDa (Genbank Accession No. NM_012433); SUB1 homolog (*S. cerevisiae*) (Genbank Accession No. NM_006713); MRNA; cDNA DKFZp56400862 (Genbank Accession No. AI278204); Amyloid beta (A4) precursor protein (peptidase nexin-II, Alzheimer disease) (Genbank Accession Nos. NM_201413, NM_000484, NM_201414); Cytochrome b-5 (Genbank Accession Nos. NM_001914, NM_148923); Cold autoinflammatory syndrome 1 (Genbank Accession No. NM_183395); Neugrin, neurite outgrowth associated (Genbank Accession Nos. NM-016645, NM_001033088); Ribosomal protein S26, 40S ribosomal protein (Genbank Accession No. XM_941927); CCR4-NOT transcription complex, subunit 6 (Genbank Accession No. NM_015455); Ubiquinol-cytochrome c reductase complex (7.2 kD) (Genbank Accession Nos. NM_013387, NM_001003684); Hepatocellular carcinoma-associated antigen 112 (Genbank Accession No. NM_018487); Kruppel-like factor 11 (Genbank Accession No. XM_001129527); GGA binding partner (Genbank Accession No. NM_018318); Cornichon homolog 4 (Drosophila) (Genbank Accession No. NM_014184); Hypothetical protein FLJ21616 (Genbank Accession No. NM_024567); *Homo sapiens* hypothetical protein FLJ1134 (Genbank Accession No. NM_018004); Nuclear prelamin A recognition factor (Genbank Accession Nos. NM_012336, NM_001038618); Erythroblast membrane-associated protein (Genbank Accession Nos. NM_018538, NM_001017922); LR8 protein (Genbank Accession No. NM_014020); Likely ortholog of mouse limb-bud and heart gene (LBH) (Genbank Accession No. NM_030915); Calmin (calponin-like, transmembrane) (Genbank Accession No. NM_024734); Chromosome 14 open reading frame 156 (Genbank Accession No. NM_031210); Guanine nucleotide binding protein (G protein) alpha 12 (Genbank Accession No. NM_007353); and SRY (sex determining region Y)-box 18 (Genbank Accession No. NR_003287) (corresponding to biomarkers listed in Table 9).

In a preferred embodiment, the one or more biomarkers is selected from the group consisting of Guanine nucleotide binding protein (G protein), beta polypeptide 1; Prothymosin, alpha (gene sequence 28); Early growth response 1; Homos sapiens leptin receptor gene-related protein (HS0BRGRP); Wiskott-Aldrich syndrome protein interacting protein; CD97 antigen; Crystallin, zeta (quinone reductase); Adaptor-related protein complex 1, sigma 2 subunit; Desmocollin 2; Chemokine (C-C motif) ligand 3; Interleukin 8 receptor, beta; ATP-binding cassette, sub-family C(CFTR/MRP), member 3; Actinin, alpha 1; NAD kinase; Platelet/endothelial cell adhesion molecule (CD31 antigen); Esterase D/formylglutathione hydrolase; Chromosome 20 open reading frame 111; Cathepsin Z; Integrin alpha-X (antigen CD11c); Lectin, galactoside-binding, soluble, 8 (galectin 8); CD86 antigen (CD28 antigen ligand 2, B7-2 antigen); Interleukin 8; Actin, gamma 1; Glucosamine (N-acetyl)-6-sulfatase (Sanfilippo disease IIID); Cell division cycle 2-like 6 (CDK8-like); Major histocompatibility complex, class II, DQ beta 1; Coagulation factor II (thrombin) receptor-like 1; Splicing factor 3b, subunit 1, 155 kDa; MRNA; cDNA DKFZp56400862; Amyloid beta (A4) precursor protein (peptidase nexin-II, Alzheimer disease); Cold autoinflammatory syndrome 1; Kruppel-like factor 11; Nuclear prelamin A recognition factor; Calmin (calponin-like, transmembrane); and SRY (sex determining region Y)-box 18 (corresponding to biomarkers listed in Table 9 that are increased in ≧80% of responders vs. non-responders). More preferably, the one or more biomarkers is selected from the group consisting of Interleukin 8 receptor, beta; Platelet/endothelial cell adhesion molecule (CD31 antigen); Integrin alpha-X (antigen CD11c); Interleukin 8; Amyloid beta (A4) precursor protein (peptidase nexin-II, Alzheimer disease); and Kruppel-like factor 11 (corresponding to biomarkers listed in Table 9 that are increased in ≧90% of responders vs. non-responders). Even more preferably, at least one of the biomarkers is Integrin alpha-X (antigen CD11c) (corresponding to a biomarker listed in Table 9 that is increased in 100% of responders vs. non-responders). In each of the embodiments, increased expression of the one or more biomarkers is predictive of responsiveness of the subject to a TNFα inhibitor.

In another preferred embodiment, the one or more biomarkers is selected from the group consisting of Aquaporin 3; Similar to ribosomal protein S24, clone MGC:8595; Transmembrane emp24 domain trafficking protein 2; Superoxide dismutase 1, soluble (amyotrophic lateral sclerosis 1; Calmodulin 1 (phosphorylase kinase, delta); *Homo sapiens* isocitrate dehydrogenase 1 (NADP+) soluble (IDH1); Tumor protein D52; *Homo sapiens* predicted osteoblast protein (GS3786); Cytochrome c oxidase subunit VIIb; CUG triplet repeat, RNA binding protein 2; Ubiquinol-cytochrome c reductase hinge protein; Glutamate-cysteine ligase, catalytic subunit; Rap guanine nucleotide exchange factor (GEF)2; Ataxin 1; Ectonucleotide pyrophosphatase/phosphodiesterase 4; MAL, T-cell differentiation protein; Glucosamine (UDP-N-acetyl)-2-epimerase/N-acetylmannosamine kinase; Carboxypeptidase A3; Charcot-Leyden crystal protein; NADH dehydrogenase (ubiquinone) 1 beta subcomplex, 1, 7 kDa; Platelet factor 4 variant 1; Poly(A) binding protein interacting protein 1; Sterol-C4-methyl oxidase-like; PIM-1 oncogene; GATA binding protein 2; Fc fragment of IgE, high affinity I, receptor for; alpha polypeptide; KIAA0746 protein; Transcription factor 4; Major histocompatibility complex, class II, DQ alpha 1; Phospholipase C-like 2; TM2 domain containing 1; SUB1 homolog (*S. cerevisiae*); Cytochrome b-5; Neugrin, neurite outgrowth associated; Ribosomal protein S26, 40S ribosomal protein; CCR4-NOT transcription complex, subunit 6; Ubiquinol-cytochrome c reductase complex (7.2 kD); Hepatocellular carcinoma-associated antigen 112; GGA binding partner; Cornichon homolog 4 (Drosophila); Hypothetical protein FLJ21616; *Homo sapiens* hypothetical protein FLJ10134; Erythroblast membrane-associated protein; LR8 protein; Likely ortholog of mouse limb-bud and heart gene (LBH); Chromosome 14 open reading frame 156; and Guanine nucleotide binding protein (G protein) alpha 12 (corresponding to biomarkers listed in Table 9 that are decreased in ≧80% of responders vs. non-responders). More preferably, the one or more biomarkers is selected from the group consisting of *Homo sapiens* predicted osteoblast protein (GS3786); Charcot-Leyden crystal protein; Neugrin, neurite outgrowth associated; Hypothetical protein FLJ21616; and *Homo sapiens* hypothetical protein FLJ10134 (corresponding to biomarkers listed in Table 9 that are decreased in ≧90% of responders vs. non-responders). Even more preferably, the one or more biomarkers is *Homo sapiens* predicted osteoblast protein (GS3786) or *Homo sapiens* hypothetical protein FLJ10134 (corresponding to biomarkers listed in Table 9 that are decreased in 100% of responders vs. non-responders). In each of these embodiments, decreased expression of the one or more biomarkers is predictive of responsiveness of the subject to a TNFα inhibitor.

In a particularly preferred aspect, the invention provides a method for predicting responsiveness to a TNFα inhibitor in a subject having an autoimmune disorder the method comprising: (i) assaying the subject for increased expression of a biomarker, which biomarker is CD11c, and (ii) predicting responsiveness of the subject to the TNFα inhibitor based on increased expression of CD11c in the subject.

In yet another particularly preferred embodiment, the invention provides a method for predicting responsiveness to a TNFα inhibitor, which TNFα inhibitor is adalimumab, in a subject having an autoimmune disorder the method comprising: (i) assaying the subject for expression of one or more biomarkers predictive of responsiveness to adalimumab in the autoimmune disorder, and (ii) predicting responsiveness of the subject to adalimumab based on expression of the one or more biomarkers in the subject. Preferably, the one or more biomarkers is encoded by a nucleic acid molecule comprising a nucleotide sequence selected from the group consisting of SEQ ID NO: 1-82 (or selected from the group consisting of the biomarkers set forth in Table 9). In more preferred embodiments, the subsets of sequences within SEQ ID NO: 1-82 that are either increased or decreased, as set forth in detail above, can be assayed.

In the methods of the invention for predicting responsiveness to a TNFα inhibitor in a subject having an autoimmune disorder, the expression of one or more biomarkers predictive of responsiveness to a TNFα inhibitor in the autoimmune disorder can be assayed in the subject using techniques well-established in the art. In a preferred embodiment, the expression of the one or more biomarkers in the subject is assayed by obtaining an mRNA sample from the subject (e.g., isolated from peripheral blood mononuclear cells, by standard methods) and detecting the expression of mRNA(s) encoding the one or more biomarkers in the mRNA sample using standard molecular biology techniques, such as PCR analysis. A preferred method of PCR analysis is revers transcriptase-polymerase chain reaction (RT-PCR). Other suitable systems for mRNA sample analysis include microarray analysis (e.g., using Affymetrix's microarray system or Illumina's BeadArray Technology).

Additionally or alternatively, in certain situations it may be possible to assay for the expression of one or more biomarkers at the protein level, using a detection reagent that detects the protein product encoded by the mRNA of the biomarker(s). For example, if an antibody reagent is available that binds specifically to the biomarker protein product to be detected, and not to other proteins, then such an antibody reagent can be used to detect the expression of the biomarker of interest in a cellular sample from the subject, or a preparation derived from the cellular sample, using standard antibody-based techniques known in the art, such as FACS analysis, ELISA and the like.

It will be readily understood by the ordinarily skilled artisan that essentially any technical means established in the art for detecting biomarkers, at either the nucleic acid or protein level, can be adapted to detection of the biomarkers discussed herein and applied in the methods of the current invention for predicting responsiveness to a TNFα inhibitor in a subject having an autoimmune disorder.

The biomarkers described herein were originally identified in patients having rheumatoid arthritis (see the Examples) and thus a particularly preferred autoimmune disorder in which to apply the methods of the invention is rheumatoid arthritis. The mechanism of action of the TNFα pathway, however, is thought to be common to a large number of autoimmune disorders and TNFα inhibitors have been shown to be effective therapy in a variety of different autoimmune disorders. Accordingly, the method of the invention for predicting responsiveness to a TNFα inhibitor can be applied to essentially any autoimmune disorder in which TNFα inhibitor therapy is applied. Other preferred autoimmune disorders include Crohn's disease, ulcerative colitis, psoriasis, psoriatic arthritis, juvenile arthritis and ankylosing spondilitis, Other non-limiting examples of autoimmune disorders include autoimmune diabetes, multiple sclerosis, systemic lupus erythematosus, rheumatoid spondylitis, gouty arthritis, allergy, autoimmune uveitis, nephrotic syndrome, multisystem autoimmune diseases, autoimmune hearing loss, adult respiratory distress syndrome, shock lung, chronic pulmonary inflammatory disease, pulmonary sarcoidosis, pulmonary fibrosis, silicosis, idiopathic interstitial lung disease, chronic obstructive pulmonary disease, asthma, restenosis, spondyloarthropathies, Reiter's syndrome, autoimmune hepatitis, inflammatory skin disorders, vasculitis of large vessels, medium vessels or small vessels, endometriosis, prostatitis and Sjogren's syndrome.

Biomarkers for Monitoring an Autoimmune Disorder in a Subject

In another aspect, the invention provides methods of monitoring an autoimmune disorder in a subject having the autoimmune disorder based on biomarker expression patterns established using microarray analysis of, for example, RA subjects vs. normal donors, RA subjects vs. RA subjects treated with a TNFα inhibitor and/or RA subjects treated with a TNFα inhibitor vs. RA responders to TNFα inhibitors. In these monitoring methods, the subject is assayed for expression of one or more biomarkers (using techniques, for example, as described in the previous section), thereby monitoring the autoimmune disorder in the subject.

In one embodiment of the monitoring method, the one or more biomarkers is encoded by a nucleic acid molecule comprising a nucleotide sequence selected from the group consisting of SEQ ID NO: 83-133 (or the biomarkers set forth by name in Table 3, namely v-maf musculoaponeurotic fibrosarcoma oncogene homolog F; Diphtheria toxin receptor (DTR); DEAH (Asp-Glu-Ala-His) box polypeptide 15; Ribonucleotide reductase M2 polypeptide; Solute carrier family 6, member 8; 6-phosphofructo-2-kinase/fructose-2,6-biphosphatase 3; Ferrochelatase (protoporphyria); Nuclear factor, interleukin 3 regulated; Thrombomodulin; Major histocompatibility complex, class II, DM beta; Forkhead box O3A; Hemoglobin, gamma A, gamma G; Synuclein, alpha (non A4 component of amyloid precursor); Hemoglobin, gamma A; Amphiregulin (schwannoma-derived growth factor); Lipoyltransferase 1; Solute carrier family 4, anion exchanger, member 1; S100 calcium binding protein A 12 (calgranulin C); Keratin 1 (epidermolytic hyperkeratosis); Carbonic anhydrase I; CD1C antigen, c polypeptide; Tumor necrosis factor, alpha-induced protein 6; Ribonuclease, RNase A family, 2; Hemoglobin, delta; Transferrin receptor (p90, CD71); Ring finger protein 10; Chromosome 1 open reading frame 63; Hemoglobin, alpha 1, alpha 2; CD69 antigen (p60, early T-cell activation antigen; APEX nuclease (multifunctional DNA repair enzyme)1; Membrane-spanning 4-domains, subfamily A, member 3; Heat shock 70 kDa protein 8; Hypothetical protein MGC12760; GABA(A) receptor-associated protein like 1, like 3; Aminolevulinate, delta-, synthase 2; Major histocompatibility complex, class II, DP alpha 1; Morf4 family associated protein 1-like 1; Aldehyde dehydrogenase 1 family, member A1; Formin binding protein 4; Zinc finger protein 24 (KOX 17); Hypothetical protein LOC54103; Selenium binding protein 1; Hematopoietically expressed homeobox; Major histocompatibility complex, class II, DM alpha; Eukaryotic translation initiation factor 2-alpha kinase 1; Ankyrin repeat domain 49; Hypothetical protein FLJ20701; Zinc finger protein 331; Membrane-spanning 4-domains, subfamily A, member 4; Tensin 1; and Family with sequence similarity 46, member A, respectively).

In another embodiment of the monitoring method, the one or more biomarkers is encoded by a nucleic acid molecule comprising a nucleotide sequence selected from the group consisting of SEQ ID NO: 134-177, 110, 112, 118, 123 and 131 (or the biomarkers set forth by name in Table 4, namely Uncharacterized hypothalamus protein HT007; Dual specificity phosphatase 22; Proteasome (prosome, macropain) subunit, beta type, 7; Membrane-spanning 4-domains, subfamily A, member 4; DKFZP434C171 protein; Protein phosphatase 1, catalytic subunit, beta isoform; Splicing factor, arginine/serine-rich 5; Sorting nexin 11; Farnesyltransferase, CAAX box, alpha; Peroxisomal D3,D2-enoyl-CoA isomerise; Fc fragment of IgE, high affinity I, receptor for; gamma polypeptide; UDP-N-acetyl-alpha-D-galactosamine: polypeptide N-acetylgalactosaminyltransferase 1; Hypothetical protein FLJ1259; APEX nuclease (multifunctional DNA repair enzyme)1; Geranylgeranyl diphosphate synthase 1; Down syndrome critical region gene 5; Calpain 7; Major histocompatibility complex, class II, DP alpha 1; Brix domain containing 5; Chromosome 21 open reading frame 59; Tumor necrosis factor (ligand) superfamily, member 10; Chromosome 10 open reading frame 86; CD1D antigen, d polypeptide; Ewing sarcoma breakpoint region 1; Ribonuclease P 40 kDa subunit; PHD finger protein 20; Thioredoxin interacting protein; Ubiquinol-cytochrome c reductase core protein II; Hypothetical protein FLJ22662; Preimplantation protein 3; DKFZP564G2022 protein; Dipeptidase 2; Hemoglobin, alpha 1, alpha 2; Frequently rearranged in advanced T-cell lymphomas; DEAD (Asp-Glu-Ala-Asp) box polypeptide 48; Tumor necrosis factor, alpha-induced protein 2; Nucleophosmin (nucleolar phosphoprotein B23, numatrin); Interleukin 13 receptor, alpha 1; Leukocyte specific transcript 1, LST1; CGI-121 protein; RAS p21 protein activator 4/hypothetical protein FLJ21767; Cathepsin S; CD63 antigen (melanoma 1 antigen); JTV1 gene; KIAA0174; Thrombospondin 1; Hypothetical protein LOC54103; Interferon regulatory factor 1; and SEC 11-like 1 (S. cerevisiae)).

More preferably, the one or more biomarkers is encoded by a nucleic acid molecule comprising a nucleotide sequence selected from the group consisting of SEQ ID NO: 134-150, 112, 118 (or the biomarkers set forth by name in Table 4 as being upregulated, namely Uncharacterized hypothalamus protein HT007; Dual specificity phosphatase 22; Proteasome (prosome, macropain) subunit, beta type, 7; Membrane-spanning 4-domains, subfamily A, member 4; DKFZP434C171 protein; Protein phosphatase 1, catalytic subunit, beta isoform; Splicing factor, arginine/serine-rich 5; Sorting nexin 11; Farnesyltransferase, CAAX box, alpha; Peroxisomal D3,D2-enoyl-CoA isomerise; Fc fragment of IgE, high affinity I, receptor for; gamma polypeptide; UDP-N-acetyl-alpha-D-galactosamine:polypeptide N-acetylgalactosaminyltransferase 1; Hypothetical protein FLJ11259; APEX nuclease (multifunctional DNA repair enzyme) 1; Geranylgeranyl diphosphate synthase 1; Down syndrome critical region gene 5; Calpain 7; Major histocompatibility complex, class II, DP alpha 1; Brix domain containing 5; and Chromosome 21 open reading frame 59), wherein expression of the one or more biomarkers is increased in the subject.

Additionally or alternatively, more preferably the one or more biomarkers is encoded by a nucleic acid molecule comprising a nucleotide sequence selected from the group consisting of SEQ ID NO: 151-177, 110 and 123 (or the biomarkers set forth by name in Table 4 as being downregulated, namely Tumor necrosis factor (ligand) superfamily, member 10; Chromosome 10 open reading frame 86; CD1D antigen, d polypeptide; Ewing sarcoma breakpoint region 1; Ribonuclease P 40 kDa subunit; PHD finger protein 20; Thioredoxin interacting protein; Ubiquinol-cytochrome c reductase core protein II; Hypothetical protein FLJ22662; Preimplantation protein 3; DKFZP564G2022 protein; Dipeptidase 2; Hemoglobin, alpha 1, alpha 2; Frequently rearranged in advanced T-cell lymphomas; DEAD (Asp-Glu-Ala-Asp) box polypeptide 48; Tumor necrosis factor, alpha-induced protein 2; Nucleophosmin (nucleolar phosphoprotein B23, numatrin); Interleukin 13 receptor, alpha 1; Leukocyte specific transcript 1, LST1; CGI-121 protein; RAS p21 protein activator 4/hypothetical protein FLJ21767; Cathepsin S; CD63 antigen (melanoma 1 antigen); JTV1 gene; KIAA0174; Thrombospondin 1; Hypothetical protein LOC54103; Interferon regulatory factor 1; and SEC 11-like 1 (*S. cerevisiae*), wherein expression of the one or more biomarkers is decreased in the subject.

In yet another embodiment of the monitoring method, the one or more biomarkers is encoded by a nucleic acid molecule comprising a nucleotide sequence selected from the group consisting of SEQ ID NO: 178-292, 91 and 97 (or the biomarkers set forth by name in Table 5, namely HLA-B associated transcript-1 (D6S81E); Interleukin enhancer binding factor 2, 45 kD (ILF2); Isolate Liv chaperone protein HSP90 beta (HSP90BETA) mRNA; Lysyl-tRNA synthetase mRNA, complete cds; nuclear gene for mitochondrial product; alternatively spliced; Tryptophanyl-tRNA synthetase (WARS); Profilin 1 (PFN1), mRNA; Seryl-tRNA synthetase (SARS); Similar to KIAA1007 protein, clone MGC:692, mRNA, complete cds; CD59 antigen p18-20 (antigen identified by monoclonal antibodies 16.3A5, EJ16, EJ30, EL32 and G344); *Homo sapiens* KIAA0064 gene product (KIAA0064), mRNA; Chromosome segregation 1 (yeast homolog)-like (CSE1L), mRNA; Protein phosphatase 1, regulatory subunit 7 (PPP1R7), mRNA; DEADH (Asp-Glu-Ala-AspHis) box polypeptide 1 (DDX1), mRNA; Threonyl-tRNA synthetase (TARS), mRNA; Dead box protein 15 mRNA, complete cds; SRY (sex determining region Y)-box 4/DEF=Human DNA sequence from clone RP3-322L4 on chromosome 6; Galactosidase, beta 1 (GLB1), mRNA; ATP-binding cassette, subfamily E (OABP), member 1; NADH dehydrogenase (ubiquinone) 1 alpha subcomplex, 6 (14 kD, B14) (NDUFA6), mRNA; Pericentriolar material 1 (PCM1), mRNA; Excision repair cross-complementing rodent repair deficiency, complementation group 3 (ERCC3), mRNA; KIAA0907 protein (KIAA0907), mRNA; v-crk avian sarcoma virus CT10 oncogene homolog; 6-phosphofructo-2-kinasefructose-2,6-biphosphatase 3 (PFKFB3), mRNA./PROD=6-phosphofructo-2-kinase-fructose-2,6-biphosphatase 3; KIAA0766 gene product (KIAA0766), mRNA; N-acetylgalactosaminidase, alpha- (NAGA), mRNA; Protein tyrosine phosphatase, non-receptor type substrate 1 (PTPNS1), mRNA; Crystallin, zeta (quinone reductase) (CRYZ), mRNA; KIAA0429 gene product (KIAA0429), mRNA; SET domain, bifurcated 1 (SETDB1), mRNA; NADH dehydrogenase (ubiquinone) 1 beta subcomplex, 3 (12 kD, B12) (NDUFB3), mRNA; Diphtheria toxin receptor (DTR); Thrombomodulin (THBD), mRNA; Protein phosphatase 1A (formerly 2C), magnesium-dependent, alpha isoform (PPM1A), mRNA; CD37 antigen (CD37), mRNA; Hemoglobin, gamma G (HBG2), mRNA; Protein phosphatase 1D magnesium-dependent, delta isoform (PPM1D), mRNA; Hematopoietically expressed homeobox (HHEX), mRNA; Amphiregulin (schwannoma-derived growth factor) (AREG), mRNA; Early growth response 2 (Krox-20 (Drosophila) homolog) (EGR2), mRNA; 2,5-oligoadenylate synthetase 1 (40-46 kD) (OAS1), transcript variant E16, mRNA; Early growth response 3 (EGR3), mRNA./PROD=early growth response 3; *Homo sapiens* MD-2 protein (MD-2), mRNA; *Homo sapiens* MAX dimerization protein (MAD), mRNA; DKFZP586A011 protein (DKFZP586A011), mRNA; 78 kDa gastrin-binding protein mRNA, complete cds; Transferrin receptor (p90, CD71), clone MGC:3151, mRNA, complete cds; *Homo sapiens* mRNA; cDNA DKFZp564N1272 (from clone DKFZp564N1272); complete cds; GABA-A receptor-associated protein like 1 (GABARAPL1) mRNA, complete cds; Translocation protein 1; *Homo sapiens* clone 016b03 My027 protein mRNA, complete cds; Protein kinase-related oncogene (PIM1 mRNA, complete cds; MADS box transcription enhancer factor 2, polypeptide C (myocyte enhancer factor 2C); eIF-2-associated p67 homolog mRNA, complete cds; Human mRNA for hCREM (cyclic AMP-responsive element modulator) type 2 protein, complete cds; Apurinic endonuclease (APE) mRNA, complete cds./PROD=apurinic endonuclease; TATA box binding protein (TBP)-associated factor, RNA polymerase II, D, 100 kD; Human mRNA for ZFM1 protein alternatively spliced product, complete cds./PROD=ZFM 1 protein, alternatively spliced product; Trachea cellular apoptosis susceptibility protein (CSE1) mRNA, complete cds; Similar to eukaryotic translation initiation factor 3, subunit 8 (110 kD), clone MGC:8693, mRNA, complete cds; GABA-A receptor-associated protein mRNA, complete cds./PROD=GABA-A receptor-associated protein; Human (clone 2-5) synuclein (NACP) mRNA, complete cds; Human putative ribosomal protein S1 mRNA; Aldehyde dehydrogenase 1, soluble (ALDH1), mRNA./PROD=aldehyde dehydrogenase 1, soluble; *Homo sapiens* mRNA for KIAA1057 protein, partial cds; RBP 1-like protein; Ring finger protein 4; KIAA0197 protein; *Homo sapiens* mRNA; cDNA DKFZp586F1323 (from clone DKFZp586F1323); *Homo sapiens* mRNA; cDNA DKFZp564I052 (from clone DKFZp564I052); *Homo sapiens* mRNA for Hmob33 protein, 3 untranslated region; *Homo sapiens* mRNA; cDNA DKFZp586F1019 (from clone DKFZp586F1019); partial cds; Myosin, light polypeptide 4, alkali; atrial, embryonic; *H. sapiens* novel gene from PAC 117P20, chromosome 1; *Homo sapiens* clone 24582 mRNA sequence; Heterogeneous nuclear ribonucleoprotein H1 (H); Tyrosine 3-monooxygenase/tryptophan 5-monooxygenase activation protein, epsilon polypeptide; Cyclin T2; cDNA: FLJ23227 fis, clone CAE00645, highly similar to AF052138; Hypothetical protein FLJ12619; C-terminal binding protein 1; SEC22, vesicle trafficking protein (*S. cerevisiae*)-like 1; Hemoglobin, alpha 1; *Homo sapiens* clone 24659 mRNA sequence/DEF=*Homo sapiens* clone 24659 mRNA sequence; Calcium channel, voltage-dependent, PQ type, alpha 1A subunit; *H. sapiens* SMA5 mRNA; *H. sapiens* HEX gene encoding homeobox related protein; Mitogen-activated protein kinase kinase kinase 4; Serine palmitoyltransferase (LCB2) mRNA, partial cds; KIAA0971 protein/DEF=*Homo sapiens* cDNA FLJ11495 fis, clone HEMBA1001950, highly similar to *Homo sapiens* mRNA for KIAA0971 protein; ESTs, Hs.97109; ESTs, Weakly similar to ALU7_HUMAN ALU; DEAD-box protein abstrakt (ABS), mRNA; KIAA1513 protein (KIAA1513), mRNA; Cell division protein FtsJ (FJH1), mRNA; F-box only protein 3 (FBXO3), mRNA; Purinergic receptor (family A group 5) (P2Y5), mRNA; Integral inner nuclear membrane protein (MAN1), mRNA; Fanconi anemia, complementation group F (FANCF), mRNA; Hypothetical protein FLJ12820 (FLJ12820), mRNA; Hypothetical protein FLJ13119 (FLJ13119), mRNA; Hypothetical protein FLJ20189 (FLJ20189), mRNA; Hypothetical protein FLJ20701 (FLJ20701), mRNA; *Homo sapiens* chromosome 12 open reading frame 5 (C12ORF5), mRNA; Hypothetical protein FLJ22555 (FLJ22555), mRNA; Hypothetical protein FLJ1110 (FLJ11110), mRNA; CGI-12 protein (LOC51001), mRNA; Triggering receptor expressed on myeloid cells 1 (TREM1), mRNA; betaGlcNAc beta 1,4-galactosyltransferase. polypeptide 5; PNAS-25 mRNA, complete cds.; *Homo sapiens* mRNA for FLJ00043 protein, partial cds; *Homo sapiens* cDNA: FLJ21737 fis, clone COLF3396; *Homo sapiens* cDNA FLJ13399 fis, clone PLACE1001395/DEF=*Homo sapiens* cDNA FLJ13399 fis, clone PLACE1001395; Novel MAFF (v-maf musculoaponeurotic fibrosarcoma (avian) oncogene family, protein F) LIKE protein; Heparin-binding EGF-like growth factor mRNA, complete cds; *E. coli* 7,8-diamino-pelargonic acid (bioA), biotin synthetase (bioB), 7-keto-8-amino-pelargonic acid synthetase (bioF), bioC protein, and dethiobiotin synthetase (bioD), complete cds; *Escherichia coli*/REF=J04423/DEF=*E coli* bioC protein corresponding to nucleotides 4609-4883 of J04423/LEN=777 (−5 and −3 represent transcript regions 5 prime and 3 prime respectively)).

More preferably, the one or more biomarkers is encoded by a nucleic acid molecule comprising a nucleotide sequence selected from the group consisting of SEQ ID NO: 178-185; 187-200, 202, 203, 205-207; 211, 213, 214, 216, 220, 221, 226, 228, 229, 231, 232, 234, 235, 238-247, 249, 250, 253, 262-265, 268-282 and 285-288 (or the biomarkers set forth by name in Table 5 as being upregulated, namely HLA-B associated transcript-1 (D6S81E); Interleukin enhancer binding factor 2, 45 kD (ILF2); Isolate Liv chaperone protein HSP90 beta (HSP90BETA) mRNA; Lysyl-tRNA synthetase mRNA, complete cds; nuclear gene for mitochondrial product; alternatively spliced; Tryptophanyl-tRNA synthetase (WARS); Profilin 1 (PFN1), mRNA; Seryl-tRNA synthetase (SARS); Similar to KIAA1007 protein, clone MGC:692, mRNA, complete cds; *Homo sapiens* KIAA0064 gene product (KIAA0064), mRNA; Chromosome segregation 1 (yeast homolog)-like (CSE1L), mRNA; Protein phosphatase 1, regulatory subunit 7 (PPP1R7), mRNA; DEADH (Asp-Glu-Ala-AspHis) box polypeptide 1 (DDX1), mRNA; Threonyl-tRNA synthetase (TARS), mRNA; Dead box protein 15 mRNA, complete cds; SRY (sex determining region Y)-box 4/DEF=Human DNA sequence from clone RP3-322L4 on chromosome 6; Galactosidase, beta 1 (GLB1), mRNA; ATP-binding cassette, sub-family E (OABP), member 1; NADH dehydrogenase (ubiquinone) 1 alpha subcomplex, 6 (14 kD, B14) (NDUFA6), mRNA; Pericentriolar material 1 (PCM1), mRNA; Excision repair cross-complementing rodent repair deficiency, complementation group 3 (ERCC3), mRNA; KIAA0907 protein (KIAA0907), mRNA; v-crk avian sarcoma virus CT10 oncogene homolog; KIAA0766 gene product (KIAA0766), mRNA; N-acetylgalactosaminidase, alpha-(NAGA), mRNA; Crystallin, zeta (quinone reductase) (CRYZ), mRNA; KIAA0429 gene product (KIAA0429), mRNA; SET domain, bifurcated 1 (SETDB1), mRNA; CD37 antigen (CD37), mRNA; Protein phosphatase 1D magnesium-dependent, delta isoform (PPM1D), mRNA; Hematopoietically expressed homeobox (HHEX), mRNA; 2,5-oligoadenylate synthetase 1 (40-46 kD) (OAS1), transcript variant E16, mRNA; DKFZP586A011 protein (DKFZP586A011), mRNA; 78 kDa gastrin-binding protein mRNA, complete cds; *Homo sapiens* clone 016b03 My027 protein mRNA, complete cds; MADS box transcription enhancer factor 2, polypeptide C (myocyte enhancer factor 2C); eIF-2-associated p67 homolog mRNA, complete cds; Apurinic endonuclease (APE) mRNA, complete cds./ PROD=apurinic endonuclease; TATA box binding protein (TBP)-associated factor, RNA polymerase II, D, 100 kD; Trachea cellular apoptosis susceptibility protein (CSE1) mRNA, complete cds; Similar to eukaryotic translation initiation factor 3, subunit 8 (110 kD), clone MGC:8693, mRNA, complete cds; Human putative ribosomal protein S1 mRNA; Aldehyde dehydrogenase 1, soluble (ALDH1), mRNA./PROD=aldehyde dehydrogenase 1, soluble; *Homo sapiens* mRNA for KIAA1057 protein, partial cds; RBP1-like protein; Ring finger protein 4; KIAA0197 protein; *Homo sapiens* mRNA; cDNA DKFZp586F1323 (from clone DKFZp586F1323); *Homo sapiens* mRNA; cDNA DKFZp564I052 (from clone DKFZp564I052); *Homo sapiens* mRNA for Hmob33 protein, 3 untranslated region; *Homo sapiens* mRNA; cDNA DKFZp586F1019 (from clone DKFZp586F1019); partial cds; *H. sapiens* novel gene from PAC 117P20, chromosome 1; *Homo sapiens* clone 24582 mRNA sequence; Cyclin T2; *H. sapiens* HEX gene encoding homeobox related protein; Mitogen-activated protein kinase kinase kinase 4; Serine palmitoyltransferase (LCB2) mRNA, partial cds; KIAA0971 protein/DEF=*Homo sapiens* cDNA FLJ11495 fis, clone HEMBA1001950, highly similar to *Homo sapiens* mRNA for KIAA0971 protein; DEAD-box protein abstrakt (ABS), mRNA; KIAA1513 protein (KIAA1513), mRNA; Cell division protein FtsJ (FJH1), mRNA; F-box only protein 3 (FBXO3), mRNA; Purinergic receptor (family A group 5) (P2Y5), mRNA; Integral inner nuclear membrane protein (MAN1), mRNA; Fanconi anemia, complementation group F (FANCF), mRNA; Hypothetical protein FLJ12820 (FLJ12820), mRNA; Hypothetical protein FLJ13119 (FLJ13119), mRNA; Hypothetical protein FLJ20189 (FLJ20189), mRNA; Hypothetical protein FLJ20701 (FLJ20701), mRNA; *Homo sapiens* chromosome 12 open reading frame 5 (C12ORF5), mRNA; Hypothetical protein FLJ22555 (FLJ22555), mRNA; Hypothetical protein FLJ11110 (FLJ11110), mRNA; CGI-12 protein (LOC51001), mRNA; PNAS-25 mRNA, complete cds.; *Homo sapiens* mRNA for FLJ00043 protein, partial cds; *Homo sapiens* cDNA: FLJ21737 fis, clone COLF3396; *Homo sapiens* cDNA FLJ13399 fis, clone PLACE1001395/ DEF=*Homo sapiens* cDNA FLJ13399 fis, clone PLACE1001395), wherein expression of the one or more biomarkers is increased in the subject.

Additionally or alternatively, more preferably the one or more biomarkers is encoded by a nucleic acid molecule comprising a nucleotide sequence selected from the group consisting of SEQ ID NO: 186, 201, 204, 208, 209, 91, 210, 212, 97, 215, 217-219, 222-225, 227, 230, 233, 236, 237, 248, 251, 252, 254-261, 266, 267, 283, 284 and 289-292 (or the biomarkers set forth by name in Table 5 as being down-regulated, namely CD59 antigen p18-20 (antigen identified by monoclonal antibodies 16.3A5, EJ16, EJ30, EL32 and G344); 6-phosphofructo-2-kinasefructose-2,6-biphosphatase 3 (PFKFB3), mRNA./PROD=6-phosphofructo-2-kinase-fructose-2,6-biphosphatase 3; Protein tyrosine phosphatase, non-receptor type substrate 1 (PTPNS1), mRNA; NADH dehydrogenase (ubiquinone) 1 beta subcomplex, 3 (12 kD, B12) (NDUFB3), mRNA; Diphtheria toxin receptor (DTR); Thrombomodulin (THBD), mRNA; Protein phosphatase 1A (formerly 2C), magnesium-dependent, alpha isoform (PPM1A), mRNA; Hemoglobin, gamma G (HBG2), mRNA; Amphiregulin (schwannoma-derived growth factor) (AREG), mRNA; Early growth response 2 (Krox-20 (Drosophila) homolog) (EGR2), mRNA; Early growth response 3 (EGR3), mRNA./PROD=early growth response 3; *Homo sapiens* MD-2 protein (MD-2), mRNA; *Homo sapiens* MAX dimerization protein (MAD), mRNA; Transferrin receptor (p90, CD71), clone MGC:3151, mRNA, complete cds; *Homo sapiens* mRNA; cDNA DKFZp564N1272 (from clone DKFZp564N1272); complete cds; GABA-A receptor-associated protein like 1 (GABARAPL1) mRNA, complete cds; Translocation protein 1; Protein kinase-related oncogene (PIM1) mRNA, complete cds; Human mRNA for hCREM (cyclic AMP-responsive element modulator) type 2 protein, complete cds; Human mRNA for ZFM1 protein alternatively spliced product, complete cds./PROD=ZFM 1 protein, alternatively spliced product; GABA-A receptor-associated protein mRNA, complete cds./PROD=GABA-A receptor-associated protein; Human (clone 2-5) synuclein (NACP) mRNA, complete cds; Myosin, light polypeptide 4, alkali; atrial, embryonic; Heterogeneous nuclear ribonucleoprotein H1 (H); Tyrosine 3-monooxygenase/tryptophan 5-monooxygenase activation protein, epsilon polypeptide; cDNA:

FLJ23227 fis, clone CAE00645, highly similar to AF052138; Hypothetical protein FLJ12619; C-terminal binding protein 1; SEC22, vesicle trafficking protein (*S. cerevisiae*)-like 1; Hemoglobin, alpha 1; *Homo sapiens* clone 24659 mRNA sequence/DEF=*Homo sapiens* clone 24659 mRNA sequence; Calcium channel, voltage-dependent, PQ type, alpha 1A subunit; *H. sapiens* SMA5 mRNA; ESTs, Hs.97109; ESTs, Weakly similar to ALU7_HUMAN ALU; Triggering receptor expressed on myeloid cells 1 (TREM1), mRNA; betaGlcNAc beta 1,4-galactosyltransferase. polypeptide 5; Novel MAFF (v-maf musculoaponeurotic fibrosarcoma (avian) oncogene family, protein F) LIKE protein; Heparin-binding EGF-like growth factor mRNA, complete cds; *E. coli* 7,8-diamino-pelargonic acid (bioA), biotin synthetase (bioB), 7-keto-8-amino-pelargonic acid synthetase (bioF), bioC protein, and dethiobiotin synthetase (bioD), complete cds; *Escherichia coli*/REF=J04423/DEF=*E coli* bioC protein corresponding to nucleotides 4609-4883 of J04423/LEN=777 (−5 and −3 represent transcript regions 5 prime and 3 prime respectively)), wherein expression of the one or more biomarkers is decreased in the subject.

In yet another embodiment of the monitoring method, the one or more biomarkers is encoded by a nucleic acid molecule comprising a nucleotide sequence selected from the group consisting of SEQ ID NO: 87, 97, 101, 293, 92, 272, 93, 107, 108, 121 and 123 (or the biomarkers set forth by name in Table 6 as pre-treatment biomarkers, namely Solute carrier family 6; Amphiregulin; Keratin 1; Hemoglobin, alpha 1; MHC-II, DM beta; Purinergic receptor P2Y, G-protein coupled 5; Forkhead box O3A; Transferrin receptor (p90, CD71); Ring finger protein 10; Formin binding protein 4; and Hypothetical protein LOC54103), wherein the subject is monitored prior to treatment with a TNFα inhibitor.

In yet another embodiment of the monitoring method, the one or more biomarkers is encoded by a nucleic acid molecule comprising a nucleotide sequence selected from the group consisting of SEQ ID NO: 290, 209, 98, 112, 116, 121, 130, 155, 92, 289, 216 and 131 (or the biomarkers set forth by name in Table 6 as post-treatment biomarkers, namely Diphteria toxin receptor; Heparin-binding EGF-like growth factor; Lipoyltransferase 1; APEX nuclease (multifunct. DNA repair enzyme)1; GABA(A) receptor-associated protein like 1/3; Formin binding protein 4; Zinc finger protein 331; Ribonuclease P 40 kDa subunit; MHC class II, DM beta; v-maf fibrosarc. oncogene homolog F (avian); 2',5'-oligoadenylate synthetase 1, 40/46 kDa; and Membrane-spanning 4-domains, subfam. A, memb. 4), wherein the subject is monitored after treatment with a TNFα inhibitor.

In yet another embodiment of the monitoring method, the one or more biomarkers is encoded by a nucleic acid molecule comprising a nucleotide sequence selected from the group consisting of SEQ ID NO: 97, 102, 29, 294, 295, 91, 131, 290, 100, 134, 296, 297, 298, 299, 136, 174 and 300 (or the biomarkers set forth by name in Table 7, namely Amphiregulin; Carbonic anhydrase 1; Charcot-Leyden crystal protein; Clusterin C; Tumor necrosis factor alpha induced protein 6; Thrombomodulin; Membrane-spanning 4-domains, subfamily A, member 4; Diptheria toxin receptor; S100 calcium binding protein A1; Uncharacterized hypothalamus protein HT007; MHC-class-II; HLA-DR alpha; Hypothetical protein LOC54103; Tumor necrosis factor alpha; Interleukin 1 beta; Proteasome subunit beta type 7 precursor; and Protein KIAA0174; Microsomal signal peptidase 18 kDa subunit).

A preferred autoimmune disorder in which to apply the methods of the invention for monitoring an autoimmune disorder is rheumatoid arthritis. However, the monitoring methods can be applied to essentially any autoimmune disorder in which TNFα inhibitor therapy is applied, including the autoimmune disorders listed in the previous section.

Selection and Use of Treatment Regimens with TNFα Inhibitors

Given the observation that the expression pattern of particular biomarkers in an autoimmune disorder subject influences the responsiveness of the subject to a TNFα inhibitor, one can select an appropriate treatment regimen for the subject based on the expression of one or more biomarkers in the subject. Accordingly, in one embodiment, the above-described method for predicting the responsiveness to a TNFα inhibitor in a subject having an autoimmune disorder further comprises selecting a treatment regimen with the TNFα inhibitor based upon expression of the one or more biomarkers in the subject. In another aspect, the method still further comprises administering the TNFα inhibitor to the subject according to the treatment regimen such that the autoimmune disorder is inhibited in the subject.

In another embodiment, the invention provides a method for selecting a treatment regimen for therapy with a TNFα inhibitor in a subject having an autoimmune disorder, the method comprising:

assaying the subject for expression of one or more biomarkers predictive of responsiveness to a TNFα inhibitor for treatment of the autoimmune disorder; and selecting a treatment regimen with a TNFα inhibitor based upon expression of the one or more biomarkers in the subject.

In yet another embodiment, the invention provides a method of treating a subject having an autoimmune disorder with a TNFα inhibitor, the method comprising:

assaying the subject for expression of one or more biomarkers predictive of responsiveness to a TNFα inhibitor for treatment of the autoimmune disorder;

selecting a treatment regimen with a TNFα inhibitor based upon expression of the one or more biomarkers in the subject; and administering the TNFα inhibitor according to the treatment regimen such that the subject is treated for the autoimmune disorder.

The treatment regimen that is selected typically includes at least one of the following parameters and more typically includes many or all of the following parameters: the type of agent chosen for administration, the dosage, the formulation, the route of administration and/or the frequency of administration.

Particularly preferred TNFα inhibitors are biologic agents that have been approved by the FDA for use in humans in the treatment of rheumatoid arthritis, which agents include adalimumab (HUMIRA™), infliximab (REMICADE™) and etanercept (ENBREL™), most preferably adalimumab (HUMIRA™).

In one embodiment, the TNFα inhibitor is an anti-tumor necrosis factor-alpha (TNFα) antibody, or antigen-binding portion thereof. For example, the anti-TNFα antibody, or antigen-binding portion thereof, can be a humanized antibody, a chimeric antibody or a multivalent antibody.

In another embodiment, the anti-TNFα antibody, or antigen-binding portion thereof, is a human antibody, preferably a human antibody, or antigen-binding portion thereof, that binds to human TNFα with high affinity and a low off rate, and has a high neutralizing capacity. Preferably, the human antibodies are recombinant, neutralizing human anti-hTNFα antibodies. The most preferred recombinant, neutralizing antibody used in the method of the invention is referred to herein as adalimumab, also referred to as HUMIRA® or D2E7 (the amino acid sequence of the adalimumab VL region is shown in SEQ ID NO: 303; the amino acid sequence of the adalimumab VH region is shown in SEQ ID NO: 304). The properties of D2E7 (adalimumab; Humira®) have been described in Salfeld et al., U.S. Pat. Nos. 6,090,382, 6,258,562, and 6,509,015, which are each incorporated by reference herein.

Other examples of TNFα antibodies include chimeric and humanized murine anti-hTNFα antibodies which have undergone clinical testing for treatment of rheumatoid arthritis (see e.g., Elliott et al. (1994) *Lancet* 344:1125-1127; Elliot et al. (1994) *Lancet* 344:1105-1110; Rankin et al. (1995) *Br. J. Rheumatol.* 34:334-342). In another embodiment, the TNFα antibody used in the invention is infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), and CNTO 148 (golimumab; Medarex and Centocor, see also WO 02/12502).

In one embodiment, the TNFα inhibitors used in the methods of the invention include adalimumab antibodies and antibody portions, adalimumab-related antibodies and antibody portions, adalimumab-related DVD-Ig or dual specific antibodies, and other human antibodies and antibody portions with equivalent properties to adalimumab, such as high affinity binding to hTNFα with low dissociation kinetics and high neutralizing capacity. In one embodiment, a treatment regimen of the invention provides treatment with an isolated human antibody, or an antigen-binding portion thereof, that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less. More preferably, the isolated human antibody, or antigen-binding portion thereof, dissociates from human TNFα with a $K_{off}$ of $5\times10^{-4}$ s$^{-1}$ or less, or even more preferably, with a $K_{off}$ of $1\times10^{-4}$ s$^{-1}$ or less. More preferably, the isolated human antibody, or antigen-binding portion thereof, neutralizes human TNFα cytotoxicity in a standard in vitro L929 assay with an $IC_{50}$ of $1\times10^{-8}$ M or less, even more preferably with an $IC_{50}$ of $1\times10^{-9}$ M or less and still more preferably with an $IC_{50}$ of $1\times10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the TNFα inhibitor used in the treatment method of the invention is a human anti-TNFα antibody that has slow dissociation kinetics for association with hTNFα and that has light and heavy chain CDR3 domains that structurally are identical to or related to those of adalimumab. Position 9 of the adalimumab VL CDR3 can be occupied by Ala or Thr without substantially affecting the $K_{off}$. Accordingly, a consensus motif for the adalimumab VL CDR3 comprises the amino acid sequence: Q-R-Y-N-R-A-P-Y-(T/A) (SEQ ID NO: 305). Additionally, position 12 of the adalimumab VH CDR3 can be occupied by Tyr or Asn, without substantially affecting the $K_{off}$. Accordingly, a consensus motif for the adalimumab VH CDR3 comprises the amino acid sequence: V-S-Y-L-S-T-A-S-S-L-D-(Y/N) (SEQ ID NO: 306). Moreover, as demonstrated in Example 2 of U.S. Pat. No. 6,090,382, the CDR3 domain of the adalimumab heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the adalimumab VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the adalimumab VL and/or VH CDR3 domains. More preferably, no more than one to three conservative amino acid substitutions are made within the adalimumab VL and/or VH CDR3 domains. Additionally, conservative amino acid substitutions should not be made at amino acid positions critical for binding to hTNFα. Positions 2 and 5 of the adalimumab VL CDR3 and positions 1 and 7 of the adalimumab VH CDR3 appear to be critical for interaction with hTNFα and thus, conservative amino acid substitutions preferably are not made at these positions (although an alanine substitution at position 5 of the adalimumab VL CDR3 is acceptable, as described above) (see U.S. Pat. No. 6,090,382).

Accordingly, in another embodiment, the antibody or antigen-binding portion thereof preferably contains the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 305, or modified from SEQ ID NO: 305 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 306, or modified from SEQ ID NO: 306 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5\times10^{-4}$ s$^{-1}$ or less. Even more preferably, the antibody, or antigen-binding portion thereof, dissociates from human TNFα with a $K_{off}$ of $1\times10^{-4}$ s$^{-1}$ or less.

In yet another embodiment, the antibody or antigen-binding portion thereof preferably contains a light chain variable region (LCVR) having a CDR3 domain comprising the amino acid sequence of SEQ ID NO: 305, or modified from SEQ ID NO: 305 by a single alanine substitution at position 1, 4, 5, 7 or 8, and with a heavy chain variable region (HCVR) having a CDR3 domain comprising the amino acid sequence of SEQ ID NO: 306, or modified from SEQ ID NO: 306 by a single alanine substitution at position 2, 3, 4, 5, 6, 8, 9, 10 or 11. Preferably, the LCVR further has a CDR2 domain comprising the amino acid sequence of SEQ ID NO: 307 (i.e., the adalimumab VL CDR2) and the HCVR further has a CDR2 domain comprising the amino acid sequence of SEQ ID NO: 308 (i.e., the adalimumab VH CDR2). Even more preferably, the LCVR further has CDR1 domain comprising the amino acid sequence of SEQ ID NO: 309 (i.e., the adalimumab VL CDR1) and the HCVR has a CDR1 domain comprising the amino acid sequence of SEQ ID NO: 310 (i.e., the adalimumab VH CDR1). The framework regions for VL preferably are from the $V_\kappa I$ human germline family, more preferably from the A20 human germline Vk gene and most preferably from the adalimumab VL framework sequences shown in FIGS. 1A and 1B of U.S. Pat. No. 6,090,382. The framework regions for VH preferably are from the $V_H 3$ human germline family, more preferably from the DP-31 human germline VH gene and most preferably from the adalimumab VH framework sequences shown in FIGS. 2A and 2B of U.S. Pat. No. 6,090,382.

Accordingly, in another embodiment, the antibody or antigen-binding portion thereof preferably contains a light chain variable region (LCVR) comprising the amino acid sequence of SEQ ID NO: 303 (i.e., the adalimumab VL) and a heavy chain variable region (HCVR) comprising the amino acid sequence of SEQ ID NO: 304 (i.e., the adalimumab VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In other embodiments, the TNFα inhibitor of the invention is etanercept (described in WO 91/03553 and WO 09/406, 476), infliximab (described in U.S. Pat. No. 5,656,272), CDP571 (a humanized monoclonal anti-TNF-alpha IgG4 antibody), CDP 870 (a humanized monoclonal anti-TNF-alpha antibody fragment), D2E7 (a human anti-TNF mAb), soluble TNF receptor Type I, or a pegylated soluble TNF receptor Type I (PEGs TNF-R1).

The TNFα antibody of the invention can be modified. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (Cl—ClO) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion of the invention can be derivatized or linked to another functional molecule (e.g., another peptide or protein). Accordingly, the antibodies and antibody portions of the invention are intended to include derivatized and otherwise modified forms of the anti-TNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Selection of the particular parameters of the treatment regimen can be based on known treatment parameters for the TNFα inhibitor previously established in the art. For example, a non-limiting example of a treatment regimen for adalimumab (HUMIRA™) is 40 mg every other week by subcutaneous injection. A non-limiting example of a treatment regimen for etanercept (ENBREL™) is 50 mg/week by subcutaneous injection. A non-limiting example of a treatment regimen for infliximab (REMICADE™) is 3 mg/kg by intravenous infusion at weeks 0, 2 and 6, then every 8 weeks. A treatment regimen can include administration of the TNFα inhibitor alone or can include combination of the TNFα inhibitor with other therapeutic agents, such as methotrexate (e.g., 10-20 mg/week) or prednisolone (e.g., 10 mg/week). Other suitable treatment regimens for the TNFα inhibitors discussed herein will be readily apparent to the ordinarily skilled artisan based on prior studies of preferred administration parameters for the TNFα inhibitor.

For administration to a subject, a TNFα inhibitor typically is formulated into a pharmaceutical composition containing the TNFα inhibitor and a pharmaceutically acceptable carrier. Therapeutic compositions typically must be sterile and stable under the conditions of manufacture and storage. Pharmaceutical compositions also can be administered in combination therapy, i.e., combined with other agents, such as other TNFα inhibitors and/or other therapeutic agents, such as traditional therapeutic agents for the treatment of autoimmune disorders, such as rheumatoid arthritis.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

The pharmaceutical compositions may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

A TNFα inhibitor of the present invention can be administered via one or more routes of administration using one or more of a variety of methods known in the art. As will be appreciated by the skilled artisan, the route and/or mode of administration will vary depending upon the desired results. A preferred route of administration, particularly for antibody agents, is by intravenous injection or infusion. Other preferred routes of administration include intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a TNFα inhibitor of the invention can be administered via a non-parenteral route, such as a topical, epidermal or mucosal route of administration, for example, intranasally, orally, vaginally, rectally, sublingually or topically.

In a preferred embodiment, the subject to be treated with the TNFα inhibitor is a human subject.

A preferred autoimmune disorder in which to apply the methods of the invention for selecting and using a treatment regimen is rheumatoid arthritis. However, these methods can be applied to essentially any autoimmune disorder in which TNFα inhibitor therapy is applied, including the autoimmune disorders listed in the previous sections Kits of the Invention In another aspect, the invention pertains to kits for carrying out the methods of the invention. For example, in one embodiment, the invention provides a kit for predicting responsiveness to a TNFα inhibitor in a subject having an autoimmune disorder. In one embodiment, the kit comprises:

a) means for isolating monocytes;

b) means for measuring expression in the subject of one or more biomarkers predictive of responsiveness to a TNFα inhibitor in an autoimmune disorder;

c) means for measuring expression of at least one housekeeping gene; and d) instructions for use of the kit to predicting responsiveness to a TNFα inhibitor in a subject having an autoimmune disorder, wherein the one or more biomarkers is encoded by a nucleic acid molecule comprising a nucleotide sequence selected from the group consisting of SEQ ID NO: 1-82 (or the biomarkers set forth by name in Table 9, as described above)

In one embodiment of the kit, the one or more biomarkers is encoded by a nucleic acid molecule comprising a nucleotide sequence selected from the group consisting of SEQ ID NOs: 6, 7, 10, 15-17, 19, 22, 24, 27, 31, 34-39, 43-47, 49, 51, 54, 55, 57, 59, 61, 62, 64, 70, 75, 79 and 82 (or the biomarkers set forth by name in Table 9 as being increased in ≧80% of responders vs. non-responders, as described above), more preferably the one or more biomarkers is encoded by a nucleic acid molecule comprising a nucleotide sequence selected from the group consisting of SEQ ID NOs: 31, 37, 44, 47, 62 and 70 (or the biomarkers set forth by name in Table 9 as being increased in ≧90% of responders vs. non-responders, as described above), and even more preferably at least one of the biomarkers is encoded by a nucleic acid molecule comprising the nucleotide sequence of SEQ ID NO: 44 (or the CD11c biomarkers set forth by name in Table 9 as being increased in 100% of responders vs. non-responders). In each of these embodiments, preferably the instructions for use of the kit instruct that increased expression of the one or more biomarkers is predictive of responsiveness of the subject to a TNFα inhibitor.

In another embodiment of the kit, the one or more biomarkers is encoded by a nucleic acid molecule comprising a nucleotide sequence selected from the group consisting of SEQ ID NOs: 1-5, 8, 9, 11-14, 18, 20, 21, 23, 25, 26, 28-30, 32, 33, 40-42, 48, 50, 52, 53, 56, 58, 60, 63, 65-69, 71-74, 76-78, 80 and 81 (or the biomarkers set forth by name in Table 9 as being decreased in ≧80% of responders vs. non-responders, as described above), more preferably the one or more biomarkers is encoded by a nucleic acid molecule comprising a nucleotide sequence selected from the group consisting of SEQ ID NOs: 11, 29, 65, 73 and 74 (or the biomarkers set forth by name in Table 9 as being decreased in ≧90% of responders vs. non-responders, as described above), and even more preferably the one or more biomarkers is encoded by a nucleic acid molecule comprising the nucleotide sequence of SEQ ID NO: 11 or SEQ ID NO: 74 (or the biomarkers set forth by name in Table 9 as being decreased in 100% of responders vs. non-responders, as described above). In each of these embodiments, preferably the instructions for use of the kit instruct that decreased expression of the one or more biomarkers is predictive of responsiveness of the subject to a TNFα inhibitor.

In another embodiment of the kit, the one or more biomarkers is encoded by a nucleic acid molecule comprising a nucleotide sequence selected from the group consisting of SEQ ID NO: 83-133 (or the biomarkers set forth by name in Table 3, as described above).

In yet another embodiment of the kit, the one or more biomarkers is encoded by a nucleic acid molecule comprising a nucleotide sequence selected from the group consisting of SEQ ID NO: 134-177, 110, 112, 118, 123 and 131 (or the biomarkers set forth by name in Table 4, as described above), more preferably SEQ ID NO: 134-150, 112, 118 (or the biomarkers set forth by name in Table 4 as being upregulated, as described above), wherein the instructions instruct that expression of the one or more biomarkers is increased in the subject, and/or more preferably SEQ ID NO: 151-177, 110 and 123 (or the biomarkers set forth by name in Table 4 as being downregulated, as described above), wherein the instructions instruct that expression of the one or more biomarkers is decreased in the subject.

In yet another embodiment of the kit, the one or more biomarkers is encoded by a nucleic acid molecule comprising a nucleotide sequence selected from the group consisting of SEQ ID NO: 178-292, 91 and 97 (or the biomarkers set forth by name in Table 5, as described above), more preferably SEQ ID NO: 178-185; 187-200, 202, 203, 205-207; 211, 213, 214, 216, 220, 221, 226, 228, 229, 231, 232, 234, 235, 238-247, 249, 250, 253, 262-265, 268-282 and 285-288 (or the biomarkers set forth by name in Table 5 as being upregulated, as described above), wherein the instructions instruct that expression of the one or more biomarkers is increased in the subject, and/or more preferably SEQ ID NO: 186, 201, 204, 208, 209, 91, 210, 212, 97, 215, 217-219, 222-225, 227, 230, 233, 236, 237, 248, 251, 252, 254-261, 266, 267, 283, 284 and 289-292 (or the biomarkers set forth by name in Table 5 as being downregulated, as described above), wherein the instructions instruct that expression of the one or more biomarkers is decreased in the subject.

In yet another embodiment of the kit, the one or more biomarkers is encoded by a nucleic acid molecule comprising a nucleotide sequence selected from the group consisting of SEQ ID NO: 87, 97, 101, 293, 92, 272, 93, 107, 108, 121 and 123 (or the biomarkers set forth by name in Table 6 as pre-treatment biomarkers, as described above), wherein the instructions instruct that the subject is monitored prior to treatment with a TNFα inhibitor. In yet another embodiment of the kit, the one or more biomarkers is encoded by a nucleic acid molecule comprising a nucleotide sequence selected from the group consisting of SEQ ID NO: 290, 209, 98, 112, 116, 121, 130, 155, 92, 289, 216 and 131 (or the biomarkers set forth by name in Table 6 as post-treatment biomarkers, as described above), wherein the instructions instruct that the subject is monitored after treatment with a TNFα inhibitor.

In yet another embodiment of the kit, the one or more biomarkers is encoded by a nucleic acid molecule comprising a nucleotide sequence selected from the group consisting of SEQ ID NO: 97, 102, 29, 294, 295, 91, 131, 290, 100, 134, 296, 297, 298, 299, 136, 174 and 300 (or the biomarkers set forth by name in Table 7, as described above).

In a preferred embodiment, the means for measuring expression in the subject of the one or more biomarkers predictive of responsiveness to a TNFα inhibitor in an autoimmune disorder comprises a nucleic acid preparation sufficient to detect expression of mRNA encoding the one or more biomarkers in a sample from the subject, such as a peripheral blood mononuclear cell sample from which mRNA is obtained by standard methods. This nucleic acid preparation includes at least one, and may include more than one, nucleic acid probe or primer, the sequence(s) of which is designed such that the nucleic acid preparation can detect the expression of mRNA encoding the biomarker(s) of interest in the sample from the subject. A preferred nucleic acid preparation includes two or more PCR primers that allow for PCR amplification of a segment of the mRNA encoding the biomarker(s) of interest. In a particularly preferred embodiment, the kit comprises a nucleic acid preparation sufficient to detect expression of CD11c mRNA in a sample from the subject.

Alternatively, the means for detecting expression in the subject of one or more biomarkers predictive of responsiveness to a TNFα inhibitor in an autoimmune disorder can comprise a reagent that detects the gene product of the mRNA encoding the biomarker(s) of interest sufficient to distinguish it from other gene products in a sample from the subject. A non-limiting example of such a reagent is a monoclonal antibody preparation (comprising one or more monoclonal antibodies) sufficient to detect protein expression of the biomarker(s) of interest in a sample from the subject, such as a peripheral blood mononuclear cell sample. In a particularly preferred embodiment, the kit comprises a monoclonal antibody preparation sufficient to detect expression of CD11c protein in a sample from the subject.

The means for measuring expression of the one or more biomarkers can also include, for example, buffers or other reagents for use in an assay for evaluating biomarker expression (e.g., at either the mRNA or protein level). The instructions can be, for example, printed instructions for performing the assay for evaluating the expression of the one or more biomarkers.

In a preferred embodiment, the means for measuring expression of at least one housekeeping gene comprises a nucleic acid preparation sufficient to detect expression of mRNA of the housekeeping gene (e.g., GAPDH) in a sample from the subject, such as a peripheral blood mononuclear cell sample from which mRNA is obtained by standard methods. This nucleic acid preparation includes at least one, and may include more than one, nucleic acid probe or primer, the sequence(s) of which is designed such that the nucleic acid preparation can detect the expression of mRNA of the housekeeping gene(s) in the sample from the subject. A preferred nucleic acid preparation includes two or more PCR primers that allow for PCR amplification of a segment of the mRNA of the housekeeping gene(s). Alternatively, the means for detecting expression in the subject of at least one housekeeping gene can comprise a reagent that detects the gene product of housekeeping gene sufficient to distinguish it from other gene products in a sample from the subject. A non-limiting example of such a reagent is a monoclonal antibody preparation (comprising one or more monoclonal antibodies) sufficient to detect protein expression of housekeeping gene product in a sample from the subject, such as a peripheral blood mononuclear cell sample.

The means for isolating monocytes can comprise one or more reagents that can be used to separate monocytes from other cell types in a sample of peripheral blood mononuclear cells, for example by positive selection of the monocytes or by negative selection in which all other cell types other than monocytes are removed. In one embodiment, a reagent that binds CD14 on monocytes (e.g., an anti-CD14 antibody) is included in the kit as means to isolate monocytes via positive selection. Alternatively, in another embodiment, reagents such as those commercially available in the Monocyte Isolation Kit II (Miltenyi Biotec, Auburn, Calif.) can be used for negative selection, in which non-monocytes (T cells, B cells, NK cells, dendritic cells, basophils) are indirectly magnetically labeled using a cocktail of biotin-conjugated antibodies against CD3, CD7, CD16, CD19, CD56, CD123 and CD235a (Glycophorin A), as well as anti-biotin MicroBeads, and then highly pure unlabeled monocytes are obtained by depletion of the magnetically labeled cells.

In another embodiment, the kit can further comprise a TNFα inhibitor for treating an autoimmune disorder in the subject. Preferred TNFα inhibitors for use in the kit include the TNFα inhibitors described in detail above with respect to treatment regimens, in particular anti-TNFα antibodies such as adalimumab, infliximab and/or golimumab, and/or Ig fusion proteins such as etanercept.

Preferably, the kit is designed for use with a human subject.

Databases and Computer Programs

In another aspect, the invention pertains to methods of building a database for use in selecting an autoimmune disorder subject for treatment with a TNFα inhibitor, or for use in selecting or monitoring a treatment regimen in an autoimmune disorder subject. The method can comprise receiving, in a computer system, biomarker expression patterns from a plurality of subjects having an autoimmune disorder; and storing the biomarker expression pattern from each subject such that the biomarker expression pattern is associated with an identifier of the subject, wherein the biomarker expression pattern reports expression in the subject of one or more biomarkers encoded by a nucleic acid molecule comprising a nucleotide sequence selected from the group consisting of SEQ ID NO: 1-82 (or the biomarkers set forth by name in Table 9, as described above). The identifier of the subject can be, for example, the name of the subject or a numerical or symbolic identifier coded to the identity of the subject. The method can further comprise receiving, in the computer system, one or more treatment regimens for treatment of an autoimmune disorder in a subject such that the treatment regimen is associated with the biomarker expression pattern of the subject and the identifier of the subject. A user can enter the subject's biomarker expression pattern, and optionally the subject's treatment regimen(s), into the computer system. Alternatively, the subject's biomarker expression pattern can be received directly from equipment used in determining the expression of one or more biomarkers in a sample from the subject.

In another aspect, the invention provides a computer program product useful for building a database for use in selecting or monitoring an autoimmune disorder subject for treatment with a TNFα inhibitor. The computer program can contain executable instructions that when executed cause a processor to perform operations comprising: receiving, in a computer system, a biomarker expression pattern of a subject at one or more biomarkers predictive of responsiveness to a TNFα inhibitor in an autoimmune disorder; and storing the biomarker expression pattern such that the biomarker expression pattern is associated with an identifier of the subject, wherein the biomarker expression pattern reports expression in the subject of one or more biomarkers encoded by a nucleic acid molecule comprising a nucleotide sequence selected from the group consisting of SEQ ID NO: 1-82 (or the biomarkers set forth by name in Table 9, as described above). Optionally, the computer program can further cause the processor to perform an operation comprising: receiving, in the computer system, a treatment regimen for treatment of an autoimmune disorder in the subject such that the treatment regimen is associated with the biomarker expression pattern of the subject and the identifier of the subject.

In another aspect, the invention provides a method of selecting an autoimmune disorder subject for a treatment with a TNFα inhibitor. The method can comprise: (i) identifying, in a database comprising a plurality of autoimmune disorder subjects, a subject whose database entry is associated with a biomarker expression pattern that is predictive of responsiveness to treatment with a TNFα inhibitor, and (ii) selecting the subject for treatment with a TNFα inhibitor, wherein the biomarker expression pattern reports expression in the subject of one or more biomarkers encoded by a nucleic acid molecule comprising a nucleotide sequence selected from the group consisting of SEQ ID NO: 1-82 (or the biomarkers set forth by name in Table 9, as described above). The method can further comprise selecting a treatment regimen by identifying, in the database, a treatment regimen that has been associated with the biomarker expression pattern of the subject and with an identifier of the subject.

In yet another aspect, the invention provides a computer program product useful for identifying and/or selecting a subject for treatment with a TNFα inhibitor. The computer program can contain executable instructions that when executed cause a processor to perform operations comprising: (i) identifying, in a database including a plurality of autoimmune disorder subjects associated with biomarker expression patterns, a subject that is associated with a biomarker expression pattern that is predictive of responsiveness to treatment with a TNFα inhibitor; and (ii) outputting the identified subject as a subject to be treated with a TNFα inhibitor; wherein the biomarker expression pattern reports expression in the subject of one or more biomarkers encoded by a nucleic acid molecule comprising a nucleotide sequence selected from the group consisting of SEQ ID NO: 1-82 (or the biomarkers set forth by name in Table 9, as described above). The computer program can further cause the processor to perform an operation comprising outputting a treatment regimen that is associated with the subject to be treated with the TNFα inhibitor.

In one embodiment of the above-described methods and computer program, the one or more biomarkers is encoded by a nucleic acid molecule comprising a nucleotide sequence selected from the group consisting of SEQ ID NOs: 6, 7, 10, 15-17, 19, 22, 24, 27, 31, 34-39, 43-47, 49, 51, 54, 55, 57, 59, 61, 62, 64, 70, 75, 79 and 82 (or the biomarkers set forth by name in Table 9 as being increased in ≧80% of responders vs. non-responders, as described above), more preferably the one or more biomarkers is encoded by a nucleic acid molecule comprising a nucleotide sequence selected from the group consisting of SEQ ID NOs: 31, 37, 44, 47, 62 and 70 (or the biomarkers set forth by name in Table 9 as being increased in ≧90% of responders vs. non-responders, as described above), and even more preferably at least one of the biomarkers is encoded by a nucleic acid molecule comprising the nucleotide sequence of SEQ ID NO: 44 (or the biomarker, CD11c antigen, set forth by name in Table 9 as being increased in 100% of responders vs. non-responders, as described above). In each of these embodiments, increased expression of the one or more biomarkers is predictive of responsiveness of the subject to a TNFα inhibitor.

In another embodiment of the above-described methods and computer programs, the one or more biomarkers is encoded by a nucleic acid molecule comprising a nucleotide sequence selected from the group consisting of SEQ ID NOs: 1-5, 8, 9, 11-14, 18, 20, 21, 23, 25, 26, 28-30, 32, 33, 40-42, 48, 50, 52, 53, 56, 58, 60, 63, 65-69, 71-74, 76-78, 80 and 81 (or the biomarkers set forth by name in Table 9 as being decreased in ≧80% of responders vs. non-responders, as described above), more preferably the one or more biomarkers is encoded by a nucleic acid molecule comprising a nucleotide sequence selected from the group consisting of SEQ ID NOs: 11, 29, 65, 73 and 74 (or the biomarkers set forth by name in Table 9 as being decreased in ≧90% of responders vs. non-responders, as described above), and even more preferably the one or more biomarkers is encoded by a nucleic acid molecule comprising the nucleotide sequence of SEQ ID NO: 11 or SEQ ID NO: 74 (or the biomarkers set forth by name in Table 9 as being decreased in 100% of responders vs. non-responders, as described above). In each of these embodiments, decreased expression of the one or more biomarkers is predictive of responsiveness of the subject to a TNFα inhibitor.

In another embodiment of the above-described methods and/or computer programs, the biomarker expression pattern(s) can be for one or more biomarkers selected from the group consisting of SEQ ID NO: 83-133 (or the biomarkers set forth by name in Table 3, as described above).

In yet another embodiment of the above-described methods and/or computer programs, the biomarker expression pattern(s) can be for one or more biomarkers selected from the group consisting of SEQ ID NO: 134-177, 110, 112, 118, 123 and 131 (or the biomarkers set forth by name in Table 4, as described above), more preferably SEQ ID NO: 134-150, 112, 118 (or the biomarkers set forth by name in Table 4 as having increased expression, as described above), wherein expression of the one or more biomarkers is increased in the subject, and/or more preferably SEQ ID NO: 151-177, 110 and 123 (or the biomarkers set forth by name in Table 4 as having decreased expression, as described above), wherein expression of the one or more biomarkers is decreased in the subject.

In yet another embodiment of the above-described methods and/or computer programs, the biomarker expression pattern(s) can be for one or more biomarkers selected from the group consisting of SEQ ID NO: 178-292, 91 and 97 (or the biomarkers set forth by name in Table 5, as described above), more preferably SEQ ID NO: 178-185; 187-200, 202, 203, 205-207; 211, 213, 214, 216, 220, 221, 226, 228, 229, 231, 232, 234, 235, 238-247, 249, 250, 253, 262-265, 268-282 and 285-288 (or the biomarkers set forth by name in Table 5 as having increased expression, as described above), wherein expression of the one or more biomarkers is increased in the subject, and/or more preferably SEQ ID NO: 186, 201, 204, 208, 209, 91, 210, 212, 97, 215, 217-219, 222-225, 227, 230, 233, 236, 237, 248, 251, 252, 254-261, 266, 267, 283, 284 and 289-292 (or the biomarkers set forth by name in Table 5 as having decreased expression, as described above), wherein expression of the one or more biomarkers is decreased in the subject.

In yet another embodiment of the above-described methods and/or computer programs, the biomarker expression pattern(s) can be for one or more biomarkers selected from the group consisting of SEQ ID NO: 87, 97, 101, 293, 92, 272, 93, 107, 108, 121 and 123 (or the biomarkers set forth by name in Table 6 as pre-treatment biomarkers, as described above), wherein the subject is monitored prior to treatment with a TNFα inhibitor. In yet another embodiment of the above-described methods and/or computer programs, the biomarker expression pattern(s) can be for one or more biomarkers selected from the group consisting of SEQ ID NO: 290, 209, 98, 112, 116, 121, 130, 155, 92, 289, 216 and 131 (or the biomarkers set forth by name in Table 6 as post-treatment biomarkers, as described above), wherein the subject is monitored after treatment with a TNFα inhibitor.

In yet another embodiment of the above-described methods and/or computer programs, the biomarker expression pattern(s) can be for one or more biomarkers selected from the group consisting of SEQ ID NO: 97, 102, 29, 294, 295, 91, 131, 290, 100, 134, 296, 297, 298, 299, 136, 174 and 300 (or the biomarkers set forth by name in Table 7, as described above).

Computer systems and database software well established in the art can be adapted for use in the methods and computer program products of the invention for building and searching a database for use in selecting or monitoring a treatment regimen for a subject having an autoimmune disorder or for selecting a particular autoimmune disorder subject for treatment with a TNFα inhibitor.

The present invention is further illustrated by the following examples which should not be construed as further limiting. The contents of all references, patents and published patent applications cited throughout this application are expressly incorporated herein by reference in their entirety.

EXAMPLES

Example 1

Materials and Methodologies

In this example, the materials and methodologies used in the subsequent Examples are described.

Patients

Purified monocytes (MO) derived from a total of 84 RA patients were used. The clinical data for the RA patients, pre- and post-anti-TNFα treatment, is summarized in Table 1. All patients fulfilled the revised American College of Rheumatology (ACR) criteria (Arnett, F. C. et al. (1988) *Arthritis Rheum.* 31:315-324). Patients were defined as responders (≧continuous ACR score 40) or non-responders (≦continuous ACR score 30) to anti-TNFα monotherapy, MTX monotherapy or combination therapy. In order to account for a gradual transition from clinical responders to non-responders to therapy, a continuous ACR response evaluation was performed by applying the ACR criteria, but by defining 10% response steps instead of the usual 20, 50, and 70% steps. This was also done to allow more detailed analyses of the correlation between the ACR response and the mRNA expression levels of the predictive marker CD11c.

For Affymetrix® microarray analysis, MO samples from 7 RA patients (RA1-RA7; all females) undergoing the Abbott DE011 trial were used (ReACT; monoclonal antibody Adalimumab®). In this multicenter, double-blinded study patients received Adalimumab® (20 mg weekly or 40 mg biweekly) in the outpatient Rheumatology Clinic of the Charité University Hospital in Berlin, Germany, for a total of 2 years. Non-steroidal anti-inflammatory drugs and 10 mg prednisolone-equivalent per week were allowed in addition to the anti-TNFα therapy. For TaqMan® real-time PCR, 26 patients (RA8-RA84 from the Abbott DE013 trial were used (ATTRACT). In this study Adalimumab®, methotrexate (MTX; 10-20 mg/week) or a combination of both therapeutics was applied.

The mean time interval between the two MO samples (blood sampling before and during therapy) was 9.4±1.8 months (mean±SEM; range 4-13.5 months), the mean age 50.3±3.9 years (range 39-70), and the mean disease duration 18.6±5.3 years (range 4-38). As controls, healthy individuals were recruited (n=7; 6 females, 1 male; mean age 36.1±7.4 years). RA patients RA1-RA84 were recruited from the Rheumatology Clinic of the Charité University Clinic, the Rheumaklinik of the Charité in Berlin-Buch, and from the Schlossparklinik in Berlin.

Separation of Peripheral Blood Mononuclear Cells, Purification of Monocytes, RNA Isolation Peripheral blood (30 to 35 ml) was obtained by venopuncture, immediately stored in heparin-containing vacutainers (Beckton-Dickinson, Rutherford, N.J., USA), and cooled to 4° C. Blood samples were subjected to a Ficoll-Hypaque gradient (d=1.077 g/ml; Biochrom, Berlin, Germany). To enrich MO, negative selection magnetic cell sorting (MACS; Miltenyi; Bergisch Gladbach, Germany) was subsequently applied. Successful purification of MO (purity of 83-90%; 1.3-3.2×10$^6$ MO/patient) was validated by FACS analysis using CD14 and CD45 antibodies (Beckman-Coulter, Krefeld, Germany). In all cases, purified MO showed >98% vitality using propidiumiodide staining (Pharmingen, San-Diego, Calif., USA). MO preparation was performed at 4° C. After purification, MO were lysed in RLT lysis buffer and total RNA was isolated using the RNeasy mini elute kit (Quiagen, Düsseldorf, Germany; yield 1.5-3.2 µg/sample). Quantification and quality control of RNA was performed at 260/280 nm using a Bioanalyzer 2100 unit (Agilent, Palo Alto, Calif., USA).

RNA Amplification and Labeling

For target synthesis, 500 ng of total RNA were amplified using the standard protocol of the manufacturer (Affymetrix®, Palo Alto, Calif., USA) and the Megascript kit (Ambion, (Cambridgeshire, UK).

Biotin-Labeling of cRNA and Gene-Chip Hybridization

Biotinylated cRNA target was generated from amplified cRNAs using the Bioarray high-yield transcription kit (Enzo, New York, N.Y., USA). Samples were hybridized to Affymetrix® test and HG-U133A GeneChip arrays.

Following washing and staining, arrays were scanned twice at 3 µm resolution using a confocal scanner with an argon laser instrument (Agilent® G2500A GeneArray Scanner; Agilent, Calif., USA).

Bioinformatic Analysis of Differentially Expressed Genes in ND and RA Patients Pre- and Post Anti-TNFα Treatment All GeneChips were analyzed for signal calculation and pairwise comparisons using the GCOS1.4 software package with standard settings provided by Affymetrix®. Scaling was performed to a target value of 150 and normalization was set to "1". Pairwise comparison data were grouped to generate a percentage level of increased and decreased comparisons. Fold-changes were calculated from the mean of the SLR values in pairwise comparisons. Filtering was performed on the basis of "increased/decreased" comparisons with a percentage cutoff as indicated in the results. For hierarchical clustering, the software tool "Gene Expression Similarity Investigation Suite" (Genesis; Sturn, A. et al. (2002) *Bioinformatics* 18:207-208; http://genome.tugraz.at/Software/Genesis Center.html) was applied using normalized signal intensities, Pearson distance correlation, and complete linkage clustering. Prediction analysis was performed using the PAM software (http://www.bioconductor.org; Khan, J. et al. (2001) *Nat. Med.* 7:673-679).

Data Sets of Publication

The complete ASCI-file datasets have been deposited in the microarray GEO database (http://www.ncbi.nlm.nih.gov/geo/).

TaqMan® Real Time PCR

Real-time PCR(RT-PC) was performed using a TaqMan® 7500 system and pre-designed TaqMan® low density gene expression primers (Applied Biosystems; Foster City, Calif., USA) or, in the case of CD11c, the primer Hs01015072_g1 (commercially available from Applied Biosystems) in a Bio-Rad iQ Real Time PCR system (Icycler; Bio-Rad; München, Germany). The housekeeping gene GAPDH was used for normalization of the cDNA content. Quantification was performed using the SDS 2.2.0 software (Applied Biosystems); results were expressed as relative quantities of the logarithm of the ΔΔACT values (logRQ), as the relative quantity of expression (RQ; fold-change in comparison to normal donor expression), or as the % expression as normalized to GAPDH.

Literature-Associated Pathway Analysis Using Ingenuity

Gene ontology and gene interaction analyses were executed using the Ingenuity® Pathway analysis tool v. 4.0 (Ingenuity, Redwood City, Calif., USA; Jenssen, T. K. et al. (2001) *Nat. Genet.* 28:21-28; http://www.ingenuity.com). Highest scoring neighborhood analysis of literature-based gene connections was performed by comparing up- and downregulated genes in anti-TNFα responders and non-responders (pre- and post-treatment). Significantly regulated genes in both comparisons were merged from the networks 1 to 5, complemented by transcription factors and finally overlayed with their relative expression values.

Expression-Based Pathway Analysis Using Kyoto Encyclopedia of Genes and Genomes (KEGG)

The KEGG pathway analysis (Kanehisa, M. and Bork, P. (2003) *Nat. Genet.* 33:305-310) was performed using selected genes from the comparison of microarray data in responders and non-responders either pre- or post-treatment with anti-TNFα. Upregulated genes and downregulated genes within the illustrated pathways were color-coded in a gradient fashion (SLR 0.5 to ≧1.5). A total of 4 pathways out of the 8 most highly ranked pathways were selected for illustration.

Statistical Analysis

The non-parametric Mann-Whitney U test was applied to analyze differences between data from RA patients and normal donors, from untreated and anti-TNFα-treated RA patients, and from responders and non-responders to anti-TNFα-therapy. Correlation analyses between experimental and clinical/laboratory parameters of the patients were performed using the Pearson test and the software SPSS 13.0™ (SPSS Inc., Chicago, Ill., USA). For the U test, statistically significant differences were accepted for P≦0.05; for correlation analyses, the acceptance level was reduced to P≦0.01 to account for multiple comparisons.

Example 2

Clinical and Laboratory Assessments for RA Patients and Normal Donors

Two of the seven anti-TNFα-treated RA patients used for microarray analysis, i.e., patients RA4 and RA6, were non-responders to therapy according to the ACR improvement criteria (≦continuous ACR 30 score). In general, this was also reflected in the respective percent-reduction of other clinical parameters of local or systemic inflammation. The group of seven RA patients employed for microarray analysis in the present study constituted a representative RA cohort, as demonstrated by well-known correlations among clinical parameters pre- and post-anti-TNFα treatment, as summarized in Table 2.

The identification of patients RA4 and RA6 as non-responders was also confirmed by hierarchical clustering of clinical parameters.

Example 3

Gene Expression Profiling and Analysis—Differential Gene Expression in Responders Versus Non-Responders to Anti-TNFα-Therapy A total of 119 differentially-expressed genes was identified by comparing RA and normal donors (ND; n=7 each; total of 49 comparisons). Hierarchical clustering of ND, as well as RA patients pre- and post-treatment with these genes also identified 5 responders and 2 non-responders (RAantiTNF4 and RAantiTNF6).

In order to select therapeutically relevant genes, a subpopulation of 51 differentially-expressed genes was then identified by the simultaneous comparison between RA versus normal donors (ND; total of 49 comparisons) and RA responders (n=5) pre- versus post-anti-TNFα therapy (25 comparisons). These genes showed an increase or decrease of the signal log ratio (SLR; between −4.36 and 4.61) in >70% of the pair-wise comparisons between RA and ND. These genes are summarized in Table 3.

Hierarchical clustering with these genes resulted in precise (100%) classification of ND, RA patients pre-treatment, and clinically-defined responders (≦continuous ACR score 40; clustered as ND) or non-responders (≦continuous ACR score 30; clustered as RA; note RAantiTNF4 and RAantiTNF6). This was confirmed by supervised pattern discovery using prediction analysis of microarrays (PAM analysis) at a threshold value of 4.3 in order to minimize the misclassification error. Table 4 summarizes the results of the PAM analysis, showing 49 selected genes, five of them overlapping with genes listed in Table 3. In this case, both non-responders (RAantiTNF4 and RAantiTNF6) were classified as RA patients, whereas the responders, RAantiTNF1-3, RAantiTNF5, and RAantiTNF7, were classified either as normals or as anti-TNFα-treated RA patients. Notably, ND showed the lowest misclassification error at the threshold value (0.00; i.e., the highest similarity among individuals), followed by pre-treatment RA patients (0.14), and anti-TNFα-treated RA patients (0.42).

Identification of responders/non-responders was also confirmed by hierarchical clustering of RA patients post-treatment. A total of 117 genes differentially expressed in RA responders versus RA non-responders was identified in post-anti-TNFα therapy samples, which showed an increase or decrease in 100% of the respective pair-wise comparisons (total of 10 comparisons). The 117 genes identified in this analysis are summarized in Table 5, three of which genes overlap with the genes summarized in Table 3. Hierarchical clustering with these genes resulted in precise (100%) classification of responders and non-responders to therapy.

A number of the differentially-expressed genes showed highly significant correlations with clinical or laboratory parameters pre- and/or post- anti-TNFα treatment, indicating a potential clinical relevance of the genes and contributing to the selection of genes for validation with TaqMan® real-time RT-PCR. These genes are summarized in Table 6.

Example 4

Real-Time RT-PCR Validation of Genes Differentiating Responders and Non-Responders Sixteen genes with a likely pathogenetic importance in RA (and 6 control genes) from Affymetrix® gene expression profiling were selected for validation by TaqMan® real-time RT-PCR (n=10 anti-TNFα-treated RA patients prior to therapy; n=14 ND). The RT-PCR results confirmed the results of Affymetrix® gene expression profiling for 17 of 22 genes (approx. 77%), summarized in Table 7. This applied to genes regarded as differentially expressed in RA versus ND by Affymetrix® analysis (decreased: <−70%; increased: >70%) and to equally expressed control genes. By real-time RT-PCR, 18 genes showed significantly differential expression (p≦0.000 for 7 genes; p≦0.041 for the remaining) in MO from RA patients responding to anti-TNFα therapy versus ND, including genes 10 upregulated in RA (Amphiregulin, Charcot-Leyden crystal protein, TNFα-induced protein 6, thrombomodulin, membrane-spanning 4-domains, subfamily A—member 4, S100 calcium binding protein A1, TNFα, IL-1β, lipoyltransferase 1, and interferon regulatory protein 1), as well as 8 genes downregulated in RA (Uncharacterized hypothalamus protein HT007, MHC class II HLA-DR-alpha, hypothetical protein LOC54103, proteasome subunit beta type 7 precursor, protein KIAA0174, microsomal signal peptidase 18 kDa subunit, ring zinc finger protein 361, and protein phosphatase 1, catalytic subunit, beta isoform). However, the expression for these genes showed no significant differences for the direct comparison between RA responders and non-responders to anti-TNFα therapy.

The potential clinical relevance of some of the differentially expressed genes is underlined by a significant correlation with the ACR response at different time points during anti-TNFα therapy, as summarized in Table 8.

Validation of the 22 selected genes by TaqMan® real-time RT-PCR confirmed the results of Affymetrix® gene expression profiling for 17 of 22 genes (approx. 77% true positives or negatives), in accordance with the rates reported in other gene expression studies and therefore underlining the validity of the present data. The 18 genes showing significantly differential expression in MO from RA patients responding to anti-TNFα therapy versus ND included several genes with a likely pathogenetic importance in RA (e.g., amphiregulin, TNFα-induced protein 6, thrombomodulin, membrane-spanning 4-domains, subfamily A—member 4, S100 calcium binding protein A1, TNFα, IL-1β, lipoyltransferase 1, interferon regulatory protein 1, MHC class II HLA-DR-alpha).

Example 5

Gene Expression Profiling and Analysis—Differential Gene Expression in Responders versus Non-Responders Prior to Anti-TNFα-Therapy (Predictive Genes)

Using a threshold of ≧80% for the pairwise comparisons between future RA responders and future RA non-responders prior to anti-TNFα therapy, a total of 82 predictive genes was identified (11 genes for a threshold of ≧90%; 3 genes for 100%). These genes are summarized in Table 9. The latter group (100%) consisted of 2 known proteins (*Homo sapiens* predicted osteoblast protein (GS3786); integrin alpha-X (antigen CD11c) and an unknown protein (*Homo sapiens* hypothetical protein FLJ10134). In particular the antigen CD11c appears highly interesting, since it is a surface molecule on human MO (and other cells of the myelomonocytic lineage), and since it has known inflammatory functions. Hierarchical clustering with the selected genes resulted again in precise (100%) predictive classification of future responders and non-responders to therapy. Marginal co-clustering of the patient RA5 with the non-responders RA4 and RA6 at the threshold values 80% and 100% possibly identified RA5 as a 'weak' responder, as also indicated by a marginal position in the hierarchical clustering of clinical parameters.

Interestingly, future responders to anti-TNFα-therapy (when directly compared to non-responders) showed a pattern shift from the recently described 'inflammatory' MO to 'resident' MO subsets (Gordon, S. et al. (2005) *Nat. Immunol.* 5:953-963) both prior to therapy and post-treatment. Although most of the individual molecules showed an identical pattern shift in both pre-treatment and post-treatment comparisons, in particular the activating (CD16a,b) and inhibiting Fcγ-receptors (CD32) displayed an opposite behavior. This pattern shift was observed despite the fact that all pre-treatment or post-treatment comparisons between RA patients (all, future responders, future non-responders) and ND indicated a dominance of 'inflammatory' MO in the respective RA groups. Post-treatment, strikingly, responders to anti-TNFα-therapy became barely distinguishable from ND in contrast to non-responders, which still showed a clear 'inflammatory' predominance. These results indicate that successful anti-TNFα-therapy acts by blocking TNFα signaling via TNFα-receptors 1 and 2 and by subsequent induction of a major change in the composition of pro-inflammatory and other MO subsets.

Example 6

Real-Time RT-PCR Validation of Predictive CD11c

TaqMan® real-time RT-PCR confirmed the discrimination of future RA responders (n=15) from future nonresponders (n=12) to anti-TNF monotherapy (at the level of continuous ACR score ≦30) on the basis of their CD11c mRNA expression in monocytes.

TaqMan® real-time RT-PCR confirmed the separation of future RA responders n 55 from future non-responders n=12 to anti-TNFα monotherapy on the basis of their CD11c mRNA expression in MO. The results are summarized in the bar graph of FIG. 1. This clear separation was lost in the case of combination therapy with anti-TNFα/MTX, possibly due to a differential importance of the CD11c mRNA expression for the anti-TNFα and MTX components.

Of the 3 genes identified by pairwise comparison between RA responders and RA non-responders prior to treatment at the level of 100% (and confirmed by TaqMan® real-time RT-PCR), the antigen CD11c appears of particular interest, since it is expressed on the surface of human MO (and other cells of the myelomonocytic lineage, e.g. dendritic cells), and since it has known functions in inflammatory reactions (e.g., as the complement receptor 4) and cell adhesion.

Figure 2:
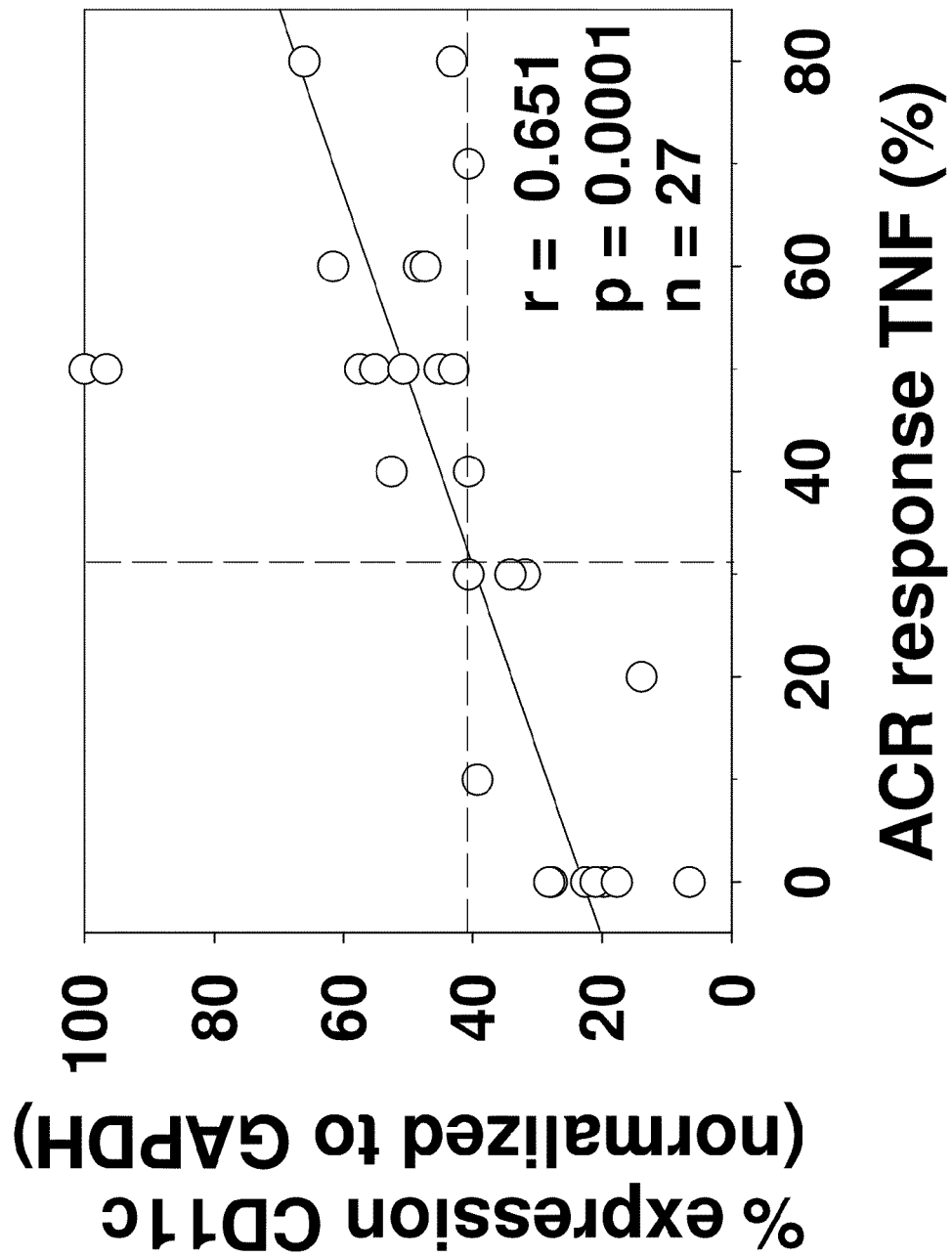
FIG. 2 is a graph showing the correlation between the mRNA expression of predictive CD11c in pre-treatment RA patients and their individual future ACR response (continuous ACR score). The horizontal and vertical broken lines indicate the thresholds for the separation between RA-responders and RA-non-responders, both in terms of the pre-treatment CD11c mRNA levels (40%) and their ACR response (continuous ACR score $\leq$30). Responders (continuous American College of Rheumatology [ACR] score $\geq$40; clustered as ND) and non-responders to anti-TNF therapy (continuous ACR score $\leq$30; clustered as RA) were defined according to the criteria of the ACR.

The validity of CD11c as a predictive biomarker is further underlined by a significant correlation (r=0.651, P=<0.0001, n=27) between the CD11c expression prior to therapy and the future percentage of the ACR response, illustrated in the graph of FIG. 2.

Except for 1 RA patient with a borderline ACR response of 30 and a CD11c mRNA level directly at the distinction threshold (who was therefore classified as a false negative), the threshold level (40%) almost fully distinguished future responders from nonresponders (100% specificity, 94% sensitivity, and 96% power). This clear separation was lost in the case of combination therapy with anti-TNF/methotrexate (MTX), possibly owing to a differential importance of the CD11c mRNA expression for the anti-TNF and MTX treatment components. This was further underlined by the fact that: i) future responders to MTX monotherapy did not significantly differ in their CD11c mRNA expression level from future nonresponders to MTX monotherapy; and ii) there was no significant correlation between the future ACR response of RA patients treated with MTX monotherapy and their CD11c mRNA expression (data not shown).

Strikingly, this was true not only for the continuous ACR score, but also for the clinically applied, discrete ACR criteria.

Figure 3:
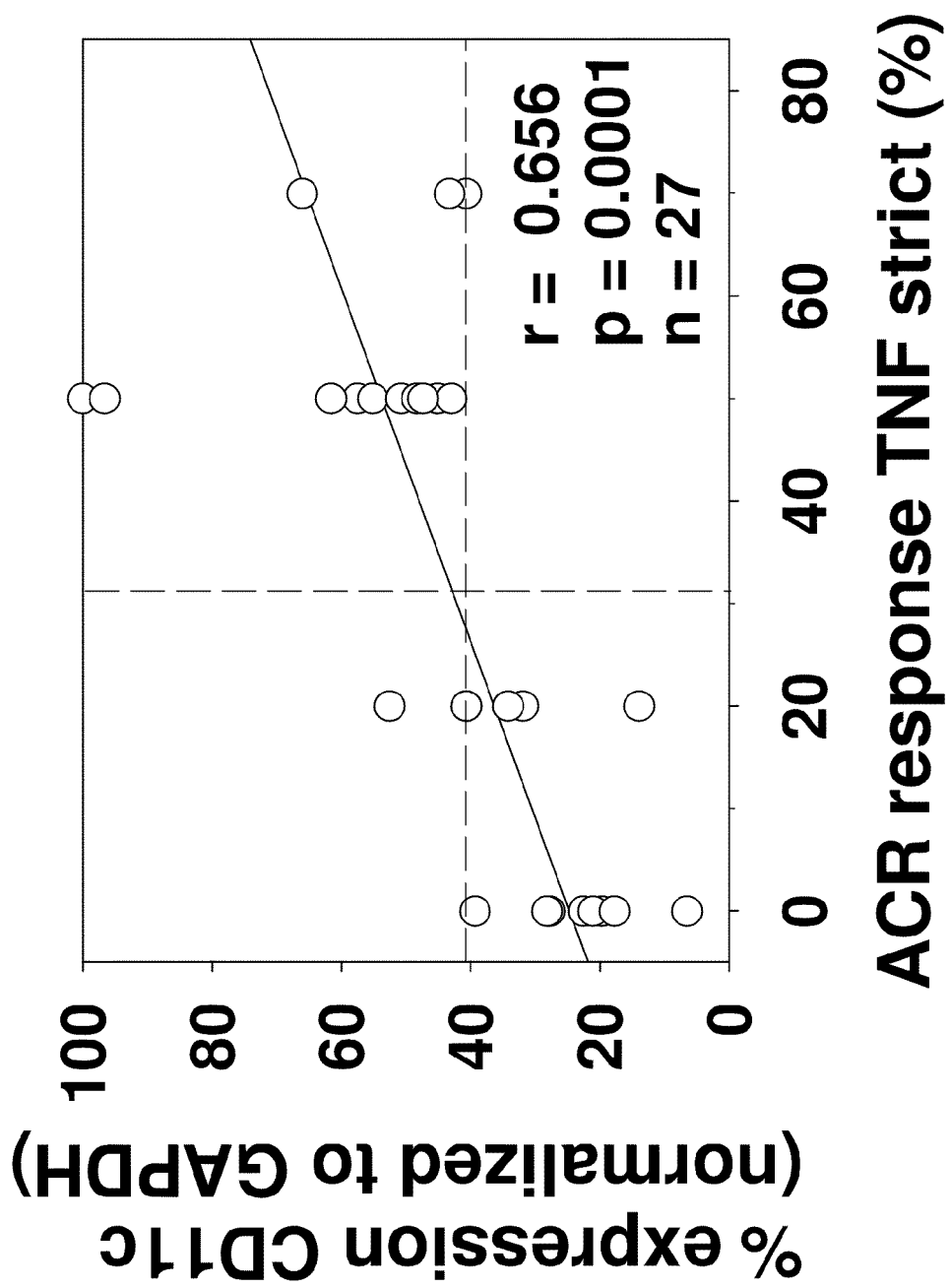
FIG. 3 is a graph showing the correlation between the mRNA expression of predictive CD11c in pre-treatment RA patients and their individual future strict ACR response in the following conventional used steps: $\geq$0%, $\geq$20%, $\geq$50%, and $\geq$70% (continuous ACR score).

A significant correlation (r=0.656, P=<0.0001, n=27) was observed between CD11c expression and the future percentage of strict ACR response, illustrated in the graph in FIG. 3. This finding complements and expands previous reports on the identification of molecules capable of predicting a future response to anti-TNFα therapy (Lequerre, T. et al. (2006) *Arthritis Res. Ther.* 8:R105; Toh, M. L. et al. (2006) *Arthritis Rheum.* 54:2109-2118).

Example 7

Ingenuity® Pathway Analysis

Ingenuity® pathway analysis of the genes in Tables 3 and 5 indicated a direct or indirect influence of anti-TNFα therapy on several molecules thought to be relevant for the pathogenesis and/or severity of RA, e.g., HLA-DMA/B (Morel, J. et al. (2004) *Ann. Rheum. Dis.* 63:1581-1586), CD69 (Marzio, R. et al. (1999) *Immunopharmacol. Immunotoxicol.* 2:565-582) thrombomodulin (Cobankara, V. et al. (2004) *Clin. Rheumatol.* 23:430-434), membrane-spanning 4-domains, subfamily A—member 4 (Fujikado, N. et al. (2006) *Arthritis Res. Ther.* 8:1-13), and forkhead box O3a (Jonsson, H. et al. (2005) *Nat. Med.* 11:666-671). The present approach, therefore, represents a powerful tool to identify gene regulation patterns applicable for diagnosis, as well as for therapy stratification and monitoring in rheumatic diseases, in particular in view of the fact that blood MO are much more easily available than synovial tissue samples. This is further supported by the fact that a high number of individual genes show significant correlations with clinical parameters in RA patients pre- and/or post-anti-TNFα treatment (see Table 6).

Pairwise comparison between RA responders and RA non-responders prior to treatment yielded a number of genes suitable for the prediction of a future response to anti-TNFα therapy (82 genes for a threshold of ≧80%; 11 genes for ≧90%; 3 genes for 100%; summarized in Table 9), resulting in exact classification of future responders and non-responders upon hierarchical clustering. Using all genes differentially expressed in the above comparison at a threshold level of 70% (256 pre-treatment; 1295 post-treatment) for Ingenuity® pathway analysis, the differences between responders and non-responders either pre-treatment or post-treatment were concentrated in the functional gene ontology terms cellular movement, haematological system development, immune response, cell-to-cell signaling and interaction, as well as immunological disease.

In particular, numerous relevant mediators were identified: i) pro-inflammatory cytokines (e.g., interleukin-8 [IL8], chemokine (C-C motif) ligand 5 [CCL5], chemokine (C-X-C motif) ligand 5 [CXCL5], and chemokine (C-X-C motif) ligand 10 [CXCL10]); ii) pro-destructive enzymes (e.g., matrix metalloproteinase 9 [MMP9]); iii) adhesion molecules and Fcγ-receptors (galectin-8 [LGALS8], integrin alpha-X [ITGAX] or CD11c, Fc-gamma receptor IIb [FCGR2B] or CD32, CD86 [CD86] and platelet/endothelial cell adhesion molecule 1 [PECAM1] or CD31); iv) signal transduction molecules (e.g., protein kinase B [AKT1], apoptosis regulator Bcl-2 [BCL2], p21-activated protein kinase 1 [PAK1]); and v) transcription factors (e.g., Mad-related protein 2 [SMAD2], interferon regulatory factor 1 [IRF1], c-myb [MYB], early growth response protein 1 [EGR1], signal transducer and activator of transcription 1 [STAT1], and nuclear factor NF-κB 1 [NFKB1]; for the remaining abbreviations see the respective gene cards [http://www.genecards.org/index.shtml]). These molecules were differentially expressed between RA responders and RA non-responders either pre-treatment or post-treatment and in some cases even inverted their expression upon anti-TNFα-therapy (see interleukin-8 receptor beta [IL8RB], Amyloid-beta A4 precursor [APP]; overexpressed in RA responders pre-treatment and underexpressed post-treatment). Similar opposite variations in transcript levels between RA responders and RA non-responders have recently been reported when comparing baseline to 3-month results (Lequerre, T. et al. (2006) *Arthritis Res. Ther.* 8:R105).

Most strikingly, the transcription of TNFα itself, as well the transcription of members of the subsequent NFKB-pathway (NFKB1 and inhibitor of NF-κB [IKBKB]), was upregulated in RA responders post-treatment. This previously unreported finding at first sight questions the central pro-inflammatory role of TNFα in RA. However, several caveats should be considered: i) The mRNA expression levels of TNFα measured in the present study may not be proportional to the levels of circulating TNFα protein and/or bioactivity, the latter apparently predictive of the clinical response to TNFα inhibition (Marotte, H. et al. (2005) *Arthritis Res. Ther.* 7:R149-155); ii) TNFα, in addition to its well-established pro-inflammatory properties, may also exhibit phase-dependent immunosuppressive properties (Kassiotis, G. et al. (2001) *J. Exp. Med.* 193:427-434).

Several interesting pathways with potential importance for the mechanisms underlying susceptibility to anti-TNFα-therapy were identified by KEGG pathway analysis; including Apotosis and the MAPK pathways.

TABLE 1

Clinical parameters of patients before and after anti-TNF treatment

| Patient | Methods Affymetrix (A) real-time (R/P) | Duration of treatment, mo | Disease duration, y | Age, y | Gender | RF | Morning stiffness, min (% reduction) | Swollen joint count 68 (% reduction) | Painful joint count 68 (% reduction) | ESR, mm/hr (% reduction) | CRP, mg/L (% reduction) | HAQ score (% reduction) | DAS28 (% reduction) | ACR improvement (% continuous score) |
|---|---|---|---|---|---|---|---|---|---|---|---|---|---|---|
| RA1-111006211 | A/P | 0 | 4 | 52 | F | + | 320 | 10 | 19 | 69 | 57.5 | 2.0 | 6.0 | |
| RA1-aTNF | A | 13.5 | | | | | 15 (95) | 3 (70) | 8 (58) | 8 (88) | 2.0 (97) | 1.3 (35) | 3.1 (48) | 50 |
| RA2-111005181 | A/P | 0 | 9 | 53 | F | + | 180 | 16 | 50 | 46 | 52.2 | 1.6 | 6.3 | |
| RA2-aTNF | A | 6 | | | | | 0 (100) | 1 (94) | 19 (62) | 12 (74) | 2.8 (94) | 1.0 (37) | 2.9 (54) | 60 |
| RA3-111005291 | A/P | 0 | 18 | 39 | F | + | 0 | 10 | 28 | 72 | 61.1 | 1.5 | 6.1 | |
| RA3-aTNF | A | 5.5 | | | | | 0 (0) | 2 (80) | 8 (29) | 16 (78) | 3.9 (93) | 1.0 (33) | 4.1 (33) | 60 |
| RA4-111005031 | A/P | 0 | 12 | 47 | F | + | 720 | 20 | 43 | 58 | 85.3 | 2.1 | 6.9 | |
| RA4-aTNF | A | 17 | | | | | 60 (92) | 19 (5) | 35 (19) | 40 (31) | 20.0 (77) | 1.3 (38) | 6.5 (6) | 0 |
| RA5-111004141 | A/P | 0 | 38 | 70 | F | + | 120 | 11 | 56 | 80 | 41.5 | 2.1 | 6.3 | |
| RA5-aTNF | A | 15 | | | | | 120 (0) | 2 (82) | 61 (0) | 11 (86) | 4.5 (88) | 1.4 (33) | 4.0 (37) | 50 |
| RA6-111004131 | A/P | 0 | 38 | 51 | F | + | 60 | 12 | 27 | 46 | 36.0 | 1.6 | 5.9 | |
| RA6-aTNF | A | 4 | | | | | 60 (0) | 4 (67) | 28 (0) | 32 (30) | 22.3 (39) | 1.6 (0) | 5.1 (14) | 10 |
| RA7-111006221 | A/P | 0 | 11 | 40 | F | + | 150 | 18 | 44 | 30 | 17.3 | 1.9 | 6.0 | |
| RA7-aTNF | A | 4.5 | | | | | 10 (93) | 5 (72) | 25 (43) | 14 (53) | 11.3 (35) | 1.3 (32) | 4.1 (32) | 40 |
| RA8-06507 | A | 0 | <1 | 28 | F | − | 120 | 14 | 17 | 30 | <3.5 | 1.6 | 6.1 | |
| RA8-aTNF/MTX | A | 6 | | | | | 0 (100) | 0 (100) | 3 (82) | 4 (87) | <3.5 (0) | 0.0 (100) | 2.4 (61) | 70 |
| RA9-06513 | R | 0 | 1 | 53 | F | − | 120 | 16 | 20 | 34 | <3.5 | 1.3 | 6.2 | |
| RA9-aTNF/MTX | R | 4.5 | | | | | 15 (87) | 12 (25) | 16 (20) | 14 (59) | <3.5 (0) | 1.4 (0) | 5.2 (26) | 20 |
| RA10-05602 | R | 0 | 1 | 48 | F | + | 180 | 8 | 40 | 31 | <3.5 | 2.2 | 7.1 | |
| RA10-MTX | R | 3.5 | | | | | 240 (0) | 10 (0) | 29 (27) | 39 (0) | <3.5 (0) | 2.3 (0) | 6.8 (4) | 0 |
| RA11-05610 | R/P | 0 | <1 | 38 | F | − | 360 | 14 | 22 | 40 | 39.2 | 1.4 | 6.5 | |
| RA11-aTNF | R | 6 | | | | | 30 (92) | 3 (79) | 9 (59) | 45 (0) | 36.4 (7) | 0.3 (79) | 4.3 (34) | 50 |
| RA12-05609 | R/P | 0 | 1 | 63 | F | + | 60 | 17 | 29 | 22 | 14.3 | 0.5 | 6.6 | |
| RA12-aTNF | R | 6 | | | | | 10 (83) | 5 (71) | 9 (69) | 30 (0) | <3.5 (100) | 0.3 (40) | 4.3 (35) | 50 |
| RA13-05608 | R | 0 | 2 | 44 | F | + | 45 | 12 | 24 | 32 | 5.1 | 0.8 | 6.1 | |
| RA13-aTNF/MTX | R | 6 | | | | | 0 (100) | 0 (100) | 1 (96) | 28 (12) | <3.5 (100) | 0.0 (100) | 2.7 (56) | 90 |
| RA14-05612 | R/P | 0 | 1 | 29 | F | + | 60 | 8 | 11 | 35 | 13.1 | 1.0 | 5.0 | |
| RA14-aTNF/MTX | R | 6 | | | | | 0 (100) | 0 (100) | 0 (100) | 8 (77) | <3.5 (100) | 0.0 (100) | 1.7 (66) | 100 |
| RA15-06504 | R/P | 0 | 2 | 47 | F | + | 60 | 10 | 23 | 28 | <3.5 | 1.8 | 6.3 | |
| RA15-aTNF | R | 6 | | | | | 20 (67) | 2 (80) | 3 (87) | 24 (14) | 4.1 (0) | 1.3 (28) | 3.5 (44) | 50 |
| RA16-06308 | R/P | 0 | <1 | 60 | F | + | 120 | 17 | 29 | 56 | <3.5 | 1.8 | 7.3 | |
| RA16-aTNF/MTX | R | 6 | | | | | 15 (87) | 1 (94) | 16 (45) | 28 (50) | <3.5 (0) | 1.3 (28) | 4.8 (44) | 40 |
| RA17-06516 | R/P | 0 | 1 | 36 | F | + | 30 | 17 | 17 | 80 | 22.8 | 1.8 | 6.5 | |
| RA17-aTNF | R | 6 | | | | | 15 (50) | 11 (35) | 0 (100) | 24 (30) | 27.5 (0) | 0.6 (67) | 3.2 (51) | 30 |
| RA18-06309 | R/P | 0 | 1 | 83 | F | + | 30 | 11 | 27 | 24 | 39.4 | 1.3 | 6.5 | |
| RA18-aTNF | R | 6 | | | | | 0 (100) | 0 (100) | 0 (100) | 8 (67) | 8.5 (78) | 0.6 (54) | 1.9 (71) | 70 |
| RA19-05613 | R/P | 0 | 2 | 63 | F | + | 120 | 25 | 43 | 53 | 31.5 | 2.3 | 8.5 | |
| RA19-aTNF | R | 6 | | | | | 15 (87) | 9 (64) | 17 (60) | 85 (0) | 40.0 (0) | 1.3 (43) | 5.6 (34) | 60 |
| RA20-06304 | R | 0 | <1 | 50 | F | − | 60 | 2 | 29 | 24 | 10.0 | 1.0 | 6.6 | |
| RA20-aTNF | R | 6 | | | | | 0 (100) | 2 (83) | 5 (83) | 16 (33) | 10.0 (0) | 1.0 (0) | 3.8 (42) | 30 |
| RA21-06514 | R/P | 0 | 2 | 56 | F | − | 30 | 21 | 52 | 34 | <3.5 | 1.4 | 8.3 | |
| RA21-aTNF/MTX | R | 6 | | | | | 30 (0) | 15 (29) | 16 (69) | 6 (82) | <3.5 (0) | 0.9 (36) | 5.4 (35) | 20 |
| RA22-05606 | R/P | 0 | <1 | 36 | F | + | 60 | 12 | 22 | 40 | 23.1 | 2.4 | 6.2 | |
| RA22-aTNF/MTX | R | 6 | | | | | 0 (100) | 2 (83) | 9 (83) | 30 (25) | 7.3 (68) | 0.8 (67) | 4.2 (32) | 50 |

TABLE 1-continued

Clinical parameters of patients before and after anti-TNF treatment

| Patient | Methods Affymetrix (A) real-time (R/P) | Duration of treatment, mo | Disease duration, y | Age, y | Gender | RF | Morning stiffness, min (% reduction) | Swollen joint count 68 (% reduction) | Painful joint count 68 (% reduction) | ESR, mm/hr (% reduction) | CRP, mg/L (% reduction) | HAQ score (% reduction) | DAS28 (% reduction) | ACR improvement (% continuous score) |
|---|---|---|---|---|---|---|---|---|---|---|---|---|---|---|
| RA23-06306 | R/P | 0 | 1 | 34 | F | + | 30 | 13 | 27 | 90 | 61.1 | 2.1 | 7.1 | |
| RA23-aTNF | R | 3 | | 18 | | | 30 (0) | 18 (0) | 27 (0) | 62 (33) | 53.4 (23) | 2.0 (5) | 7.2 (0) | 0 |
| RA24-06305 | R | 0 | n.d. | | F | + | 30 | 14 | 20 | 22 | 29.1 | 0.3 | 4.7 | |
| RA24-MTX | R | 6 | | | | | 60 (0) | 2 (86) | 8 (60) | 20 (10) | 31.3 (0) | 0.1 (33) | 4.1 (13) | 20 |
| RA25-06515 | R/P | 0 | <1 | 54 | M | − | 45 | 22 | 43 | 34 | <3.5 | 1.0 | 8.0 | |
| RA25-aTNF | R | 6 | | | | | 20 (66) | 7 (68) | 28 (35) | 9 (74) | <3.5 (0) | 1.6 (0) | 5.8 (27) | 0 |
| RA26-06506 | R/P | 0 | 1 | 50 | F | − | 60 | 9 | 23 | 16 | <3.5 | 1.5 | 5.9 | |
| RA26-aTNF | R | 6 | | | | | 120 (0) | 20 (0) | 45 (0) | 50 (0) | <3.5 (0) | 1.9 (0) | 8.3 (0) | 0 |
| RA27-05601 | R/P | 0 | 1 | 42 | F | + | 60 | 8 | 24 | 30 | 6.8 | 1.1 | 5.8 | |
| RA27-aTNF | R | 6.5 | | | | | 60 (0) | 7 (12) | 30 (0) | 58 (0) | 16.9 (0) | 1.5 (0) | 6.7 (0) | 0 |
| RA28-1110004171 | P | 0 | n.d. | 34 | F | + | 60 | 20 | 47 | 30 | 7.0 | 1.8 | 6.2 | |
| RA28-aTNF | | 3.5 | | | | | 0 (100) | 4 (80) | 4 (91) | 16 (47) | 6.9 (1) | 0.4 (78) | 3.6 (42) | 80 |
| RA29-1110011271 | P | 0 | 11 | 62 | F | + | 120 (0) | 8 | 35 | 19 | 16.5 | n.d. | 4.3 | |
| RA29-aTNF/MTX | | 0.5 | | | | | 120 (0) | 9 (0) | 44 (0) | 9 (53) | 3.0 (72) | n.d. | 4.1 (13) | 0 |
| RA30-1110010101 | P | 0 | 7 | 35 | F | + | 120 | 8 | 12 | 52 | 42.6 | n.d. | 5.3 | |
| RA30-aTNF/MTX | | 10 | | | | | 0 (100) | 2 (75) | 7 (42) | 17 (63) | 10.1 (76) | n.d. | 2.6 (51) | 50 |
| RA31-1110004121 | P | 0 | 13 | 33 | F | + | 30 | 11 | 27 | 33 | 7.8 | 1.3 | 5.2 | |
| RA31-aTNF | | 6 | | | | | 20 (67) | 2 (82) | 7 (74) | 18 (45) | 5.9 (24) | 0.9 (31) | 3.4 (35) | 40 |
| RA32-1110008092 | P | 0 | 20 | 43 | F | + | 60 | 14 | 38 | 29 | 18.4 | n.d. | 6.8 | |
| RA32-aTNF | | 6.5 | | | | | 0 (100) | 6 (57) | 7 (72) | 28 (3) | 21.0 (0) | n.d. | 3.4 (50) | 50 |
| RA33-1110005121 | P | 0 | 8 | 61 | F | − | 180 | 19 | 59 | 27 | 22.4 | 1.8 | 6.3 | |
| RA33-aTNF | | 17.5 | | | | | 120 (66) | 2 (89) | 12 (81) | 26 (7) | 14.0 (36) | 1.9 (0) | 4.1 (35) | 20 |
| RA34-1110111281 | P | 0 | 12 | 66 | F | + | 90 | 10 | 5 | 18 | 9.0 | 1.43 | 4.29 | |
| RA34-MTX | | 12 | | | | | 120 (0) | 8 (20) | 9 (0) | 13 (28) | 12.0 (0) | 0.74 (49) | 5.10 (0) | 0 |
| RA35-1110112121 | P | 0 | 6 | 63 | F | + | 180 | 8 | 20 | 17 | 66.0 | 2.67 | 6.3 | |
| RA35-MTX | | 9 | | | | | 0 | 3 (63) | 4 (80) | 12 (29) | <3.5 (100) | 0.67 (76) | 3.5 (45) | 60 |
| RA36-1110201231 | P | 0 | 10 | 36 | F | 0 | 60 | 30 | 19 | 38 | 45.0 | 2.33 | 6.3 | |
| RA36-MTX | | 4 | | | | | 30 (50) | 0 (100) | 0 (100) | 17 (55) | 5.0 (89) | 0.33 (86) | 2.1 (67) | 80 |
| RA37-1110211051 | P | 0 | 1 | 59 | F | + | 180 | 2 | 21 | 27 | 11.0 | 2.44 | 5.5 | |
| RA37-MTX | | 3 | | | | | 0 (100) | 0 (100) | 0 (100) | 8 (70) | 5.0 (55) | 1.44 (41) | 2.9 (47) | 40 |
| RA38-1110309012 | P | 0 | <1 | 32 | F | + | 15 (92) | 7 | 29 | 20 | 8.1 | 1.11 | 5.4 | |
| RA38-MTX | | 0 | | | | | 180 | 1 (85) | 3 (90) | 10 (50) | 1.2 (85) | 0.44 (60) | 2.5 (54) | 50 |
| RA39-1110309122 | P | 0 | 1 | 26 | F | + | 180 | 6 | 23 | 101 | 33.0 | 2.67 | 6.5 | |
| RA39-MTX | | 3 | | | | | 0 (100) | 1 (83) | 2 (88) | 12 (29) | 22.0 (0) | 2.10 (21) | 3.1 (43) | 80 |
| RA40-1110310302 | P | 0 | 1 | 45 | F | + | 15 (92) | 10 | 17 | 81 (20) | 44.5 (0) | 2.1 | 5.6 (14) | |
| RA40-MTX | | 4 | | | | | 10 | 0 (100) | 0 (100) | 72 | 77.6 | 1.1 (49) | 6.8 | 20 |
| RA41-1110411251 | P | 0 | <1 | 58 | F | 0 | 0 (100) | 6 | 16 | 18 (75) | 6.9 (91) | 2.4 | 3.4 (50) | 50 |
| RA41-MTX | | 3 | | | | | 180 | 0 (100) | 2 (88) | 17 | <3.5 | | 5.4 | |
| RA42-1110409071 | P | 0 | 1 | 52 | F | + | 0 | 9 | 4 | 37 | 22.0 | 2.1 | 5.7 | |
| RA42-MTX | | 3 | | | | | 0 (0) | 0 (100) | 0 (100) | 5 (87) | 6.6 (70) | 0.4 (81) | 1.1 (81) | 80 |
| RA43-110409141 | P | 0 | <1 | 58 | M | + | 10 | 8 | 22 | 27 | 32.0 | 2.3 | 5.9 | |
| RA43-MTX | | 3 | | | | | 10 (0) | 0 (100) | 5 (77) | 3 (89) | 4.6 (86) | 2.0 (13) | 1.7 (71) | 70 |
| RA44-1110409223 | P | 0 | 1 | 67 | F | 0 | 60 | 12 | 20 | 55 | 62.6 | 1.33 | 3.13 | |
| RA44-MTX | | 3 | | | | | 0 (100) | 0 (100) | 4 (80) | 12 (78) | 3.80 (94) | 1.40 (0) | 4.93 (0) | 70 |
| RA45-1110411291 | P | 0 | <1 | 44 | F | 0 | 30 | 25 | 43 | 34 | 18.0 | 1.4 | 4.9 | |
| RA45-MTX | | 3 | | | | | 0 (100) | 9 (64) | 17 (60) | 20 (41) | 12.6 (30) | 0 (100) | 2.2 (65) | 60 |

TABLE 1-continued

Clinical parameters of patients before and after anti-TNF treatment

| Patient | Methods Affymetrix (A) real-time (R/P) | Duration of treatment, mo | Disease duration, y | Age, y | Gender | RF | Morning stiffness, min (% reduction) | Swollen joint count 68 (% reduction) | Painful joint count 68 (% reduction) | ESR, mm/hr (% reduction) | CRP, mg/L (% reduction) | HAQ score (% reduction) | DAS28 (% reduction) | ACR improvement (% continuous score) |
|---|---|---|---|---|---|---|---|---|---|---|---|---|---|---|
| RA46-1110602212 | P | 0 | 10 | 45 | F | + | 120 | 3 | 13 | 74 | 17.8 | 1.7 | 5.8 | |
| RA46-aTNF/MTX | | 6 | | | | | 120 (0) | 0 (100) | 21 (0) | 20 (63) | 2.7 (85) | 1.1 (35) | 4.4 (24) | 30 |
| RA47-1110503081 | P | 0 | 21 | 57 | F | + | 360 | 8 | 10 | 74 | <3.5 | 2.0 | 6.5 | |
| RA47-TNF | | 6 | | | | | 180 (50) | 7 (14) | 11 (0) | 20 (0) | <3.5 (0) | 2.8 (0) | 6.7 (0) | 0 |
| RA48-1110703082 | P | 0 | 7 | 60 | F | + | 240 | 0 | 10 | 28 | 106.0 | 1.1 | 6.2 | |
| RA48-TNF | | 6 | | | | | 120 (50) | 0 (0) | 5 (50) | 120 (12) | 83.6 (21) | 1.0 (9) | 4.1 (34) | 0 |
| RA49-1110309122 | P | 0 | 1 | 26 | F | + | 180 | 6 | 24 | 40 | 33.0 | 0.9 | 6.6 | |
| RA49-MTX | | 9 | | | | | 15 (92) | 1 (83) | 9 (62) | 40 (0) | 34.5 (0) | 0.7 (22) | 5.7 (14) | 10 |
| RA50-1100308202 | P | 0 | 6 | 63 | F | + | 0 | 0 | 18 | 28 | 9.8 | 1.4 | 4.6 | |
| RA50-MTX | | 3 | | | | | 0 (0) | 1 (0) | 2 (89) | 21 (25) | 9.9 (0) | 1.7 (0) | 4.0 (13) | 0 |
| RA51-1110309111 | P | 0 | 2 | 45 | M | + | 180 | 16 | 30 | 10 | 4.0 | 2.2 | 6.1 | |
| RA51-MTX | | 3 | | | | | 120 (33) | 9 (44) | 24 (20) | 5 (50) | 1.3 (77) | 2.1 (5) | 5.1 (16) | 0 |
| RA52-1110401081 | P | 0 | 1 | 62 | F | + | 0 | 0 | 18 | 30 | 6.5 | 1.1 | 4.4 | |
| RA52-MTX | | 5.5 | | | | | 0 (0) | 0 (0) | 0 (100) | 25 (17) | 4.8 (26) | 0.1 (91) | 2.3 (48) | 90 |
| RA53-1110406011 | P | 0 | 1 | 61 | F | + | 30 | 10 | 33 | 10 | 23.0 | 1.78 | 6.4 | |
| RA53-MTX | | 3 | | | | | 5 (83) | 0 (100) | 1 (97) | 0 (100) | 3.1 (87) | 0.3 (83) | 2.4 (62) | 80 |
| RA54-1110406112 | P | 0 | 3 | 61 | M | + | 10 | 6 | 22 | 10 | 9.0 | 0.7 | 5.2 | |
| RA54-MTX | | 3 | | | | | 0 (100) | 0 (100) | 5 (77) | 20 (0) | 16.7 (0) | 1.9 (0) | 3.3 (37) | 40 |
| RA55-1110406111 | P | 0 | <1 | 57 | F | + | 60 | 2 | 12 | 25 | 24.8 | 1.9 | 5.4 | |
| RA55-MTX | | 3 | | | | | 0 (100) | 0 (100) | 2 (83) | 12 (52) | 6.7 (73) | 0.3 (84) | 2.4 (56) | 80 |
| RA56-1110407131 | P | 0 | 1 | 63 | F | + | 30 | 9 | 30 | 55 | 37.8 | 1.67 | 8.8 | |
| RA56-MTX | | 3 | | | | | 0 (100) | 0 (100) | 6 (80) | 14 (75) | 1.0 (97) | 1.10 (34) | 3.7 (58) | 30 |
| RA57-1110407281 | P | 0 | 2 | 56 | F | + | 0 | 7 | 19 | 21 | 3.9 | 1.6 | 5.5 | |
| RA57-MTX | | 3 | | | | | 0 (0) | 0 (100) | 2 (89) | 10 (52) | <3.5 (100) | 0.2 (87) | 2.5 (55) | 70 |
| RA58-1110409201 | P | 0 | 1 | 61 | F | + | 10 | 5 | 16 | 20 | <3.5 | 2.2 | 4.3 | |
| RA58-MTX | | 3 | | | | | 0 (100) | 0 (100) | 4 (75) | 14 (30) | <3.5 (0) | 0.4 (82) | 2.0 (53) | 70 |
| RA59-1110410271 | P | 0 | 6 | 35 | M | + | 15 | 0 | 5 | 12 | <3.5 | 0.8 | 2.6 | |
| RA59-MTX | | 3 | | | | | 0 (100) | 0 (0) | 2 (60) | 25 (0) | 7.9 (0) | 0.8 (0) | 2.7 (0) | 30 |
| RA60-1110503231 | P | 0 | 1 | 71 | F | + | 30 | 6 | 23 | 14 | 5.6 | 2 | 5.9 | |
| RA60-MTX | | 3 | | | | | 45 (0) | 12 (0) | 5 (78) | 8 (43) | 4.9 (12) | 0.9 (55) | 3.1 (47) | 40 |
| RA61-1110504061 | P | 0 | 1 | 51 | F | + | 45 | 12 | 27 | 16 | <3.5 | 2.5 | 7.0 | |
| RA61-MTX | | 3 | | | | | 0 (100) | 0 (100) | 0 (100) | 4 (75) | <3.5 (0) | 0.4 (84) | 1.0 (86) | 70 |
| RA62-1110505301 | P | 0 | 1 | 59 | F | + | 120 | 2 | 9 | 10 | <3.5 | 2.1 | 4.7 | |
| RA62-MTX | | 3 | | | | | 0 (100) | 0 (100) | 0 (100) | 6 (40) | <3.5 (0) | 1.1 (48) | 3.2 (26) | 40 |
| RA63-1110507281 | P | 0 | 2 | 43 | F | + | 30 | 10 | 17 | 68 | 42.0 | 1.8 | 6.0 | |
| RA63-MTX | | 3 | | | | | 0 (100) | 6 (40) | 15 (12) | 20 (71) | 33.0 (21) | 1.1 (39) | 4.0 (33) | 30 |
| RA64-1110511281 | P | 0 | <1 | 69 | F | + | 90 | 7 | 21 | 25 | 14.5 | 1.2 | 5.8 | |
| RA64-MTX | | 3 | | | | | 15 (50) | 1 (86) | 2 (90) | 10 (60) | 27.0 (0) | 0.9 (25) | 3.0 (48) | 20 |
| RA65-1110405273 | P | 0 | 5 | 55 | F | + | 0 | 4 | 2 | 6 | <3.5 | 1.2 | 3.0 | |
| RA65-aTNF/MTX | | 4 | | | | | 0 (100) | 0 (100) | 16 (0) | 12 (0) | <3.5 (0) | 0.8 (33) | 4.7 (0) | 0 |
| RA66-1110502091 | P | 0 | 36 | 62 | F | 0 | 10 (0) | 13 | 14 | 10 | <3.5 | 1.9 | 4.2 | |
| RA66-aTNF/MTX | | 30 | | | | | 30 | 2 (85) | 14 (0) | 12 (0) | 4.2 (0) | 0 (100) | 4.1 (2) | 40 |
| RA67-1110507261 | P | 0 | 25 | 43 | F | + | 15 (50) | 4 | 5 | 32 | 11.4 | 1.7 | 4.4 | |
| RA67-aTNF/MTX | | 25 | | | | | 0 | 1 (80) | 7 | 16 (50) | 7.7 (32) | 1.1 (35) | 2.8 (36) | 30 |
| RA68-1110603141 | P | 0 | 12 | 72 | F | + | 30 | 7 | 0 (100) | 72 | 4.8 | 1.3 | 4.7 | |
| RA68-aTNF | | 12 | | | | | 60 (0) | 0 (100) | | 4 (94) | <3.5 (100) | 0.0 (100) | 2.4 (49) | 30 |

TABLE 1-continued

Clinical parameters of patients before and after anti-TNF treatment

| Patient | Methods Affymetrix (A) real-time (R/P) | Duration of treatment, mo | Disease duration, y | Age, y | Gender | RF | Morning stiffness, min (% reduction) | Swollen joint count 68 (% reduction) | Painful joint count 68 (% reduction) | ESR, mm/hr (% reduction) | CRP, mg/L (% reduction) | HAQ score (% reduction) | DAS28 (% reduction) | ACR improvement (% continuous score) |
|---|---|---|---|---|---|---|---|---|---|---|---|---|---|---|
| RA69-111051018l | P | 0 | 2 | 33 | F | + | 50 | 6 | 6 | 12 | 9.0 | 3.0 | 4.7 | |
| RA69-aTNF/MTX | | 12 | | | | | 0 (100) | 0 (100) | 0 (100) | 26 (0) | <3.5 (100) | 1.1 (63) | 2.4 (49) | 80 |
| RA70-06303 | P | 0 | 1 | 53 | F | + | 30 | 14 | 17 | 26 | 31.9 | 1.3 | 5.8 | |
| RA70-aTNF/MTX | | 6 | | | | | 10 (66) | 0 (100) | 0 (100) | 6 (77) | 0 (100) | 0.1 (92) | 1.6 (73) | 70 |
| RA71-06516 | P | 0 | 3 | 79 | F | + | 30 | 17 | 17 | 80 | 22.8 | 1.8 | 6.5 | |
| RA71-TNF | | 6 | | | | | 15 (50) | 0 (100) | 11 (35) | 24 (70) | 7.5 (67) | 0.6 (67) | 3.2 (49) | 30 |
| RA72-06510 | P | 0 | 3 | 68 | F | + | 10 | 25 | 34 | 80 | 41.6 | 2.1 | 8.2 | |
| RA72-TNF | | 6 | | | | | 10 (0) | 2 (92) | 0 (100) | 58 (27) | 21.4 (49) | 1.5 (29) | 2.6 (68) | 70 |
| RA73-06309 | P | 0 | 1 | 36 | F | 0 | 45 | 11 | 27 | 24 | 39.4 | 1.3 | 6.5 | |
| RA73-TNF/MTX | | 6 | | | | | 0 (100) | 0 (100) | 0 (100) | 8 (75) | 8.5 (78) | 0.6 (54) | 1.9 (71) | 70 |
| RA74-06310 | P | 0 | 3 | 48 | F | 0 | 360 | 14 | 22 | 30 | 21.9 | 3.0 | 8.1 | |
| RA74-TNF | | 12 | | | | | 15 | 6 (57) | 14 (36) | 13 (57) | 14.3 (35) | 2.3 (23) | 2.9 (64) | 50 |
| RA75-06307 | P | 0 | 2 | 51 | F | + | 360 | 16 | 22 | 64 | 83.4 | 2.6 | 7.0 | |
| RA75-MTX | | 6 | | | | | 0 (100) | 2 (87) | 3 (86) | 22 (66) | 11.5 (86) | 0.8 (69) | 2.2 (69) | 70 |
| RA76-06311 | P | 0 | 3 | 43 | F | + | 120 | 14 | 36 | 32 | 53.1 | 0.8 | 7.0 | |
| RA76-TNF | | 3 | | | | | 0 (100) | 0 (100) | 0 (100) | 8 (75) | 4.9 (91) | 0.1 (87) | 1.7 (75) | 80 |
| RA77-06513 | P | 0 | 1 | 53 | F | 0 | 120 | 16 | 20 | 34 | <3.5 | 1.3 | 6.2 | |
| RA77-TNF/MTX | | 4.5 | | | | | 15 (87) | 12 (25) | 16 (20) | 14 (59) | <3.5 (0) | 1.4 (0) | 5.3 (15) | 20 |
| RA78-06512 | P | 0 | 1 | 83 | F | 0 | 30 | 15 | 53 | 33 | 7.4 | 2.4 | 6.7 | |
| RA78-MTX | | 5.5 | | | | | 15 (50) | 15 | 63 (0) | 8 (76) | 4.9 (34) | 3.0 (0) | 8.3 (0) | 0 |
| RA79-06514 | P | 0 | 2 | 56 | F | 0 | 30 | 27 (0) | 52 | 34 | 4.9 | 1.3 | 8.3 | |
| RA79-TNF/MTX | | 6 | | | | | 30 (0) | 15 (29) | 16 (69) | 6 (82) | <3.5 (0) | 0.9 (31) | 5.4 (35) | 20 |
| RA80-111050524l | P | 0 | 4 | 47 | F | + | 24 | 5 | 9 | 24 | 10.2 | 1.3 | 4.4 | |
| RA80-TNF/MTX | | 3.5 | | | | | 36 (0) | 4 (20) | 4 (56) | 36 (0) | <3.5 (100) | 1.1 (15) | 4.1 (7) | 20 |
| RA81-06305 | P | 0 | 1 | 18 | F | + | 30 | 8 | 20 | 22 | 29.1 | 0.3 | 6.0 | |
| RA81-MTX | | 6 | | | | | 60 (0) | 2 (75) | 14 (70) | 20 (9) | 31.3 (0) | 0.1 (33) | 4.1 (32) | 20 |
| RA82-05602 | P | 0 | 1 | 48 | F | + | 180 | 29 | 40 | 31 | <3.5 | 2.1 | 4.0 | |
| RA82-MTX | | 3.5 | | | | | 240 (0) | 10 (66) | 8 (20) | 39 (0) | <3.5 (0) | 2.3 (0) | 6.5 (0) | 0 |
| RA83-05607 | P | 0 | 3 | 61 | M | + | 120 | 25 | 40 | 29 | 4.6 | 2.5 | 7.8 | |
| RA83-MTX | | 8 | | | | | 0 (100) | 3 (88) | 3 (92) | 12 (59) | 0 (100) | 1.3 (52) | 3.1 (60) | 60 |
| RA84-06302 | P | 0 | 3 | 42 | F | + | 60 | 16 | 39 | 30 | 9.6 | 2.5 | 7.4 | |
| RA84-MTX | | 6 | | | | | 10 (83) | 6 (62) | 18 (51) | 24 ( ) | <3.5 (100) | 0.8 (68) | 5.3 (28) | 60 |

A = Affymetrix;
R = real-time RT-PCR (validation of gene expression);
P = real-time RT-PCR (validation of predictive gene);
RF = rheumatoid factor;;
ESR = erythrocyte sedimentation rate;
CRP = C-reactive protein concentration,
HAQ = Health Assessment Questionnaire;
DAS28 = disease activity score (28 joints);
+ = positive;
− = negative;
n.d. = not determined;
aTNF = anti-TNF monoclonal antibody therapy;
MTX = methotrexate therapy

TABLE 2

Correlations among clinical parameters (Pearson correlation test; pre- and post-anti-TNFα treatment)

| | r-value | p-value |
|---|---|---|
| Morning stiffness/Swollen joint count 28 | 0.718 | 0.004 |
| Morning stiffness/Swollen joint count 68 | 0.664 | 0.010 |
| Swollen joint count 28/Swollen joint count 68 | 0.990 | 0.000 |
| Painful joint count 28/Painful joint count 68 | 0.794 | 0.001 |
| ESR/CRP | 0.854 | 0.000 |
| ESR/VAS (physician) | 0.764 | 0.001 |
| ESR/DAS 28 | 0.813 | 0.000 |
| CRP/Morning stiffness | 0.733 | 0.003 |
| CRP/Swollen joint count 28 | 0.762 | 0.002 |
| CRP/Swollen joint count 68 | 0.728 | 0.003 |
| CRP/DAS 28 | 0.786 | 0.001 |
| DAS 28/Swollen joint count 28 | 0.891 | 0.000 |
| DAS 28/Swollen joint count 68 | 0.878 | 0.000 |
| DAS 28/Painful joint count 28 | 0.660 | 0.010 |
| VAS (physician)/Swollen joint count 68 | 0.672 | 0.008 |
| VAS (physician)/Painful joint count 28 | 0.697 | 0.006 |
| VAS (physician)/DAS 28 | 0.790 | 0.001 |

Different clinical parameters showed correlations in RA patients pre- and post anti-TNFα treatment (n = 14 in all cases).
ESR = erythrocyte sedimentation rate;
CRP = C-reactive protein;
DAS 28 = disease activity score (28 joints); and
VAS (physician) = visual analogue score (physican's global assessment)

TABLE 3

Genes differentially regulated in peripheral blood monocytes of both RA patients versus normal donors and RA patients pre- versus post-anti-TNFα

| Affymetrix ID | Gene name | Increased (%) | Decreased (%) RA vs. ND | Fold change | SLR | Increased (%) | Decreased (%) RA-aTNF vs. RA (all) | Fold change | SLR | Increased (%) | Decreased (%) RA-aTNF vs. RA (responder) | Fold change | SLR |
|---|---|---|---|---|---|---|---|---|---|---|---|---|---|
| 36711_at | v-maf musculoaponeurotic fibrosarcoma oncogene homolog F | 71.43 | 14.29 | 3.44 | 1.78 | 28.57 | 61.22 | -2.78 | -1.48 | 12.00 | 80.00 | -5.88 | -2.56 |
| 38037_at | Diphtheria toxin receptor (DTR) | 71.43 | 10.20 | 2.87 | 1.52 | 12.24 | 73.47 | -2.59 | -1.37 | — | 84.00 | -3.70 | -1.89 |
| 201386_s_at | DEAH (Asp-Glu-Ala-His) box polypeptide 15 | 2.04 | 73.47 | -1.66 | -0.73 | 44.90 | 14.29 | 1.43 | 0.51 | 60.00 | — | 1.81 | 0.85 |
| 201890_at | Ribonucleotide reductase M2 polypeptide | 81.63 | 8.16 | 4.39 | 2.13 | 2.04 | 69.39 | -3.86 | -1.95 | 4.00 | 64.00 | -3.88 | -1.96 |
| 202219_at | Solute carrier family 6, member 8 | 71.43 | 8.16 | 8.44 | 3.08 | 12.24 | 59.18 | -5.17 | -2.37 | 4.00 | 72.00 | -6.96 | -2.80 |
| 202464_s_at | 6-phosphofructo-2-kinase/fructose-2,6-biphosphatase 3 | 81.63 | — | 2.74 | 1.46 | 12.24 | 69.39 | -2.18 | -1.12 | — | 84.00 | -3.01 | -1.59 |
| 203115_at | Ferrochelatase (protoporphyria) | 83.67 | 8.16 | 3.87 | 1.95 | 20.41 | 63.27 | -2.18 | -1.12 | 16.00 | 72.00 | -2.25 | -1.17 |
| 203574_at | Nuclear factor, interleukin 3 regulated | 77.55 | — | 2.16 | 1.11 | 10.20 | 53.06 | -1.54 | -0.62 | — | 76.00 | -2.06 | -1.04 |
| 203887_s_at | Thrombomodulin | 71.43 | 16.33 | 2.49 | 1.32 | 12.24 | 65.31 | -2.34 | -1.23 | — | 76.00 | -3.14 | -1.65 |
| 203932_at | Major histocompatibility complex, class II, DM beta | 2.04 | 75.51 | -1.82 | -0.87 | 63.27 | 4.08 | 1.64 | 0.71 | 84.00 | — | 1.68 | 0.75 |
| 204131_s_at | Forkhead box O3A | 77.55 | 4.08 | 2.21 | 1.14 | 18.37 | 55.10 | -1.42 | -0.50 | 4.00 | 64.00 | -1.41 | -0.50 |
| 204419_x_at | Hemoglobin, gamma A, gamma G | 75.51 | 6.12 | 2.88 | 1.52 | 14.29 | 75.51 | -3.18 | -1.67 | 8.00 | 92.00 | -4.16 | -2.04 |
| 204467_s_at | Synuclein, alpha (non A4 component of amyloid precursor) | 71.43 | 4.08 | 3.60 | 1.85 | 24.49 | 65.31 | -2.26 | -1.18 | 16.00 | 80.00 | -2.93 | -1.55 |
| 204848_x_at | Hemoglobin, gamma A | 75.51 | 6.12 | 3.83 | 1.94 | 16.33 | 65.31 | -3.22 | -1.69 | 4.00 | 80.00 | -4.63 | -2.21 |
| 205239_at | Amphiregulin (schwannoma-derived growth factor) | 81.63 | 4.08 | 6.13 | 2.62 | 20.41 | 71.43 | -3.36 | -1.75 | — | 96.00 | -5.91 | -2.56 |
| 205571_at | Lipoyltransferase 1 | — | 79.59 | -1.90 | -0.93 | 51.02 | 12.24 | 1.35 | 0.44 | 72.00 | — | 1.61 | 0.69 |
| 205592_at | Solute carrier family 4, anion exchanger, member 1 | 77.55 | 10.20 | 4.83 | 2.27 | 16.33 | 65.31 | -3.81 | -1.93 | 8.00 | 76.00 | -5.63 | -2.49 |
| 205863_at | S100 calcium binding protein A12 (calgranulin C) | 71.43 | 4.08 | 1.69 | 0.76 | 14.29 | 55.10 | -1.49 | -0.58 | 8.00 | 56.00 | -1.56 | -0.64 |
| 205900_at | Keratin 1 (epidermolytic hyperkeratosis) | 75.51 | 6.12 | 4.03 | 2.01 | 20.41 | 67.35 | -2.31 | -1.21 | 16.00 | 84.00 | -3.18 | -1.67 |
| 205950_s_at | Carbonic anhydrase I | 81.63 | 4.08 | 5.88 | 2.56 | 22.45 | 67.35 | -2.87 | -1.52 | 16.00 | 84.00 | -4.14 | -2.05 |
| 205987_at | CD1C antigen, c polypeptide | — | 87.76 | -2.93 | -1.55 | 63.27 | 2.04 | 1.72 | 0.79 | 68.00 | — | 1.72 | 0.78 |
| 206025_s_at | Tumor necrosis factor, alpha-induced protein 6 | 71.43 | — | 3.85 | 1.94 | 12.24 | 59.18 | -1.97 | -0.98 | 4.00 | 72.00 | -2.74 | -1.46 |
| 206111_at | Ribonuclease, RNase A family, 2 | 73.47 | 10.20 | 1.95 | 0.97 | 8.16 | 67.35 | -1.59 | -0.67 | — | 72.00 | -1.68 | -0.75 |
| 206834_at | Hemoglobin, delta | 83.67 | 2.04 | 4.08 | 2.03 | 20.41 | 65.31 | -3.13 | -1.64 | 16.00 | 80.00 | -4.59 | -2.20 |
| 207332_s_at | Transferrin receptor (p90, CD71) | 81.63 | 6.12 | 2.35 | 1.23 | 2.04 | 79.59 | -2.45 | -1.29 | — | 84.00 | -2.57 | -1.36 |
| 208632_at | Ring finger protein 10 | 71.43 | 6.12 | 2.06 | 1.04 | 12.24 | 59.18 | -1.71 | -0.78 | 4.00 | 68.00 | -1.69 | -0.76 |
| 209007_s_at | Chromosome 1 open reading frame 63 | 4.08 | 73.47 | -2.14 | -1.10 | 57.14 | 14.29 | 1.54 | 0.62 | 76.00 | 4.00 | 1.87 | 0.90 |
| 209458_x_at | Hemoglobin, alpha 1, alpha 2 | 85.71 | 2.04 | 3.00 | 1.59 | 8.16 | 63.27 | -2.09 | -1.06 | 4.00 | 76.00 | -2.60 | -1.38 |
| 209795_at | CD69 antigen (p60, early T-cell activation antigen | 71.43 | 12.24 | 2.95 | 1.56 | 14.29 | 75.51 | -3.18 | -1.67 | 16.00 | 76.00 | -3.77 | -1.92 |
| 210027_s_at | APEX nuclease (multifunctional DNA repair enzyme) 1 | — | 75.51 | -1.93 | -0.94 | 67.35 | 10.20 | 1.64 | 0.72 | 84.00 | — | 2.02 | 1.02 |
| 210254_at | Membrane-spanning 4-domains, subfamily A, member 3 | 73.47 | 16.33 | 3.41 | 1.77 | 14.29 | 79.59 | -4.56 | -2.19 | 20.00 | 76.00 | -3.69 | -1.88 |
| 210338_s_at | Heat shock 70 kDa protein 8 | 6.12 | 71.43 | -2.09 | -1.06 | 55.10 | 18.37 | 1.57 | 0.66 | 68.00 | 4.00 | 2.04 | 1.03 |
| 211038_s_at | Hypothetical protein MGC12760 | — | 71.43 | -2.07 | -1.05 | 42.86 | 16.33 | 1.29 | 0.37 | 56.00 | 4.00 | 1.46 | 0.55 |
| 211458_s_at | GABA(A) receptor-associated protein like 1, like 3 | 71.43 | — | 1.95 | 0.96 | 16.33 | 65.31 | -1.92 | -0.94 | — | 84.00 | -2.75 | -1.46 |

TABLE 3-continued

Genes differentially regulated in peripheral blood monocytes of both RA patients versus normal donors and RA patients pre- versus post-anti-TNFα

| Affymetrix ID | Gene name | Increased (%) | Decreased (%) RA vs. ND | Fold change | SLR | Increased (%) | Decreased (%) RA-aTNF vs. RA (all) | Fold change (all) | SLR | Increased (%) | Decreased (%) RA-aTNF vs. RA (responder) | Fold change (responder) | SLR |
|---|---|---|---|---|---|---|---|---|---|---|---|---|---|
| 211560_s_at | Aminolevulinate, delta-, synthase 2 | 87.76 | 4.08 | 24.35 | 4.61 | 16.33 | 75.51 | −10.81 | −3.43 | 8.00 | 80.00 | −20.53 | −4.36 |
| 211991_s_at | Major histocompatibility complex, class II, DP alpha 1 | 4.08 | 79.59 | −3.01 | −1.59 | 75.51 | 8.16 | 2.37 | 1.24 | 80.00 | 4.00 | 2.54 | 1.34 |
| 212199_at | Morf4 family associated protein 1-like 1 | 2.04 | 75.51 | −1.94 | −0.96 | 59.18 | 10.20 | 1.56 | 0.64 | 80.00 | — | 2.11 | 1.08 |
| 212224_at | Aldehyde dehydrogenase 1 family, member A1 | 4.08 | 75.51 | −2.56 | −1.36 | 71.43 | 12.24 | 2.28 | 1.19 | 92.00 | — | 2.74 | 1.45 |
| 212232_at | Formin binding protein 4 | — | 77.55 | −1.83 | −0.87 | 48.98 | 14.29 | 1.27 | 0.35 | 72.00 | — | 1.57 | 0.65 |
| 212534_at | Zinc finger protein 24 (KOX 17) | 6.12 | 71.43 | −1.49 | −0.58 | 53.06 | 4.08 | 1.35 | 0.43 | 76.00 | — | 1.45 | 0.53 |
| 213142_x_at | Hypothetical protein LOC54103 | 4.08 | 73.47 | −1.77 | −0.82 | 51.02 | 12.24 | 1.25 | 0.32 | 72.00 | — | 1.51 | 0.60 |
| 214433_s_at | Selenium binding protein 1 | 71.43 | 10.20 | 4.59 | 2.20 | 18.37 | 65.31 | −3.08 | −1.62 | 12.00 | 68.00 | −3.55 | −1.83 |
| 215933_s_at | Hematopoietically expressed homeobox | — | 75.51 | −1.83 | −0.87 | 55.10 | 6.12 | 1.51 | 0.59 | 76.00 | 0.00 | 1.85 | 0.88 |
| 217478_s_at | Major histocompatibility complex, class II, DM alpha | 4.08 | 73.47 | −2.02 | −1.01 | 61.22 | 12.24 | 1.68 | 0.75 | 64.00 | 8.00 | 1.85 | 0.88 |
| 217736_s_at | Eukaryotic translation initiation factor 2-alpha kinase 1 | 75.51 | — | 1.97 | 0.98 | 14.29 | 51.02 | −1.46 | −0.54 | 8.00 | 60.00 | −1.41 | −0.50 |
| 219069_at | Ankyrin repeat domain 49 | — | 73.47 | −1.59 | −0.67 | 57.14 | 12.24 | 1.30 | 0.38 | 84.00 | — | 1.58 | 0.66 |
| 219093_at | Hypothetical protein FLJ20701 | — | 85.71 | −3.32 | −1.73 | 71.43 | 8.16 | 2.43 | 1.28 | 84.00 | — | 2.59 | 1.37 |
| 219228_at | Zinc finger protein 331 | 77.55 | 8.16 | 3.94 | 1.98 | 10.20 | 71.43 | −3.26 | −1.70 | 12.00 | 80.00 | −4.62 | −2.21 |
| 219607_s_at | Membrane-spanning 4-domains, subfamily A, member 4 | 91.84 | — | 2.96 | 1.57 | 6.12 | 73.47 | −1.95 | −0.96 | — | 80.00 | −2.06 | −1.04 |
| 221748_s_at | Tensin 1 | 81.63 | 4.08 | 4.29 | 2.10 | 24.49 | 65.31 | −2.12 | −1.08 | 16.00 | 80.00 | −2.42 | −1.28 |
| 221766_s_at | Family with sequence similarity 46, member A | — | 71.43 | −1.71 | −0.77 | 53.06 | 10.20 | 1.30 | 0.38 | 80.00 | — | 1.66 | 0.73 |

The table presents the percentage of pairwise comparisons between the respective groups showing an increase or decrease for the fold-change/Signal Log Ratio (SLR; 51 candidate genes were selected); n = 7 each for the comparisons RA vs. ND and RA-αTNF vs. RA (all); n = 5 for the comparison RA-αTNF vs. RA (responder).
The pairwise comparison RA-aTNF vs. RA (all) is shown in the central 4 columns to assess the effect of treatment on differential gene expression in all TNFα-treated RA patients.
RA = rheumatoid arthritis (pre-anti-TNFα treatment);
ND = normal donor;
RA-αTNF = rheumatoid arthritis (post-anti-TNFα treatment)

TABLE 4

Genes differentially regulated in peripheral blood monocytes of both RA patients versus normal donors and RA patients pre- versus post-anti-TNFα therapy (PAM analysis)

| Affymetrix ID | Gene title | RA score |
|---|---|---|
| 221622_s_at | Uncharacterized hypothalamus protein HT007 | 0.7405 |
| 218845_at | Dual specificity phosphatase 22 | 0.6694 |
| 200786_at | Proteasome (prosome, macropain) subunit, beta type, 7 | 0.5297 |
| 219607_s_at | Membrane-spanning 4-domains, subfamily A, member 4 | 0.4449 |
| 212886_at | DKFZP434C171 protein | 0.2690 |
| 201407_s_at | Protein phosphatase 1, catalytic subunit, beta isoform | 0.2653 |
| 212266_s_at | Splicing factor, arginine/serine-rich 5 | 0.1771 |
| 53912_at | Sorting nexin 11 | 0.1277 |
| 200090_at | Farnesyltransferase, CAAX box, alpha | 0.1167 |
| 218025_s_at | Peroxisomal D3,D2-enoyl-CoA isomerase | 0.1032 |
| 204232_at | Fc fragment of IgE, high affinity I, receptor for; gamma polypeptide | 0.0993 |
| 201722_s_at | UDP-N-acetyl-alpha-D-galactosamine:polypeptide N-acetylgalactosaminyltransferase 1 | 0.0942 |
| 218627_at | Hypothetical protein FLJ11259 | 0.0841 |
| 210027_s_at | APEX nuclease (multifunctional DNA repair enzyme) 1 | 0.0817 |
| 202322_s_at | Geranylgeranyl diphosphate synthase 1 | 0.0646 |
| 221689_s_at | Down syndrome critical region gene 5 | 0.0549 |
| 203356_at | Calpain 7 | 0.0535 |
| 211991_s_at | Major histocompatibility complex, class II, DP alpha 1 | 0.0515 |
| 218462_at | Brix domain containing 5 | 0.0378 |
| 218123_at | Chromosome 21 open reading frame 59 | 0.0173 |
| 214329_x_at | Tumor necrosis factor (ligand) superfamily, member 10 | −0.0025 |
| 219067_s_at | Chromosome 10 open reading frame 86 | −0.0046 |
| 205789_at | CD1D antigen, d polypeptide | −0.0104 |
| 209214_s_at | Ewing sarcoma breakpoint region 1 | −0.0111 |
| 213427_at | Ribonuclease P 40 kDa subunit | −0.0471 |
| 209422_at/206567_s_at | PHD finger protein 20 | −0.0480/−0.0698 |
| 201010_s_at | Thioredoxin interacting protein | −0.0520 |
| 200883_at | Ubiquinol-cytochrome c reductase core protein II | −0.0521 |
| 218454_at | Hypothetical protein FLJ22662 | −0.0544 |
| 202918_s_at | Preimplantation protein 3 | −0.0574 |
| 212204_at | DKFZP564G2022 protein | −0.0698 |
| 219452_at | Dipeptidase 2 | −0.0800 |
| 209458_x_at | Hemoglobin, alpha 1, alpha 2 | −0.0809 |
| 219889_at | Frequently rearranged in advanced T-cell lymphomas | −0.0832 |
| 201303_at | DEAD (Asp-Glu-Ala-Asp) box polypeptide 48 | −0.0836 |
| 202510_s_at | Tumor necrosis factor, alpha-induced protein 2 | −0.0872 |
| 221705_s_at | Nucleophosmin (nucleolar phosphoprotein B23, numatrin) | −0.0902 |
| 201887_at | Interleukin 13 receptor, alpha 1 | −0.1075 |
| 211582_x_at | Leukocyte specific transcript 1, LST1 | −0.1193 |
| 219030_at | CGI-121 protein | −0.1259 |
| 212706_at | RAS p21 protein activator 4/hypothetical protein FLJ21767 | −0.1393 |
| 202902_s_at | Cathepsin S | −0.1644 |
| 200663_at | CD63 antigen (melanoma 1 antigen) | −0.1764 |
| 202138_x_at/209971_x_at | JTV1 gene | −0.1950/−0.2868 |
| 200851_s_at | KIAA0174 | −0.2019 |
| 201109_at | Thrombospondin 1 | −0.2079 |
| 213142_x_at | Hypothetical protein LOC54103 | −0.2285 |
| 202531_at | Interferon regulatory factor 1 | −0.2904 |
| 216274_s_at | SEC11-like 1 (*S. cerevisiae*) | −0.6951 |

Positive RA scores indicate genes overexpressed in RA, negative RA scores indicate those underexpressed in RA.
PAM = Prediction analysis of microarrays;
bold and underlined letters indicate genes overlapping with the 51 genes identified by Affymetrix ® gene expression profiling and analysis (see Table 3).

TABLE 5

Genes differentially regulated in RA-anti-TNFα responders versus RA-anti-TNFα non-responders (post anti-TNFα therapy)

| Affymetrix ID | Increased (%) | Decreased (%) | Gene title | Fold change | SLR |
|---|---|---|---|---|---|
| 200041_s_at | 100 | 0 | HLA-B associated transcript-1 (D6S81E) | 2.53 | 1.34 |
| 200052_s_at | 100 | 0 | Interleukin enhancer binding factor 2, 45 kD (ILF2) | 3.73 | 1.90 |
| 200064_at | 100 | 0 | Isolate Liv chaperone protein HSP90 beta (HSP90BETA) mRNA | 2.66 | 1.41 |
| 200079_s_at | 100 | 0 | Lysyl-tRNA synthetase mRNA, complete cds; nuclear gene for mitochondrial product; alternatively spliced | 2.16 | 1.11 |
| 200629_at | 100 | 0 | Tryptophanyl-tRNA synthetase (WARS) | 2.14 | 1.10 |
| 200634_at | 100 | 0 | Profilin 1 (PFN1), mRNA | 2.16 | 1.11 |
| 200802_at | 100 | 0 | Seryl-tRNA synthetase (SARS) | 2.20 | 1.14 |
| 200860_s_at | 100 | 0 | Similar to KIAA1007 protein, clone MGC: 692, mRNA, complete cds | 2.11 | 1.08 |
| 200983_x_at | 0 | 100 | CD59 antigen p18-20 (antigen identified by monoclonal antibodies 16.3A5, EJ16, EJ30, EL32 and G344) | −2.43 | −1.28 |
| 200991_s_at | 100 | 0 | *Homo sapiens* KIAA0064 gene product (KIAA0064), mRNA | 2.71 | 1.44 |

TABLE 5-continued

Genes differentially regulated in RA-anti-TNFα responders versus RA-anti-TNFα non-responders (post anti-TNFα therapy)

| Affymetrix ID | Increased (%) | Decreased (%) | Gene title | Fold change | SLR |
|---|---|---|---|---|---|
| 201112_s_at | 100 | 0 | Chromosome segregation 1 (yeast homolog)-like (CSE1L), mRNA | 2.01 | 1.01 |
| 201214_s_at | 100 | 0 | Protein phosphatase 1, regulatory subunit 7 (PPP1R7), mRNA | 2.17 | 1.12 |
| 201241_at | 100 | 0 | DEADH (Asp-Glu-Ala-AspHis) box polypeptide 1 (DDX1), mRNA | 2.30 | 1.20 |
| 201263_at | 100 | 0 | Threonyl-tRNA synthetase (TARS), mRNA | 2.14 | 1.10 |
| 201386_s_at | 100 | 0 | Dead box protein 15 mRNA, complete cds | 2.22 | 1.15 |
| 201417_at | 100 | 0 | SRY (sex determining region Y)-box 4 /DEF = Human DNA sequence from clone RP3-322L4 on chromosome 6 | 3.18 | 1.67 |
| 201576_s_at | 100 | 0 | Galactosidase, beta 1 (GLB1), mRNA | 2.00 | 1.00 |
| 201872_s_at | 100 | 0 | ATP-binding cassette, sub-family E (OABP), member 1 | 2.28 | 1.19 |
| 201892_s_at | 100 | 0 | NADH dehydrogenase (ubiquinone) 1 alpha subcomplex, 6 (14 kD, B14) (NDUFA6), mRNA | 2.19 | 1.13 |
| 202174_s_at | 100 | 0 | Pericentriolar material 1 (PCM1), mRNA | 2.08 | 1.06 |
| 202176_at | 100 | 0 | Excision repair cross-complementing rodent repair deficiency, complementation group 3 (ERCC3), mRNA | 2.93 | 1.55 |
| 202220_at | 100 | 0 | KIAA0907 protein (KIAA0907), mRNA | 2.39 | 1.26 |
| 202225_at | 100 | 0 | v-crk avian sarcoma virus CT10 oncogene homolog | 2.10 | 1.07 |
| 202464_s_at | 0 | 100 | 6-phosphofructo-2-kinasefructose-2,6-biphosphatase 3 (PFKFB3), mRNA. /PROD = 6-phosphofructo-2-kinase-fructose-2,6-biphosphatase 3 | −3.25 | −1.70 |
| 202545_at | 100 | 0 | KIAA0766 gene product (KIAA0766), mRNA | 1.38 | 0.46 |
| 202838_at | 100 | 0 | N-acetylgalactosaminidase, alpha-(NAGA), mRNA | 1.82 | 0.86 |
| 202896_s_at | 0 | 100 | Protein tyrosine phosphatase, non-receptor type substrate 1 (PTPNS1), mRNA | −2.00 | −1.00 |
| 202950_at | 100 | 0 | Crystallin, zeta (quinone reductase) (CRYZ), mRNA | 2.51 | 1.33 |
| 203037_s_at | 100 | 0 | KIAA0429 gene product (KIAA0429), mRNA | 2.41 | 1.27 |
| 203155_at | 100 | 0 | SET domain, bifurcated 1 (SETDB1), mRNA | 4.23 | 2.08 |
| 203371_s_at | 0 | 100 | NADH dehydrogenase (ubiquinone) 1 beta subcomplex, 3 (12 kD, B12) (NDUFB3), mRNA | −2.13 | −1.09 |
| 203821_at | 0 | 100 | Diphtheria toxin receptor (DTR) | −3.63 | −1.86 |
| 203887_s_at | 0 | 100 | Thrombomodulin (THBD), mRNA | −2.75 | −1.46 |
| 203966_s_at | 0 | 100 | Protein phosphatase 1A (formerly 2C), magnesium-dependent, alpha isoform (PPM1A), mRNA | −2.73 | −1.45 |
| 204192_at | 100 | 0 | CD37 antigen (CD37), mRNA | 3.66 | 1.87 |
| 204419_x_at | 0 | 100 | Hemoglobin, gamma G (HBG2), mRNA | −5.50 | −2.46 |
| 204566_at | 100 | 0 | Protein phosphatase 1D magnesium-dependent, delta isoform (PPM1D), mRNA | 2.00 | 1.00 |
| 204689_at | 100 | 0 | Hematopoietically expressed homeobox (HHEX), mRNA | 2.04 | 1.03 |
| 205239_at | 0 | 100 | Amphiregulin (schwannoma-derived growth factor) (AREG), mRNA | −3.38 | −1.04 |
| 205249_at | 0 | 100 | Early growth response 2 (Krox-20 (Drosophila) homolog) (EGR2), mRNA | −2.55 | −1.35 |
| 205552_s_at | 100 | 0 | 2,5-oligoadenylate synthetase 1 (40-46 kD) (OAS1), transcript variant E16, mRNA | 2.08 | 1.06 |
| 206115_at | 0 | 100 | Early growth response 3 (EGR3), mRNA. /PROD = early growth response 3 | −6.54 | −2.71 |
| 206584_at | 0 | 100 | Homo sapiens MD-2 protein (MD-2), mRNA | −2.16 | −1.11 |
| 206877_at | 0 | 100 | Homo sapiens MAX dimerization protein (MAD), mRNA | −3.92 | −1.97 |
| 207170_s_at | 100 | 0 | DKFZP586A011 protein (DKFZP586A011), mRNA | 2.20 | 1.14 |
| 208631_s_at | 100 | 0 | 78 kDa gastrin-binding protein mRNA, complete cds | 2.04 | 1.03 |
| 208691_at | 0 | 100 | Transferrin receptor (p90, CD71), clone MGC: 3151, mRNA, complete cds | −2.30 | −1.20 |
| 208868_s_at | 0 | 100 | Homo sapiens mRNA; cDNA DKFZp564N1272 (from clone DKFZp564N1272); complete cds | −3.18 | −1.67 |
| 208869_s_at | 0 | 100 | GABA-A receptor-associated protein like 1 (GABARAPL1) mRNA, complete cds | −3.29 | −1.72 |
| 208942_s_at | 0 | 100 | Translocation protein 1 | −2.93 | −1.55 |
| 209092_s_at | 100 | 0 | Homo sapiens clone 016b03 My027 protein mRNA, complete cds | 2.07 | 1.05 |
| 209193_at | 0 | 100 | Protein kinase-related oncogene (PIM1) mRNA, complete cds | −2.51 | −1.33 |
| 209200_at | 100 | 0 | MADS box transcription enhancer factor 2, polypeptide C (myocyte enhancer factor 2C) | 2.48 | 1.31 |
| 209861_s_at | 100 | 0 | eIF-2-associated p67 homolog mRNA, complete cds | 2.55 | 1.35 |
| 209967_s_at | 0 | 100 | Human mRNA for hCREM (cyclic AMP-responsive element modulator) type 2 protein, complete cds | −3.07 | −1.62 |
| 210027_s_at | 100 | 0 | Apurinic endonuclease (APE) mRNA, complete cds. /PROD = apurinic endonuclease | 2.23 | 1.16 |
| 210053_at | 100 | 0 | TATA box binding protein (TBP)-associated factor, RNA polymerase II, D, 100 kD | 2.23 | 1.16 |
| 210172_at | 0 | 100 | Human mRNA for ZFM1 protein alternatively spliced product, complete cds. /PROD = ZFM1 protein, alternatively spliced product | −2.16 | −1.11 |
| 210766_s_at | 100 | 0 | Trachea cellular apoptosis susceptibility protein (CSE1) mRNA, complete cds | 2.28 | 1.19 |
| 210949_s_at | 100 | 0 | Similar to eukaryotic translation initiation factor 3, subunit 8 (110 kD), clone MGC: 8693, mRNA, complete cds | 2.53 | 1.34 |
| 211458_s_at | 0 | 100 | GABA-A receptor-associated protein mRNA, complete cds. /PROD = GABA-A receptor-associated protein | −3.18 | −1.67 |
| 211546_x_at | 0 | 100 | Human (clone 2-5) synuclein (NACP) mRNA, complete cds | −4.92 | −2.30 |
| 212199_at | 100 | 0 | Human putative ribosomal protein S1 mRNA | 2.22 | 1.15 |
| 212224_at | 100 | 0 | Aldehyde dehydrogenase 1, soluble (ALDH1), mRNA. /PROD = aldehyde dehydrogenase 1, soluble | 3.18 | 1.67 |
| 212388_at | 100 | 0 | Homo sapiens mRNA for KIAA1057 protein, partial cds | 3.10 | 1.63 |
| 212591_at | 100 | 0 | RBP1-like protein | 2.03 | 1.02 |
| 212696_s_at | 100 | 0 | Ring finger protein 4 | 3.05 | 1.61 |
| 212709_at | 100 | 0 | KIAA0197 protein | 2.10 | 1.07 |
| 212714_at | 100 | 0 | Homo sapiens mRNA; cDNA DKFZp586F1323 (from clone DKFZp586F1323) | 2.13 | 1.09 |
| 212893_at | 100 | 0 | Homo sapiens mRNA; cDNA DKFZp564I052 (from clone DKFZp564I052) | 2.01 | 1.01 |
| 212989_at | 100 | 0 | Homo sapiens mRNA for Hmob33 protein, 3 untranslated region | 2.25 | 1.17 |
| 213410_at | 100 | 0 | Homo sapiens mRNA; cDNA DKFZp586F1019 (from clone DKFZp586F1019); partial cds | 2.53 | 1.34 |
| 213515_x_at | 0 | 100 | Myosin, light polypeptide 4, alkali; atrial; embryonic | −4.69 | −2.23 |
| 213528_at | 100 | 0 | H. sapiens novel gene from PAC 117P20, chromosome 1 | 2.87 | 1.52 |

TABLE 5-continued

Genes differentially regulated in RA-anti-TNFα responders versus RA-anti-TNFα non-responders (post anti-TNFα therapy)

| Affymetrix ID | Increased (%) | Decreased (%) | Gene title | Fold change | SLR |
|---|---|---|---|---|---|
| 213604_at | 100 | 0 | *Homo sapiens* clone 24582 mRNA sequence | 2.07 | 1.05 |
| 213619_at | 0 | 100 | Heterogeneous nuclear ribonucleoprotein H1 (H) | −2.48 | −1.31 |
| 213655_at | 0 | 100 | Tyrosine 3-monooxygenase/tryptophan 5-monooxygenase activation protein, epsilon polypeptide | −3.03 | −1.60 |
| 213743_at | 100 | 0 | Cyclin T2 | 2.08 | 1.06 |
| 213788_s_at | 0 | 100 | cDNA: FLJ23227 fis, clone CAE00645, highly similar to AF052138 | −2.20 | −1.14 |
| 213872_at | 0 | 100 | Hypothetical protein FLJ12619 | −4.29 | −2.1 |
| 213979_s_at | 0 | 100 | C-terminal binding protein 1 | −4.41 | −2.14 |
| 214257_s_at | 0 | 100 | SEC22, vesicle trafficking protein (*S. cerevisiae*)-like 1 | −2.97 | −1.57 |
| 214414_x_at | 0 | 100 | Hemoglobin, alpha 1 | −2.04 | −1.03 |
| 214696_at | 0 | 100 | *Homo sapiens* clone 24659 mRNA sequence /DEF = *Homo sapiens* clone 24659 mRNA sequence | −2.93 | −1.55 |
| 214933_at | 0 | 100 | Calcium channel, voltage-dependent, PQ type, alpha 1A subunit | −2.17 | −1.12 |
| 215043_s_at | 0 | 100 | *H. sapiens* SMA5 mRNA | −4.08 | −2.03 |
| 215933_s_at | 100 | 0 | *H. sapiens* HEX gene encoding homeobox related protein | 2.17 | 1.12 |
| 216199_s_at | 100 | 0 | Mitogen-activated protein kinase kinase kinase 4 | 2.77 | 1.47 |
| 216202_s_at | 100 | 0 | Serine palmitoyltransferase (LCB2) mRNA, partial cds | 2.75 | 1.46 |
| 216996_s_at | 100 | 0 | KIAA0971 protein /DEF = *Homo sapiens* cDNA FLJ11495 fis, clone HEMBA1001950, highly similar to *Homo sapiens* mRNA for KIAA0971 protein | 2.20 | 1.14 |
| 217554_at | 0 | 100 | ESTs, Hs.97109 | −3.63 | −1.86 |
| 217682_at | 0 | 100 | ESTs, Weakly similar to ALU7_HUMAN ALU | −3.01 | −1.59 |
| 217840_at | 100 | 0 | DEAD-box protein abstrakt (ABS), mRNA | 2.39 | 1.26 |
| 218229_s_at | 100 | 0 | KIAA1513 protein (KIAA1513), mRNA | 2.07 | 1.05 |
| 218356_at | 100 | 0 | Cell division protein FtsJ (FJH1), mRNA | 2.20 | 1.14 |
| 218432_at | 100 | 0 | F-box only protein 3 (FBXO3), mRNA | 2.16 | 1.11 |
| 218589_at | 100 | 0 | Purinergic receptor (family A group 5) (P2Y5), mRNA | 2.68 | 1.42 |
| 218604_at | 100 | 0 | Integral inner nuclear membrane protein (MAN1), mRNA | 2.04 | 1.03 |
| 218689_at | 100 | 0 | Fanconi anemia, complementation group F (FANCF), mRNA | 8.94 | 3.16 |
| 218889_at | 100 | 0 | Hypothetical protein FLJ12820 (FLJ12820), mRNA | 2.01 | 1.01 |
| 218973_at | 100 | 0 | Hypothetical protein FLJ13119 (FLJ13119), mRNA | 2.07 | 1.05 |
| 219069_at | 100 | 0 | Hypothetical protein FLJ20189 (FLJ20189), mRNA | 2.23 | 1.16 |
| 219093_at | 100 | 0 | Hypothetical protein FLJ20701 (FLJ20701), mRNA | 3.32 | 1.73 |
| 219099_at | 100 | 0 | *Homo sapiens* chromosome 12 open reading frame 5 (C12ORF5), mRNA | 2.13 | 1.09 |
| 219176_at | 100 | 0 | Hypothetical protein FLJ22555 (FLJ22555), mRNA | 2.13 | 1.09 |
| 219243_at | 100 | 0 | Hypothetical protein FLJ11110 (FLJ11110), mRNA | 2.07 | 1.05 |
| 219363_s_at | 100 | 0 | CGI-12 protein (LOC51001), mRNA | 2.31 | 1.21 |
| 219434_at | 0 | 100 | Triggering receptor expressed on myeloid cells 1 (TREM1), mRNA | −4.35 | −2.12 |
| 221485_at | 0 | 100 | betaGlcNAc beta 1,4-galactosyltransferase. polypeptide 5 | −2.71 | −1.44 |
| 221652_s_at | 100 | 0 | PNAS-25 mRNA, complete cds. | 2.55 | 1.35 |
| 221755_at | 100 | 0 | *Homo sapiens* mRNA for FLJ00043 protein, partial cds | 3.44 | 1.09 |
| 221970_s_at | 100 | 0 | *Homo sapiens* cDNA: FLJ21737 fis, clone COLF3396 | 2.41 | 1.27 |
| 222127_s_at | 0.1 | 0 | *Homo sapiens* cDNA FLJ13399 fis, clone PLACE1001395 /DEF = *Homo sapiens* cDNA FLJ13399 fis, clone PLACE1001395 | 2.31 | 1.21 |
| 36711_at | 0 | 100 | Novel MAFF (v-maf musculoaponeurotic fibrosarcoma (avian) oncogene family, protein F) LIKE protein | −3.54 | −1.16 |
| 38037_at | 0 | 100 | Heparin-binding EGF-like growth factor mRNA, complete cds | −3.63 | −1.86 |
| AFFX-BioB-M_at | 0 | 100 | *E. coli* 7,8-diamino-pelargonic acid (bioA), biotin synthetase (bioB), 7-keto-8-amino-pelargonic acid synthetase (bioF), bioC protein, and dethiobiotin synthetase (bioD), complete cds | −4.69 | −2.58 |
| AFFX-r2-Ec-bioC-3_at | 0 | 100 | *Escherichia coli* /REF = J04423 /DEF = *E coli* bioC protein corresponding to nucleotides 4609-4883 of J04423 /LEN = 777 (−5 and −3 represent transcript regions 5 prime and 3 prime respectively) | −4.22 | −1.86 |

The listed genes (n = 117) show differential expression in 100% of the pairwise comparisons; bold and underlined letters indicate genes overlapping with the 51 genes identified by Affymetrix ® gene expression profiling and analysis (see Table 3)

TABLE 6

Correlations between clinical parameters and differentially expressed genes (Pearson correlation test; pre- and post-anti-TNFα treatment; n = 7 for all; bold letters identify genes occurring twice, bold and italics letters identify genes occurring ≥ 3 times)

|  | Affymetrix_ID | Gene title | r-value | p-value |
|---|---|---|---|---|
| \multicolumn{5}{l}{Pre-anti-TNFα treatment} | | | | |
| Leuko/ | 202219—at | Solute carrier family 6 | 0.901 | 0.006 ** |
|  | 205239_at | Amphiregulin | 0.879 | 0.009 ** |
| Thromb/ | 205900—at | Keratin 1 | 0.923 | 0.003 ** |
| Mono/ | 204018_x_at | Hemoglobin, alpha 1 | −0.908 | 0.005 ** |
| GPT/ | 203932—at | MHC-II, DM beta | −0.912 | 0.004 ** |
|  | 218589_s_at | Purinergic receptor P2Y, G-protein coupled 5 | −0.919 | 0.003 ** |
| Hb/ | 205900—at | Keratin 1 | −0.944 | 0.001 ** |
| MoStiff/ | 202219—at | Solute carrier family 6 | 0.893 | 0.007 ** |
|  | 203932—at | MHC-II, DM beta | −0.898 | 0.006 ** |
|  | 204131_s_at | Forkhead box O3A | 0.917 | 0.004 ** |
|  | 205239—at | Amphiregulin | 0.954 | 0.001 ** |
|  | 207332_s_at | Transferrin receptor (p90, CD71) | 0.926 | 0.003 ** |
|  | 208632_at | Ring finger protein 10 | 0.913 | 0.004 ** |
| DisDur/ | 212232_at | Formin binding protein 4 | 0.955 | 0.001 ** |
|  | 213142_x_at | Hypothetical protein LOC54103 | 0.877 | 0.009 ** |
| \multicolumn{5}{l}{Post-anti-TNFα treatment} | | | | |
| ESR/ | *38037_at* | *Diphteria toxin receptor* | *0.928* | *0.003*** |
|  | *203821_at* | *Heparin-binding EGF-like growth factor* | *0.928* | *0.003*** |
|  | *205571_at* | *Lipoyltransferase 1* | *−0.898* | *0.006*** |
|  | *210027_s_at* | *APEX nuclease (multifunct. DNA repair enzyme) 1* | *−0.944* | *0.001*** |
|  | *211458_s_at* | *GABA(A) receptor-associated protein like 1/3* | *0.947* | *0.001*** |
|  | *212232_at* | *Formin binding protein 4* | *−0.890* | *0.007*** |
|  | 219228_at | Zinc finger protein 331 | 0.894 | 0.007 ** |
| CRP/ | *38037_at* | *Diphteria toxin receptor* | *0.968* | *0.000*** |
|  | *203821_at* | *Heparin-binding EGF-like growth factor* | *0.963* | *0.001*** |
|  | *205571_at* | *Lipoyltransferase 1* | *−0.946* | *0.001*** |
|  | *210027_s_at* | *APEX nuclease (multifunct. DNA repair enzyme) 1* | *−0.950* | *0.001*** |
|  | *211458_s_at* | *GABA(A) receptor-associated protein like 1/3* | *0.948* | *0.001*** |
|  | *212232_at* | *Formin binding protein 4* | *−0.908* | *0.005*** |
| Thromb/ | *205571_at* | *Lipoyltransferase 1* | *−0.934* | *0.002*** |
|  | *212232_at* | *Formin binding protein 4* | *−0.921* | *0.003*** |
| Granulo/ | 213427_at | Ribonuclease P 40 kDa subunit | −0.875 | 0.010 ** |
| Hb/ | *38037_at* | *Diphteria toxin receptor* | *−0.930* | *0.002*** |
|  | *203821_at* | *Heparin-binding EGF-like growth* factor | *−0.948* | *0.001*** |
|  | 203932_at | MHC class II, DM beta | 0.885 | 0.008 ** |
|  | *210027_s_at* | *APEX nuclease (multifunct. DNA repair enzyme) 1* | *0.971* | *0.000*** |
|  | *211458_s_at* | *GABA(A) receptor-associated protein like 1/3* | *−0.951* | *0.001*** |
| Dis_act | 36711_at | v-maf fibrosarc. oncogene homolog F (avian) | 0.932 | 0.002 ** |
|  | 205552_s_at | 2′,5′-oligoadenylate synthetase 1, 40/46 kDa | −0.951 | 0.001 ** |
|  | *211458_s_at* | *GABA(A) receptor-associated protein like 1/3* | *0.896* | *0.006*** |
|  | *212232_at* | *Formin binding protein 4* | *−0.898* | *0.006*** |
| DAS28/ | 36711 | v-maf fibrosarc. oncogene homolog F (avian) | 0.940 | 0.002 ** |
|  | 205552_s_at | 2′,5′-oligoadenylate synthetase 1, 40/46 kDa | −0.898 | 0.006 ** |
|  | *205571_at* | *Lipoyltransferase 1* | *−0.937* | *0.002*** |
|  | *211458_s_at* | *GABA(A) receptor-associated protein like 1/3* | *0.897* | *0.006*** |
|  | *212232_at* | *Formin binding protein 4* | *−0.973* | *0.000*** |
| Sw28/ | 219607_s_at | Membrane-spanning 4-domains, subfam. A, memb. 4 | 0.931 | 0.002 ** |

GPT = glutamate pyruvic transferase;
Hb = haemoglobin;
MoStiff = Morning stiffness (minutes);
DisDur = Disease duration (years);
ESR = erythrocyte sedimentation rate;
CRP = C-reactive protein;
DAS 28 = disease activity score (28 joints);
Sw = number of swollen joints (28 joints)

TABLE 7

TaqMan PCR validation in anti-TNFα-treated RA patients and normal donors

| Time point | Gene Description | Gene title | Applera ID | PCR RA-αTNF (responder) versus ND (RQ: Means ± SEM) | Max-ΔRQ (Therapy) | p value (U-Test) | Affymetrix ID | Affymetrix RA-αTNF (responder) versus ND (% of comp.) | FC RA-αTNF (responder) versus ND (Means) | RA-αTNF all versus ND (% of comp.) | FC RA-αTNF all versus ND (Means) |
|---|---|---|---|---|---|---|---|---|---|---|---|
| | | | | Validated genes | | | | | | | |
| BL | AREG | Amphiregulin | Hs00155832_m1 | 10.23 ± 2.93 | −7.60 | 0.000 | 205239_at | 82.86 | 5.48 | 81.63 | 6.13 |
| BL | CA-1 | Carbonic anhydrase 1 | Hs00266139_m1 | 6.83 ± 3.49 | −5.93 | n.s. | 205950_s_at | 88.57 | 4.92 | 81.63 | 5.88 |
| BL | CLC | Charcot-Leyden crystal protein | Hs00171342_m1 | 5.36 ± 4.82 | −3.26 | 0.041 | 206207_at | 62.86 | 2.46 | 73.47 | 3.97 |
| BL | CLU | Clusterin C | Hs00156548_m1 | 3.94 ± 2.87 | −2.77 | n.s. | 222043_at | 68.57 | 2.57 | 75.51 | 2.68 |
| BL | TNFAIP6 | Tumor necrosis factor alpha induced protein 6 | Hs00218482_m1 | 1.71 ± 0.40 | 0.82 | 0.000 | 206026_s_at | 62.86 | 2.07 | 73.27 | 2.24 |
| BL | THBD | Thrombomodulin | Hs00264920_s1 | 1.58 ± 1.08 | −0.53 | 0.041 | 203887_s_at | 74.29 | 2.64 | 71.43 | 2.49 |
| BL | MS4A4A | Membrane-spanning 4-domains, subfamily A, member 4 | Hs00254770_m1 | 1.54 ± 0.42 | 0.71 | 0.041 | 219607_s_at | 88.57 | 2.66 | 91.84 | 2.96 |
| BL | DTR | Diphtheria toxin receptor | Hs00181813_m1 | 1.21 ± 0.44 | −1.10 | n.s. | 38037_at | 68.57 | 2.91 | 71.43 | 2.87 |
| BL | S100A12 | S100 calcium binding protein A1 | Hs00194525_m1 | 1.07 ± 0.21 | 0.11 | 0.041 | 205863_at | 62.86 | 1.50 | 71.43 | 1.69 |
| BL | HT007 | Uncharacterized hypothalamus protein HT007 | Hs00218482_m1 | 0.51 ± −0.09 | 0.01 | 0.000 | 221622_s_at | −88.57 | −1.74 | −85.71 | −1.66 |
| BL | HLA-DR | MHC-class-II; HLA-DR alpha | Hs00219578_m1 | 0.59 ± −0.15 | 0.09 | 0.000 | 208894_at | −65.71 | −1.77 | −75.51 | −2.15 |
| BL | LOC54103 | Hypothetical protein LOC54103 | Hs00367929_m1 | 0.90 ± −0.21 | −0.24 | 0.041 | 222150_s_at | −80.00 | −1.84 | −73.47 | −1.71 |
| *BL* | *TNF* | *Tumor necrosis factor alpha* | *Hs00174128_m1* | *1.22 ± 0.53* | *−0.84* | *0.041* | *207113_s_at* | *34.29* | *1.03* | *−46.94* | *−1.28* |
| *BL* | *IL1B* | *Interleukin 1 beta* | *Hs00174097_m1* | *1.14 ± 0.42* | *−0.28* | *0.041* | *205067_at* | *57.14* | *1.62* | *51.02* | *1.44* |
| *BL* | *PSMB7* | *Proteasome subunit beta type 7 precursor* | *Hs00160607_m1* | *0.72 ± −0.19* | *0.16* | *0.041* | *200786_at* | *−54.29* | *−1.27* | *−57.14* | *−1.27* |
| BL | KIAA0174 | Protein KIAA0174 | Hs00796085_sh | 0.89 ± 0.30 | 0.08 | 0.041 | 200851_s_at | −42.86 | −1.17 | −46.94 | −1.23 |
| *BL* | *SPC18* | *Microsomal signal peptidase 18 kDa subunit* | *Hs00819308_m1* | *0.96 ± 0.11* | *−0.25* | *0.041* | *201290_at* | *−17.14* | *−1.04* | *−12.24* | *−1.03* |
| | | | | Discrepancies between Affymetrix and TaqMan PCR | | | | | | | |
| BL | LIPT1 | Lipoyltransferase 1 | Hs00376962_m1 | 2.17 ± 0.54 | −0.68 | 0.000 | 205571_at | −74.29 | −1.74 | −79.59 | −1.90 |
| BL | ZNF361 | Ring zinc finger protein 361 | Hs00367929_m1 | 0.55 ± −0.11 | −0.14 | 0.000 | 219228_at | 77.14 | 4.19 | 77.55 | 3.94 |
| BL | THBS1 | Thrombospondin-1 | Hs00170236_m1 | 0.88 ± 0.25 | −0.34 | n.s. | 201110_s_at | 85.71 | 16.35 | 77.55 | 12.60 |
| *BL* | *IRF1* | *Interferon regulatory protein 1* | *Hs00233698_m1* | *4.95 ± 0.18* | *3.37* | *0.000* | *202531_at* | *−40.00* | *−1.30* | *−55.10* | *−1.44* |
| *BL* | *PPP1CB* | *Protein phosphatase 1, catalytic subunit, beta isoform* | *Hs00160349_m1* | *0.93 ± 0.09* | *−0.28* | *0.041* | *201409_s_at* | *60.00* | *1.63* | *57.14* | *1.69* |

Validation of 22 selected genes from Affymetrix ® gene expression profiling by Taqman real-time RT-PCR (10 anti-TNFα-treated RA patients prior to therapy; 14 normal donors - ND); genes differentially expressed (decreased: <−70%; increased: >70%) in RA versus ND according to the Affymetrix ® analysis are shown in normal type; equally-expressed genes are displayed in italics;
RQ = relative quantity;
FC = fold-change;
BL = baseline (pre-antiTNFα therapy)

TABLE 8

Correlations between TaqMan PCR results and the ACR response in anti-TNFα-treated RA patients

| Gene description | Time point | Gene title | Applera ID | r-value | p | n |
|---|---|---|---|---|---|---|
| CA1 | w 12 | Carbonic anhydrase 1 | Hs00266139_m1 | 0.642 | 0.045 | 10 |
| CA1 | w 26 | | | 0.962 | 0.000 | 9 |
| CLC | w 4 | Charcot-Leyden crystal protein | Hs00171342_m1 | 0.766 | 0.027 | 8 |
| THBD | w 4 | Thrombomodulin | Hs00264920_s1 | 0.766 | 0.027 | 8 |
| THBS1 | w 26 | Thrombospondin 1 | Hs00170236_m1 | −0.710 | 0.032 | 9 |
| IRF1 | w 4 | Interferon regulatory factor 1 | Hs00233698_m1 | 0.778 | 0.023 | 8 |

TABLE 9

Genes differentially regulated in RA-anti-TNFα responders versus RA-anti-TNFα non-responders (pre-anti-TNFα therapy; predictive genes)

| Affymetrix ID | Gene title | Increased (%) | Decreased (%) | Fold-Change | SLR |
|---|---|---|---|---|---|
| 39248_at | Aquaporin 3 | 10 | 80 | −4.6 | −2.19 |
| 200061_s_at | Similar to ribosomal protein S24, clone MGC: 8595 | 0 | 80 | −1.39 | −0.47 |
| 200087_s_at | Transmembrane emp24 domain trafficking protein 2 | 0 | 80 | −1.6 | −0.63 |
| 200642_at | Superoxide dismutase 1, soluble (amyotrophic lateral sclerosis 1 | 0 | 80 | −1.8 | −0.84 |
| 200655_s_at | Calmodulin 1 (phosphorylase kinase, delta) | 0 | 80 | −1.5 | −0.59 |
| 200745_s_at | Guanine nucleotide binding protein (G protein), beta polypeptide 1 | 80 | 0 | 1.6 | 0.66 |
| 200772_x_at | Prothymosin, alpha (gene sequence 28) | 80 | 0 | 1.7 | 0.75 |
| 201193_at | *Homo sapiens* isocitrate dehydrogenase 1 (NADP+) soluble (IDH1) | 0 | 80 | −1.4 | −0.49 |
| 201690_s_at | Tumor protein D52 | 0 | 80 | −3.3 | −1.73 |
| 201693_s_at | Early growth response 1 | 80 | 0 | 3.1 | 1.61 |
| 201889_at | ***Homo sapiens* predicted osteoblast protein (GS3786) | 0 | *100*** | −1.7 | −0.74 |
| 202110_at | Cytochrome c oxidase subunit VIIb | 0 | 80 | −1.6 | −0.64 |
| 202157_s_at | CUG triplet repeat, RNA binding protein 2 | 0 | 80 | −1.6 | −0.64 |
| 202233_s_at | Ubiquinol-cytochrome c reductase hinge protein | 0 | 80 | −1.7 | −0.74 |
| 202378_s_at | *Homos spaiens* leptin receptor gene-related protein (HS0BRGRP) | 80 | 20 | 1.15 | 0.20 |
| 202664_at | Wiskott-Aldrich syndrome protein interacting protein | 80 | 0 | 1.9 | 0.91 |
| 202910_s_at | CD97 antigen | 80 | 10 | 1.6 | 0.70 |
| 202922_at | Glutamate-cysteine ligase, catalytic subunit | 0 | 80 | −2.3 | −1.17 |
| 202950_at | Crystallin, zeta (quinone reductase) | 80 | 0 | 2.2 | 1.16 |
| 203097_s_at | Rap guanine nucleotide exchange factor (GEF) 2 | 20 | 80 | −1.3 | −0.38 |
| 203231_s_at | Ataxin 1 | 0 | 80 | −8.2 | −3.03 |
| 203300_x_at | Adaptor-related protein complex 1, sigma 2 subunit | 80 | 20 | 1.9 | 0.89 |
| 204160_s_at | Ectonucleotide pyrophosphatase/phosphodiesterase 4 | 10 | 80 | −2.4 | −1.27 |
| 204750_s_at | Desmocollin 2 | 80 | 0 | 12.9 | 3.69 |
| 204777_s_at | MAL, T-cell differentiation protein | 10 | 80 | −2.6 | −1.39 |
| 205042_at | Glucosamine (UDP-N-acetyl)-2-epimerase/N-acetylmannosamine kinase | 0 | 80 | −1.9 | −0.95 |
| 205114_s_at | Chemokine (C-C motif) ligand 3 | 80 | 0 | 2.0 | 0.96 |
| 205624_at | Carboxypeptidase A3 | 0 | 80 | −4.0 | −2.00 |
| 206207_at | Charcot-Leyden crystal protein | 0 | 90 | −4.9 | −2.29 |
| 206790_s_at | NADH dehydrogenase (ubiquinone) 1 beta subcomplex, 1, 7 kDa | 0 | 80 | −1.5 | −0.61 |
| 207008_at | Interleukin 8 receptor, beta | 90 | 0 | 4.0 | 2.00 |
| 207815_at | Platelet factor 4 variant 1 | 20 | 80 | −2.4 | −1.28 |
| 208051_s_at | Poly(A) binding protein interacting protein 1 | 0 | 80 | −1.6 | −0.68 |
| 208161_s_at | ATP-binding cassette, sub-family C (CFTR/MRP), member 3 | 80 | 0 | 4.3 | 2.10 |
| 208637_x_at | Actinin, alpha 1 | 80 | 0 | 2.4 | 1.24 |
| 208918_s_at | NAD kinase | 80 | 0 | 1.5 | 0.59 |
| 208982_at | Platelet/endothelial cell adhesion molecule (CD31 antigen) | 90 | 0 | 1.6 | 0.71 |
| 209009_at | Esterase D/formylglutathione hydrolase | 80 | 20 | 1.5 | 0.54 |
| 209020_at | Chromosome 20 open reading frame 111 | 80 | 20 | 1.5 | 0.54 |
| 209146_at | Sterol-C4-methyl oxidase-like | 0 | 80 | −1.9 | −0.89 |
| 209193_at | PIM-1 oncogene | 10 | 80 | −2.3 | −1.19 |
| 209710_at | GATA binding protein 2 | 20 | 80 | −3.5 | −1.81 |
| 210042_s_at | Cathepsin Z | 80 | 20 | 1.9 | 0.94 |
| 210184_at | *Integrin alpha-X (antigen CD11c)* | *100* | 0 | 2.3 | 1.22 |
| 210732_s_at | Lectin, galactoside-binding, soluble, 8 (galectin 8) | 80 | 0 | 2.4 | 1.23 |
| 210895_s_at | CD86 antigen (CD28 antigen ligand 2, B7-2 antigen) | 80 | 10 | 1.9 | 0.92 |
| 211506_s_at | Interleukin 8 | 90 | 0 | 3.2 | 1.67 |
| 211734_s_at | Fc fragment of IgE, high affinity I, receptor for; alpha polypeptide | 0 | 80 | −5.0 | −2.31 |
| 211995_x_at | Actin, gamma 1 | 80 | 0 | 1.4 | 0.46 |
| 212314_at | KIAA0746 protein | 10 | 80 | −1.7 | −0.73 |
| 212335_at | Glucosamine (N-acetyl)-6-sulfatase (Sanfilippo disease IIID) | 80 | 0 | 1.5 | 0.54 |
| 212386_at | Transcription factor 4 | 0 | 80 | −2.5 | −1.29 |
| 212671_s_at | Major histocompatibility complex, class II, DQ alpha 1 | 10 | 80 | −3.3 | −1.72 |
| 212897_at | Cell division cycle 2-like 6 (CDK8-like) | 80 | 0 | 1.8 | 0.83 |
| 212999_x_at | Major histocompatibility complex, class II, DQ beta 1 | 80 | 20 | 1.8 | 0.88 |
| 213309_at | Phospholipase C-like 2 | 0 | 80 | −1.9 | −0.9 |
| 213506_at | Coagulation factor II (thrombin) receptor-like 1 | 80 | 0 | 2.4 | 1.23 |
| 213883_s_at | TM2 domain containing 1 | 10 | 80 | −1.4 | −0.46 |

TABLE 9-continued

Genes differentially regulated in RA-anti-TNFα responders versus RA-anti-TNFα non-responders (pre-anti-TNFα therapy; predictive genes)

| Affymetrix ID | Gene title | Increased (%) | Decreased (%) | Fold-Change | SLR |
|---|---|---|---|---|---|
| 214305_s_at | Splicing factor 3b, subunit 1, 155 kDa | 80 | 20 | 1.5 | 0.62 |
| 214512_s_at | SUB1 homolog (*S. cerevisiae*) | 0 | 80 | −1.7 | −0.76 |
| 214807_at | MRNA; cDNA DKFZp564O0862 | 80 | 10 | 1.7 | 0.79 |
| 214953_s_at | Amyloid beta (A4) precursor protein (peptidase nexin-II, Alzheimer disease) | *90* | 0 | 1.9 | 0.93 |
| 215726_s_at | Cytochrome b-5 | 0 | 80 | −2.1 | −1.08 |
| 216016_at | Cold autoinflammatory syndrome 1 | 80 | 0 | 6.1 | 2.60 |
| 217722_s_at | Neugrin, neurite outgrowth associated | 0 | *90* | −1.9 | −0.91 |
| 217753_s_at | Ribosomal protein S26, 40S ribosomal protein | 10 | 80 | −2.9 | −1.51 |
| 217970_s_at | CCR4-NOT transcription complex, subunit 6 | 0 | 80 | −1.9 | −0.91 |
| 218190_s_at | Ubiquinol-cytochrome c reductase complex (7.2 kD) | 0 | 80 | −2.0 | −1.03 |
| 218345_at | Hepatocellular carcinoma-associated antigen 112 | 10 | 80 | −3.9 | −1.95 |
| 218486_at | Kruppel-like factor 11 | *90* | 0 | 2.1 | 1.06 |
| 218545_at | GGA binding partner | 0 | 80 | −1.6 | −0.67 |
| 218728_s_at | Cornichon homolog 4 (*Drosophila*) | 0 | 80 | −1.8 | −0.84 |
| 219269_at | Hypothetical protein FLJ21616 | 0 | 90 | −2.1 | −1.06 |
| 219410_at | *Homo sapiens hypothetical protein FLJ10134* | 0 | *100* | −4.7 | −2.33 |
| 219862_s_at | Nuclear prelamin A recognition factor | 80 | 0 | 1.5 | 0.62 |
| 219905_at | Erythroblast membrane-associated protein | 0 | 80 | −1.8 | −0.85 |
| 220532_s_at | LR8 protein | 10 | 80 | −5.2 | −2.39 |
| 221011_s_at | Likely ortholog of mouse limb-bud and heart gene (LBH) | 0 | 80 | −2.8 | −1.47 |
| 221042_s_at | Calmin (calponin-like, transmembrane) | 80 | 0 | 1.9 | 0.89 |
| 221434_s_at | Chromosome 14 open reading frame 156 | 0 | 80 | −1.7 | −0.72 |
| 221737_at | Guanine nucleotide binding protein (G protein) alpha 12 | 10 | 80 | −2.0 | −1.96 |
| AFFX-M27830_5_at | SRY (sex determining region Y)-box 18 | 80 | 0 | 4.3 | 2.09 |

The criterion for gene selection (total of 82) was the percentage of pairwise comparisons between future RA responders and future RA non-responders to anti-TNFα therapy showing an increase or decrease for the fold-change/Signal Log Ratio prior to therapy; bold letters indicate a percentage of 80% for the pairwise comparisons (total of 10), bold and italic letters *90%*, bold, italic, and underlined letters *100%*; in the latter case, also the gene names are shown in bold, italic, and underlined letters.

---

What is claimed is:

1. A method for predicting responsiveness to a TNFα inhibitor in a subject having an autoimmune disorder, the method comprising:
   (i) assaying the subject for expression of one or more biomarkers predictive of responsiveness to a TNFα inhibitor in an autoimmune disorder, and
   (ii) predicting responsiveness of the subject to the TNFα inhibitor based on expression of the one or more biomarkers in the subject, wherein the one or more biomarkers is encoded by a nucleic acid molecule comprising a nucleotide sequence selected from the group consisting of SEQ ID NOs:11, 29, 44, 62, 65, and 74,
   wherein decreased expression of the one or more biomarkers encoded by a nucleic acid molecule comprising a nucleotide sequence selected from the group consisting of SEQ ID NOs:11, 29, 65, and 74 is predictive of responsiveness of the subject to a TNFα inhibitor and/or wherein increased expression of the one or more biomarkers encoded by a nucleic acid molecule comprising a nucleotide sequence selected from the group consisting of SEQ ID NOs:44 and 62 is predictive of responsiveness of the subject to a TNFα inhibitor.

2. The method of claim 1, wherein a sample from the subject is assayed for expression of an mRNA encoding the one or more biomarkers.

3. The method of claim 1, which further comprises selecting a treatment regimen with the TNFα inhibitor based upon expression of the one or more biomarkers in the subject or administering the TNFα inhibitor to the subject according to the treatment regimen such that the autoimmune disorder is inhibited in the subject.

4. The method of claim 1, wherein the TNFα inhibitor is an anti-tumor necrosis factor-alpha (TNFα) antibody, or antigen-binding portion thereof.

5. The method of claim 4, wherein the anti-TNFα antibody, or antigen-binding portion thereof, is selected from the group consisting of a human antibody, a humanized antibody, a chimeric antibody, or a multivalent antibody.

6. The method of claim 4, wherein the anti-TNFα antibody, or antigen-binding portion thereof, is adalimumab.

7. The method of claim 4, wherein the anti-TNFα antibody, or antigen-binding portion thereof, is infliximab.

8. The method of claim 4, wherein the anti-TNFα antibody, or antigen-binding portion thereof, is golimumab.

9. The method of claim 5, wherein the human anti-TNFα antibody, or antigen-binding portion thereof, is selected from the group consisting of
   i) an isolated human antibody that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less;
   ii) an isolated human antibody with the following characteristics:
      a) dissociates from human TNFα with a $K_{off}$ rate constant of $1\times10^{-3}$ s$^{-1}$ or less, as determined by surface plasmon resonance;
      b) has a light chain CDR3 domain comprising the amino acid sequence of SEQ ID NO: 305, or modified from SEQ ID NO: 305 by a single alanine substitution at position 1, 4, 5, 7 or 8 or by one to five conservative amino acid substitutions at positions 1, 3, 4, 6, 7, 8 and/or 9;
      c) has a heavy chain CDR3 domain comprising the amino acid sequence of SEQ ID NO: 306, or modified from SEQ ID NO: 306 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12; and
   iii) an isolated human antibody with a light chain variable region (LCVR) comprising the amino acid sequence of SEQ ID NO: 303 and a heavy chain variable region (HCVR) comprising the amino acid sequence of SEQ ID NO: 304.

10. The method of claim 1, wherein the TNFα inhibitor is etanercept.

11. The method of claim 1, wherein the one or more biomarkers is encoded by a nucleic acid molecule comprising a nucleotide sequence of SEQ ID NO:44.

12. The method of claim 1, wherein the one or more biomarkers is encoded by a nucleic acid molecule comprising a nucleotide sequence selected from the group consisting of SEQ ID NOs:11 and 74.

13. The method of claim 1, wherein a sample from the subject is assayed for protein expression of the one or more biomarkers.

14. The method of claim 1, wherein the subject is a human.

15. The method of claim 1, wherein the autoimmune disorder is rheumatoid arthritis.

16. A method for predicting responsiveness to a TNFα inhibitor in a subject having an autoimmune disorder, the method comprising:
   (i) assaying the subject for expression of one or more biomarkers predictive of responsiveness to a TNFα inhibitor in an autoimmune disorder, and
   (ii) predicting responsiveness of the subject to the TNFα inhibitor based on expression of the one or more biomarkers in the subject, wherein the one or more biomarkers is selected from the group consisting of Homo sapiens predicted osteoblast protein (GS3786) (Genbank Accession Nos. NM_014888, NM_001040020); Charcot-Leyden crystal protein (Genbank Accession No. NM_001828); Integrin alpha-X (antigen CD11c) (Genbank Accession No. NM_000887); Amyloid beta (A4) precursor protein (peptidase nexin-II, Alzheimer disease) (Genbank Accession Nos. NM_201413, NM_000484, NM_201414); Neugrin, neurite outgrowth associated (Genbank Accession Nos. NM_016645, NM_001033088); and Homo sapiens hypothetical protein FLJ10134 (Genbank Accession No. NM_018004), wherein increased expression of the one or more biomarkers selected from the group consisting of Integrin alpha-X (antigen CD11c); and Amyloid beta (A4) precursor protein (peptidase nexin-II, Alzheimer disease) is predictive of responsiveness of the subject to a TNFα inhibitor and/or wherein decreased expression of the one or more biomarkers selected from the group consisting of Homo sapiens predicted osteoblast protein (GS3786); Charcot-Leyden crystal protein; Neugrin, neurite outgrowth associated; and *Homo sapiens* hypothetical protein FLJ10134 is predictive of responsiveness of the subject to a TNFα inhibitor.

17. The method of claim 16, wherein the one or more biomarkers is Integrin alpha-X (antigen CD11c).

18. The method of claim 16, wherein the one or more biomarkers is selected from the group consisting of Homo sapiens predicted osteoblast protein (GS3786) and *Homo sapiens* hypothetical protein FLJ10134.

19. The method of claim 16, wherein the TNFα inhibitor is an anti-tumor necrosis factor-alpha (TNFα) antibody, or antigen-binding portion thereof.

20. The method of claim 16, wherein a sample from the subject is assayed for protein expression of the one or more biomarkers.

21. The method of claim 16, wherein the subject is a human.

22. The method of claim 16, wherein the autoimmune disorder is rheumatoid arthritis.

23. The method of claim 16, wherein a sample from the subject is assayed for expression of an mRNA encoding the one or more biomarkers.

24. The method of claim 16, which further comprises selecting a treatment regimen with the TNFα inhibitor based upon expression of the one or more biomarkers in the subject or administering the TNFα inhibitor to the subject according to the treatment regimen such that the autoimmune disorder is inhibited in the subject.

25. A method for predicting responsiveness to a TNFα inhibitor in a subject having an autoimmune disorder, the method comprising:
(i) assaying the subject for increased expression of a biomarker, which biomarker is Integrin alpha-X (antigen CD11c), and
(ii) predicting responsiveness of the subject to the TNFα inhibitor based on increased expression of Integrin alpha-X (antigen CD11c) in the subject.

26. The method of claim 25, wherein the TNFα inhibitor is an anti-tumor necrosis factor-alpha (TNFα) antibody, or antigen-binding portion thereof.

27. The method of claim 25, wherein a sample from the subject is assayed for protein expression of the one or more biomarkers.

28. The method of claim 25, wherein the subject is a human.

29. The method of claim 25, wherein the autoimmune disorder is rheumatoid arthritis.

30. The method of claim 25, wherein a sample from the subject is assayed for expression of an mRNA encoding the one or more biomarkers.

31. The method of claim 25, which further comprises selecting a treatment regimen with the TNFα inhibitor based upon expression of the one or more biomarkers in the subject or administering the TNFα inhibitor to the subject according to the treatment regimen such that the autoimmune disorder is inhibited in the subject.

32. A method for predicting responsiveness to a TNFα inhibitor, which TNFα inhibitor is adalimumab, in a subject having an autoimmune disorder, the method comprising:
(i) assaying the subject for expression of one or more biomarkers predictive of responsiveness to adalimumab in an autoimmune disorder, wherein the one or more biomarkers is encoded by a nucleic acid molecule comprising a nucleotide sequence selected from the group consisting of SEQ ID NOs:11, 29, 44, 62, 65, and 74, and
(ii) predicting responsiveness of the subject to adalimumab based on expression of the one or more biomarkers in the subject,
wherein decreased expression of the one or more biomarkers encoded by a nucleic acid molecule comprising a nucleotide sequence selected from the group consisting of SEQ ID NOs:11, 29, 65, and 74 is predictive of responsiveness of the subject to a TNFα inhibitor and/or wherein increased expression of the one or more biomarkers encoded by a nucleic acid molecule comprising a nucleotide sequence selected from the group consisting of SEQ ID NOs:44 and 62 is predictive of responsiveness of the subject to a TNFα inhibitor.

33. The method of claim 32, wherein a sample from the subject is assayed for protein expression of the one or more biomarkers.

34. The method of claim 32, wherein the subject is a human.

35. The method of claim 32, wherein the autoimmune disorder is rheumatoid arthritis.

36. The method of claim 32, wherein a sample from the subject is assayed for expression of an mRNA encoding the one or more biomarkers.

37. A method of monitoring an autoimmune disorder in a subject having the autoimmune disorder, the method comprising: assaying the subject for expression of one or more biomarkers following treatment with a TNFα inhibitor, wherein the one or more biomarkers is encoded by a nucleic acid molecule comprising a nucleotide sequence selected from the group consisting of SEQ ID NOs:29, 91, and 176, thereby monitoring the autoimmune disorder in the subject.

38. The method of claim 37, further comprising monitoring the subject prior to treatment with a TNFα inhibitor.

39. The method of claim 37, wherein a sample from the subject is assayed for protein expression of the one or more biomarkers.

40. The method of claim 37, wherein the subject is a human.

41. The method of claim 37, wherein the autoimmune disorder is rheumatoid arthritis.

42. The method of claim 37, wherein a sample from the subject is assayed for expression of an mRNA encoding the one or more biomarkers.

* * * * *

UNITED STATES PATENT AND TRADEMARK OFFICE
CERTIFICATE OF CORRECTION

| | | |
|---|---|---|
| PATENT NO. | : 8,092,998 B2 | Page 1 of 1 |
| APPLICATION NO. | : 12/130373 | |
| DATED | : January 10, 2012 | |
| INVENTOR(S) | : Stuhlmuller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 8 days.

Signed and Sealed this
Twenty-sixth Day of June, 2012

David J. Kappos
*Director of the United States Patent and Trademark Office*

SEQUENCE LISTING

<160> NUMBER OF SEQ ID NOS: 310

<210> SEQ ID NO 1
<211> LENGTH: 279
<212> TYPE: DNA
<213> ORGANISM: Homo sapiens
<220> FEATURE:
<221> NAME/KEY: misc_feature
<222> LOCATION: (1)..(279)
<223> OTHER INFORMATION: AffymetrixID: 39248_at

<400> SEQUENCE: 1

```
cttctacagg cttttgggaa gtagggtgga tgtgggtagg gctgggagga gggggccaca     60
gcttaggttt ggagctctgg atgtacatac ataagtagga gcagtgggac gtgtttctgt    120
cataatgcag gcatgaaggg tggagtgaag tcaggtcata agtttcatgt ttgcttttgt    180
tttgttttgt ttttaatgta tgtagcagat gttacagtct tagggatccg ggatgggaga    240
ccccacttta gaaagggtcg tcactccttt aatcctcta                            279
```

<210> SEQ ID NO 2
<211> LENGTH: 483
<212> TYPE: DNA
<213> ORGANISM: Homo sapiens
<220> FEATURE:
<221> NAME/KEY: misc_feature
<222> LOCATION: (1)..(483)
<223> OTHER INFORMATION: AffymetrixID: 200061_s_at

<400> SEQUENCE: 2

```
agatcgccat catgaacgac accgtaacta tccgcactag aaagttcatg accaaccgac     60
tacttcagag gaaacaaatg gtcattgatg tccttcaccc cgggaaggcg acagtgccta    120
```

```
agacagaaat tcgggaaaaa ctagccaaaa tgtacaagac cacaccggat gtcatctttg    180
tatttggatt cagaactcat tttggtggtg gcaagacaac tggcttttggc atgatttatg   240 attccctgga ttatgcaaag aaaaatgaac ccaaacatag acttgcaaga catggcctgt    300
atgagaagaa aaagacctca agaaagcaac gaaaggaacg caagaacaga atgaagaaag    360
tcagggggac tgcaaaggcc aatgttggtg ctggcaaaaa gtgagctgga gattggatca    420
cagccgaagg agtaaaggtg ctgcaatgat gttagctgtg gccactgtgg attttttcgca   480 aga                                                                  483

<210> SEQ ID NO 3
<211> LENGTH: 474
<212> TYPE: DNA
<213> ORGANISM: Homo sapiens
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (1)..(474)
<223> OTHER INFORMATION: AffymetrixID: 200087_s_at

<400> SEQUENCE: 3
gggtactgac catcagtgtc agcattaggg ttttggtttt tgtttctttt gggtatttct     60
tttttggcac atgtgaatct tgttttgtgt aaaatgaaat tactttctct tgttctctga   120
tgatgggttt aaaattaaaa gagcatccgg ttttggtatg gggatgatcc aggattatgt   180
tgtgactgat acatattagt tacttgtgct tttttttttt tttttttngga tctttgcaag   240 ggcaaaacta caagtaacga gttttatata attaatttaa atttgttaca ggttttcatg    300
ttcaggataa accatacttc caccttgggt gagaacactt gcaacagttt attaatgagg   360
tgactttcac cttaggacaa ctgttgcatg ccaagttttt tgtgtgtgtg aaacacttca   420
aaactgattt aaaagatgta aatttaaaat tggttgtatc taatatgccc cagg         474

<210> SEQ ID NO 4
<211> LENGTH: 452
<212> TYPE: DNA
<213> ORGANISM: Homo sapiens
<220> FEATURE:
<221> NAME/KEY: misc_feature
<222> LOCATION: (1)..(452)
<223> OTHER INFORMATION: AffymetrixID: 200642_at

<400> SEQUENCE: 4
ctgaagggcg acggcccagt gcagggcatc atcaatttcg agcagaagga aagtaatgga    60
ccagtgaagg tgtggggaag cattaaagga ctgactgaag gcctgcatgg attccatgtt   120
catgagtttg gagataatac ggcaggctgt accagtgcag gtcctcactt taatcctcta   180
tccagaaaac acggtgggcc aaaggatgaa gagaggcatg ttggagactt gggcaatgtg   240
actgctgaca aagatggtgt ggccgatgtg tctattgaag attctgtgat ctcactctca   300
ggagaccatt gcatcattgg ccgcacactg gtggtccatg aaaaagcaga tgacttgggc   360
aaaggtggaa atgaagaaag tacaaagaca ggaaacgctg gaagtcgttt ggcttgtggt   420
gtaattggga tcgcccaata aacattccct tg                                 452

<210> SEQ ID NO 5
<211> LENGTH: 457
<212> TYPE: DNA
<213> ORGANISM: Homo sapiens
```

```
<220> FEATURE:
<221> NAME/KEY: misc_feature
<222> LOCATION: (1)..(457)
<223> OTHER INFORMATION: AffymetrixID:  200655_s_at

<400> SEQUENCE: 5
acctattcaa atgggttcta gttcaatttg tttagtataa attgtcatag ctggtttact      60
gaaaacaaac acatttaaaa ttggtttacc tcaggatgac gtgcagaaaa atgggtgaag     120
gataaaccgt tgagacgtgg ccccactggt aggatggtcc tcttgtactt cgtgtgctcc     180
gacccatggt gacgatgaca caccctggtg gcatgcccgt gtatgttggt ttagcgttgt     240
ctgcattgtt ctagagtgaa acaggtgtca ggctgtcact gttcacacaa attttttaata    300 agaaacattt accaagggag catctttgga ctctctgttt ttaaaacctt ctgaaccatg     360
acttggagcc ggcagagtag gctgtggctg tggacttcag cacaaccatc aacattgctg     420
ttcaaagaaa ttacagttta cgtccattcc aagttgt                              457

<210> SEQ ID NO 6
<211> LENGTH: 507
<212> TYPE: DNA
<213> ORGANISM: Homo sapiens
<220> FEATURE:
<221> NAME/KEY: misc_feature
<222> LOCATION: (1)..(507)
<223> OTHER INFORMATION: AffymetrixID:  200745_s_at

<400> SEQUENCE: 6
gcgtgatcag agaatccttc accttatgct gaaaagtgag ctcagatcca gcaccaatgt      60
tcctcctgac ccatcctgtc tatcttctca gttgagtttt taatctcact ttgggtttcc     120
ttgtgaagtt ggagggaagt tttataatagc ctaacactac cccaccccca actaggagga    180
acctctgttt tcaagagaga tgcctgtcct gtgcttggat agtcagtcaa ttatttgtgt     240
atgaaacaat gtacaaatca atgttttgaa aataatgatc tcagactttc taagttaaag    300
ttttaaaaat tttgattgtt tgccatattg ggtgggttta ctcttagaat cgcatgctgt     360
agaaaatgct caaagtgca tatgggactc agtccttagg tgttcttttt cttttaagaa      420
ataacctctt acagttgtaa ccattgcggc tctgtccact tctcgttgct gctctgtggc     480
acatatcgga agcagtacag cgcgcgg                                         507

<210> SEQ ID NO 7
<211> LENGTH: 540
<212> TYPE: DNA
<213> ORGANISM: Homo sapiens
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
```

```
<222> LOCATION: (266)..(267)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (292)..(293)
<223> OTHER INFORMATION: n is a, c, g, or t
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (334)..(334)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (389)..(389)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
```

```
<222> LOCATION: (403)..(403)
<223> OTHER INFORMATION: n is a, c, g, or t
<220> FEATURE:
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (1)..(540)
<223> OTHER INFORMATION: AffymetrixID: 200772_x_at

<400> SEQUENCE: 7
gaaaagccat ctttgcattg ttcctcatcc gncctccttg ctcngccgca gccgcctccg      60
ccgcgcgcct cctccgccgc cgcggactnc cggcagcttt atcgccagag tccctgaact     120
ctcgctttct ttttaatccc cntgcatcgg atcaccggcg tgccccacca tgtcagacgc     180
agccgtagac accagctccg aaatcaccac caaggactta aaggagaaga aggaagttgt     240
ggaagaggca gaaanatgga agagann cgc ccctgctnaa cgggnaatgc tnnananant     300
gaggaanaat ggggnagcag gaggctngac aatngaggta gacgaangaa ganggaagan     360
anggtgggga nggaangagg anggaggana gaangaaggt gantggtgan ggaangagga     420
ntggangant gaangatgag gaagctgagt cagctacggg caagcgggca gctgaangat     480
gatgaggatg acgatgtcga taccaangaa gcagaagacc gacgaggatg actagacagc     540

<210> SEQ ID NO 8
<211> LENGTH: 492
<212> TYPE: DNA
<213> ORGANISM: Homo sapiens
<220> FEATURE:
<221> NAME/KEY: misc_feature
<222> LOCATION: (1)..(492)
<223> OTHER INFORMATION: AffymetrixID: 201193_at

<400> SEQUENCE: 8
tagccacagt attgctccct aaaatatgca taaagtagaa attcactgcc ttccctcct      60 gtccatgacc ttgggcacag ggaagttctg gtgtcataga tatcccgttt tgtgaggtag    120
agctgtgcat taaacttgca catgactgga acgaagtatg agtgcaactc aaatgtgttg    180
aagatactgc agtcattttt gtaaagacct tgctgaatgt ttccaataga ctaaatactg    240
tttaggccgc aggagagttt ggaatccgga ataaatacta cctggagtct tgtcctctcc    300
```

```
atttttctct ttctcctcct ggcctggcct gaatattata ctactctaaa tagcatattt    360
catccaagtg caataatgta agctgaatct tttttggact tctgctggcc tgttttattt    420
cttttatata aatgtgattt ctcagaaatt gatattaaac actatcttat cttctcctga    480
actgttgatt tt                                                        492
```

```
<210> SEQ ID NO 9
<211> LENGTH: 391
<212> TYPE: DNA
<213> ORGANISM: Homo sapiens
<220> FEATURE:
<221> NAME/KEY: misc_feature
<222> LOCATION: (1)..(391)
<223> OTHER INFORMATION: AffymetrixID:  201690_s_at

<400> SEQUENCE: 9
atgatactgt agaacctgtc tcctactttg aaaactgaat gtcagggctg agtgaatcaa     60
agtgtctaga catatttgca tagaggccaa ggtattctat tctaataact gcttactcaa    120
cactaccacc ttttccttat actgtatatg attatggcct acaatgttgt atttgttatt    180
tattaaattg tgattgtttt attattgttt atgccaaatg ttaactgcca agcttggagt    240
gacctaaagc attttttaaa agcatggcta gatttacttc agtataaatt atcttatgaa    300
aaccaaattt taaaagccac aggtgttgat tgttataaaa taacatgctg ccattcttga    360
ttgctagagt ttttgttagt actttggatg c                                   391
```

```
<210> SEQ ID NO 10
<211> LENGTH: 501
<212> TYPE: DNA
<213> ORGANISM: Homo sapiens
<220> FEATURE:
<221> NAME/KEY: misc_feature
<222> LOCATION: (1)..(501)
<223> OTHER INFORMATION: AffymetrixID:  201693_s_at

<400> SEQUENCE: 10
gggctttcgg acatgacagc aaccttttct cccaggacaa ttgaaatttg ctaaagggaa     60
aggggaaaga aagggaaaag ggagaaaaag aaacacaaga gacttaaagg acaggaggag    120
gagatggcca taggagagga gggttcctct taggtcagat ggaggttctc agagccaagt    180
cctccctctc tactggagtg gaaggtctat tggccaacaa tcctttctgc ccacttcccc    240
ttccccaatt actattccct ttgacttcag ctgcctgaaa cagccatgtc caagttcttc    300
acctctatcc aaagaacttg atttgcatgg attttggata aatcatttca gtatcatctc    360
catcatatgc ctgacccctt gctcccttca atgctagaaa atcgagttgg caaaatgggg    420
tttgggcccc tcagagccct gccctgcacc cttgtacagt gtctgtgcca tggatttcgt    480
ttttcttggg gtactcttga t                                              501
```

```
<210> SEQ ID NO 11
<211> LENGTH: 489
<212> TYPE: DNA
<213> ORGANISM: Homo sapiens
<220> FEATURE:
<221> NAME/KEY: misc_feature
<222> LOCATION: (1)..(489)
<223> OTHER INFORMATION: AffymetrixID:  201889_at

<400> SEQUENCE: 11
ttgaccccaa atgactttat acccaattct acataaaaat atagaagatc tatctttttt     60
tgttaccttc agatgttcac taaataactc agttttttaag cagaagtttt cagggcatta   120
```

```
aatatatgtt gtgtatgaag tatctcaaac tggaacataa atttagtgat caaactgcca      180
ttcacagtgt aaggcagcac ttaaatttcg aacctaaagt ttagatgcat tgtataaaaa      240
aacctaaaag cagtatctgt tatttagctg taaaccaagt tggaagctat tcggataatt      300
tcttaaatat tgatgaactt tggagtactg tttcttcctt caaactgaat gtaattaatt      360
catgaataaa tgcaccttat atgtttaaac aatctttgta tacttttggg atttttggtg      420
cttatatgct aaatcacatt cagcatgtgt attttgacat ttaaaatact tccctcaatt      480
ctgtaaatt                                                             489

<210> SEQ ID NO 12
<211> LENGTH: 409
<212> TYPE: DNA
<213> ORGANISM: Homo sapiens
<220> FEATURE:
<221> NAME/KEY: misc_feature
<222> LOCATION: (1)..(409)
<223> OTHER INFORMATION: AffymetrixID:  202110_at

<400> SEQUENCE: 12
tcagctcact tcaagggtac ctgaagcgaa ttggcaccaa agcagcagct gtattgccgc      60
agttctagct tcaccttcac gatgtttccc ttggtcaaaa gcgcactaaa tcgtctccaa     120
gttcgaagca ttcagcaaac aatggcaagg cagagccacc agaaacgtac acctgatttt     180
catgacaaat acggtaatgc tgtattagct agtggagcca ctttctgtat tgttacatgg     240
acatatgtag caacacaagt cggaatagaa tggaacctgt cccctgttgg cagagttacc     300
ccaaaggaat ggaggaatca gtaatcatcc cagctggtgt aataatgaat tgtttaaaaa     360
acagctcata attgatgcca aattaaagca ctgtgtaccc attaagata               409

<210> SEQ ID NO 13
<211> LENGTH: 511
<212> TYPE: DNA
<213> ORGANISM: Homo sapiens
<220> FEATURE:
<221> NAME/KEY: misc_feature
<222> LOCATION: (1)..(511)
<223> OTHER INFORMATION: AffymetrixID:  202157_s_at

<400> SEQUENCE: 13
tgtggcaaaa acgtttcttt cttatttttt ttcttttcct aaaacagact tgaaagtatt      60
atacagggat tggcattctt cccggtcact ggtaacaata gcaatatgtg tccagggaca     120
cagaatgttg gtttctaaca gactacttcc aaaaacagtt tgagaaaaaa actgtctgat     180
tttaagtctc tagaggtctg taatagtttt tacattttc aggcagtgta aagttttttg      240
ataaggccat tttaggtggc tcactttctc attaagatat atatatagaa ccacttttg     300 tagattagta taagaaaaat atttaccctg ttttggggca aatgctacct atttgtgtca     360 cctttttgctg aactcacagt tagacaatcc atggtttaat gcacatgaaa ttacctatat     420
tttatactgt ttcaatgtac aggagaaagg ttactgtaaa ctgtgttatg ttggtgcttc     480
tgtgaattaa gttgtggttt catcatgagt c                                    511

<210> SEQ ID NO 14
<211> LENGTH: 480
<212> TYPE: DNA
<213> ORGANISM: Homo sapiens
<220> FEATURE:
<221> NAME/KEY: misc_feature
<222> LOCATION: (1)..(480)
<223> OTHER INFORMATION: AffymetrixID:  202233_s_at
```

<400> SEQUENCE: 14

```
gctcgtgttg aatctagaac cgtagccaga catgggactg gaggacgagc aaaagatgct      60
taccgaatcc ggagatcctg aggaggagga agaggaagag gaggaattag tggatcccct     120
aacaacagtg agagagcaat gcgagcagtt ggagaaatgt gtaaaggccc gggagcggct     180
agagctctgt gatgagcgtg attcctctcg atcacataca gaagaggatt gcacggagga     240
gctctttgac ttcttgcatg cgagggacca ttgcgtggcc cacaaactct ttaacaactt     300
gaaataaatg tgtggactta agttgcaccc cagtcttcat catctgggca tcagaatatt     360
tccttatggt tttggatgta ccatttgttt cttatttgtg taactgtaag ttcacatcaa     420
cctcatgggt ttggcttgag gctggtagct tctatgtaat tcgcaatgat tccatctaaa     480
```

<210> SEQ ID NO 15
<211> LENGTH: 556
<212> TYPE: DNA
<213> ORGANISM: Homo sapiens
<220> FEATURE:
<221> NAME/KEY: misc_feature
<222> LOCATION: (1)..(556)
<223> OTHER INFORMATION: AffymetrixID: 202378_s_at

<400> SEQUENCE: 15

```
acatgtgcac atgcggcatt ttactatgaa atttaatatg ctgggttttt taatacccttt     60
atatatcatg ttcactttaa gaaagacttc ataagtagga gatgagtttt attctcagca    120
aatagacctg tcaaatttag attatgttac tcaaattatg ttacttgttt ggctgttcat    180
gtagtcacgg tgctctcaga aaatatatta acgcagtctt gtaggcagct gccaccttat    240
gcagtgcatc gaaacctttt gcttggggat gtgcttggag aggcagataa cgctgaagca    300
ggcctctcat gacccaggaa ggccggggtg gatccctctt tgtgttgtag tccatgctat    360
taaaagtgtg gcccacagac caagagcctc aacattcct agagccttat tagaaatgca    420
gaatctgaag ccccactctg gacccaggac attttgatga gatccaaagg agttgtatgc    480
acatgaaagt ttgagaagca tcatcataga gaagtaaaca tcacacccaa cttccttatc    540
tttccagtgg ctaaac                                                     556
```

<210> SEQ ID NO 16
<211> LENGTH: 529
<212> TYPE: DNA
<213> ORGANISM: Homo sapiens
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (1)..(529)
<223> OTHER INFORMATION: AffymetrixID: 202664_at

<400> SEQUENCE: 16

```
gaaatcagag cttacatgtg tgttttttta taacattttc agataaatgt attcaacatg      60
taatacagta ttttnacatt cacctcttat tttatattga aatgtattac agtattaaaa    120
ctcagtgttc agtatttatt tcactatgca ttttatttag taaagccag gagaaatgtt    180
taatccaatg gtgccttact ttgtgattta aagaaatca actttttttt atgtctaagt    240
agtagattat ttgcatattt gtaaaaactg ttaggtcttt atattttaaa gtgtaatacc    300
agttttgtta tttagtagc agaaatggga tgattgttaa agttccccaa aaatgttggc    360
atgaaattaa ttttccctc cttatagtca aggaccgtag aggaagaaaa acttttttt    420
```

```
catatcatgc actatgtaaa cagacacatt ttgctatctg tgtcatcagg atagtgtaag    480
tggtagggta gagactaccc tagacatctg catctttgta agttagcca               529

<210> SEQ ID NO 17
<211> LENGTH: 478
<212> TYPE: DNA
<213> ORGANISM: Homo sapiens
<220> FEATURE:
<221> NAME/KEY: misc_feature
<222> LOCATION: (1)..(478)
<223> OTHER INFORMATION: AffymetrixID:  202910_s_at

<400> SEQUENCE: 17
ctgtggccac agcagctttg tacacgaaga ccatccatcc tcccttcgtc caccactcta    60
ctccctccac cctccctccc tgatcccgtg tgccaccagg agggagtggc agctatagtc   120
tggcaccaaa gtccaggaca cccagtgggg tggagtcgga gccactggtc ctgctgctgg   180
ctgcctctct gctccacctt gtgacccagg gtggggacag gggctggccc agggctgcaa   240
tgcagcatgt tgccctggca cctgtggcca gtactcggga cagactaagg gcgcttgtcc   300
catcctggac ttttcctctc atgtctttgc tgcagaactg aagagactag gcgctggggc   360
tcagcttccc tcttaagcta agactgatgt cagaggcccc atggcgaggc cccttggggc   420
cactgcctga ggctcacggt acagaggcct gccctgcctg gccgggcagg aggttctc    478

<210> SEQ ID NO 18
<211> LENGTH: 276
<212> TYPE: DNA
<213> ORGANISM: Homo sapiens
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (1)..(276)
<223> OTHER INFORMATION: AffymetrixID:  202922_at

<400> SEQUENCE: 18
aaaaatggcg ttcttctctt gtggcctgtt attctgattg ctgctgtata cagtttngtc    60
actctttagt tttagttaa gcatactgat agactttcct ctaaaagcca ttcactccag   120 atttttacctg gggaatattc tacatactgc ttactttctc tataaaactc atcaataaat   180
catgaaaggc actgagtttt gtaaatcagg accctaaatg tttaattgta aataagtttc   240
agataattat tatagctttg cgttgaagtt tgttgt                             276

<210> SEQ ID NO 19
<211> LENGTH: 486
<212> TYPE: DNA
<213> ORGANISM: Homo sapiens
<220> FEATURE:
<221> NAME/KEY: misc_feature
<222> LOCATION: (1)..(486)
<223> OTHER INFORMATION: AffymetrixID:  202950_at

<400> SEQUENCE: 19
taacatgtta gttgtcattt ggcatgagtg tgcattccag taattcttaa ttgatatttg    60
attaattcca tacctttgat taaaacatgc tagttcaaaa taagactgct cagttttcaa   120
gggttttcaa gcctacttac ctttataaag gttctctagt ctctgattag ccatgactgt   180
attggacttt gaacattttc tgaactaaaa acctctattc taaactaatc tcatttggat   240
gtgtaagtct tttgtaaagg caagaataaa taatatccag gacaatttat tagttttctc   300
```

```
agtattttcc caaatattag aatatttact tcattattgg ttggctgcca atgacccat      360 atgttctgtg agaatagtag ctttatcttt gatataatac atagtctcca aataggtaat     420
acttcgcaat tgattagatt ttcagagtag atttagagtt atctgttttt ctggtgaggg     480
tcaaat                                                                486

<210> SEQ ID NO 20
<211> LENGTH: 539
<212> TYPE: DNA
<213> ORGANISM: Homo sapiens
<220> FEATURE:
<221> NAME/KEY: misc_feature
<222> LOCATION: (1)..(539)
<223> OTHER INFORMATION: AffymetrixID: 203097_s_at

<400> SEQUENCE: 20
tttccattaa attcagctga tcatattgat cagtagataa acgtaaatag cttcaaattt     60
taaaagtgga attgcagtgt tttttcactg tatcaaacaa tgtcagtgct ttatttaata    120
attctcttct gtatcatggc atttgtctac ttgcttatta cattgtcaat tatgcatttg    180
taattttaca tgtaatatgc attatttgcc agtttttatta tataggctat ggacctcatg   240
tgcatataga aagacagaaa tctagctcta ccacaagttg cacaaatgtt atctaagcat    300
taagtaattg tagaacatag gactgctaat ctcagttcgc tctgtgatgt caagtgcaga    360
atgtacaatt aactggtgat ttcctcatac ttttgatact acttgtacct gtatgtcttt    420
tagaaagaca ttggtggagt ctgtatccct tttgtatttt taatacaata attgtacata    480
ttggttatat ttttgttgaa gatggtagaa atgtactatg tttatgcttc tacatccag     539

<210> SEQ ID NO 21
<211> LENGTH: 444
<212> TYPE: DNA
<213> ORGANISM: Homo sapiens
<220> FEATURE:
<221> NAME/KEY: misc_feature
<222> LOCATION: (1)..(444)
<223> OTHER INFORMATION: AffymetrixID: 203231_s_at

<400> SEQUENCE: 21
tgcaccaggt gaaaacaggg ccagcagact ccatggccca attcggtttc ttcggtggtg     60
atgtgaaagg agagaattac acttttttttt tttttaagtg gcgtggaggc ctttgcttcc   120
acatttgttt ttaacccaga atttctgaaa tagagaattt aagaacacat caagtaataa    180
atatacagag aatatacttt tttataaagc acatgcatct gctattgtgt tgggttggtt    240
tcctctcttt tccacggaca gtgttgtgtt tctggcatag ggaaactcca aacaacttgc    300
acacctctac tccggagctg agatttcttt tacatagatg acctcgcttc aaatacgtta    360
ccttactgat gataggatct tttcttgtag cactatacct tgtgggaatt ttttttttaaa   420 tgtacacctg atttgagaag ctga                                          444

<210> SEQ ID NO 22
<211> LENGTH: 526
<212> TYPE: DNA
<213> ORGANISM: Homo sapiens
<220> FEATURE:
<221> NAME/KEY: misc_feature
<222> LOCATION: (1)..(526)
<223> OTHER INFORMATION: AffymetrixID: 203300_x_at

<400> SEQUENCE: 22
gaacttgttc agaccgtttt agcacggaaa cctaaaatgt gcagcttcct tgagtggcga     60
```

```
gatctgaaga ttgtttacaa aagatatgct agtctgtatt tttgctgtgc tattgaggat    120
caggacaatg aactaattac cctggaaata attcatcgtt atgtggaatt acttgacaag    180
tatttcggca gtgtctgtga actagatatc atctttaatt ttgagaaggc ttattttatt    240
ttggatgagt ttcttttggg aggggaagtt caggaaacat ccaagaaaaa tgtccttaaa    300
gcaattgagc aggctgatct actgcaggag gaagctgaaa ccccacgtag tgttcttgaa    360
gaaattggac tgacataact ctcctccctt gttgatgact tcttgtggca tttcacacac    420
tgtagatggt cactcccttc atgtccatgt tagctcatgg tgtaagatga tgtcttgtca    480
gtattactgt tttgctaagc cgcttcattc atgcctacac aatttt              526

<210> SEQ ID NO 23
<211> LENGTH: 502
<212> TYPE: DNA
<213> ORGANISM: Homo sapiens
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (1)..(502)
<223> OTHER INFORMATION: AffymetrixID:  204160_s_at

<400> SEQUENCE: 23
ttgtggttgt tgagaggcat tttcaaaccc tgtataaata atccatgctg ttggtcataa     60
gttaactgta ttaagaacag taaaataaat aaaaaccaat agtactaatt tngctttaaa    120
aaaatttcta attttttttca cataaaacaa ttatcctaaa ggttaatagt tgatcgaaac    180
agaataatag aaaaattctn ctttaatttc cattaaaaag caaatagcat tgacacattt    240
aaagcttttc atttaaagta gtggatgttt ttgaagtatc taaaatagta gcagaatatt    300
ttatacttgg tccttgcaat ggtgtgagtt ttaatgattg cattatcgtg attggtggtt    360
atgagtttca gaaatctata cttggcatcc aactcatgag tggatttttat ataggatgga    420 acaggaaggt atgtcctgtc agtatcttaa ccctttcaac aagacattta cctatttgtc    480
tttccttacg ttctcaaaat at                                             502

<210> SEQ ID NO 24
<211> LENGTH: 244
<212> TYPE: DNA
<213> ORGANISM: Homo sapiens
<220> FEATURE:
<221> NAME/KEY: misc_feature
<222> LOCATION: (1)..(244)
<223> OTHER INFORMATION: AffymetrixID:  204750_s_at

<400> SEQUENCE: 24
gaccctcgcg atcttaatat ttgccagtga tgcctgcaaa aatgtgacat tacatgttcc     60
ctccaaacta gatgccgaga aacttgttgg tagagttaac ctgaaagagt gctttacagc    120
tgcaaatcta attcattcaa gtgatcctga cttccaaatt ttggaggatg gttcagtcta    180
tacaacaaat actattctat tgtcctcgga gaagagaagt tttaccatat tactttccaa    240
cact                                                                 244

<210> SEQ ID NO 25
<211> LENGTH: 504
```

```
<212> TYPE: DNA
<213> ORGANISM: Homo sapiens
<220> FEATURE:
<221> NAME/KEY: misc_feature
<222> LOCATION: (1)..(504)
<223> OTHER INFORMATION: AffymetrixID: 204777_s_at

<400> SEQUENCE: 25
ggaagtcttc ataaagccgc agtagaactt gagctgaaaa cccagatggt gttaactggc      60
cgccccactt tccggcataa cttttagaa aacagaaatg cccttgatgg tggaaaaaag     120
aaaacaacca ccccccact gcccaaaaaa aaaagccctg ccctgttgct cgtgggtgct     180
gtgtttactc tcccgtgtgc cttcgcgtcc gggttgggag cttgctgtgt ctaacctcca    240
actgctgtgc tgtctgctag ggtcacctcc tgtttgtgaa aggggacctt cttgttcggg    300
ggtgggaagt ggcgaccgtg acctgagaag gaaagaaaga tcctctgctg accctggag    360
cagctctcga gaactacctg ttggtattgt ccacaagctc tcccgagcgc cccatcttgt    420
gccatgtttt aagtcttcat ggatgttctg catgtcatgg ggactaaaac tcacccaaca    480
gatctttcca gaggtccatg gtgg                                            504

<210> SEQ ID NO 26
<211> LENGTH: 268
<212> TYPE: DNA
<213> ORGANISM: Homo sapiens
<220> FEATURE:
<221> NAME/KEY: misc_feature
<222> LOCATION: (1)..(268)
<223> OTHER INFORMATION: AffymetrixID: 205042_at

<400> SEQUENCE: 26
ttacatttga actatatcct tcctagtggg ttagtgtgaa aaagagtttg gctgattcct     60
aaaactctgc cagccctgca gtaatctcca ggcctggtta ttgttcagac attccatggt   120
gattcctggg aaggaagctt ggctgctcag tttctgagtc tggggtgaga taatgttctg   180
gaaggacatc tgttctttgg tgtaatctct catggtgaaa tctgctctgt acatcagaca   240
attgcattgc taccaagttt cataccaa                                       268

<210> SEQ ID NO 27
<211> LENGTH: 507
<212> TYPE: DNA
<213> ORGANISM: Homo sapiens
<220> FEATURE:
<221> NAME/KEY: misc_feature
<222> LOCATION: (1)..(507)
<223> OTHER INFORMATION: AffymetrixID: 205114_s_at

<400> SEQUENCE: 27
gattccacag aatttcatag ctgactactt tgagacgagc agccagtgct ccaagcccgg     60
tgtcatcttc ctaaccaagc gaagccggca ggtctgtgct gacccagtg aggagtgggt    120
ccagaaatat gtcagcgacc tagagctgag tgcctgaggg gtccagaagc ttcgaggccc    180
agcgacctcg gtgggccagt ggggaggagc aggagcctga ccttgggaa acatgcgtgt    240
gacctccaca gctacctctt ctatggactg gttgttgcca acagccaca ctgtgggact    300
cttcttaact taaattttaa tttatttata ctatttagtt tttgtaattt atttcgatt     360
tcacagtgtg tttgtgattg tttgctctga gagttccccct gtcccctccc ccttccctca    420
caccgcgtct ggtgacaacc gagtggctgt catcagcctg tgtaggcagt catggcacca    480
aagccaccag actgacaaat gtgtatc                                        507
```

```
<210> SEQ ID NO 28
<211> LENGTH: 565
<212> TYPE: DNA
<213> ORGANISM: Homo sapiens
<220> FEATURE:
<221> NAME/KEY: misc_feature
<222> LOCATION: (1)..(565)
<223> OTHER INFORMATION: AffymetrixID:  205624_at

<400> SEQUENCE: 28
tatgaaaccc gctacatcta tgcccaata gaatcaacaa tttacccgat atcaggttct      60
tctttagact gggcttatga cctgggcatc aaacacacat ttgcctttga gctccgagat    120
aaaggcaaat ttggttttct ccttccagaa tcccggataa agccaacgtg cagagagacc    180
atgctagctg tcaaatttat tgccaagtat atcctcaagc atacttccta agaactgcc     240 ctctgtttgg aataagccaa ttaatccttt tttgtgcctt tcatcagaaa gtcaatcttc    300
agttatcccc aaatgcagct tctatttcac ctgaatcctt ctcttgctca tttaagtccc    360
atgttactgc tgtttgcttt tacttacttt cagtagcacc ataacgaagt agctttaagt    420 gaaaccttt aactacctt ctttgctcca agtgaagttt ggacccagca gaaagcatta     480
ttttgaaagg tgatatacag tggggcacag aaaacaaatg aaaaccctca gtttctcaca    540
gattttcacc atgtggcttc atcaa                                         565

<210> SEQ ID NO 29
<211> LENGTH: 493
<212> TYPE: DNA
<213> ORGANISM: Homo sapiens
<220> FEATURE:
<221> NAME/KEY: misc_feature
<222> LOCATION: (1)..(493)
<223> OTHER INFORMATION: AffymetrixID:  206207_at

<400> SEQUENCE: 29
aggagacaac aatgtccctg ctacccgtgc catacacaga ggctgcctct ttgtctactg      60
gttctactgt gacaatcaaa gggcgaccac ttgtctgttt cttgaatgaa ccatatctgc    120
aggtggattt ccacactgag atgaaggagg aatcagacat tgtcttccat ttccaagtgt    180
gctttggtcg tcgtgtggtc atgaacagcc gtgagtatgg ggcctggaag cagcaggtgg    240
aatccaagaa catgcccttt caggatggcc aagaatttga actgagcatc tcagtgctgc    300
cagataagta ccaggtaatg gtcaatggcc aatcctctta cacctttgac catagaatca    360
agcctgaggc tgtgaagatg gtgcaagtgt ggagagatat ctccctgacc aaatttaatg    420
tcagctattt aaagagataa ccagacttca tgttgccaag gaatccctgt ctctacgtga    480
acttgggatt cca                                                       493

<210> SEQ ID NO 30
<211> LENGTH: 218
<212> TYPE: DNA
<213> ORGANISM: Homo sapiens
<220> FEATURE:
<221> NAME/KEY: misc_feature
<222> LOCATION: (1)..(218)
<223> OTHER INFORMATION: AffymetrixID:  206790_s_at

<400> SEQUENCE: 30
gaacttactt cagattgtgc gggaccactg ggttcatgtt cttgtcccta tgggatttgt      60
cattggatgt tatttagaca gaaagagtga tgaacggcta actgccttcc ggaacaagag    120
tatgttattt aaaagggaat tgcaacccag tgaagaagtt acctggaagt aaagactggc    180
tagattatcg aatgttcaca ttttaaagtt ctgagaga                           218
```

<210> SEQ ID NO 31
<211> LENGTH: 453
<212> TYPE: DNA
<213> ORGANISM: Homo sapiens
<220> FEATURE:
<221> NAME/KEY: misc_feature
<222> LOCATION: (1)..(453)
<223> OTHER INFORMATION: AffymetrixID: 207008_at

<400> SEQUENCE: 31

| | | | | | |
|---|---|---|---|---|---|
| acctaacgaa | gtatccttca | gcctgaaaga | ggaatgaagt | actcatacat | gttacaacac | 60 |
| ggacgaacct | tgaaaacttt | atgctaagtg | aaataagcca | gacatcaaca | gataaatagt | 120 |
| ttatgattcc | acctacatga | ggtactgaga | gtgaacaaat | ttacagagac | agaaagcaga | 180 |
| acagtgatta | ccagggactg | aggggagggg | agcatgggaa | gtgacggttt | aatgggcaca | 240 |
| gggtttatgt | ttaggatgtt | gaaaaagttc | tgcagataaa | cagtagtgat | agttgtaccg | 300 |
| caatgtgact | taatgccact | aaattgacac | ttaaaaatgg | tttaaatggt | caattttgtt | 360 |
| atgtatattt | tatatcaatt | taaaaaaaaa | cctgagcccc | aaaaggtatt | ttaatcacca | 420 |
| aggctgatta | aaccaaggct | agaaccacct | gcc | | | 453 |

<210> SEQ ID NO 32
<211> LENGTH: 385
<212> TYPE: DNA
<213> ORGANISM: Homo sapiens
<220> FEATURE:
<221> NAME/KEY: misc_feature
<222> LOCATION: (1)..(385)
<223> OTHER INFORMATION: AffymetrixID: 207815_at

<400> SEQUENCE: 32

| | | | | | |
|---|---|---|---|---|---|
| caagccctgc | tgtacaagaa | aatcattaag | gaacatttgg | agagttagct | actagctgcc | 60 |
| taagtgtgca | ctttcaatct | aactgtgaaa | gaatcttctg | atgtttgtat | tatccttctt | 120 |
| atattatatt | aacaaaataa | atcaagttgt | ggtatagtca | atctatttct | taataatact | 180 |
| gcaaaaataa | tgctgacaca | tcacaatttc | atattttaaa | atttccagaa | ttttaagcaa | 240 |
| aaagcattat | gaaggaaggc | ttggtttaat | aaagactgat | tttgttcagt | gttatatgtt | 300 |
| agctgataca | tatttgttca | tttatgtgat | tgcagtactt | tatagctaca | tatttacctt | 360 |
| gaatgttaca | attagcttgc | caata | | | | 385 |

<210> SEQ ID NO 33
<211> LENGTH: 491
<212> TYPE: DNA
<213> ORGANISM: Homo sapiens
<220> FEATURE:
<221> NAME/KEY: misc_feature
<222> LOCATION: (1)..(491)
<223> OTHER INFORMATION: AffymetrixID: 208051_s_at

<400> SEQUENCE: 33

| | | | | | |
|---|---|---|---|---|---|
| gaactcccag | ctaaacaacc | aagacttcac | tgaagattta | ttccaattct | agaattgttc | 60 |
| ttttttatt | ttttatttt | tcaactgact | aacttcatta | ccttaaagcc | tagaacatta | 120 |
| ttctgcttta | tttatatggc | tttctcaatt | ttattttgta | gcatgggttg | aatcgaactt | 180 |
| tttactagag | aattttacta | gatatttgtc | attcaagttt | tcatctgctt | tataattgat | 240 |
| acaccttgag | ggtcactttt | ctaatacttt | tacctataat | gtggtaccca | cctcagcccc | 300 |
| taataaaataa | tatttttacc | ctaatgtcaa | atcttttttcc | caggctaact | aaaaactgtg | 360 |
| tacaaaagga | ttgcttgtaa | atatgcatgt | aaatagttct | gttaataacc | cactgtttta | 420 |

```
catttggtac atctgtgtct gctaatacag ttagctttct cacttttctg cttgtttgtt    480
cagtctgaat t                                                         491
```

```
<210> SEQ ID NO 34
<211> LENGTH: 382
<212> TYPE: DNA
<213> ORGANISM: Homo sapiens
<220> FEATURE:
<221> NAME/KEY: misc_feature
<222> LOCATION: (1)..(382)
<223> OTHER INFORMATION: AffymetrixID:  208161_s_at

<400> SEQUENCE: 34
gatagcaaac actgggggca ccttaagatt ttgcacctgt aaagtgcctt acagggtaac     60
tgtgctgaat gctttagatg aggaaatgat ccccaagtgg tgaatgacac gcctaaggtc    120
acagctagtt tgagccagtt agactagtcc cccggtctcc cgattcccaa ctgagtgtta    180
tttgcacact gcactgtttt caaataacga ttttatgaaa tgacctctgt cctccctctg    240
atttttcata ttttcctaaa gtttcgtttc tgttttttaa taaaaagctt tttcctcctg    300
gaacagaaga cagctgctgg gtcaggccac ccctaggaac tcagtcctgt actctggggt    360
gctgcctgaa tccattaaaa at                                             382
```

```
<210> SEQ ID NO 35
<211> LENGTH: 543
<212> TYPE: DNA
<213> ORGANISM: Homo sapiens
<220> FEATURE:
<221> NAME/KEY: misc_feature
<222> LOCATION: (1)..(543)
<223> OTHER INFORMATION: AffymetrixID:  208637_x_at

<400> SEQUENCE: 35
ggtcccgagg agttcaaagc ctgcctcatc agcttgggtt atgatattgg caacgacccc     60
cagggagaag cagaatttgc ccgcatcatg agcattgtgg accccaaccg cctgggggta    120
gtgacattcc aggccttcat tgacttcatg tcccgcgaga cagccgacac agatacagca    180
gaccaagtca tggcttcctt caagatcctg gctggggaca agaactacat taccatggac    240
gagctgcgcc gcgagctgcc acccgaccag gctgagtact gcatcgcgcg gatggccccc    300
tacaccggcc ccgactccgt gccaggtgct ctggactaca tgtccttctc cacggcgctg    360
tacggcgaga gtgaccctcta atccaccccg cccggccgcc ctcgtcttgt gcgccgtgcc    420
ctgccttgca cctccgccgt cgcccatctc ctgcctgggt tcggtttcag ctcccagcct    480
ccacccgggt gagctggggc ccacgtggca tcgatcctcc ctgcccgcga agtgacagtt    540
tac                                                                  543
```

```
<210> SEQ ID NO 36
<211> LENGTH: 165
<212> TYPE: DNA
<213> ORGANISM: Homo sapiens
<220> FEATURE:
<221> NAME/KEY: misc_feature
<222> LOCATION: (1)..(165)
<223> OTHER INFORMATION: AffymetrixID:  208918_s_at

<400> SEQUENCE: 36
gaaatgggct gggagtgctt ctgtcctgct gacaccccgc ggtgggtccc tggagcgcgg     60
cctccagctg ccgcaatttc catgccagga tattttccg caaatcagtc ggttgaaatt    120
cagaggagtc agaatgactc gacctgtcct tcaatgttga taata                    165
```

<210> SEQ ID NO 37
<211> LENGTH: 189
<212> TYPE: DNA
<213> ORGANISM: Homo sapiens
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (1)..(189)
<223> OTHER INFORMATION: AffymetrixID: 208982_at

<400> SEQUENCE: 37

| | | | | | |
|---|---|---|---|---|---|
| attgcttgct | aaagaagtgg | tctcctgagg | tcttaagaca | ttcctgacag | tgtcttgagt | 60 |
| gggtgggaga | gaggntgctg | tcattgcgct | gtggaatttc | acagatgaga | accacgccta | 120 |
| gccaaaatca | cttttcctgt | ttgcctcagt | gacacagctg | cagggaccct | cgtggatgtt | 180 |
| gtattaaat | | | | | | 189 |

<210> SEQ ID NO 38
<211> LENGTH: 355
<212> TYPE: DNA
<213> ORGANISM: Homo sapiens
<220> FEATURE:
<221> NAME/KEY: misc_feature
<222> LOCATION: (1)..(355)
<223> OTHER INFORMATION: AffymetrixID: 209009_at

<400> SEQUENCE: 38

| | | | | | |
|---|---|---|---|---|---|
| gagcttcccc | aactcataaa | tgccaatttt | ccagtggatc | cccaaaggat | gtctattttt | 60 |
| ggccactcca | tgggaggtca | tggagctctg | atctgtgctt | tgaaaaatcc | tggaaaatac | 120 |
| aaatctgtgt | cagcatttgc | tccaatttgc | aaccctgtac | tctgtccctg | ggcaaaaaa | 180 |
| gcctttagtg | gatatttggg | aacagatcaa | agtaaatgga | aggcttatga | tgctacccac | 240 |
| cttgtgaaat | cctatccagg | atctcagctg | gacatactaa | ttgatcaagg | gaaagatgac | 300 |
| cagtttcttt | tagatggaca | gttactccct | gataacttca | tagctgcctg | tacag | 355 |

<210> SEQ ID NO 39
<211> LENGTH: 564
<212> TYPE: DNA
<213> ORGANISM: Homo sapiens
<220> FEATURE:
<221> NAME/KEY: misc_feature
<222> LOCATION: (1)..(564)
<223> OTHER INFORMATION: AffymetrixID: 209020_at

<400> SEQUENCE: 39

| | | | | | |
|---|---|---|---|---|---|
| caggggcagt | cgttgagcct | ttgagaactt | ctgttccaag | gctcccatca | gagagtaaga | 60 |
| aggaagactc | ctctgacgct | acccaagtcc | cccaagcaag | tctcaaagcc | agtgatctct | 120 |
| ctgactttca | atcagtttcc | aagctaaacc | aggggcaagc | catgcacatg | cataggcaag | 180 |
| gaatgccagt | gtaagagatg | gcatgatatg | gaagtgtatt | cctttcagg | cctgcagagt | 240 |
| gtccctccct | tggctccaga | acgaagatcc | acacttgagg | actactctca | gtcgctgcac | 300 |
| gccagaactc | tgtctggctc | tccccgatcc | tgttctgagc | aagctcgagt | cttcgtggat | 360 |
| gatgtgacca | ttgaggacct | gtcaggctac | atggagtatt | acttgtatat | tcccaagaaa | 420 |
| atgtcccaca | tgggcagaaa | tgatgtacac | ctgatagcaa | gaagctaatt | catatgcttt | 480 |
| aaaccaatga | aggcttgtca | aagagattta | gttaatggca | gaccttgtgg | ccactttgtg | 540 |
| tgagaagaca | tctctttctg | ctca | | | | 564 |

<210> SEQ ID NO 40
<211> LENGTH: 339
<212> TYPE: DNA
<213> ORGANISM: Homo sapiens
<220> FEATURE:
<221> NAME/KEY: misc_feature
<222> LOCATION: (1)..(339)
<223> OTHER INFORMATION: AffymetrixID: 209146_at

<400> SEQUENCE: 40

```
gaacctcatc aattgatagc agtgagtgac tgaagcttcc aaatcaagaa aagccggcac      60
caagaacttc cattctaatc tagagctgac cagtttgagc tgattctctc tttgaagagt     120
ccttcttgat tgcagtgcag tactggcatt tctgaatgga tgtaagtgga gtattttagt     180
ctaaaggctt ttcaaattac ttgaattttt ttaaaaattg aggagcttta tttctattta     240
cccttccatt tttgtatatc aaatttccat tgtcattaaa aactgtatct tgaaactttg     300
tgaactgact tgctgtattt gcactttgag ctcttgaaa                            339
```

<210> SEQ ID NO 41
<211> LENGTH: 465
<212> TYPE: DNA
<213> ORGANISM: Homo sapiens
<220> FEATURE:
<221> NAME/KEY: misc_feature
<222> LOCATION: (1)..(465)
<223> OTHER INFORMATION: AffymetrixID: 209193_at

<400> SEQUENCE: 41

```
gattgtagtg gatctaattt ttcagaaatt ttgcctttaa gttatttttac ctgttttttgt     60 ttcttgtttt gaaagatgcg cattctaacc tggaggtcaa tgttatgtat ttatttattt    120
atttatttgg ttcccttcct attccaagct tccatagctg ctgccctagt tttcttttcct    180 cctttcctcc tctgacttgg ggaccttttg ggggagggct gcgacgcttg ctctgttttgt    240 ggggtgacgg gactcaggcg ggacagtgct gcagctccct ggcttctgtg gggcccctca    300
cctacttacc caggtgggtc ccggctctgt gggtgatggg gagggggcatt gctgactgtg    360 tatataggat aattatgaaa agcagttctg gatggtgtgc cttccagatc ctctctgggg    420
ctgtgttttg agcagcaggt agcctggctg gttttatctg agtga                    465
```

<210> SEQ ID NO 42
<211> LENGTH: 535
<212> TYPE: DNA
<213> ORGANISM: Homo sapiens
<220> FEATURE:
<221> NAME/KEY: misc_feature
<222> LOCATION: (1)..(535)
<223> OTHER INFORMATION: AffymetrixID: 209710_at

<400> SEQUENCE: 42

```
gatcccacag ccctagtatg aaagctgggg gtggggaggg gcctttgctg cccttggttt     60
ctgggggctg gttggcattt gctggcctgg caggggtga aggcaggagt tgggggcagg    120
tcaggaccag gacccaggga gaggctgtgt ccctgctggg gtctcaggtc cagctttact    180
gtggctgtct ggatccttcc caaggtacag ctgtatataa acgtgtcccg agcttagatt    240
ctgtatgcgt tgacggcggg gtgtggtggc ctgtgagggg ccctggccc aggaggagga    300 ttgtgctgat gtagtgacca agtgcaatat gggcgggcag tcgctgcagg gagcaccacg    360
gccagaagta acttatttttg tactagtgtc cgcataagaa aaagaatcgg cagtattttc    420 tgttttttatg ttttattttgg cttgtttttat tttggattag tgaactaagt tattgttaat    480
```

| | |
|---|---|
| tatgtacaac atttatatat tgtctgtaaa aaatgtatgc tatcctctta ttcct | 535 |

```
<210> SEQ ID NO 43
<211> LENGTH: 527
<212> TYPE: DNA
<213> ORGANISM: Homo sapiens
<220> FEATURE:
<221> NAME/KEY: misc_feature
<222> LOCATION: (1)..(527)
<223> OTHER INFORMATION: AffymetrixID: 210042_s_at

<400> SEQUENCE: 43
```

| | |
|---|---|
| gaaatctacg caaatggtcc catcagctgt ggaataatgg caacagaaag actggcaaac | 60 |
| tacaccggag gcatctatgc cgaataccag gacaccacat atataaacca tgtcgtttcc | 120 |
| gtggctgggt ggggcatcag tgatgggact gagtactgga ttgtccggaa ttcatggggt | 180 |
| gaaccatggg gcgagagagg ctggctgagg atcgtgacca gcacctataa ggatgggaag | 240 |
| ggcgccagat acaaccttgc catcgaggag cactgtacat ttggggaccc catcgtttaa | 300 |
| ggccatgtca ctagaagcgc agtttaagaa aaggcatggt gacccatgac cagaggggat | 360 |
| cctatggtta tgtgtgccag gctggctggc aggaactggg gtggctatca atattggatg | 420 |
| gcgaggacag cgtggtactg gctgcgagtg ttcctgagag ttgaaagtgg gatgacttat | 480 |
| gacacttgca cagcatggct ctgcctcaca atgatgcagt cagccac | 527 |

```
<210> SEQ ID NO 44
<211> LENGTH: 536
<212> TYPE: DNA
<213> ORGANISM: Homo sapiens
<220> FEATURE:
<221> NAME/KEY: misc_feature
<222> LOCATION: (1)..(536)
<223> OTHER INFORMATION: AffymetrixID: 210184_at

<400> SEQUENCE: 44
```

| | |
|---|---|
| cagttctgaa tatgctgctc atccccacct gtcttcaaca gctccccatt accctcagga | 60 |
| caatgtctga actctccagc ttcgcgtgag aagtcccctt ccatcccaga gggtgggctt | 120 |
| cagggcgcac agcatgagag cctctgtgcc cccatcaccc tcgtttccag tgaattagtg | 180 |
| tcatgtcagc atcagctcag ggcttcatcg tggggctctc agttccgatt ccccaggctg | 240 |
| aattgggagt gagatgcctg catgctgggt tctgcacagc tggcctcccg cggttgggtc | 300 |
| aacattgctg gcctggaagg gaggagcgcc ctctagggag ggacatggcc ccggtgcggc | 360 |
| tgcagctcac cagccccagg ggcagaagag acccaaccac ttcctatttt ttgaggctat | 420 |
| gaatatagta cctgaaaaaa tgccaagcac tagattattt ttttaaaaag cgtactttaa | 480 |
| atgtttgtgt taatacacat taaaacatcg cacaaaaacg atgcatctac cgctcc | 536 |

```
<210> SEQ ID NO 45
<211> LENGTH: 132
<212> TYPE: DNA
<213> ORGANISM: Homo sapiens
<220> FEATURE:
<221> NAME/KEY: misc_feature
<222> LOCATION: (1)..(132)
<223> OTHER INFORMATION: AffymetrixID: 210732_s_at

<400> SEQUENCE: 45
```

| | |
|---|---|
| cccagcttcc tagtaataga ggaggagaca tttctaaaat cgcacccaga actgtctaca | 60 |
| ccaagagcaa agattcgact gtcaatcaca ctttgacttg caccaaaata ccacctatga | 120 |
| actatgtgtc aa | 132 |

<210> SEQ ID NO 46
<211> LENGTH: 398
<212> TYPE: DNA
<213> ORGANISM: Homo sapiens
<220> FEATURE:
<221> NAME/KEY: misc_feature
<222> LOCATION: (1)..(398)
<223> OTHER INFORMATION: AffymetrixID: 210895_s_at

<400> SEQUENCE: 46
gtgtacataa atttgacctg ctcatctata cacggttacc cagaacctaa gaagatgagt     60
gttttgctaa gaaccaagaa ttcaactatc gagtatgatg gtattatgca gaaatctcaa    120
gataatgtca cagaactgta cgacgtttcc atcagcttgt ctgtttcatt ccctgatgtt    180
acgagcaata tgaccatctt ctgtattctg gaaactgaca gacgcggct tttatcttca     240 cctttctcta tagagcttga ggaccctcag cctcccccag accacattcc ttggattaca    300
gctgtacttc caacagttat tatatgtgtg atggttttct gtctaattct atggaaatgg    360
aagaagaaga agcggcctcg caactcttat aaatgtgg                            398

<210> SEQ ID NO 47
<211> LENGTH: 216
<212> TYPE: DNA
<213> ORGANISM: Homo sapiens
<220> FEATURE:
<221> NAME/KEY: misc_feature
<222> LOCATION: (1)..(216)
<223> OTHER INFORMATION: AffymetrixID: 211506_s_at

<400> SEQUENCE: 47
gtgtgaaggt gcagttttgc caaggagtgc taaagaactt agatgtcagt gcataaagac     60
atactccaaa cctttccacc ccaaatttat caaagaactg agagtgattg agagtggacc    120
acactgcgcc aacacagaaa ttattgtaaa gctttctgat ggaagagagc tctgtctgga    180
ccccaaggaa aactgggtgc agagggttgt ggagaa                              216

<210> SEQ ID NO 48
<211> LENGTH: 378
<212> TYPE: DNA
<213> ORGANISM: Homo sapiens
<220> FEATURE:
<221> NAME/KEY: misc_feature
<222> LOCATION: (1)..(378)
<223> OTHER INFORMATION: AffymetrixID: 211734_s_at

<400> SEQUENCE: 48
acatctccat tacaaatgcc acagttgaag acagtggaac ctactactgt acgggcaaag     60
tgtggcagct ggactatgag tctgagcccc tcaacattac tgtaataaaa gctccgcgtg    120
agaagtactg gctacaattt tttatcccat tgttggtggt gattctgttt gctgtggaca    180
caggattatt tatctcaact cagcagcagg tcacatttct cttgaagatt aagagaacca    240
ggaaaggctt cagacttctg aacccacatc ctaagccaaa ccccaaaaac aactgatata    300
attactcaag aaatatttgc aacattagtt tttttccagc atcagcaatt gctactcaat    360
tgtcaaacac agcttgca                                                  378

<210> SEQ ID NO 49
<211> LENGTH: 529
<212> TYPE: DNA
<213> ORGANISM: Homo sapiens
<220> FEATURE:
<221> NAME/KEY: misc_feature

```
<222> LOCATION: (1)..(529)
<223> OTHER INFORMATION: AffymetrixID: 211995_x_at

<400> SEQUENCE: 49
agtactcggt gtggatcggt ggctccatcc tggcctcact gtccaccttc cagcagatgt    60
ggattagcaa gcaggagtac gacgagtcgg gcccctccat cgtccaccgc aaatgcttct   120
aaacggactc agcagatgcg tagcatttgc tgcatgggtt aattgagaat agaaatttgc   180
ccctggcaaa tgcacacacc tcatgctagc ctcacgaaac tggaataagc cttcgaaaag   240
aaattgtcct tgaagcttgt atctgatatc agcactggat tgtagaactt gttgctgatt   300
ttgaccttgt attgaagtta actgttcccc ttggtatttg tttaataccc tgtacatatc   360
tttgagttca accttagta cgtgtggctt ggtcacttcg tggctaaggt aagaacgtgc     420
ttgtggaaga caagtctgtg gcttggtgag tctgtgtggc cagcagcctc tgatctgtgc   480
agggtattaa cgtgtcaggg ctgagtgttc tgggatttct ctagaggct               529

<210> SEQ ID NO 50
<211> LENGTH: 535
<212> TYPE: DNA
<213> ORGANISM: Homo sapiens
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (1)..(535)
<223> OTHER INFORMATION: AffymetrixID: 212314_at

<400> SEQUENCE: 50
tattttggta cctgtgcttg ccacagccct gttcctcaaa gctgaattga tagatttctc    60
tttgacttcc aagacctagc agttataagg caccttgaaa taaattgttt gtgcctggaa   120
atgcagggag ggcaatagct ttgtaaattg gtttacatt ttctccttga attttttctag   180 ggtcctagtg cttccgaatc atttaatggc attgtcggat atcttttaca tttcaattgc   240
aatccatgaa attacattta gaagattctt agtacttaac tgtagtcttc tccatgaatt   300
acacgttaga atagactggc agcaacngaa tatgcagcaa gtaagcctct agcttatagt   360
ttcatcccta cccctcatgc ctgcgtgagt ctgtacaggg atatgtgtgt gtgtgtgtgt   420
gtgtgtgtgt tagagaggaa gaggaagagc agaatgtctg tatactacat gctgctaagg   480
tagtgaataa atcagtaatg caatattgtg ggtccaaact actctttgca ctact        535

<210> SEQ ID NO 51
<211> LENGTH: 475
<212> TYPE: DNA
<213> ORGANISM: Homo sapiens
<220> FEATURE:
<221> NAME/KEY: misc_feature
<222> LOCATION: (1)..(475)
<223> OTHER INFORMATION: AffymetrixID: 212335_at

<400> SEQUENCE: 51
accacgcttg gctaagaaca cctaaatttt tatgtttctt ggctcaaaaa ccagttccat    60
ttctaatgtt gtcctcacaa gaaggctaat tggtggtgag acagcagggg aggaggaaga   120
gctgtggttt gtaacttgtt caactcaggc aataagcgat tttagcttta tttaaagtct   180
tctgtccagc tttaagcact ttgtaagaca tggctgaaag tagcttttct atcagaattg   240
cagatagtca tgttgggcta acagtcaatt ggatatattc ctttacctca catgaccca    300 gcaactgtgg tggtatctag aggtgaaaca ggcaagtgaa atggacacct ctgctgtgaa   360
```

```
tgttttagag aaggaaattc aaaaaatgtt gtaactgaaa gcactgttga atatgggtat      420
cggctttctt tttcactttg actcttaaca ttatcagtca acttccacat taatg          475
```

<210> SEQ ID NO 52
<211> LENGTH: 179
<212> TYPE: DNA
<213> ORGANISM: Homo sapiens
<220> FEATURE:
<221> NAME/KEY: misc_feature
<222> LOCATION: (1)..(179)
<223> OTHER INFORMATION: AffymetrixID: 212386_at

<400> SEQUENCE: 52

```
gagatttacc atgtatcagt gcctggcttt ttgttataaa gctttgtttg tctagtgctc      60
ttttgctata aaatagactg tagtacaccc tagtaggaaa aaaaaaaaac taaatttaaa     120
aataaaaaat atatttggct tattttttcgc aggagcaatc cttttatacc atgaatatt     179
```

<210> SEQ ID NO 53
<211> LENGTH: 295
<212> TYPE: DNA
<213> ORGANISM: Homo sapiens
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t
<220> FEATURE:
<221> NAME/KEY: misc_feature
<222> LOCATION: (1)..(295)
<223> OTHER INFORMATION: AffymetrixID: 212671_s_at

<400> SEQUENCE: 53

```
accaatgagg ttcctgaggt cacagtgttt tccaagtctc ccgtgacact gggtcagccc      60
aacaccctca tctgtcttgt ggacaacatc tttcctcctg tggtcaacat cacntggctg    120
agcaatgggc actcagtcac agaaggtgtt tctgagacca gcttcctctc caagagtgat    180
cattccttct tcaagatcag ttacctcacc ttcctccctt ctgntgatga gatttatgac    240
tgcaaggtgg agcactgggg cctggatgag cctcttctga aacactggga gcctg          295
```

<210> SEQ ID NO 54
<211> LENGTH: 565
<212> TYPE: DNA
<213> ORGANISM: Homo sapiens
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (1)..(565)
<223> OTHER INFORMATION: AffymetrixID: 212897_at

<400> SEQUENCE: 54

```
aaggagacct ttgaagcttt ttgagggcaa actttacctt tgtggtcccc aaatgatggc      60
atttctcttt gaatttatt agatactgtt atgtcccca agggtacagg aggggcatcc      120
ctcagcctat gggnaacacc caaactagga ggggttattg acaggaagga atgaatccaa    180
gtgaaggctt tctgctcttc gtgttacaaa ccagtttcag agttagcttt ctggggaggt    240
gtgtgtttgt gaaaggaatt caagtgttgc aggacagatg agctcaaggt aaggtagctt    300
tggcagcagg gctgatacta tgaggctgaa acaatccttg tgatgaagta gatcatgcag    360
```

-continued

```
tgacatacaa agaccaagga ttatgtatat ttttatatct ctgtggtttt gaaactttag    420
tacttagaat tttggccttc tgcactactc ttttgctctt acgaacataa tggactctta    480
agaatggaaa gggatgacat ttacctatgt gtgctgcctc attcctggtg aagcaactgc    540
tacttgttct ctatgcctct aaaat                                         565
```

```
<210> SEQ ID NO 55
<211> LENGTH: 358
<212> TYPE: DNA
<213> ORGANISM: Homo sapiens
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (218)..(218)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
```

```
<222> LOCATION: (1)..(358)
<223> OTHER INFORMATION: AffymetrixID: 212999_x_at

<400> SEQUENCE: 55
cactgcagaa tgaaggaaca tcccttgagg tgacccagcc aacctgtggc cagaaggagg      60
nttgtacctt gaaaagacac tgaaagcatt ttggngtgtn aagtaagggt gggcagagga     120
ggtagaaaat caattcaatt gtcgcatcat tcatggttct ttaatattga tgctcagtgc     180
antggcctna gaatatccca gcctctcttc tggtttgntg agtgctntnt aagtaagcat     240
ggtngaattg tttggggnca natatagtga nccttggtca ctggtgtttc aaacattctg     300
gnaagtcaca tcnatcaaga atanttttta nttttaagaa agcataacca gcaataaa      358

<210> SEQ ID NO 56
<211> LENGTH: 441
<212> TYPE: DNA
<213> ORGANISM: Homo sapiens
<220> FEATURE:
<221> NAME/KEY: misc_feature
<222> LOCATION: (1)..(441)
<223> OTHER INFORMATION: AffymetrixID: 213309_at

<400> SEQUENCE: 56
gtatgtagca atcctgcgtg tgaaggcaaa taaactcttt aacaggcaat tatattgctg      60
gccaaaatat gctatatttg tatacaaaga cattctaact cagttccagt atgaagaaag     120
attattcact ctagctccac tgagaaacat tttcctaagt gaaaacaatt tcttaagatg     180
gaaatggatt ggattgtcaa attattattt attggagaaa aaaacctgat ctacacattt     240
ttacttatat ggggttgcca gagtctctgg gttctagatg attttggtgg catgcttgct     300
gagccataat tactaaagag aatgtaagtg gacgggttcc ctgaatcccc ggggtccttg     360
gagagccatc gaggagaatg tgcaattgga ctgaagctcc ctggctgaag atacatgccg     420
agtcagcaca tgggtagaga t                                                441

<210> SEQ ID NO 57
<211> LENGTH: 431
<212> TYPE: DNA
<213> ORGANISM: Homo sapiens
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (1)..(431)
<223> OTHER INFORMATION: AffymetrixID: 213506_at

<400> SEQUENCE: 57
gcacacagag atttgagaac cattgttctg aatgctgctt ccatttgaca aagtgccgtg      60 ataattttg aaaagagaag caaacaatgg tgtctctttt atgttcagct tataatgaaa     120
tctgtttgtt gacttattag gactttgaat tatttcttta ttaaccctct gagttttngt     180
atgtattatt attaaagaaa aatgcaatca ggattttaaa catgtaaata caaattttgt     240
ataacttttg atgacttcag tgaaattttc aggtagtctg agtaatagat tgttttgcca     300
cttagaatag catttgccac ttagtatttt aaaaaataat tgttggagta tttattgtca     360
gttttgttca cttgttatct aatacaaaat tataaagcct tcagagggtt tggaccacat     420
ctctttggaa a                                                           431

<210> SEQ ID NO 58
<211> LENGTH: 251
```

```
<212> TYPE: DNA
<213> ORGANISM: Homo sapiens
<220> FEATURE:
<221> NAME/KEY: misc_feature
<222> LOCATION: (1)..(251)
<223> OTHER INFORMATION: AffymetrixID:  213883_s_at

<400> SEQUENCE: 58
agagaacttc tagtgtatgg atttaaagat ttctcttttt cattcatata ccattttatg      60
agttctgtat aattttttgt ggttttttgtt ttgttgagtt aaagtatatt attgtgagat    120
ttatttaata ggacttcctt tgaaagctgt ataatagtgt ttctcgggct tctgtctcta    180
tgagagatag cttattactc tgatactctt taatctttta caaaggcaag ttgccacttg    240 tcattttgt t                                                           251

<210> SEQ ID NO 59
<211> LENGTH: 332
<212> TYPE: DNA
<213> ORGANISM: Homo sapiens
<220> FEATURE:
<221> NAME/KEY: misc_feature
<222> LOCATION: (1)..(332)
<223> OTHER INFORMATION: AffymetrixID:  214305_s_at

<400> SEQUENCE: 59
gttctgaccc ctggaaagac accaattggc acaccagcca tgaacatggc taccctact      60 ccaggtcaca taatgagtat gactcctgaa cagcttcagg cttggcggtg ggaaagagaa    120
attgatgaga gaaatcgccc actttctgat gaggaattag atgctatgtt cccagaagga    180
tataaggtac ttcctcctcc agctggttat gttcctattc gaactccagc tcgaaagctg    240
acagctactc caaacccttt gggtggtatg actggtttcc acatgcaaac tgaagatcga    300
actatgaaaa gtgttaatga ccagccatct gg                                   332

<210> SEQ ID NO 60
<211> LENGTH: 241
<212> TYPE: DNA
<213> ORGANISM: Homo sapiens
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (1)..(241)
<223> OTHER INFORMATION: AffymetrixID:  214512_s_at

<400> SEQUENCE: 60
gaccaagagg gtgttcgact gctagagccg ancgaagcga tgcctaaatc aaaggaactt      60
gtttcttcaa gctcttctgg cagtgattct gacagtgagg ttgacaaaaa gttaaagagg    120
aaaaagcaag ttgctccaga aaacctgta aagaaacaaa agacaggtga gacttcgaga     180
gccctgtcat cttctaaaca gagcagcagc agcagagatg ataacatgtt tcagattggg    240
a                                                                     241

<210> SEQ ID NO 61
<211> LENGTH: 436
<212> TYPE: DNA
<213> ORGANISM: Homo sapiens
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
```

```
<222> LOCATION: (244)..(244)
<223> OTHER INFORMATION: n is a, c, g, or t
<220> FEATURE:
<221> NAME/KEY: misc_feature
<222> LOCATION: (250)..(252)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (304)..(304)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (1)..(436)
<223> OTHER INFORMATION: AffymetrixID:  214807_at

<400> SEQUENCE: 61
tcttcattcc acgagaattt tgattttaa cagcagtctc tcttttctc agcattgcaa      60 atatatatgt atatatacat tcatgaccaa agtatcgctt actgaccatg cagctgtaaa    120
ccttctgtgc ctatcaaaca aatacatagc atgaanctaa ttttagaagt tcatggggg    180 aattttaggg gaaagtataa acctaagagt gagtgaatgg agatgattca tggaaaaaaa    240
aaanaaaaan nnanatgtgc tatnaggcag agttattaac ttcttttagt tgttgtttga    300
gatngngttc tgctcttgtt ncccaggctg gagtgcantg gcgtgatctc gtctcnctgc    360
aacctccgcc tcccaggttc aagcgattct cctgccccag ctactttgga ggctgaagtg    420
taagagttgc ttgagc                                                   436

<210> SEQ ID NO 62
<211> LENGTH: 448
<212> TYPE: DNA
<213> ORGANISM: Homo sapiens
<220> FEATURE:
<221> NAME/KEY: misc_feature
<222> LOCATION: (1)..(448)
<223> OTHER INFORMATION: AffymetrixID:  214953_s_at

<400> SEQUENCE: 62
atagattctc tcctgattat ttatcacata gccccttagc cagttgtata ttattcttgt     60
ggtttgtgac ccaattaagt cctactttac atatgcttta agaatcgatg ggggatgctt    120
catgtgaacg tgggagttca gctgcttctc ttgcctaagt attccttcc tgatcactat     180 gcattttaaa gttaaacatt tttaagtatt tcagatgctt tagagagatt ttttttccat   240
gactgcattt tactgtacag attgctgctt ctgctatatt tgtgatatag gaattaagag   300
gatacacacg tttgtttctt cgtgcctgtt ttatgtgcac acattaggca ttgagacttc   360
```

```
aagcttttct tttttgtcc acgtatcttt gggtctttga taaagaaaag aatccctgtt    420
cattgtaagc acttttacgg ggcgggtg                                      448

<210> SEQ ID NO 63
<211> LENGTH: 383
<212> TYPE: DNA
<213> ORGANISM: Homo sapiens
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (1)..(383)
<223> OTHER INFORMATION: AffymetrixID:  215726_s_at

<400> SEQUENCE: 63
gacagaccaa agttaaacaa gcctccggaa actcttatca ctactattga ttctagttcc    60
agttggtgga ccaactgggt gatccctgcc atctctgcag tggccgtcgc cttgatgtat   120
cgcctataca tggcagagga ctgaacacct cctcagaagt cagcgcagga agagcctgct   180
ttggacacgg gagaaaagaa gccattgcta actacttcaa ctgacagaaa ccttcacttg   240
aaaacaatga ttttaatata tctctttctt tttcttccga cattagaaac aaaacaaaaa   300
gaactgtcct ttctgcgcnc aaattttttcg agtgtgcctt tttattcatc tactttattt   360
tgatgtttcc ttaatgtgta att                                           383

<210> SEQ ID NO 64
<211> LENGTH: 492
<212> TYPE: DNA
<213> ORGANISM: Homo sapiens
<220> FEATURE:
<221> NAME/KEY: misc_feature
<222> LOCATION: (1)..(492)
<223> OTHER INFORMATION: AffymetrixID:  216016_at

<400> SEQUENCE: 64
gccaatgcta aaaagctgca gatccagccc agccagctgg aattgttcta ctgtttgtac    60
gagatgcagg aggaggactt cgtgcaaagg gccatggact atttccccaa gattgagatc   120
aatctctcca ccagaatgga ccacatggtt tcttcctttt gcattgagaa ctgtcatcgg   180
gtggagtcac tgtccctggg gtttctccat aacatgccca aggaggaaga ggaggaggaa   240
aaggaaggcc gacaccttga tatggtgcag tgtgtcctcc caagctcctc tcatgctgcc   300
tgttctcatg ggtaaggaaa ctcggcttcc aggtgcttcc tcctgcttcc tcgccagctt   360
cttcttggca cctgcctcct ctcatctctt ttcaactatc ttccaaatac tgttgccaca   420
gctacatcat aatgccacca ctgtctgttt gagactcctt catgagcaaa gattgatgta   480
tggtaggtgg at                                                       492

<210> SEQ ID NO 65
<211> LENGTH: 275
<212> TYPE: DNA
<213> ORGANISM: Homo sapiens
<220> FEATURE:
<221> NAME/KEY: misc_feature
<222> LOCATION: (1)..(275)
<223> OTHER INFORMATION: AffymetrixID:  217722_s_at

<400> SEQUENCE: 65
ggagatgcct cgtgaaacac agctgggcaa gtattaatgt atatggaaca gcctggattt    60
ctgcatatgg ataagccacc ttggaatagg aagaggtgtt gagcctggac tgtgggagga   120
```

```
aagagctgcg tggatagatt caaacttcct gtggtagtgc tcccagtctg acctctgtag    180
accttcagta ctcactcttc ttgcttaggc tctctgtgtg ttgaaagcca tcccgtgttg    240
catgtgttgt tacaattttc tgtgatactt gcaat                               275
```

<210> SEQ ID NO 66
<211> LENGTH: 339
<212> TYPE: DNA
<213> ORGANISM: Homo sapiens
<220> FEATURE:
<221> NAME/KEY: misc_feature
<222> LOCATION: (1)..(339)
<223> OTHER INFORMATION: AffymetrixID: 217753_s_at

<400> SEQUENCE: 66

```
tggtcgtgcc aaaaagggcc gcggccacgt gcagcctatt cgctgcacta actgtgcccg     60
atgcgtgccc aaggacaagg ccattaagaa attcgtcatt cgaaacatag tggaggccgc    120
agcagtcagg gacatttctg aagcgagcgt cttcgatgcc tatgtgcttc ccaagctgta    180
tgtgaagcta cattactgtg tgagttgtgc aattcacagc aaagtagtca ggaatcgatc    240
tcgtgaagcc cgcaaggacc gaacacccCC accCcgattt agacctgcgg gtgctgcccC    300
agctccccca ccaaagccca tgtaaggagc tgagttctt                           339
```

<210> SEQ ID NO 67
<211> LENGTH: 532
<212> TYPE: DNA
<213> ORGANISM: Homo sapiens
<220> FEATURE:
<221> NAME/KEY: misc_feature
<222> LOCATION: (1)..(532)
<223> OTHER INFORMATION: AffymetrixID: 217970_s_at

<400> SEQUENCE: 67

```
tgagctggag ctggttggac taatgagact gaggaagcag cttttcctac gatctgcatt     60
atgtaatcac aggtccagag agctttatgg aagcgggaga ggaggagcac ttactcatgt    120
tgtatttgtt aatggaggat gtcatctttt catagatgct agaactagag tgcacttgtt    180
agatgctaaa ggtttgagct ttacacaaaa tgtcttcatc tgtatttgtt attgtctaca    240
atatatttga atttggggca gcatattaag atgtaatggc ctgttatgtc ttgaaaatac    300
ttgttttgcc tcttccaggc atactgcatt ctgtggatca gtttgaacag cttctccacc    360
ttatttggac agtgataaat tgaaccaaga gtgtagattt acaagtgtaa ccttcaaaag    420
aggaagaact atttggggtc tgtaggtaat gaacagtcac accaaaatag actatgatgc    480
ttttgttaag aaaggtttca tgttttagat attttccgtg tcctaaataa tt            532
```

<210> SEQ ID NO 68
<211> LENGTH: 379
<212> TYPE: DNA
<213> ORGANISM: Homo sapiens
<220> FEATURE:
<221> NAME/KEY: misc_feature
<222> LOCATION: (1)..(379)
<223> OTHER INFORMATION: AffymetrixID: 218190_s_at

<400> SEQUENCE: 68

```
tgaagaaaca tggcggccgc gacgttgact tcgaaattgt actccctgct gttccgcagg     60
acctccacct tcgccctcac catcatcgtg ggcgtcatgt tcttcgagcg cgccttcgat    120
caaggcgcgg acgctatcta cgaccacatc aacgagggga agctgtggaa acacatcaag    180
cacaagtatg agaacaagta gttccttgga ggcccccatc caggccagaa ggaccaggtc    240
```

```
cacccagcag ctgtttgccc agagctggag cctcagcttg aagatgatgc tcaaggtact    300
cttcatggac caccattcgc tgttggcaag aaacggcttt acttacaaaa cagactcttt    360
accttctgct gtgtttgaa                                                 379

<210> SEQ ID NO 69
<211> LENGTH: 545
<212> TYPE: DNA
<213> ORGANISM: Homo sapiens
<220> FEATURE:
<221> NAME/KEY: misc_feature
<222> LOCATION: (1)..(545)
<223> OTHER INFORMATION: AffymetrixID:  218345_at

<400> SEQUENCE: 69
gatttccgat atggctactc ttattacaac agtgcctgcc gcatctccag ctcgagtgac     60
tggaacactc cagcccccac tcagagtcca gaagaagtca aaggctaca cctatgtacc    120 tccttcatgg acatgctgaa ggccttgttc agaacccttc aggccatgct cttgggtgtt    180
tggattctgc tgcttctggc atctctggcc cctctgtggc tgtactgctg gagaatgttc    240
ccaaccaaag ggaaaagaga ccagaaggaa atgttggaag tgagtggaat ctagccatgc    300
ctctcctgat tattagtgcc tggtgcttct gcaccgggcg tccctgcatc tgactgctgg    360
aagaagaacc agactgagga aaagaggctt ttcaacagcc ccagttatcc tggccccatg    420
accgtggcca cagccctgct ccagcagcac ttgcccattc cttacacccc ttccccatcc    480
tgctccgctt catgtcccct cctgagtagt catgtgataa taaactctca tgttattgtt    540
cccag                                                                545

<210> SEQ ID NO 70
<211> LENGTH: 557
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (1)..(557)
<223> OTHER INFORMATION: AffymetrixID:  218486_at

<400> SEQUENCE: 70
gactgtacac actataaatg gcatcaaatt tggatatttt tcttaattat gacatgcaaa     60
gtaatgtgag tcctgccagt attctggtgg ataaggtctt ntgagtattt ggttgcttgt    120
cacaacattc tccaagcagt gatatttcta aagaggagat acatgttgaa aacggtttta    180
atttacactt ccatttcctg attacatttg gaaatacttt gtgtaaacca tcccccttcc    240
acctccattt gtctgttgaa agattttaag ttggaaacag ttcctgtctg aaaactcttc    300
tgagaaccac aaaccttgtg tatggattcg gcatggagcc ctcagctggc ggctctgggt    360
gctgacggcc gctggagagg tgggctcccc tcgtgcactt tattgcctgg gcagttttgc    420
ttgatctttt gtgactttga gccttttaag tagtttgaat gataagactt aaaatgtttc    480
ataattatgt tttatgtaac agactttgac attatttaaa cgagcatgtg taatgtaact    540
tttctctttg aatcata                                                   557

<210> SEQ ID NO 71
<211> LENGTH: 541
<212> TYPE: DNA
<213> ORGANISM: Homo sapiens
```

```
<220> FEATURE:
<221> NAME/KEY: misc_feature
<222> LOCATION: (1)..(541)
<223> OTHER INFORMATION: AffymetrixID:  218545_at

<400> SEQUENCE: 71
agcatggatt tcaacatcac ttatttatct gtataattgg aaataaaaca ccgatatgat    60
agagaatcat tccggcatta cctaacctct tctgcagttg gatctatgta ttttcattgg   120
tctactgaaa acgaacaata caattaaaag cactaaagat tattatatta attcaacttt   180
gatctgatat atcacttaaa ctaaaggggt gtgtgtggtg tatgcttgtt tcctatttct   240 gctcttttaaa gatactttga atcaataaaa ccattagtct acaaatcaaa ttgtgaactt   300
aatctctaga aagagaatat aactcagcca tttataggaa tttaggttca agtacaggat   360
atatgaaatc ttttcccagt atttcagaat gtacttaatt cacaggcagg atgcttcaat   420
gcaaaatcat gaatatttt aattcaaaac taaaatgtca ttaatatgta tgtatgcaaa   480
tgttttatct tattttctga aatgcatcta ctttcatggg ctttgtacgt ttctgagatt   540
t                                                                   541

<210> SEQ ID NO 72
<211> LENGTH: 160
<212> TYPE: DNA
<213> ORGANISM: Homo sapiens
<220> FEATURE:
<221> NAME/KEY: misc_feature
<222> LOCATION: (1)..(160)
<223> OTHER INFORMATION: AffymetrixID:  218728_s_at

<400> SEQUENCE: 72
atatcgatac attatggtgc cgagtggtaa catgggagtg tttgatccaa cagaaataca    60
caatcgaggg cagctgaagt cacacatgaa agaagccatg atcaagcttg gtttccactt   120
gctctgcttc ttcatgtatc tttatagtat gatcttagct                         160

<210> SEQ ID NO 73
<211> LENGTH: 461
<212> TYPE: DNA
<213> ORGANISM: Homo sapiens
<220> FEATURE:
<221> NAME/KEY: misc_feature
<222> LOCATION: (1)..(461)
<223> OTHER INFORMATION: AffymetrixID:  219269_at

<400> SEQUENCE: 73
aggctagaaa atcttgctgc tccgtcttag cattccaaga gagtgcttcc aggtatttag    60
atagccctca gttctcaaat attagactac gtgtaaaatc ttgggtacct ttagattctt   120
gtaacactag tctgtactcc cttttccttc cccaagactg ataggatgca agctgaggtc   180
gtggcacagg aatgacagac accatttggg gagtatccac agagtcaaag gaacactaga   240
atccccacct cagcgtgagg ataattgatt tccagctgca ataagccgtg cctcattata   300
gccacactgt ggctagatta tacttctttg ggtgctgtgc taagaatgtc aatggaaaaa   360
gccgatctca gattttgttt gaagttaaca tgcctgacac agacatcctt tcctctcaca   420
agctgtgtga cttagtagat aaaatactgc cttctgcctt t                       461

<210> SEQ ID NO 74
<211> LENGTH: 563
<212> TYPE: DNA
<213> ORGANISM: Homo sapiens
<220> FEATURE:
<221> NAME/KEY: misc_feature
```

```
<222> LOCATION: (1)..(563)
<223> OTHER INFORMATION: AffymetrixID: 219410_at

<400> SEQUENCE: 74
tgtttctcac catatgcttt tgttggcatt atgcagtaac cattgtcatc gttggaatga      60
attatgcttt cattacctgg ttggttaaat ctagacttaa gaggctctgc tcctcagaag     120
ttggacttct gaaaaatgct gaacgagaac aagaatcaga agaagaaatg tgactttgat     180
gagcttccag ttttttctaga taaacctttt cttttttaca ttgttcttgg ttttgtttct    240
cgatcttttg tttggagaac agctggctaa ggatgactct aagtgtactg tttgcatttc     300
caatttggtt aaagtatttg aatttaaata ttttctttttt agctttgaaa atattttggg    360
tgatactttc attttgcaca tcatgcacat catggtattc aggggctaga gtgattttt     420
tccagattat ctaaagttgg atgcccacac tatgaaagaa atatttgttt tatttgcctt     480
atagatatgc tcaaggttac tgggcttgct actatttgta actccttgac catggaatta    540
tacttgttta tcttgttgct gca                                             563

<210> SEQ ID NO 75
<211> LENGTH: 472
<212> TYPE: DNA
<213> ORGANISM: Homo sapiens
<220> FEATURE:
<221> NAME/KEY: misc_feature
<222> LOCATION: (1)..(472)
<223> OTHER INFORMATION: AffymetrixID: 219862_s_at

<400> SEQUENCE: 75
cggccaagga gctgttcaac gaggatgtgg aggaggtcac ttaccgagcc ctgagaaaca      60
aagacttcca agaggtcacc cttgagaaga acgagaggg ggtgttacgc tttgctgcag     120
cctatggctt tcgaaacatc cagaacatga tcctgaagct taagaagggc aagttcccat     180
tccactttgt ggaggtcctc gcctgtgctg gaggatgctt aaatggcaga ggccaagccc     240
agactccaga cggacatgcg gataaggccc tgctgcggca gatggaaggc atttacgctg     300
acatccctgt gcggcgtccg gagtccagtg cacacgtgca ggagctgtac caggagtggc     360
tggaggggat caactccccc aaggcccgag aggtgctgca taccacgtac cagagccagg     420
agcgtggcac acacagcctg gacatcaagt ggtgaagtca ggccagggcc tt            472

<210> SEQ ID NO 76
<211> LENGTH: 396
<212> TYPE: DNA
<213> ORGANISM: Homo sapiens
<220> FEATURE:
<221> NAME/KEY: misc_feature
<222> LOCATION: (1)..(396)
<223> OTHER INFORMATION: AffymetrixID: 219905_at

<400> SEQUENCE: 76
ggctcacgtg attatggagg cggttaaatc ccaagatctg caggataagt cagcaagatg      60
gagtcccatg agagctgatg gtttagttcc agtctgatgg cagcaggctt gacgccaagg     120
aagagatgat gtttaattca agtccgaagg caaggaaaaa gctgatggtc ctgtccaaag     180
gctattaggc aggaagaatt ctcttagggc agagttagct cttttgttct attcaggcct    240
tcaactgatt cagcaaggcc cgcccacatt gggaggaca gtctgcatta ctcagtctac     300
tgatttgaat gttaatgtca ttgcgaaaca ccctcacagg aacactcaga ataatgtttg     360
accaaatagc tgggcatctt gtgacccagt taagtg                               396
```

<210> SEQ ID NO 77
<211> LENGTH: 533
<212> TYPE: DNA
<213> ORGANISM: Homo sapiens
<220> FEATURE:
<221> NAME/KEY: misc_feature
<222> LOCATION: (1)..(533)
<223> OTHER INFORMATION: AffymetrixID: 220532_s_at

<400> SEQUENCE: 77

| | | | | | |
|---|---|---|---|---|---|
| atctggcaaa | ctgaaccctt | tttatacatc | gacactgtgt | gtgatcgctc | agaccctgtc | 60 |
| ttccctacca | ctgggtacag | atggatgcgg | cgaagtcaag | agaaccaatg | gcagaaggag | 120 |
| gagtgtagag | cttacatgca | gatgctgagg | aagttgttca | cagcaatccg | tgccctgttc | 180 |
| ctggctgtct | gtgtcttgaa | ggtcattgtg | tccttggttt | ccttgggagt | aggtcttcga | 240 |
| aacttgtgtg | gccagagctc | ccagcccctg | aatgaggaag | gatcagagaa | gaggctactg | 300 |
| ggggagaatt | cagtgccccc | ttcgccctct | agggagcaga | cctccactgc | cattgtcctg | 360 |
| tgagccgcca | aagaccccac | ggggtgcccg | catgtccctg | tctagggcag | cccagggccc | 420 |
| ccactcctgg | ctcctcacac | ttgcctcccc | tatggccgct | ctccagaccc | tcctcctttc | 480 |
| ttctccccac | atccgcacct | gctgttccca | ctctggggtt | ctcaagtcca | tga | 533 |

<210> SEQ ID NO 78
<211> LENGTH: 488
<212> TYPE: DNA
<213> ORGANISM: Homo sapiens
<220> FEATURE:
<221> NAME/KEY: misc_feature
<222> LOCATION: (1)..(488)
<223> OTHER INFORMATION: AffymetrixID: 221011_s_at

<400> SEQUENCE: 78

| | | | | | |
|---|---|---|---|---|---|
| gagtggttca | tccatactct | cattccctcg | cctcccttg | tggacggggg | tcttgccttt | 60 |
| tcaattcctg | tgttttggtg | tcttccctta | tctgctaccc | tgaatcacct | gtcctggtct | 120 |
| tgctgtgtga | tgggaacatg | cttgtaaact | gcgtaacaaa | tctactttgt | gtatgtgtct | 180 |
| gtttatgggg | gtggtttatt | attttttgctg | gtccctagac | cactttgtat | gaccgtttgc | 240 |
| agtctgagca | ggccagggc | tgacagctaa | tgtcaggacc | ctcagcggtg | gagcctgctg | 300 |
| ggggacccca | gctgctcttg | gacaagtggc | tgagctccta | tctggcctcc | tcttttttt | 360 |
| ttttttcaag | taatttgtgt | gtatttctaa | ctgattgtat | tgaaaaaatt | cctagtattt | 420 |
| cagtaaaaat | gcctgttgtg | agatgaacct | cctgtaactt | ctatctgttc | tttttttgagg | 480 |
| ctcaggga | | | | | | 488 |

<210> SEQ ID NO 79
<211> LENGTH: 526
<212> TYPE: DNA
<213> ORGANISM: Homo sapiens
<220> FEATURE:
<221> NAME/KEY: misc_feature
<222> LOCATION: (1)..(526)
<223> OTHER INFORMATION: AffymetrixID: 221042_s_at

<400> SEQUENCE: 79

| | | | | | |
|---|---|---|---|---|---|
| tgacccatg | gacagccatc | agtcccagga | atccccaaac | ctggaaaaca | tagcaaaccc | 60 |
| cctagaagaa | aatgtaacga | aagaatcaat | cagtagtaaa | aaaaaggaaa | aaggaaaca | 120 |
| tgtggaccac | gtagaaagtt | cactatttgt | agcaccagga | agtgttcaat | cctcagatga | 180 |
| cctagaagaa | gacagtagcg | actacagcat | tccttccagg | actagtcaca | gtgactccag | 240 |
| catttacctt | cgacgacata | ctcataggtc | ttcggaatcg | gatcatttta | gctatgttca | 300 |

| | | |
|---|---|---|
| gttgaggaac gcagcagatc tggatgacag aagaaaccga atattaacca ggaaggccaa | 360 | |
| cagctcagga gaagccatgt cactggggag ccacagcccg cagagtgact ccctgacaca | 420 | |
| gcttgtccag cagccggata tgatgtattt tattctcttc ctgtggctcc tggtgtactg | 480 | |
| cttgctgctc ttcccacaac tggatgttag caggctctga tacgtg | 526 | |

```
<210> SEQ ID NO 80
<211> LENGTH: 230
<212> TYPE: DNA
<213> ORGANISM: Homo sapiens
<220> FEATURE:
<221> NAME/KEY: misc_feature
<222> LOCATION: (1)..(230)
<223> OTHER INFORMATION: AffymetrixID: 221434_s_at

<400> SEQUENCE: 80
```

| | | |
|---|---|---|
| cctcagcagc gcgaggtgct gcggcgctgc gtagaagtat caatcagccg gttgcttttg | 60 | |
| tgagaagaat tccttggact gcggcgtcga gtcagctgaa agaacacttt gcacagttcg | 120 | |
| gccatgtcag aagtgcatt ttaccttttg acaaggagac tggctttcac agaggtttgg | 180 | |
| gttgggttca gttttcttca gaagaaggac ttcggaatgc actacaacag | 230 | |

```
<210> SEQ ID NO 81
<211> LENGTH: 350
<212> TYPE: DNA
<213> ORGANISM: Homo sapiens
<220> FEATURE:
<221> NAME/KEY: misc_feature
<222> LOCATION: (1)..(350)
<223> OTHER INFORMATION: AffymetrixID: 221737_at

<400> SEQUENCE: 81
```

| | | |
|---|---|---|
| gaaatctatt tttaactctt atgttcgtag agaaattgtt tcaaggkattt tgagtcatag | 60 | |
| gtctgtaatt tatagagatc tctagaattc ttattgtaat tttcctactt ctttgataaa | 120 | |
| agaaaaataa gtcagattgt taactccaag attgaaaaaa aaaactcttg aaagaagatt | 180 | |
| attagttgta actaatttgg gggttctggg cacagacatc taacctggta ttgtaaggca | 240 | |
| gaggctccca ttggaatggt agtggtccgg gtcagttgtt catggtgtaa gctttgcaca | 300 | |
| gtgtattaac attgggaggg tctggcttga aaatttggcc accctcagcc | 350 | |

```
<210> SEQ ID NO 82
<211> LENGTH: 97
<212> TYPE: DNA
<213> ORGANISM: Homo sapiens
<220> FEATURE:
<221> NAME/KEY: misc_feature
<222> LOCATION: (1)..(97)
<223> OTHER INFORMATION: AffymetrixID: AFFX-M27830_5_at

<400> SEQUENCE: 82
```

| | | |
|---|---|---|
| tagtttacc ctactgatga tgtgttgttg ccatggtaat cctgctcagt acgagaggaa | 60 | |
| ccgcaggttc agacatttgg tgtatgtgct tggctga | 97 | |

```
<210> SEQ ID NO 83
<211> LENGTH: 535
<212> TYPE: DNA
<213> ORGANISM: Homo sapiens
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
```

```
<222> LOCATION: (43)..(44)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (171)..(465)
<223> OTHER INFORMATION: n is a, c, g, or t
<220> FEATURE:
<221> NAME/KEY: misc_feature
<222> LOCATION: (1)..(535)
<223> OTHER INFORMATION: AffymetrixID:  36711_at

<400> SEQUENCE: 83
ttgcacggat ctaagttatt ctccccagcc agagcccgng ctnnctgctc ccngggaaaa      60
gntggcgtan tggncctgag ctgggnttta tattttatat ctgcaaataa atnacatttt     120
atcntanatt tagggaaagc cngagagnaa caacaaaaaa tgtttaagcc nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnntattg cccggctcct     480
agaatttatt tatttcctga cttacagcaa gcgagttatc gtcttctgta ttttg          535

<210> SEQ ID NO 84
<211> LENGTH: 494
<212> TYPE: DNA
<213> ORGANISM: Homo sapiens
<220> FEATURE:
<221> NAME/KEY: misc_feature
<222> LOCATION: (124)..(124)
<223> OTHER INFORMATION: n is a, c, g, or t
```

```
<220> FEATURE:
<221> NAME/KEY: misc_feature
<222> LOCATION: (184)..(184)
<223> OTHER INFORMATION: n is a, c, g, or t
<220> FEATURE:
<221> NAME/KEY: misc_feature
<222> LOCATION: (237)..(262)
<223> OTHER INFORMATION: n is a, c, g, or t
<220> FEATURE:
<221> NAME/KEY: misc_feature
<222> LOCATION: (447)..(464)
<223> OTHER INFORMATION: n is a, c, g, or t
<220> FEATURE:
<221> NAME/KEY: misc_feature
<222> LOCATION: (1)..(494)
<223> OTHER INFORMATION: AffymetrixID: 38037_at

<400> SEQUENCE: 84
ccactctatg agttggactt cagtcttgcc taggcgattt tgtctaccat ttgtgttttg      60
aaagcccaag gtgctgatgt caaagtgtaa cagatatcag tgtctccccg tgtcctctcc     120
ctgncaagtc tcagaagagg ttgggcttcc atgcctgtag ctttcctggt ccctcacccc     180
catngcccca ggcccacagc gtgggaactc actttccctt gtgtcaagac atttctnnnn     240
nnnnnnnnnn nnnnnnnnnn nnactccatg caggggtcag tgcagcagag gacagtctgg     300
agaaggtatt agcaaagcaa aaggctgaga aggaacaggg aacattggag ctgactgttc     360
ttggtaactg attacctgcc aattgctacc gagaaggttg gaggtgggga aggctttgta     420
taatcccacc cacctcacca aaacgannnn nnnnnnnnnn nnnngtcctt tctggaagtt     480
tctggtgcca tttc                                                      494

<210> SEQ ID NO 85
<211> LENGTH: 492
<212> TYPE: DNA
<213> ORGANISM: Homo sapiens
<220> FEATURE:
<221> NAME/KEY: misc_feature
<222> LOCATION: (1)..(492)
<223> OTHER INFORMATION: AffymetrixID: 201386_s_at

<400> SEQUENCE: 85
ggagatcatc tgacactgct gaacgtctac catgctttta aacaaaatca tgaatcggtt      60
cagtggtgtt atgacaactt cattaactac aggtccctga tgtccgcaga caatgtacgc     120
cagcagctat ctcgaattat ggacagattt aatttgcctc gtcgaagtac tgactttaca     180
agcagggact attatattaa tataagaaaa gctttggtta ctgggtattt tatgcaggtg     240
gcacatttag aacgaacagg gcattactta actgtgaaag ataaccaggt ggttcagttg     300
catccctcta ctgttcttga ccacaaacct gaatgggtgc tttataatga gtttgttcta     360
acaacaaaga attcatccg gacatgtaca gatatcaagc cagaatggtt ggtgaaaatt     420
gcccctcaat attatgacat gagcaatttc ccacagtgtg aagcaaagag acagttggac     480
cgcatcattg cc                                                        492

<210> SEQ ID NO 86
<211> LENGTH: 378
<212> TYPE: DNA
<213> ORGANISM: Homo sapiens
<220> FEATURE:
<221> NAME/KEY: misc_feature
<222> LOCATION: (1)..(378)
<223> OTHER INFORMATION: AffymetrixID: 201890_at

<400> SEQUENCE: 86
gctactttga attaatctgc ctttatgttt gggagaagaa agctgagaca ttgcatgaaa      60
```

```
gatgatgaga gataaatgtt gatcttttgg ccccatttgt taattgtatt cagtatttga    120
acgtcgtcct gtttattgtt agttttcttc atcatttatt gtatagacaa ttttttaaatc  180 tctgtaatat gatacatttt cctatctttt aagttattgt tacctaaagt taatccagat   240
tatatggtcc ttatatgtgt acaacattaa aatgaaaggc tttgtcttgc attgtgaggt   300
acaggcggaa gttggaatca ggttttagga ttctgtctct cattagctga ataatgtgag   360
gattaacttc tgccagct                                                  378
```

<210> SEQ ID NO 87
<211> LENGTH: 448
<212> TYPE: DNA
<213> ORGANISM: Homo sapiens
<220> FEATURE:
<221> NAME/KEY: misc_feature
<222> LOCATION: (1)..(448)
<223> OTHER INFORMATION: AffymetrixID: 202219_at

<400> SEQUENCE: 87

```
aagcttcgag ctgttgcgtg tgtgagtctg ttgtgtggat gtgcgtgtgt ggtccccagc    60
cccagactgg attggaaaag tgcatggtgg gggcctcggg gctgtcccca cgctgtccct   120
ttgccacaag tctgtggggc aagaggctgc aatattccgt cctgggtgtc tgggctgcta   180
acctggcctg ctcaggcttc ccaccctgtg cggggcacac ccccaggaag ggaccctgga   240
cacggctccc acgtccaggc ttaaggtgga tgcacttccc gcacctccag tcttctgtgt   300
agcagcttta acccacgttt gtctgtcacg tccagtcccg agacggctga gtgaccccaa   360
gaaaggcttc cccgacaccc agacagaggc tgcagggctg gggctgggtg agggtggcgg   420
gcctgcgggg acattctact gtgctaaa                                      448
```

<210> SEQ ID NO 88
<211> LENGTH: 371
<212> TYPE: DNA
<213> ORGANISM: Homo sapiens
<220> FEATURE:
<221> NAME/KEY: misc_feature
<222> LOCATION: (1)..(371)
<223> OTHER INFORMATION: AffymetrixID: 202464_s_at

<400> SEQUENCE: 88

```
tattctgtcc tgagaccacg ggcaaagctc ttccattttg agagagaaga aaaactgttt   60
ggaaccacac caatgatatt tttctttgta atacttgaaa tttatttttt tattattttg  120
atagcagatg tgctatttat ttatttaata tatgtataag gagtcctaaa caatagaaag  180
ctgtagaagc tgtagagata ggcttcagtt gttaattggt ttggagcctc ctatgtgtga  240
cttatgactc tctgtgttct gtgtatttgt ctgaattaat gacctgggat ataaagctat  300
gctagctttc aaacaggaga tgccttcaga aagctttgta tattttgcag ttgccagacc  360
aataaaatac c                                                        371
```

<210> SEQ ID NO 89
<211> LENGTH: 530
<212> TYPE: DNA
<213> ORGANISM: Homo sapiens
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (1)..(530)
<223> OTHER INFORMATION: AffymetrixID: 203115_at -continued

<400> SEQUENCE: 89

| aactccaatt | caggagccct | tgcgagtata | tctgaagcac | ttatttgcta | aggaaacctg | 60 |
| aattgatanc | agtactgtgc | tgtctggaat | aatgtccttg | atactgagtt | gggaccagac | 120 |
| tggcttttat | agtgacaggc | aaagaggaat | ttattgagat | cactgctcat | ggcatttgtt | 180 |
| gctgtaagaa | gtgttgcctt | tgattgttac | taaccacgga | tgggtaacgg | tcatacatta | 240 |
| ggctagtgtt | tggtaggaca | aaatcttttt | agagctttga | gaattgtcat | cctgttggtc | 300 |
| aactttgaaa | tacaaatgtt | tgccctggta | attagcaatg | aactgctggc | agttcttca | 360 |
| gctgtgtata | tacggatctg | gcttttaatt | gatgaatcaa | cttctacaga | aacttttgca | 420 |
| gggacagtgt | tgatgaggca | gtttagcttg | ccagggtgat | gataaagccc | aggtccctgc | 480 |
| atgtatagtg | ctcttctaaa | gaatatgcat | tcttgaacta | cttaactttt | | 530 |

<210> SEQ ID NO 90
<211> LENGTH: 497
<212> TYPE: DNA
<213> ORGANISM: Homo sapiens
<220> FEATURE:
<221> NAME/KEY: misc_feature
<222> LOCATION: (1)..(497)
<223> OTHER INFORMATION: AffymetrixID: 203574_at

<400> SEQUENCE: 90

| gtatggtaca | ttcttctctt | actcctttct | cagtgcaagt | gactaacatt | caagattggt | 60 |
| ctctcaaatc | ggagcactgg | catcaaaaag | aactgagtgg | caaaactcag | aatagtttca | 120 |
| aaactggagt | tgttgaaatg | aaagacagtg | gctacaaagt | ttctgaccca | gagaacttgt | 180 |
| atttgaagca | ggggatagca | aacttatctg | cagaggttgt | ctcactcaag | agacttatag | 240 |
| ccacacaacc | aatctctgct | tcagactctg | gtaaattac | tactgagtaa | gagctgggca | 300 |
| tttagaaaga | tgtcatttgc | aatagagcag | tccatttttgt | attatgctga | attttcactg | 360 |
| gacctgtgat | gtcatttcac | tgtgatgtgc | acatgttgtc | tgtttggtgt | cttttttgtgc | 420 |
| acagattatg | atgaagatta | gattgtgtta | tcactctgcc | tgtgtatagt | cagatagtcc | 480 |
| atgcgaaggc | tgtatat | | | | | 497 |

<210> SEQ ID NO 91
<211> LENGTH: 326
<212> TYPE: DNA
<213> ORGANISM: Homo sapiens
<220> FEATURE:
<221> NAME/KEY: misc_feature
<222> LOCATION: (1)..(326)
<223> OTHER INFORMATION: AffymetrixID: 203887_s_at

<400> SEQUENCE: 91

| caggggtgt | gtctgctcag | taatttgagg | acaaccattc | cagactgctt | ccaatttttct | 60 |
| ggaatacatg | aaatatagat | cagttataag | tagcaggcca | agtcaggccc | ttattttcaa | 120 |
| gaaactgagg | aattttcttt | gtgtagcttt | gctctttggt | agaaaaggct | aggtacacag | 180 |
| ctctagacac | tgccacacag | ggtctgcaag | gtctttggtt | cagctaagct | aggaatgaaa | 240 |
| tcctgcttca | gtgtatggaa | ataaatgtat | catagaaatg | taacttttgt | aagacaaagg | 300 |
| ttttcctctt | ctattttgta | aactca | | | | 326 |

<210> SEQ ID NO 92
<211> LENGTH: 533
<212> TYPE: DNA
<213> ORGANISM: Homo sapiens

```
<220> FEATURE:
<221> NAME/KEY: misc_feature
<222> LOCATION: (1)..(533)
<223> OTHER INFORMATION: AffymetrixID:  203932_at

<400> SEQUENCE: 92
tcttacgggg acacttacac ctgtgtggta gagcacattg gggctcctga gcccatcctt      60
cgggactgga cacctgggct gtcccccatg cagaccctga aggtttctgt gtctgcagtg     120
actctgggcc tgggcctcat catcttctct cttggtgtga tcagctggcg gagagctggc     180
cactctagtt acactcctct tcctgggtcc aattattcag aaggatggca catttcctag     240
aggcagaatc ctacaacttc cactccaagt gagaaggaga ttcaaactca atgatgctac     300
catgcctctc caacatcttc aaccccctga cattatcttg gatcctatgg tttctccatc     360
caattctttg aatttcccag tctcccctat gtaaaactta gcaacttggg ggacctcatt     420
cctgggacta tgctgtaacc aaattattgt ccaaggctat atttctggga tgaatataat     480
ctgaggaagg gagttaaaga ccctcctggg gctctcagtg tgccatagag gac            533

<210> SEQ ID NO 93
<211> LENGTH: 419
<212> TYPE: DNA
<213> ORGANISM: Homo sapiens
<220> FEATURE:
<221> NAME/KEY: misc_feature
<222> LOCATION: (1)..(419)
<223> OTHER INFORMATION: AffymetrixID:  204131_s_at

<400> SEQUENCE: 93
ttaccattcc gggttcgagc atcacaagct tttgagcgca tggaactcca taaactaaca      60
aattacataa actaaagggg gattttcttt cttcttttgt ttggtagaaa attatccttt     120
tctaaaaact gaacaatggc acaattgttt gctatgtgca cccgtccagg acagaaccgt     180
gcataggcaa aaggagtgga gcacagcgtc cggcccagtg tgtttccggt tctgagtcag     240
ggtgatctgt ggacgggacc ccagcaccaa gtctacgggt gccagatcag tagggcctgt     300
gatttcctgt cagtgtcctc agctaatgtg aacagtgttg gtctgctggt tagaaactag     360
aatattgata ttttcaggaa agaaatcagc tcagctctcc actcattgcc aaatgtcac     419

<210> SEQ ID NO 94
<211> LENGTH: 507
<212> TYPE: DNA
<213> ORGANISM: Homo sapiens
<220> FEATURE:
<221> NAME/KEY: misc_feature
<222> LOCATION: (1)..(507)
<223> OTHER INFORMATION: AffymetrixID:  204419_x_at

<400> SEQUENCE: 94
acactcgctt ctggaacgtc tgaggttatc aataagctcc tagtccagac gccatgggtc      60
atttcacaga ggaggacaag gctactatca caagcctgtg gggcaaggtg aatgtggaag     120
atgctggagg agaaaccctg ggaaggctcc tggttgtcta cccatggacc cagaggttct     180
ttgacagctt tggcaacctg tcctctgcct ctgccatcat gggcaacccc aaagtcaagg     240
cacatggcaa gaaggtgctg acttccttgg gagatgccat aaagcacctg gatgatctca     300
agggcacctt tgcccagctg agtgaactgc actgtgacaa gctgcatgtg gatcctgaga     360
acttcaagct cctgggaaat gtgctggtga ccgttttggc aatccatttc ggcaaagaat     420
tcacccctga ggtgcaggct tcctggcaga agatggtgac tggagtggcc agtgccctgt     480
cctccagata ccactgagct cactgcc                                         507
```

<210> SEQ ID NO 95
<211> LENGTH: 309
<212> TYPE: DNA
<213> ORGANISM: Homo sapiens
<220> FEATURE:
<221> NAME/KEY: misc_feature
<222> LOCATION: (1)..(309)
<223> OTHER INFORMATION: AffymetrixID: 204467_s_at

<400> SEQUENCE: 95

```
ctcggaattc cctgaagcaa cactgccaga agtgtgtttt ggtatgcact ggttccttaa      60
gtggctgtga ttaattattg aaagtggggt gttgaagacc ccaactacta ttgtagagtg     120
gtctatttct cccttcaatc ctgtcaatgt ttgctttatg tattttgggg aactgttgtt     180
tgatgtgtat gtgtttataa ttgttataca tttttaattg agccttttat taacatatat     240
tgttattttt gtctcgaaat aattttttag ttaaaatcta ttttgtctga tattggtgtg     300
aatgctgta                                                             309
```

<210> SEQ ID NO 96
<211> LENGTH: 521
<212> TYPE: DNA
<213> ORGANISM: Homo sapiens
<220> FEATURE:
<221> NAME/KEY: misc_feature
<222> LOCATION: (1)..(521)
<223> OTHER INFORMATION: AffymetrixID: 204848_x_at

<400> SEQUENCE: 96

```
acactcgctt ctggaacgtc tgagattatc aataagctcc tagtccagac gccatgggtc      60
atttcacaga ggaggacaag gctactatca caagcctgtg gggcaaggtg aatgtggaag     120
atgctggagg agaaaccctg ggaaggctcc tggttgtcta cccatggacc cagaggttct     180
ttgacagctt tggcaacctg tcctctgcct ctgccatcat gggcaacccc aaagtcaagg     240
cacatggcaa gaaggtgctg acttccttgg gagatgccat aaagcacctg atgatctca      300
agggcacctt tgcccagctg agtgaactgc actgtgacaa gctgcatgtg atcctgaga     360
acttcaagct cctgggaaat gtgctggtga ccgttttggc aatccatttc ggcaaagaat     420
tcacccctga ggtgcaggct tcctggcaga agatggtgac tgcagtggcc agtgccctgt     480
cctccagata ccactgagcc tcttgcccat gattcagagc t                        521
```

<210> SEQ ID NO 97
<211> LENGTH: 472
<212> TYPE: DNA
<213> ORGANISM: Homo sapiens
<220> FEATURE:
<221> NAME/KEY: misc_feature
<222> LOCATION: (1)..(472)
<223> OTHER INFORMATION: AffymetrixID: 205239_at

<400> SEQUENCE: 97

```
atttcaaaat ttctgcattc acggagaatg caaatatata gagcacctgg aagcagtaac      60
atgcaaatgt cagcaagaat atttcggtga acggtgtggg gaaaagtcca tgaaaactca     120
cagcatgatt gacagtagtt tatcaaaaat tgcattagca gccatagctg cctttatgtc     180
tgctgtgatc ctcacagctg ttgctgttat tacagtccag cttagaagac aatacgtcag     240
gaaatatgaa ggagaagctg aggaacgaaa gaaacttcga caagagaatg gaaatgtaca     300
tgctatagca taactgaaga taaaattaca ggatatcaca ttggagtcac tgccaagtca     360
tagccataaa tgatgagtcg gtcctctttc cagtggatca taagacaatg gacccttttt     420
```

```
gttatgatgg ttttaaactt tcaattgtca cttttttatgc tatttctgta ta              472

<210> SEQ ID NO 98
<211> LENGTH: 477
<212> TYPE: DNA
<213> ORGANISM: Homo sapiens
<220> FEATURE:
<221> NAME/KEY: misc_feature
<222> LOCATION: (1)..(477)
<223> OTHER INFORMATION: AffymetrixID:  205571_at

<400> SEQUENCE: 98
gatcaggagc aatgccactg ctagcatacc ttccttagtg aaaaatcttt tggaaaagga       60
tcccactctg acctgtgaag tactaatgaa tgctgttgct acagagtatg ctgcctatca      120
tcaaattgat aatcacattc acctaataaa cccaacggat gagacactgt ttcctggaat      180
aaatagcaaa gccaaagaac tgcaaacttg ggagtggata tatggcaaaa ctccaaagtt      240
tagtataaat acttcctttc atgtgttata tgaacagtca cacttggaaa ttaaagtatt      300
catagacata aagaatggaa gaattgaaat ttgtaatatt gaagcacctg atcattggtt      360
gccattggaa atacgtgaca aattaaattc aagtcttatt ggcagtaagt tttgcccaac      420
tgaaactacc atgctaacaa atatattact tagaacatgt ccacaagacc acaaact        477

<210> SEQ ID NO 99
<211> LENGTH: 422
<212> TYPE: DNA
<213> ORGANISM: Homo sapiens
<220> FEATURE:
<221> NAME/KEY: misc_feature
<222> LOCATION: (1)..(422)
<223> OTHER INFORMATION: AffymetrixID:  205592_at

<400> SEQUENCE: 99
tgggggccac agactcaaca tgtgtgtgtg gtggggttcc agcccaacat agagtaacat       60
tatttgtacc tcccaggcta gctcagtcca tgggaggctc tcctgtccct gaaagctgac      120
acccaccttt caccacttcg cccatgctac agttcagttt cctcgtctgt aaaatgggga      180
tgataatggt acctaccttg cagtgttgtt ataaggatta aaggagacag tgcaagaaaa      240
ggccttggtt ggtgaagagc ccaacctcgg aggggagctg ctgggatcct ccttatcttg      300
actgggatgt ccctgtctcc ccctcccctt gctccttgaa catggccaag gaaagtgaaa      360
aacaaaaatt attcactctg ctagcaccct tccccttgat gcctgggaat aggttttgcc      420
aa                                                                    422

<210> SEQ ID NO 100
<211> LENGTH: 362
<212> TYPE: DNA
<213> ORGANISM: Homo sapiens
<220> FEATURE:
<221> NAME/KEY: misc_feature
<222> LOCATION: (1)..(362)
<223> OTHER INFORMATION: AffymetrixID:  205863_at

<400> SEQUENCE: 100
tagctccaca ttcctgtgca ttgagggggtt aacattaggc tgggaagatg acaaaacttg      60
aagagcatct ggagggaatt gtcaatatct tccaccaata ctcagttcgg aaggggcatt     120
ttgacaccct ctctaagggt gagctgaagc agctgcttac aaaggagctt gcaaacacca     180
tcaagaatat caaagataaa gctgtcattg atgaaatatt ccaaggcctg gatgctaatc     240
aagatgaaca ggtcgacttt caagaattca tatccctggt agccattgcg ctgaaggctg     300
```

```
cccattacca cacccacaaa gagtaggtag ctctctgaag gcttttacc cagcaatgtc    360
ct                                                                  362

<210> SEQ ID NO 101
<211> LENGTH: 416
<212> TYPE: DNA
<213> ORGANISM: Homo sapiens
<220> FEATURE:
<221> NAME/KEY: misc_feature
<222> LOCATION: (1)..(416)
<223> OTHER INFORMATION: AffymetrixID:  205900_at

<400> SEQUENCE: 101
tcaagtcctc tggtggcagt tccagcgtga ggtttgtttc taccacttat tccggagtaa    60
ccagataaag agatgccctc tgtttcatta gctctagttc tcccccagca tcactaacaa   120
atatgcttgg caagaccgag gtcgatttgt cccagcctta ccggagaaaa gagctatggt   180
tagttacact agctcatcct attccccag ctctttcttt tctgctgttt cccaatgaag    240
ttttcagatc agtggcaatc tcagttccct tgctatgacc ctgctttgtt ctttcccgag   300
aaacagttca gcagtgacca ccacccacat gacatttcaa gcaccacctt aagccagcca   360
gagtaggacc agttagacct agggtgtgga cagctccttg catcttaaca ctgtgc        416

<210> SEQ ID NO 102
<211> LENGTH: 560
<212> TYPE: DNA
<213> ORGANISM: Homo sapiens
<220> FEATURE:
<221> NAME/KEY: misc_feature
<222> LOCATION: (1)..(560)
<223> OTHER INFORMATION: AffymetrixID:  205950_s_at

<400> SEQUENCE: 102
gagccccatt cacaaatttt gacccctcta ctctccttcc ttcatccctg gatttctgga    60
cctaccctgg ctctctgact catcctcctc tttatgagag tgtaacttgg atcatctgta   120
aggagagcat cagtgtcagc tcagagcagc tggcacaatt ccgcagcctt ctatcaaatg   180
ttgaaggtga taacgctgtc cccatgcagc acaacaaccg cccaacccaa cctctgaagg   240
gcagaacagt gagagcttca ttttgatgat tctgagaaga aacttgtcct tcctcaagaa   300
cacagccctg cttctgacat aatccagtta aaataataat ttttaagaaa taaatttatt   360
tcaatattag caagacagca tgccttcaaa tcaatctgta aaactaagaa acttaaattt   420
tagttcttac tgcttaattc aaataataat tagtaagcta gcaaatagta atctgtaagc   480
ataagcttat cttaaattca agtttagttt gaggaattct ttaaaattac aactaagtga   540
tttgtatgtc tatttttttc                                               560

<210> SEQ ID NO 103
<211> LENGTH: 447
<212> TYPE: DNA
<213> ORGANISM: Homo sapiens
<220> FEATURE:
<221> NAME/KEY: misc_feature
<222> LOCATION: (1)..(447)
<223> OTHER INFORMATION: AffymetrixID:  205987_at

<400> SEQUENCE: 103
ccagctgttg ctggtttgtc atgcctccgg cttctaccca aagcctgttt gggtgacatg    60
gatgcggaat gaacaggagc aactgggcac taaacatggt gatattcttc ctaatgctga   120
tgggacatgg tatcttcagg tgatcctgga ggtggcatct gaggagcctg ctggcctgtc   180
```

-continued

| | |
|---|---|
| ttgtcgagtg agacacagca gtctaggagg ccaggacatc atcctctact ggggacacca | 240 |
| ctcttccatg aattggattg ccttggtagt gatagtgccc ttggtgattc taatagtcct | 300 |
| tgtgttatgg tttaagaagc actgctcata tcaggacatc ctgtgagact cttcccctg | 360 |
| actcccccat tgtgttaaga acccagcaac ccaggagcct agtacaatat agtgatgcca | 420 |
| tcccgtcgac tctccattta aattgtt | 447 |

```
<210> SEQ ID NO 104
<211> LENGTH: 490
<212> TYPE: DNA
<213> ORGANISM: Homo sapiens
<220> FEATURE:
<221> NAME/KEY: misc_feature
<222> LOCATION: (1)..(490)
<223> OTHER INFORMATION: AffymetrixID: 206025_s_at

<400> SEQUENCE: 104
```

| | |
|---|---|
| ggataccca ttgtgaagcc agggcccaac tgtggatttg gaaaaactgg cattattgat | 60 |
| tatggaatcc gtctcaatag gagtgaaaga tgggatgcct attgctacaa cccacacgca | 120 |
| aaggagtgtg gtggcgtctt tacagatcca aagcaaattt ttaaatctcc aggcttccca | 180 |
| aatgagtacg aagataacca atctgctac tggcacatta gactcaagta tggtcagcgt | 240 |
| attcacctga gttttttaga ttttgacctt gaagatgacc caggttgctt ggctgattat | 300 |
| gttgaaatat atgacagtta cgatgatgtc catggctttg tgggaagata ctgtggagat | 360 |
| gagcttccag atgacatcat cagtacagga aatgtcatga ccttgaagtt tctaagtgat | 420 |
| gcttcagtga cagctggagg tttccaaatc aaatatgttg caatggatcc tgtatccaaa | 480 |
| tccagtcaag | 490 |

```
<210> SEQ ID NO 105
<211> LENGTH: 479
<212> TYPE: DNA
<213> ORGANISM: Homo sapiens
<220> FEATURE:
<221> NAME/KEY: misc_feature
<222> LOCATION: (1)..(479)
<223> OTHER INFORMATION: AffymetrixID: 206111_at

<400> SEQUENCE: 105
```

| | |
|---|---|
| gtttacctgg gctcaatggt ttgaaaccca gcacatcaat atgacctccc agcaatgcac | 60 |
| caatgcaatg caggtcatta acaattatca acggcgatgc aaaaaccaaa atactttcct | 120 |
| tcttacaact tttgctaacg tagttaatgt ttgtggtaac ccaaatatga cctgtcctag | 180 |
| taacaaaact cgcaaaaatt gtcaccacag tggaagccag gtgcctttaa tccactgtaa | 240 |
| cctcacaact ccaagtccac agaatatttc aaactgcagg tatgcgcaga caccagcaaa | 300 |
| catgttctat atagttgcat gtgacaacag agatcaacga cgagaccctc cacagtatcc | 360 |
| ggtggttcca gttcacctgg atagaatcat ctaagctcct gtatcagcac tcctcatcat | 420 |
| cactcatctg ccaagctcct caatcatagc caagatccca tctctccata tactttggg | 479 |

```
<210> SEQ ID NO 106
<211> LENGTH: 524
<212> TYPE: DNA
<213> ORGANISM: Homo sapiens
<220> FEATURE:
<221> NAME/KEY: misc_feature
<222> LOCATION: (1)..(524)
<223> OTHER INFORMATION: AffymetrixID: 206834_at

<400> SEQUENCE: 106
```

```
ggagaagact gctgtcaatg ccctgtgggg caaagtgaac gtggatgcag ttggtggtga      60
ggccctgggc agattactgg tggtctaccc ttggacccag aggttctttg agtcctttgg     120
ggatctgtcc tctcctgatg ctgttatggg caacccaag gtgaaggctc atggcaagaa      180
ggtgctaggt gcctttagtg atggcctggc tcacctggac aacctcaagg gcactttttc     240
tcagctgagt gagctgcact gtgacaagct gcacgtggat cctgagaact tcaggctctt     300
gggcaatgtg ctggtgtgtg tgctggcccg caactttggc aaggaattca ccccacaaat     360
gcaggctgcc tatcagaagg tggtggctgg tgtggctaat gccctggctc acaagtacca     420
ttgagatcct ggactgtttc ctgataacca taagaagacc ctatttccct agattctatt     480
ttctgaactt gggaacacaa tgcctacttc aagggtatgg cttc                      524
```

```
<210> SEQ ID NO 107
<211> LENGTH: 560
<212> TYPE: DNA
<213> ORGANISM: Homo sapiens
<220> FEATURE:
<221> NAME/KEY: misc_feature
<222> LOCATION: (1)..(560)
<223> OTHER INFORMATION: AffymetrixID:  207332_s_at

<400> SEQUENCE: 107
aaggagagtc ccctgaaggt ctgacacgtc tgcctaccca ttcgtggtga tcaattaaat      60
gtaggtatga ataagttcga agctccgtga gtgaaccatc atataaacgt gtagtacagc    120
tgtttgtcat agggcagttg gaaacggcct cctaggaaaa agttcatagg gtctcttcag    180
gttcttagtg tcacttacct agatttacag cctcacttga atgtgtcact actcacagtc    240
tctttaatct tcagttttat ctttaatctc ctctttatc ttggactgac atttagcgta     300
gctaagtgaa aaggtcatag ctgagattcc tggttcgggt gttacgcaca cgtacttaaa    360
tgaaagcatg tggcatgttc atcgtataac acaatatgaa tacagggcat gcattttgca    420
gcagtgagtc tcttcagaaa acccttttct acagttaggg ttgagttact tcctatcaag    480
ccagtacgtg ctaacaggct caatattcct gaatgaaata tcagactagt gacaagctcc    540
tggtcttgag atgtcttctc                                                 560
```

```
<210> SEQ ID NO 108
<211> LENGTH: 482
<212> TYPE: DNA
<213> ORGANISM: Homo sapiens
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (1)..(482)
<223> OTHER INFORMATION: AffymetrixID:  208632_at

<400> SEQUENCE: 108
aacccagaat ggcacacact gctctgctgt agcatcatgt cagggcttcc tggactcagt      60
acacctctca gtttgtcttt taaaaaacag ctgaatcttt actacctatt tagttctcct    120
tgttaaagaa acaggggtgg gaataaaatg gatttaggna cacccagttt gaattgcagt    180
tttttttttt ctgacacatg gccaggctgt ggtgccagct taatgagta ggctgtcctt     240 ggcacttgca tgtgtgaaag gagggttttg cctcttcttg agcatggctt gagttggtaa    300
ggaaagctgt aactcacgaa gccctgagac ctgctacccc taagatcgag cttgttttca    360
gtgactggct tgagtcatag gaggaggagt ctggtacagc tgcaggagag cagggccatc    420
```

```
tgaagcggta gcattgccac catctccctc tcatctagag cagttttctt atgccttggt    480
tt                                                                  482

<210> SEQ ID NO 109
<211> LENGTH: 494
<212> TYPE: DNA
<213> ORGANISM: Homo sapiens
<220> FEATURE:
<221> NAME/KEY: misc_feature
<222> LOCATION: (1)..(494)
<223> OTHER INFORMATION: AffymetrixID:  209007_s_at

<400> SEQUENCE: 109
gaagatggaa ctcgaaatcc caatgaaaaa cctacccagc aaagaagcat agcttttagc     60
tctaataatt ctgtagcaaa gccaatacaa aaatcagcta aagctgccac agaagaggca    120
tcttcaagat caccaaaaat agatcagaaa aaaagtccat atggactgtg gatacctatc    180
taaaagaaga aaactgatgg ctaagtttgc atgaaaactg cactttattg caagttagtg    240
tttctagcat tatcccatcc ctttgagcca ttcaggggta cttgtgcatt taaaaaccaa    300
cacaaaaaga tgtaaatact taacactcaa atattaacat tttaggtttc tcttgcagat    360
atgagagata gcacagatgg accaaaggtt atgcacaggt gggagtcttt tgtatatagt    420
tgtaaatatt gtcttggtta tgtaaaaatg aaattttta  gacacagtaa ttgaactgta    480
ttcctgtttt gtat                                                     494

<210> SEQ ID NO 110
<211> LENGTH: 445
<212> TYPE: DNA
<213> ORGANISM: Homo sapiens
<220> FEATURE:
<221> NAME/KEY: misc_feature
<222> LOCATION: (1)..(445)
<223> OTHER INFORMATION: AffymetrixID:  209458_x_at

<400> SEQUENCE: 110
agagaaccca ccatggtgct gtctcctgcc gacaagacca cgtcaaggc cgcctggggt      60 aaggtcggcg cgcacgctgg cgagtatggt gcggaggccc tggagaggat gttcctgtcc    120
ttccccacca ccaagaccta cttcccgcac ttcgacctga gccacggctc tgcccaggtt    180
aagggccacg gcaagaaggt ggccgacgcg ctgaccaacg ccgtggcgca cgtggacgac    240
atgcccaacg cgctgtccgc cctgagcgac ctgcacgcgc acaagcttcg ggtggacccg    300
gtcaacttca agctcctaag ccactgcctg ctggtgaccc tggccgccca cctccccgcc    360
gagttcaccc ctgcggtgca cgcctccctg gacaagttcc tggcttctgt gagcaccgtg    420
ctgacctcca ataccgtta agctg                                          445

<210> SEQ ID NO 111
<211> LENGTH: 432
<212> TYPE: DNA
<213> ORGANISM: Homo sapiens
<220> FEATURE:
<221> NAME/KEY: misc_feature
<222> LOCATION: (1)..(432)
<223> OTHER INFORMATION: AffymetrixID:  209795_at

<400> SEQUENCE: 111
tagtctaatt gaatccctta aactcaggga gcatttataa atggcaaatg cttatgaaac     60
taagatttgt aatatttctc tcttttaga gaaatttgcc aatttacttt gttatttttc    120
cccaaaaaga atgggatgat cgtgtattta tttttttact tcctcagctg tagacaggtc    180
```

```
cttttcgatg gtacatattt ctttgccttt ataatctttt atacagtgtc ttacagagaa    240
aagacataag caaagactat gaggaatatt tgcaagacat agaatagtgt tggaaaatgt    300
gcaatatgtg atgtggcaaa tctctattag gaaatattct gtaatcttca gacctagaat    360
aatactagtc ttataatagg tttgtgactt tcctaaatca attctattac gtgcaatact    420
tcaatacttc at                                                        432
```

<210> SEQ ID NO 112
<211> LENGTH: 535
<212> TYPE: DNA
<213> ORGANISM: Homo sapiens
<220> FEATURE:
<221> NAME/KEY: misc_feature
<222> LOCATION: (1)..(535)
<223> OTHER INFORMATION: AffymetrixID: 210027_s_at

<400> SEQUENCE: 112

```
tgggatgaag cctttcgcaa gttcctgaag ggcctggctt cccgaaagcc ccttgtgctg     60
tgtggagacc tcaatgtggc acatgaagaa attgaccttc gcaacccccaa ggggaacaaa   120 aagaatgctg gcttcacgcc acaagagcgc caaggcttcg gggaattact gcaggctgtg   180
ccactggctg acagctttag gcacctctac cccaacacac cctatgccta cacctttttgg  240 acttatatga tgaatgctcg atccaagaat gttggttggc gccttgatta cttttttgttg  300 tcccactctc tgttacctgc attgtgtgac agcaagatcc gttccaaggc cctcgcgagt   360
gatcactgtc ctatcaccct atacctagca ctgtgacacc accccctaaat cactttgagc   420 ctgggaaata agccccctca actaccattc cttctttaaa cactcttcag agaaatctgc    480
attctatttc tcatgtataa aacgaggaat cctccaacca ggctcctgtg ataga         535
```

<210> SEQ ID NO 113
<211> LENGTH: 368
<212> TYPE: DNA
<213> ORGANISM: Homo sapiens
<220> FEATURE:
<221> NAME/KEY: misc_feature
<222> LOCATION: (220)..(220)
<223> OTHER INFORMATION: n is a, c, g, or t
<220> FEATURE:
<221> NAME/KEY: misc_feature
<222> LOCATION: (1)..(368)
<223> OTHER INFORMATION: AffymetrixID: 210254_at

<400> SEQUENCE: 113

```
atacaccagc agggcaatta gcagcttggg gaagttggaa gtctcgatgt tgtgatagta     60
gaccacggag gtgacagcag ccatgaacgc catcccggct ggcatgtaca ggtgcagatg    120
gtgggattcg gtcaccccat cagacaggat gccctctgca atctcacaca ccaggacgaa    180
gagcagcatg aaggtcagga tccaccgcag gttgtgcccn gggaaatgaa gccatgtgct    240
gtggtggatg tgcaccttgg agctctgact tccccatcca atgaagagga tggggaaggt    300
gatgaagagt aggaagacgt gcggcaccac gttgagcgcg tccacaaagc agccgttgtt    360
gaggaccc                                                              368
```

<210> SEQ ID NO 114
<211> LENGTH: 414
<212> TYPE: DNA
<213> ORGANISM: Homo sapiens
<220> FEATURE:
<221> NAME/KEY: misc_feature
<222> LOCATION: (1)..(414)
<223> OTHER INFORMATION: AffymetrixID: 210338_s_at

<400> SEQUENCE: 114

| | | | | |
|---|---|---|---|---|
| gaactgaatg | ctgacctgtt | ccgtggcacc | ctggacccag | tagagaaagc | ccttcgagat | 60 |
| gccaaactag | acaagtcaca | gattcatgat | attgtcctgg | ttggtggttc | tactcgtatc | 120 |
| cccaagattc | agaagcttct | ccaagacttc | ttcaatggaa | agaactgaa | taagagcatc | 180 |
| aaccctgatg | aagctgttgc | ttatggtgca | gctgtccagg | cagccatctt | gtctggagac | 240 |
| aagtctgaga | atgttcaaga | tttgctgctc | ttggatgtca | ctcctctttc | ccttggtatt | 300 |
| gaaactgctg | gtggagtcat | gactgtcctc | atcaagcgta | ataccaccat | tcctaccaag | 360 |
| cagacacaga | ccttcactac | ctattctgac | aaccagcctg | gtgtgcttat | tcag | 414 |

<210> SEQ ID NO 115
<211> LENGTH: 557
<212> TYPE: DNA
<213> ORGANISM: Homo sapiens
<220> FEATURE:
<221> NAME/KEY: misc_feature
<222> LOCATION: (1)..(557)
<223> OTHER INFORMATION: AffymetrixID: 211038_s_at

<400> SEQUENCE: 115

| | | | | |
|---|---|---|---|---|
| tggtgttcct | tgaatgccta | tcttcctttt | gtgcctcgga | acctctcacg | cctgccacaa | 60 |
| gttactcttt | tccttggtag | ttctgaactt | taaataaggt | aatgcctgta | agaatgccat | 120 |
| aaatgctcaa | taattgtcat | ctgttattat | tttcatcagt | aacatcatct | gaatcatcag | 180 |
| tattgtctgc | ttttaacagc | tgcattttc | attgtccaaa | tatagtcaca | tacatttgac | 240 |
| cattttataa | ttattgaata | ataaattcgt | tctgctattt | tacaatgaaa | ataatgctg | 300 |
| cagagagcat | ttttgcacat | gtatcgtggc | agatgtaggc | cagaggctct | tctttatcca | 360 |
| tcctatggcc | aacctatgaa | tgtatacacg | tttaatgaga | ttttgccagc | aatcaaagcc | 420 |
| ttcagggaaa | atgtccctag | ctctttacta | catcagatca | aggactctgg | ataattggca | 480 |
| taacatcctg | gaatagctga | aacagagata | ttattctctg | ctgtcctctg | ttgtctttgt | 540 |
| cttttcacgt | cttaata | | | | | 557 |

<210> SEQ ID NO 116
<211> LENGTH: 545
<212> TYPE: DNA
<213> ORGANISM: Homo sapiens
<220> FEATURE:
<221> NAME/KEY: misc_feature
<222> LOCATION: (1)..(545)
<223> OTHER INFORMATION: AffymetrixID: 211458_s_at

<400> SEQUENCE: 116

| | | | | |
|---|---|---|---|---|
| aaatagcatt | aaactggaat | tgacagagtg | agttgagcat | ctctgtctaa | cctgctcttt | 60 |
| ctctctggtg | ctcctcatct | caccectacc | ttggaattta | ataagcttca | ggcatttcca | 120 |
| attgcagact | aaaaccactt | ctaccatctc | ctctagtatt | ttccatgtat | caggacagag | 180 |
| atgtcttatg | tagggaaggg | gcaggtatga | agtgaggtag | attatctata | cctctcactc | 240 |
| attcaggatt | ctcgctccca | tgctgctgtc | ccttcattct | cacactcaca | ggaatgctat | 300 |
| gtgatggcca | gctgcttccc | ttcttggtta | tccactgcag | ctgctagtta | gaaaggtttg | 360 |
| cagggatgac | ttttagtaaa | tcatgggat | tttattgatt | tattatcact | ataggatt | 420 |
| tgtggggtgg | gagtggggag | caggaattgc | actcagacat | gacatttcaa | ttcatctctg | 480 |
| caaatgaaaa | gggttcttcc | tcttggggga | aatctgtgtg | tcagttctgt | cagctgcaag | 540 |
| ttctt | | | | | | 545 |

<210> SEQ ID NO 117
<211> LENGTH: 441
<212> TYPE: DNA
<213> ORGANISM: Homo sapiens
<220> FEATURE:
<221> NAME/KEY: misc_feature
<222> LOCATION: (1)..(441)
<223> OTHER INFORMATION: AffymetrixID: 211560_s_at

<400> SEQUENCE: 117

```
tccccatccg ggtgggcaat gcagcactca acagcaagct ctgtgatctc ctgctctcca      60
agcatggcat ctatgtgcag gccatcaact acccaactgt cccccggggt gaagagctcc     120
tgcgcttggc accctccccc caccacagcc ctcagatgat ggaagatttt gtggagaagc     180
tgctgctggc ttggactgcg gtggggctgc cctccagga tgtgtctgtg gctgcctgca      240
atttctgtcg ccgtcctgta cactttgagc tcatgagtga gtgggaacgt tcctacttcg     300
ggaacatggg gccccagtat gtcaccacct atgcctgaga agccagctgc ctaggattca     360
caccccacct gcgcttcact tgggtccagg cctactcctg tcttctgctt tgttgtgtgc     420
ctctagctga attgagccta a                                               441
```

<210> SEQ ID NO 118
<211> LENGTH: 131
<212> TYPE: DNA
<213> ORGANISM: Homo sapiens
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (1)..(131)
<223> OTHER INFORMATION: AffymetrixID: 211991_s_at

<400> SEQUENCE: 118

```
gcactgggag gcccaagagc caatccagat gcctgagaca acggagactg tgctctgtgc      60
cctgggcctg gtgctgggcc tagtnggcat catcgtgggc accgtcctca tcataaagtc     120
tctgcgttct g                                                          131
```

<210> SEQ ID NO 119
<211> LENGTH: 482
<212> TYPE: DNA
<213> ORGANISM: Homo sapiens
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (1)..(482)
<223> OTHER INFORMATION: AffymetrixID: 212199_at

<400> SEQUENCE: 119

```
attttgctgt taccttttgtg acctgattgt tttttggaac acgtcaagac gtgggatcag      60
aatcttccaa ctttagaggt gcaatggaag acactacgct acttggttga gcctggtgaa     120
gaatgtatta atgagactgc tttgcataaa actgggaaga agagaagac agttggagat       180
ggaagatggt tttgtatata ttttggaact ttagttcctc tgtgagacga aagaggagag     240
ctatgttttg tgtcacattg tctgatatat attgtgtaac ctgtcaggtg agttgattta     300
gacaacatag ctgacctttt atgacaaggc agtttgaata gggactattg taataccctc     360
acacattata ggggcancag agaatggcat ggaagagaca gtctacagag agctttaaga     420
```

```
ggccggagaa aggaaaagac attatcaggg cctggaaagt ctcttccagt tcatcagggt      480
ag                                                                     482

<210> SEQ ID NO 120
<211> LENGTH: 419
<212> TYPE: DNA
<213> ORGANISM: Homo sapiens
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (1)..(419)
<223> OTHER INFORMATION: AffymetrixID:  212224_at

<400> SEQUENCE: 120
acagtgttct ctaatgttac agatgagatg cgcattgcca agaggagat ttttggacca       60 gtgcagcaaa tcatgaagtt taaatcttta gatgacgtga tcaaaagagc aaacaatact     120
ttctatggct tatcagcagg agtgtttacc aaagacattg ataaagccat aacaatctcc     180
tctgctctgc aggcaggaac agtgtgggtg aattgctatg cgtggtaag tgcccagtgc      240 ccctttggnt gggattcaag atgtctggaa atggaagaga actgggagag tacggtttcc     300
atgaatatac agaggtcaaa acagtcacag tgaaaatctc tcagaagaac tcataaagaa     360
aatacaagag tggagagaag ctcttcaata gctaagcatc tccttacagt cactaatat     419

<210> SEQ ID NO 121
<211> LENGTH: 343
<212> TYPE: DNA
<213> ORGANISM: Homo sapiens
<220> FEATURE:
<221> NAME/KEY: misc_feature
<222> LOCATION: (1)..(343)
<223> OTHER INFORMATION: AffymetrixID:  212232_at

<400> SEQUENCE: 121
agaaggcagc tctgcattct accttgcttg actggaattg tctgaagctt tttctggcct      60
cttttctcta gtcggccacc cctgaagtgc tgaggtctaa gtggtttacc tcgtgctgat    120
agatggccac actctttaga gtagttctca taagttctag aactggtagc tcggtcgttt    180
cgcacactag gtggcataca ggcagcagca ggtgttcata tccttgattt tgagaatttc    240
ccctcaagta tgtggcagta aatacaacaa gacactctat gtattaatgt ctccattgtc    300
ttaaccctgt tccaaaacaa aattcacctc ctttctttat gtg                      343

<210> SEQ ID NO 122
<211> LENGTH: 427
<212> TYPE: DNA
<213> ORGANISM: Homo sapiens
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (1)..(427)
<223> OTHER INFORMATION: AffymetrixID:  212534_at

<400> SEQUENCE: 122
gtggattgtt tgtatccctt acctgctttc tattgggtta tgtgtggata tattgttttt      60
atttgttcag catctccttc cccatcttct ggtaacacaa cctttattta tttgtgggga    120
acctattccc tgtggcttag gtgagcatgt gaccaggcct ggcctcctga gtcccacagc    180
```

```
ttcctagcca cagtgataaa agaatgggnt atataactta agccaggcta aggaaagccc      240
ttaacagaac ttctgctgga actactggaa agaaggcttt atggagatcc caggaaccaa      300
ggaccatgta agcctgaatt tgtgccatgt ggagagagtc tgtctgagga gaaactcgga      360
tgctagcaga aatggaaaga gaactaagtt ctgatgtcat ttttctggag ccctagatc       420 cagctgt                                                               427

<210> SEQ ID NO 123
<211> LENGTH: 497
<212> TYPE: DNA
<213> ORGANISM: Homo sapiens
<220> FEATURE:
<221> NAME/KEY: misc_feature
<222> LOCATION: (1)..(497)
<223> OTHER INFORMATION: AffymetrixID: 213142_x_at

<400> SEQUENCE: 123
ctgctgccat tttaatcttg ctcattaacc ttactccttt gagaattctt taacaatatt       60
taaaattggt aacaaaaata gtttagccat aattgtttag ccatgtgagt ttcaggttgg      120
tacacgttca gacagaactg ctgtatcaca ttccaatttt gaatagccag tgagcaatca      180
agtgtagaga aatgataaat ggcctaagaa ggcatacagt ggcataaacg atgctcttcc      240
tagtagctta ataggccaca agctagtttc tgttgcactc tgaaataaaa tatgctttaa      300
aaatgtaggg aacagtgctt agaaaagcaa aaactaggtg tgtcattgaa ataataggca      360
taaaaattaa atgttacata agaacactat ttggaaagag ggtccttta aaaactgaat       420 ttgtactaaa tcagatttgc catgtccagt acagaataat ttgtacttag tatttgcagc      480
agggtttgtc tttgtga                                                    497

<210> SEQ ID NO 124
<211> LENGTH: 543
<212> TYPE: DNA
<213> ORGANISM: Homo sapiens
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (1)..(543)
<223> OTHER INFORMATION: AffymetrixID: 214433_s_at

<400> SEQUENCE: 124
cttcctcgga ggcagcattg ttaagggagg ccctgtgcaa gtgctggagg acgaggaact       60
aaagtcccag ccagagcccc tagtggtcaa gggaaaacgg gtggctggag ccctcagat      120 gatccagctc agcctggatg ggaagcgcct ctacatcacc acgtcgctgt acagtgcctg      180
ggacaagcag ttttaccctg atctcatcag ggaaggctct gtgatgctgc aggttgatgt      240
agacacagta aaaggagggc tgaagttgaa ccccaacttc ctggtggact tcgggaagga      300
gcccccttgg ccagcccttg cccnatgagc tccgctaccc tggggcgat tgtagctctg       360 acatctggat ttgaaggctc caccctcatc acccacactc cctattttgg gccctcactt      420
ccttggggac ctggcttcat tctgctctct cttggcaccc gacccttggc agcatgtacc      480
acacagccaa gctgagactg tggcaatgtg ttgagtcata tacatttact gaccactgtt      540
gct                                                                  543

<210> SEQ ID NO 125
<211> LENGTH: 501
```

```
<212> TYPE: DNA
<213> ORGANISM: Homo sapiens
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (1)..(501)
<223> OTHER INFORMATION: AffymetrixID: 215933_s_at

<400> SEQUENCE: 125
ggacagttcc tgtgatcaga ggcaagattt gcccagngaa cagaataaag gtgcttcttt      60
ggatagctct caatgttcgc cctccctgc ctcccaggaa gaccttgaat cagagatttc     120
agaggattct gatcaggaag tggacattga gggcgataaa agctatttta atgctggatg     180
atgaccactg gcattggcat gttcagaaaa ctggatttag gaataatgtt ttgctacaga     240
aaatcttcat agaagaactg gaaggctata taagaaaggg aatcaattct ctggtattct     300
ggaaacctaa aaatatttgg tgcactgctc aattaacaaa cctacatgga gaccttaatt     360
ttgacttaac aaatagttta tgtactgctc ttaggttgtt ttgataaagt gacattatag     420
tgattaaatt ctttccnctt taaaaaaaca gntagtggtt ttcactattt ataaatagga     480
ccttcttgaa cgacttttct g                                               501

<210> SEQ ID NO 126
<211> LENGTH: 424
<212> TYPE: DNA
<213> ORGANISM: Homo sapiens
<220> FEATURE:
<221> NAME/KEY: misc_feature
<222> LOCATION: (1)..(424)
<223> OTHER INFORMATION: AffymetrixID: 217478_s_at

<400> SEQUENCE: 126
ctgttttgtc agtaatctct tcccacccat gctgacagtg aactggcagc atcattccgt      60
ccctgtggaa ggatttgggc ctactttgt ctcagctgtc gatggactca gcttccaggc     120
cttttcttac ttaaacttca caccagaacc ttctgacatt ttctcctgca ttgtgactca     180
cgaaattgac cgctacacag caattgccta ttgggtaccc cggaacgcac tgccctcaga     240
tctgctggag aatgtgctgt gtggcgtggc ctttggcctg ggtgtgctgg gcatcatcgt     300
gggcattgtt ctcatcatct acttccggaa gccttgctca ggtgactgat tcttccagac     360
cagagtttga tgccagcagc ttcggccatc caaacagagg atgctcagat ttctcacatc     420
ctgc                                                                  424

<210> SEQ ID NO 127
<211> LENGTH: 530
<212> TYPE: DNA
<213> ORGANISM: Homo sapiens
<220> FEATURE:
<221> NAME/KEY: misc_feature
<222> LOCATION: (1)..(530)
<223> OTHER INFORMATION: AffymetrixID: 217736_s_at

<400> SEQUENCE: 127
tctgtctggt cttcctctag aaggttctac cgcagaaatt gatgtgtgct ccctgccctc      60
```

-continued

```
gtcactgccc aagcccgggc ctgcacatac tcactggact gttccagttt tgacagctgc      120
cagtcttcct gccccttcca cactgcagct gaagttcatt acctgaagga cgcctcatca      180
tttcattcct tggctccaaa ccttctgctg cctctaagat aaaagctcaa cttcttaaca      240
gtgtacagtg tgcaacttcc aaccttttta tctgttctct ccaccttcag tttagcgtca      300
ttccaaaacc acaccttgc  aaagctttgt actccgcacc ccagatgatc tccaggcagc      360
tcagatctct ttcctgcctt tgccctgcac tgttccccgg tacttcctcc tttattgtag      420
cactcagctc cccagccaat ctgtacatcc ctcagaggca gcgatctgat gaattggttt      480
ttgaatccca gaaagggtct gccatggagt tggcagtcat cacggtagat                 530
```

<210> SEQ ID NO 128
<211> LENGTH: 262
<212> TYPE: DNA
<213> ORGANISM: Homo sapiens
<220> FEATURE:
<221> NAME/KEY: misc_feature
<222> LOCATION: (1)..(262)
<223> OTHER INFORMATION: AffymetrixID: 219069_at

<400> SEQUENCE: 128

```
gaatattgta tactgcatcc cctaccacaa tttacacaat cctgtggata gtcctacctc       60
accctggtca acctacatga tccttaagct aatggcgaat cacgatgacc ttgtagacat      120
gcacacaact atacctttgt ccaacagatc ataatatatc tgctatccaa ctggttttac      180
ctgcctaatc ctactgattt gggcactgct tgtatagtct ctcaagttca caggaaatgt      240
tgattttcta aggtcctcat tt                                               262
```

<210> SEQ ID NO 129
<211> LENGTH: 490
<212> TYPE: DNA
<213> ORGANISM: Homo sapiens
<220> FEATURE:
<221> NAME/KEY: misc_feature
<222> LOCATION: (1)..(490)
<223> OTHER INFORMATION: AffymetrixID: 219093_at

<400> SEQUENCE: 129

```
tagagaccca tgtcatctta acctaaaggg aaatcttatt gcgttatcat aaaattgatg       60
atatcttagg gtcagaattg cccttttttt tattttgaat gggaagctct cactaaaaca      120
atcctgagat ttcttaattt catggttctt taaatattat aaacacagag tcaacataga      180
atgaaattgt atttgttaaa atacacacat tggaggacaa gagcagatga ctacttttcg      240
aagtaatgct gctccttcct aaaagtctgt tttcaatcct ggtaatatta ggggcactgc      300
ggcacctaag aagccttaaa tgagagctaa tccaatttag agagcgatgg tgtcagcatt      360
tcggtctgca tatctgtgtg tccgtatctg cgtttgtgtg cgtgtacgtg tgcccctgtg      420
tgtgggccca gttttcaggc atgtagaata agcatggagt catattgagg aggactcact      480
tcttgaagat                                                             490
```

<210> SEQ ID NO 130
<211> LENGTH: 446
<212> TYPE: DNA
<213> ORGANISM: Homo sapiens
<220> FEATURE:
<221> NAME/KEY: misc_feature
<222> LOCATION: (1)..(446)
<223> OTHER INFORMATION: AffymetrixID: 219228_at

<400> SEQUENCE: 130

```
ggggttcgag cctcgttaag cacgagagga tacatacggg cgagaagccg tacaagtgca      60
cagaatgtgg gaaggccttc aattgtggct atcacctcac tcagcacgag agaatccaca     120
caggcgaaac cccgtataaa tgtaaggagt gtgggaaggc tttcatttat ggatcgagcc     180
tcgtgaaaca tgagagaatt cataccgggg tgaaaccta  tgggtgtaca gaatgtggga     240
agagctttag tcacggccat cagcttacac aacatcagaa acgcacagt  ggggcgaaat     300 cctacgaatg taaggagtgc gggaaggcat gtaaccacct aaaccatctc cgagaacatc     360
agaggatcca caacagttga agagcctttt gaacgcagta gcccgctcgt atctatggtt     420
tcgctttcca cagtttgtta cctgca                                          446
```

\<210\> SEQ ID NO 131
\<211\> LENGTH: 331
\<212\> TYPE: DNA
\<213\> ORGANISM: Homo sapiens
\<220\> FEATURE:
\<221\> NAME/KEY: misc_feature
\<222\> LOCATION: (1)..(331)
\<223\> OTHER INFORMATION: AffymetrixID: 219607_s_at

\<400\> SEQUENCE: 131

```
atcaacacat ttagcttggc gttttattca ttccatcacc cttactgtaa ctactatggc      60
aactcaaata attgtcatgg gactatgtcc atcttaatgg gtctggatgg catggtgctc     120
ctcttaagtg tgctggaatt ctgcattgct gtgtccctct ctgcctttgg atgtaaagtg     180
ctctgttgta cccctggtgg ggttgtgtta attctgccat cacattctca catggcagaa     240
acagcatctc ccacaccact taatgaggtt tgaggccacc caaagatcaa cagacaaatg     300
ctccagaaat ctatgctgac tgtgacacaa g                                    331
```

\<210\> SEQ ID NO 132
\<211\> LENGTH: 149
\<212\> TYPE: DNA
\<213\> ORGANISM: Homo sapiens
\<220\> FEATURE:
\<221\> NAME/KEY: misc_feature
\<222\> LOCATION: (55)..(55)
\<223\> OTHER INFORMATION: n is a, c, g, or t
\<220\> FEATURE:
\<221\> NAME/KEY: misc_feature
\<222\> LOCATION: (1)..(149)
\<223\> OTHER INFORMATION: AffymetrixID: 221748_s_at

\<400\> SEQUENCE: 132

```
atattttgta tcatcgtgcc tatagccgct gccaccgtgt ataaatcctg gtgtntgctc      60
cttatcctgg acatgaatgt attgtacact gacgcgtccc cactcctgta cagctgcttt     120
gtttctttgc aatgcattgt atggcttta                                       149
```

\<210\> SEQ ID NO 133
\<211\> LENGTH: 534
\<212\> TYPE: DNA
\<213\> ORGANISM: Homo sapiens
\<220\> FEATURE:
\<221\> NAME/KEY: misc_feature
\<222\> LOCATION: (120)..(120)
\<223\> OTHER INFORMATION: n is a, c, g, or t
\<220\> FEATURE:
\<221\> NAME/KEY: misc_feature
\<222\> LOCATION: (308)..(308)
\<223\> OTHER INFORMATION: n is a, c, g, or t
\<220\> FEATURE:
\<221\> NAME/KEY: misc_feature
\<222\> LOCATION: (1)..(534)
\<223\> OTHER INFORMATION: AffymetrixID: 221766_s_at

<400> SEQUENCE: 133

| gatttccagg aagcctttga tcacctttgt aacaagatca ttgccaccag gaacccagag | 60 |
| gaaatccgag ggggaggcct gcttaagtac tgcaacctct tggtgagggg ctttaggccn | 120 |
| gcctctgatg aaatcaagac ccttcaaagg tatatgtgtt ccaggttttt catcgacttc | 180 |
| tcagacattg gagagcagca gagaaaactg gagtcctatt tgcagaacca ctttgtggga | 240 |
| ttggaagacc gcaagtatga gtatctcatg acccttcatg gagtggtaaa tgagagcaca | 300 |
| gtgtgccntg atgggacatg aaagaagaca gactttaaac cttatcacca tgctggctat | 360 |
| ccgggtgtta gctgaccaaa atgtcattcc taatgtggct aatgtcactt gctattacca | 420 |
| gccagccccc tatgtagcag atgccaactt tagcaattac tacattgcac aggttcagcc | 480 |
| agtattcacg tgccagcaac agacctactc cacttggcta ccctgcaatt aaga | 534 |

<210> SEQ ID NO 134
<211> LENGTH: 503
<212> TYPE: DNA
<213> ORGANISM: Homo sapiens
<220> FEATURE:
<221> NAME/KEY: misc_feature
<222> LOCATION: (1)..(503)
<223> OTHER INFORMATION: AffymetrixID: 221622_s_at

<400> SEQUENCE: 134

| atgcatcatt ggctacactt ccattttgt ctactgttgt tactgacaag cttttgtaa | 60 |
| ttgatgcttt gtattcagat aatataagca aggaaaactg tgttttcaga agctcactga | 120 |
| ttggcatagt ttgtggtgtt ttctatccca gttctttggc ttttactaaa aatggacgcc | 180 |
| tggcaaccaa gtatcatacc gttccactgc caccaaaagg aagggtttta atccattgga | 240 |
| tgacgctttg tcaaacacaa atgaaattaa ttgcgattcc tctagtcttt cagattatgt | 300 |
| ttggaatatt aaatggctat accattatgc aagtatttga agagacact tgagaaaact | 360 |
| atacatgaag agtaaccaaa aaaatgaatg gttgctaact tagcaaaatg aagtttctat | 420 |
| aaagaggact caggcattgc tgaaagagtt aaaagtaact gtgaacaaat aatttgttct | 480 |
| gtgccttttg cctggtatat agc | 503 |

<210> SEQ ID NO 135
<211> LENGTH: 515
<212> TYPE: DNA
<213> ORGANISM: Homo sapiens
<220> FEATURE:
<221> NAME/KEY: misc_feature
<222> LOCATION: (1)..(515)
<223> OTHER INFORMATION: AffymetrixID: 218845_at

<400> SEQUENCE: 135

| aaaacattct ggccgctcca ggaattctga agttctgggc ctttctcaga agactgtaat | 60 |
| gtacctgaag tttctgaaat attgcaaacc cacagagttt aggctggtgc tgccaaaaag | 120 |
| aaaagcaaca tagagtttaa gtatccagta gtgatttgta aacttgtttt tcatttgaag | 180 |
| ctgaatatat acgtagtcat gtttatgttg agaactaagg atattcttta gcaagagaaa | 240 |
| atattttccc cttatcccca ctgctgtgga ggtttctgta cctcgcttgg atgcctgtaa | 300 |
| ggatcccggg agccttgccg cactgccttg tgggtggctt ggcgctcgtg attgcttcct | 360 |
| gtgaacgcct cccaaggacg agccagtgt agttgtgtgg gcgtgaactc tgcccgtgtg | 420 |
| ttctcaaatt ccccagcttg ggaaatagcc cttggtgtgg gttttatctc tggtttgtgt | 480 |
| tctccgtggt ggaattgacc gaaagctcta tgttt | 515 |

<210> SEQ ID NO 136
<211> LENGTH: 504
<212> TYPE: DNA
<213> ORGANISM: Homo sapiens
<220> FEATURE:
<221> NAME/KEY: misc_feature
<222> LOCATION: (1)..(504)
<223> OTHER INFORMATION: AffymetrixID: 200786_at

<400> SEQUENCE: 136

```
gttacattgg tgcagccta gttttagggg gagtagatgt tactggacct cacctctaca    60
gcatctatcc tcatggatca actgataagt tgccttatgt caccatgggt tctggctcct   120
tggcagcaat ggctgtattt gaagataagt ttaggccaga catggaggag gaggaagcca   180
agaatctggt gagcgaagcc atcgcagctg gcatcttcaa cgacctgggc tccggaagca   240
acattgacct ctgcgtcatc agcaagaaca agctggattt tctccgccca tacacagtgc   300
ccaacaagaa ggggaccagg cttggccggt acaggtgtga gaaagggact actgcagtcc   360
tcactgagaa aatcactcct ctggagattg aggtgctgga agaaacagtc caaacaatgg   420
acacttcctg aatggcatca gtgggtggct ggccgcggtt ctggaaggtg gtgagcattg   480
aggcccagta agacactcat gtgg                                          504
```

<210> SEQ ID NO 137
<211> LENGTH: 492
<212> TYPE: DNA
<213> ORGANISM: Homo sapiens
<220> FEATURE:
<221> NAME/KEY: misc_feature
<222> LOCATION: (1)..(492)
<223> OTHER INFORMATION: AffymetrixID: 212886_at

<400> SEQUENCE: 137

```
acaggcacat caggctgcag aatgcgcttt agaaagcatt gttttagtcc aggcacagtg    60
gctcacgcct gtaatcccag cactttggga ggccgaggtg ggtggatcac aaggttggga   120
gattgagacc atcctggcta acacagtgaa accctgtctc tactaaaaaa atacaaaaaa   180
ttagcttggc gtggtggtgg gcgcctgtag tcccagcagc ttgggaggct gaggctggag   240
aatggtgtga acccaggagg cggagcttgc agtgagccaa gatcgcgcca ctgcactcca   300
gcccgggtga cagagcaaga ctccgtctca aaaaaaagaa aagaaaaaag aaagcattgt   360
tttaattgag aggggcaggg ctggagaagg agcaagttgt ggggagccag gcttccctca   420
cgcagcctgt ggtggatgtg ggaaggagat caacttctcc tcactctggg acagacgatg   480
tatggaaact aa                                                       492
```

<210> SEQ ID NO 138
<211> LENGTH: 316
<212> TYPE: DNA
<213> ORGANISM: Homo sapiens
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (1)..(316)
<223> OTHER INFORMATION: AffymetrixID: 201407_s_at

<400> SEQUENCE: 138

```
ggatgtgatt ctaaaagctt ttattgagca ttgtcaaatt tgtaagcttc atagggatgg    60
acatcatatc tataatgccc ttctatatgt gctaccatag atgtgacatt tttgacctta   120
```

```
atatcgtctt tgaaaatgtt aaattgagaa acctgttaac ttacatttta tgnattggca      180
cattgtatta cttactgcaa gagatatttc attttcagca cagtgcaaaa gttcttaaa       240 atgcatatgt cttttttct aattccgttt tgttttaaag cacattttaa atgtagtttt        300
ctcatttagt aaaagt                                                      316
```

```
<210> SEQ ID NO 139
<211> LENGTH: 525
<212> TYPE: DNA
<213> ORGANISM: Homo sapiens
<220> FEATURE:
<221> NAME/KEY: misc_feature
<222> LOCATION: (1)..(525)
<223> OTHER INFORMATION: AffymetrixID: 212266_s_at

<400> SEQUENCE: 139
gttgagtttg cctcttatgg tgacttaaag aatgctattg aaaaactttc tggaaaggaa      60
ataaatggga gaaaataaaa attaattgaa ggcagcaaaa ggcacagtag gtcaagaagc     120
aggtctcgat cccggaccag aagttcctct aggtctcgta gccgatcccg ttcccgtagt     180
cgcaaatctt acagccggtc aagaagcagg agcaggagcc ggagccggag caagtcccgt     240
tctgttagta ggtctcccgt gcctgagaag agccagaaac gtggttcttc aagtagatct     300
aagtctccag catctgtgga tcgccagagg tcccggtccc gatcaaggtc cagatcagtt     360
gacagtggca attaaactgt aaataacttg ccctgggggc cttttttaa aaaacaaaaa      420 ccacaaaaat tcccaaacca tacttgctaa aaattctggt aagtatgtgc ttttctgtgg      480
gggtgggatt tggaagggg gttgggttgg gctggatatc tttgt                      525
```

```
<210> SEQ ID NO 140
<211> LENGTH: 581
<212> TYPE: DNA
<213> ORGANISM: Homo sapiens
<220> FEATURE:
<221> NAME/KEY: misc_feature
<222> LOCATION: (72)..(74)
<223> OTHER INFORMATION: n is a, c, g, or t
<220> FEATURE:
<221> NAME/KEY: misc_feature
<222> LOCATION: (239)..(253)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (270)..(305)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t
<220> FEATURE:
<221> NAME/KEY: misc_feature
<222> LOCATION: (446)..(526)
<223> OTHER INFORMATION: n is a, c, g, or t
<220> FEATURE:
<221> NAME/KEY: misc_feature
<222> LOCATION: (1)..(581)
<223> OTHER INFORMATION: AffymetrixID: 53912_at

<400> SEQUENCE: 140
acaatgaggc attctgtcct cctgctgcca ttcttcatct ccactgagag ccagagctgg      60
taggagccga gnnnccacag gcattctgca ttgctctact cttaggtttg tgtgtgtgat     120
ccttcccctc cctgtcgccc actcctccct cctctggcta tcctaccctg tctgtgggct     180
```

```
cttttactac cagcctatgc tgtgggactg tcatggcatt tagttcagag tggaggggnn    240
nnnnnnnnnn nnnaaatgca agtatttnan nnnnnnnnnn nnnnnnnnnn nnnnnnnnnn    300
nnnnnaanat tgttgttgca atttgtgtct aacaagctgt agcagagaag gagggagtga    360
gcgctggcag tatttccttt cataaatcat gaatttatca gtgtggaaat aatgcttcag    420
aactgtgctc tgtagccctc ctgcannnnn nnnnnnnnnn nnnnnnnnnn nnnnnnnnnn    480
nnnnnnnnnn nnnnnnnnnn nnnnnnnnnn nnnnnnnnnn nnnnngcgt gaaccttgtt    540 aggtatactt tacctgatgc tgcttccatc ctcgcagtct g                       581

<210> SEQ ID NO 141
<211> LENGTH: 377
<212> TYPE: DNA
<213> ORGANISM: Homo sapiens
<220> FEATURE:
<221> NAME/KEY: misc_feature
<222> LOCATION: (1)..(377)
<223> OTHER INFORMATION: AffymetrixID:  200090_at

<400> SEQUENCE: 141 tcccttttgcc tgtggtgtaa aagtgcatca cacaggtatt gcttttaac aagaactgat    60 gctccttggg tgctgctgct actcagacta gctctaagta atgtgattct tctaaagcaa    120
agtcattgga tgggaggagg aagaaaaagt cccataaagg aacttttgta gtcttatcaa    180
catataatct aatcccttag catcagctcc tccctcagtg gtacatgcgt caagatttgt    240
agcagtaata actgcaggtc acttgtatgt aatggatgtg aggtagccga agtttggttc    300
agtaagcagg gaatacagtc gttccatcag agctggtctg cacactcaca ttatcttgct    360
atcactgtaa ccaacta                                                 377

<210> SEQ ID NO 142
<211> LENGTH: 494
<212> TYPE: DNA
<213> ORGANISM: Homo sapiens
<220> FEATURE:
<221> NAME/KEY: misc_feature
<222> LOCATION: (1)..(494)
<223> OTHER INFORMATION: AffymetrixID:  218025_s_at

<400> SEQUENCE: 142
ctccttgggc tattcgatgc cgtgtatgca tctgacaggg caacatttca tacaccattt    60
agtcacctag gccaaagtcc ggaaggatgc tcctcttaca cttttccgaa gataatgagc    120
ccagccaagg caacagagat gcttattttt ggaaagaagt taacagcggg agaggcatgt    180
gctcaaggac ttgttactga agttttccct gatagcactt ttcagaaaga agtctggacc    240
aggctgaagg catttgcaaa gcttcccccca aatgccttga gaatttcaaa agaggtaatc    300
aggaaaagag agagagaaaa actacacgct gttaatgctg aagaatgcaa tgtccttcag    360
ggaagatggc tatcagatga atgcacaaat gctgtggtga acttcttatc cagaaaatca    420
aaactgtgat gaccactaca gcagagtaaa gcatgtccaa ggaaggatgt gctgttacct    480
ctgatttcca gtac                                                    494

<210> SEQ ID NO 143
<211> LENGTH: 540
<212> TYPE: DNA
<213> ORGANISM: Homo sapiens
<220> FEATURE:
<221> NAME/KEY: misc_feature
<222> LOCATION: (1)..(540)
<223> OTHER INFORMATION: AffymetrixID:  204232_at
```

<400> SEQUENCE: 143

```
cgatctccag cccaagatga ttccagcagt ggtcttgctc ttactccttt tggttgaaca      60
agcagcggcc ctgggagagc ctcagctctg ctatatcctg gatgccatcc tgtttctgta     120
tggaattgtc ctcaccctcc tctactgtcg actgaagatc caagtgcgaa aggcagctat     180
aaccagctat gagaaatcag atggtgttta cacgggcctg agcaccagga accaggagac     240
ttacgagact ctgaagcatg agaaaccacc acagtagctt tagaatagat gcggtcatat     300
tcttctttgg cttctggttc ttccagccct catggttggc atcacatatg cctgcatgcc     360
attaacacca gctggcccta ccctataat gatcctgtgt cctaaattaa tatacaccag      420
tggttcctcc tccctgttaa agactaatgc tcagatgctg tttacggata tttatattct     480
agtctcactc tcttgtccca cccttcttct cttccccatt cccaactcca gctaaaatat     540
```

<210> SEQ ID NO 144
<211> LENGTH: 559
<212> TYPE: DNA
<213> ORGANISM: Homo sapiens
<220> FEATURE:
<221> NAME/KEY: misc_feature
<222> LOCATION: (1)..(559)
<223> OTHER INFORMATION: AffymetrixID: 201722_s_at

<400> SEQUENCE: 144

```
attttgtttt catctgtgat agtcatggat gcttttattt tccttggggt gctgaaattg      60
agctgaaaaa aaaaggctct ttgaatatag ttttaatttc tctctacagt ttttttttgtt    120
tggtttgtgg gctgttggaa ttgtaatttt taattgcctt ctaaaaaatg gaaatttaac     180
aatgtctgat ctcagctgaa caaattagat gtttcagttg ctcttgggtc aactggctta     240
cagatttaca tgtgcacaca cacacaaatt tcttatcaca ttttcgactt cttcacttga     300
cctaactgat tatgcgaaat acccaagatt catgctactg taccacagat ttgttttcac     360
agcaataaat cttcagttct gttgtttatg attccactta acaaaaggcc tgcagaagtg     420
atttattatt tgggtatttg gagataatac atttgatggt tttttggaaa acctttttca     480
ctccatactc agatatgctt cattgtcaaa tgcatattta gattagatta ttgaattgta     540
atgtttatct gctgctttt                                                  559
```

<210> SEQ ID NO 145
<211> LENGTH: 453
<212> TYPE: DNA
<213> ORGANISM: Homo sapiens
<220> FEATURE:
<221> NAME/KEY: misc_feature
<222> LOCATION: (1)..(453)
<223> OTHER INFORMATION: AffymetrixID: 218627_at

<400> SEQUENCE: 145

```
taatcatttc tgggttcact gcgactcact gtagtgctgg ggatcccct tgtaacactg       60
gaactgaaag gcagtgatga aagctatgtc aagcattcat tattctgaag aggaggagaa     120
atgccacata cctttcccat gggacctgtg gtggaatgaa tccatacttc tgcctcactt     180
cgagcagact tttgttctcg gcgctcctca cgatggagtt tcatgcttca ttttcacatc     240
tctctgcaca attagattgg gagctccttg agggcagagt acgtgcctta atctttatct     300
ttgtaatgcc acaatgaaca gagtgcctcc tggtacactg taggagctta agaaatactc     360
actgaatgca tgaatgaatg aatgaacaaa tgaaggaatg actaaggatg tttgtagtgc     420
tataatatag aatgggattt actctgcttt acc                                  453
```

<210> SEQ ID NO 146
<211> LENGTH: 553
<212> TYPE: DNA
<213> ORGANISM: Homo sapiens
<220> FEATURE:
<221> NAME/KEY: misc_feature
<222> LOCATION: (1)..(553)
<223> OTHER INFORMATION: AffymetrixID: 202322_s_at

<400> SEQUENCE: 146

```
gttctcattt cctactattc atgctatttg gtcaaggcct gaaagcaccc aggtgcagaa      60
tatcttgcgc cagagaacag aaaacataga tataaaaaaa tactgtgtac attatcttga     120
ggatgtaggt tcttttgaat acactcgtaa taccttaaa gagcttgaag ctaaagccta     180
taaacagatt gatgcacgtg gtgggaaccc tgagctagta gccttagtaa aacacttaag     240
taagatgttc aaagaagaaa atgaataatg ttaagccatt cttgattgga cctcatagct     300
tattttagtt aatctttttt ttgtctttta gccttaccac cttttaaaaa atttgttatt     360
ctccagaaac agtaaatagg tgagtagggg tggtgcaagt gaattcgttt tcatttagaa     420
gcccctctgt acagataatc aaaattcaaa gttgaaagaa tcaaaagcag ccacagttat     480
gtaggtctga tttgaatgtc ataattgcag tgacaggaca ttgccaccaa ctctatccta     540
ctaccatcaa tgt                                                        553
```

<210> SEQ ID NO 147
<211> LENGTH: 530
<212> TYPE: DNA
<213> ORGANISM: Homo sapiens
<220> FEATURE:
<221> NAME/KEY: misc_feature
<222> LOCATION: (1)..(530)
<223> OTHER INFORMATION: AffymetrixID: 221689_s_at

<400> SEQUENCE: 147

```
accgtcgcca ttgccagaaa gagcgattta tggctttgtt cttttcttaa gctcccaatt      60
tggcttcata ctttacctcg tgtgggcctt tattcctgaa tcttggctaa actcttagg     120
tttaacctat tggcctcaaa aatattgggc agttgcatta cctgtctacc tccttattgc     180
tatagtaatt ggctacgtgc tcttgtttgg gattaacatg atgagtacct ctccactcga     240
ctccatccat acaatcacag ataactatgc aaaaaatcaa cagcagaaga ataccaaga     300
ggaggccatt ccagccttaa gagatatttc tattagtgaa gtaaaccaaa tgttctttct     360
tgcagccaaa gaactttaca ccaaaaactg aactgtgtgt aaccatagta acaccaagca     420
cgtatttatt tataagtttt tgccattata attttgacca taattaatt tgaccatctc     480
tcttattaat agagaagtaa aaaatgtaag ttgaccttct cttagattat                530
```

<210> SEQ ID NO 148
<211> LENGTH: 563
<212> TYPE: DNA
<213> ORGANISM: Homo sapiens
<220> FEATURE:
<221> NAME/KEY: misc_feature
<222> LOCATION: (1)..(563)
<223> OTHER INFORMATION: AffymetrixID: 203356_at

<400> SEQUENCE: 148

```
tatacatctt gggcaactag ttaccaaatg aattgtgcca ccataactga ttttaatttt      60
gcattattta tgattttaaa atatttgttg cccaggtgtt atgaaagaat aaagctttta     120
agtatagact accttagcat gaagatgctc atgcctaaga atgaaaattg ttgaggttat     180
```

```
ctcccattca atcatgtagc aagaacttaa agaaattcac tactgcagtt tttatttta      240 aaaaacagta attgagatat tgaagacatt acaatttagt ttgtgtggtc ttttttaaa      300 ttgctgtatc gttcagtctc ttgtggcaat agcactttga agaaaataga gaatttaata    360
tatggtgatt gggatatgta gcattcaaaa aaagtgaatt gccaagatac tggtgtcatg    420
taaattccca ctttacataa aaacccatca ggacagaatg atgctcaata tttttaaaatt  480 ctaaaaatag ggtgggattt ttcattgtct ctactttata attatcaaaa cttattttgt   540
attgctacta ccttaaattg aaa                                            563
```

```
<210> SEQ ID NO 149
<211> LENGTH: 544
<212> TYPE: DNA
<213> ORGANISM: Homo sapiens
<220> FEATURE:
<221> NAME/KEY: misc_feature
<222> LOCATION: (1)..(544)
<223> OTHER INFORMATION: AffymetrixID: 218462_at

<400> SEQUENCE: 149
aaatgagcag tgttcgtctt cgtaaagaaa ttaagagaag aggcaaggac cccacagaac     60
acatacctga ataattctg ataattttta caacacggct gggtcattca attggacgta    120
tgtttgcatc tctctttcct cataatcctc aatttatcgg aaggcaggtt gccacattcc   180
acaatcaacg ggattacata ttcttcagat ttcacagata catattcagg agtgaaaaga   240
aagtgggaat tcaggaactt ggaccacgtt ttaccttaaa attaaggtct cttcagaaag   300
gaacctttga ttctaaatat ggagagtatg aatgggtcca taagccccgg gaaatggata   360
caagtagaag aaaattccat ttataaagta ctgagagaat gatattggat tttgctgaac   420
aggcctatct tgaactttgg taaattattt ttgacagaat actcttttca aaatggcatt   480
tgctgatttc ataaaccttt cacgtctgga cgaattacca aatgccatga attgccactg   540
tgtg                                                                 544
```

```
<210> SEQ ID NO 150
<211> LENGTH: 519
<212> TYPE: DNA
<213> ORGANISM: Homo sapiens
<220> FEATURE:
<221> NAME/KEY: misc_feature
<222> LOCATION: (1)..(519)
<223> OTHER INFORMATION: AffymetrixID: 218123_at

<400> SEQUENCE: 150
gtggaagccg gtgtctgtgt taccatggag atggtgaaag atgccttgga ccagcttcga     60
ggcgcggtga tgattgttta ccccatgggg ttgccaccgt atgatcccat ccgcatggag   120
tttgaaaata aggaagactt gtcgggaaca caggcagggc tcaacgtcat taagaggca   180 gaggcgcagc tgtggtgggc agccaaggag ctgagaagaa cgaagaagct ttcagactac   240
gtggggaaga atgaaaaaac caaaattatc gccaagattc agcaaggggg acagggagct   300
ccagcccgag agcctattat tagcagtgag gagcagaagc agctgatgct gtactatcac   360
agaagacaag aggagctcaa gagattggaa gaaaatgatg atgatgccta tttaaactca   420 ccatgggcg ataacactgc tttgaaaaga cattttcatg gagtgaaaga cataaagtgg    480
agaccaagat gaagttcacc agctgatgac acttccaaa                           519
```

```
<210> SEQ ID NO 151
<211> LENGTH: 272
```

```
<212> TYPE: DNA
<213> ORGANISM: Homo sapiens
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (1)..(272)
<223> OTHER INFORMATION: AffymetrixID:   214329_x_at

<400> SEQUENCE: 151
aggttgcagt gtggtgagat catgccacta cactccagcc tggcgacaga gcgagacttg     60
gtttcnaaaa aaaaaaaaaa aaaaacttca gtaagtacgt gttatttttt tcaataaaat    120
tctattacag tatgtcatgt ttgctgtagt gctcatattt attgttgttt ttgttttagt    180
actcacttgt ttcataatat caagattact aaaaatgggg gaaaggactt ctaatctttt    240
tttcataata tctttgacac atattacaga ag                                  272

<210> SEQ ID NO 152
<211> LENGTH: 386
<212> TYPE: DNA
<213> ORGANISM: Homo sapiens
<220> FEATURE:
<221> NAME/KEY: misc_feature
<222> LOCATION: (1)..(386)
<223> OTHER INFORMATION: AffymetrixID:   219067_s_at

<400> SEQUENCE: 152
cgagaagatc ctgatacccc aatgtccttc tttgactttg tggttgatcc tcattctttc     60
ccccgtacag tggaaaacat cttcatgtt tccttcatta tacgggatgg ttttgcaaga    120
ataagacttg accaagaccg actgccagta atagagcctg ttagtattaa tgaagaaaat    180
gagggatttg aacataacac acaagttaga aatcaaggaa ttatagcttt gagttaccgt    240
gactgggagg agattgtgaa gacctttgag atttcagagc ctgtgattac tccaagtcag    300
aggcagcaga agccaagtgc ttgatgctag ctgaaggact caaatggata gtgaagtcca    360
aaacggaaag cggcatgtat tgtaca                                        386

<210> SEQ ID NO 153
<211> LENGTH: 462
<212> TYPE: DNA
<213> ORGANISM: Homo sapiens
<220> FEATURE:
<221> NAME/KEY: misc_feature
<222> LOCATION: (1)..(462)
<223> OTHER INFORMATION: AffymetrixID:   205789_at

<400> SEQUENCE: 153
gtcatgaggc agctttcatc acacccttt aacatttatc taaaagaatt taaattcttt     60
ttcaaaaatt acactacaag tttataagcc caaatggctc tgtgaaatca gaagtgcaaa    120
ggtgtgcaaa cttgtatctg aagacctacc agggacaagg aggtaagagc tgatgtgagt    180
gtgtgtgatg ggatctgtaa ggaactggaa cacacatgtc ctatccaaag gaatcagctg    240
cagctgcttg ttgtcaagta taaagtcagg acctggcttg gctttaaccg ttttcaaga    300 aaactggaaa tctggatttt cagcgaacat gcctgatttt aaaaggttga ctcaagtttt    360
tacaaaatac tatgtgggac acctcaaata catacctact gactgatgac aaacccagga    420
gtttgtgtgt ctttttataaa aagtttgccc tggatgtcat at                     462

<210> SEQ ID NO 154
<211> LENGTH: 546
```

```
<212> TYPE: DNA
<213> ORGANISM: Homo sapiens
<220> FEATURE:
<221> NAME/KEY: misc_feature
<222> LOCATION: (1)..(546)
<223> OTHER INFORMATION: AffymetrixID:  209214_s_at

<400> SEQUENCE: 154
cagtgtccca atccggggttg tggaaaccag aacttcgcct ggagaacaga gtgcaaccag      60
tgtaaggccc caaagcctga aggcttcctc ccgccaccct ttccgccccc gggtggtgat     120
cgtggcagag gtggccctgg tggcatgcgg ggaggaagag gtggcctcat ggatcgtggt     180
ggtcccggtg gaatgttcag aggtggccgt ggtggagaca gaggtggctt ccgtggtggc     240
cggggcatgg accgaggtgg ctttggtgga ggaagacgag gtggccctgg ggggcccct      300 ggacctttga tggaacagat gggaggaaga agaggaggac gtggaggacc tggaaaaatg     360
gataaaggcg agcaccgtca ggagcgcaga gatcggccct actagatgca gagacccgc      420 agagctgcat tgactaccag atttattttt taaaccagaa aatgttttaa atttataatt     480
ccatatttat aatgttggcc acaacattat gattattcct tgtctgtact ttagtatttt     540
tcacca                                                                 546

<210> SEQ ID NO 155
<211> LENGTH: 428
<212> TYPE: DNA
<213> ORGANISM: Homo sapiens
<220> FEATURE:
<221> NAME/KEY: misc_feature
<222> LOCATION: (1)..(428)
<223> OTHER INFORMATION: AffymetrixID:  213427_at

<400> SEQUENCE: 155
cgttgagaga tctccagtgc ccagtgctgc agagcagcga gctggaggga acgccagagg      60
tgtcctgccg ggctctggag ctcttcgact ggctcggcgc cgtcttcagt aatgtcgacc     120
taaataatga gcctaataat ttcatatcaa cctattgctg tcctgagcca agcacagtgg     180
tggcaaaagc ttatttgtgt acaatcactg gcttcatact tccagagaag atctgtctcc     240
tattggaaca tctctgtcac tactttgatg aaccgaagtt agctccatgg gttacactgt     300
ccgttcaagg ctttgcagac agccctgttt cttgggaaaa aaatgaacat ggttttcgaa     360
aaggaggaga acatttatat aactttgtga ttttttaataa tcaggactat tggcttcaga     420
tggctgtt                                                              428

<210> SEQ ID NO 156
<211> LENGTH: 315
<212> TYPE: DNA
<213> ORGANISM: Homo sapiens
<220> FEATURE:
<221> NAME/KEY: misc_feature
<222> LOCATION: (1)..(315)
<223> OTHER INFORMATION: AffymetrixID:  209422_at

<400> SEQUENCE: 156
cagctcgggc gacaactgca agactccatc tcaaaaaaat aaaataaaa gaaagaaag       60 aaatatgtgc actacctaag ttttgtcttt agaaaaacta tccacctata aaaattacc     120 ttgacaaaaa tagttccggt ttgactaatc attttgtttc tttaagtggt aagtgtatgc     180
aaggtggatc cttgatgagc caacattgca ctgtggatac atatctatgt ttacgcgcta     240
ttagaacaga aggcgctgta tatagaaatg ttgctttgaa gcaatatttg caaaacacgc     300
agacttctgt atctg                                                      315
```

<210> SEQ ID NO 157
<211> LENGTH: 543
<212> TYPE: DNA
<213> ORGANISM: Homo sapiens
<220> FEATURE:
<221> NAME/KEY: misc_feature
<222> LOCATION: (1)..(543)
<223> OTHER INFORMATION: AffymetrixID: 201010_s_at

<400> SEQUENCE: 157

```
gtgttctcct actgcaaata ttttcatatg ggaggatggt tttctcttca tgtaagtcct      60
tggaattgat tctaaggtga tgttcttagc actttaattc ctgtcaaatt ttttgttctc     120
cccttctgcc atcttaaatg taagctgaaa ctggtctact gtgtctctag ggttaagcca     180
aaagacaaaa aaaattttac tacttttgag attgccccaa tgtacagaat tatataattc     240
taacgcttaa atcatgtgaa agggttgctg ctgtcagcct tgcccactgt gacttcaaac     300
ccaaggagga actcttgatc aagatgccca accctgtgat cagaacctcc aaatactgcc     360
atgagaaact agagggcagg tgttcataaa agccctttga accccttcc tgccctgtgt      420
taggagatag ggatattggc ccctcactgc agctgccagc acttggtcag tcactctcag     480
ccatagcact tgttcactg tcctgtgtca gagcactgag ctccacccttt ttctgagagt     540
tat                                                                   543
```

<210> SEQ ID NO 158
<211> LENGTH: 181
<212> TYPE: DNA
<213> ORGANISM: Homo sapiens
<220> FEATURE:
<221> NAME/KEY: misc_feature
<222> LOCATION: (1)..(181)
<223> OTHER INFORMATION: AffymetrixID: 200883_at

<400> SEQUENCE: 158

```
ttgccaaggc aactcagcag ccatttgatg tttctgcatt taatgccagt tactcagatt      60
ctggactctt tgggatttat actatctccc aggccacagc tgctggagat gttatcaagg     120
ctgcctataa tcaagtaaaa agaatagctc aaggaaacct ttccaacaca gatgtccaag     180
c                                                                     181
```

<210> SEQ ID NO 159
<211> LENGTH: 503
<212> TYPE: DNA
<213> ORGANISM: Homo sapiens
<220> FEATURE:
<221> NAME/KEY: misc_feature
<222> LOCATION: (1)..(503)
<223> OTHER INFORMATION: AffymetrixID: 218454_at

<400> SEQUENCE: 159

```
gtggctatcc actgttagtt cagaagctgg gcttggacta ctcttatgat ttagctccac      60
gagccaaaat tttccggcgt gaccaaggga aagtgactga tacggcatcc atgaaatata     120
tcatgcgata caacaattat aagaaggatc cttacagtag aggtgacccc tgtaatacca     180
tctgctgccg tgaggacctg aactcaccta acccaagtcc tggaggttgt atgacacaa      240
aggtggcaga tatctaccta gcatctcagt acacatccta tgccataagt ggtcccacag     300
tacaaggtgg cctccctgtt tttcgctggg accgtttcaa caaaactcta catcagggca     360
tgccagaggt ctacaacttt gattttatta ccatgaaacc aattttgaaa cttgatataa     420
aatgaaggag ggagatgacg gactagaaga ctgtaaataa gataccaaag gcactatttt     480
```

```
agctatgttt tcccatcag aat                                           503
```

<210> SEQ ID NO 160
<211> LENGTH: 530
<212> TYPE: DNA
<213> ORGANISM: Homo sapiens
<220> FEATURE:
<221> NAME/KEY: misc_feature
<222> LOCATION: (1)..(530)
<223> OTHER INFORMATION: AffymetrixID: 202918_s_at

<400> SEQUENCE: 160

```
gagtgtcctg ctatagacta tactagacac acacttgatg gtgctgcatg tcttctgaat    60
agcaataaat attttcccag cagggttagc ataaaggaat catctgtagc gaaactagga   120
tcagtatgcc gtaggattta cagaatattt tcacatgctt attttcatca tcggcagata   180
tttgatgaat atgaaaatga aacattttg tgtcatcggt ttactaagtt tgtgatgaaa    240
tacaatttga tgtccaagga taacctgatt gtaccaattt tagaagagga agtacagaat   300
tcagtttctg gggaaagtga agcatgaagg gaatcatagg aaaaatgtac tgatcatata   360
attaacatta tgtactgtat atatcatttt agacacatca atcatgtatc catattatag   420
cttctttgtt tagtataggt ttttgtatgc tgggtttgcc tttaaaatg ggaaatactt    480
tttaagttat tcataagctg tatattcacc agtgtggcac tcatggtttt              530
```

<210> SEQ ID NO 161
<211> LENGTH: 403
<212> TYPE: DNA
<213> ORGANISM: Homo sapiens
<220> FEATURE:
<221> NAME/KEY: misc_feature
<222> LOCATION: (1)..(403)
<223> OTHER INFORMATION: AffymetrixID: 212204_at

<400> SEQUENCE: 161

```
gcttaactct tttgacatct gctattgtga cacatcccat tgctggcaat gtggtgcaca    60
ctccgaaact tttaactact gttttgtaag cctccaaggg tggcattgca gggtccttag   120
gcaatgtttt gtttgccttt atgcagagag gtgctccaag tgctgtgatt gagcaccgtg   180
ctagaggaac tgtaatgctt cagaagttgt agcttataca aaggaaacag gtcctgctgg   240
cttaatttaa acagttattg catgaagtag cgtggaggcc ctggactgct gctcgttctt   300
taggatggac tgttctggta tctggtattg gtttagagac tgttaataag ggacatcaca   360
aggtgatggg attcatttga agcactctat ttctgtttta atg                     403
```

<210> SEQ ID NO 162
<211> LENGTH: 499
<212> TYPE: DNA
<213> ORGANISM: Homo sapiens
<220> FEATURE:
<221> NAME/KEY: misc_feature
<222> LOCATION: (1)..(499)
<223> OTHER INFORMATION: AffymetrixID: 219452_at

<400> SEQUENCE: 162

```
atcacttcga ccacatcaag gctgtcattg gatccaagtt catcgggatt ggtggagatt    60
atgatgggggc cggcaaattc cctcaggggc tggaagacgt gtccacatac ccggtcctga   120
tagaggagtt gctgagtcgt ggctggagtg aggaagagct tcagggtgtc cttcgtggaa   180
acctgctgcg ggtcttcaga caagtggaaa aggtacagga agaaaacaaa tggcaaagcc   240
ccttggagga caagttcccg gatgagcagc tgagcagttc ctgccactcc gacctctcac   300
```

```
gtctgcgtca gagacagagt ctgacttcag gccaggaact cactgagatt cccatacact      360
ggacagccaa gttaccagcc aagtggtcag tctcagagtc ctcccccac atggcccag        420 tccttgcagt tgtggccacc ttcccagtcc ttattctgtg gctctgatga cccagttagt      480
cctgccagat gtcactgta                                                   499

<210> SEQ ID NO 163
<211> LENGTH: 424
<212> TYPE: DNA
<213> ORGANISM: Homo sapiens
<220> FEATURE:
<221> NAME/KEY: misc_feature
<222> LOCATION: (1)..(424)
<223> OTHER INFORMATION: AffymetrixID: 219889_at

<400> SEQUENCE: 163
tactcaagcg ggtggctctg ggatcctggg ggcctgggtt gggggctagg gagacgccat       60
gtgatggaca ctccagggac acacagccta gcacagcagc ttataatggg ctctccgggg     120
ccatttgcaa taacagctgc aattccctgg atagacgagt tgatttcctc cctctgcccc     180
tcccccagcc atgccagctg gcctttgtaa gtgcaggaaa ccgagtagaa aatgtgaccc     240
tccaaatgga gaagctgcca gctttgccat tgtgaaccat ggtgaagtgc ttggaacata     300
ctgttcactc actctaaagg cgctgagact gtgctgttgt tctcgttttt atagtcaatg     360
gcttgttcat catccagatg tggctactga catatctaca cttcgcaccg gagtgtctgg     420
aatt                                                                  424

<210> SEQ ID NO 164
<211> LENGTH: 464
<212> TYPE: DNA
<213> ORGANISM: Homo sapiens
<220> FEATURE:
<221> NAME/KEY: misc_feature
<222> LOCATION: (1)..(464)
<223> OTHER INFORMATION: AffymetrixID: 201303_at

<400> SEQUENCE: 164
caacttcact gtatcctcaa tgcatggaga catgccccag aaagagcggg agtccatcat       60
gaaggagttc cggtcgggcg ccagccgagt gcttatttct acagatgtct gggccagggg     120
gttggatgtc ccctcaggtgt ccctcatcat taactatgat ctccctaata acagagaatt     180
gtacatacac agaattggga gatcaggtcg atacggccgg aagggtgtgg ccattaactt     240
tgtaaagaat gacgacatcc gcatcctcag agatatcgag cagtactatt ccactcagat     300
tgatgagatg ccgatgaacg ttgctgatct tatctgaagc agcagatcag tgggatgagg     360
gagactgttc acctgctgtg tactcctgtt tggaagtatt tagatccaga ttctacttaa     420
tggggtttat atggactttc ttctcataaa tggcctgccg tctc                      464

<210> SEQ ID NO 165
<211> LENGTH: 454
<212> TYPE: DNA
<213> ORGANISM: Homo sapiens
<220> FEATURE:
<221> NAME/KEY: misc_feature
<222> LOCATION: (1)..(454)
<223> OTHER INFORMATION: AffymetrixID: 202510_s_at

<400> SEQUENCE: 165
gtcgtcttcc tattttcagg tcagctgatt agccacctta gttccatctg caactttagt       60
tcccactggc tgtgtaacct aacatagtca caggctctgg ggactgtcac gtggacatct     120
```

| | | |
|---|---|---|
| ttgggaggcc gttattctgc ccaccgcacc ctccgttcat cccctgccct gccgggcacc | 180 | |
| tcgctctacc ccaggaaaat gtgagctcgt tttcctgctc ggcatgtgct cccctaagg | 240 | |
| ctctgctcct ccctgggcct gaaagttcct tctcagcctg agaggggggcc cttcgatctc | 300 | |
| aggcatgact cagcccggct gatgcctctg cagtgctgag tcaggatttg gggccggctc | 360 | |
| tcttgggtct gtccccttt cccaggtact gccttacaaa gctgtggcca ggaagtggcc | 420 | |
| ggtataaagg atgcccaagg tctttgtacg tgtg | 454 | |

<210> SEQ ID NO 166
<211> LENGTH: 239
<212> TYPE: DNA
<213> ORGANISM: Homo sapiens
<220> FEATURE:
<221> NAME/KEY: misc_feature
<222> LOCATION: (1)..(239)
<223> OTHER INFORMATION: AffymetrixID: 221923_s_at

<400> SEQUENCE: 166

| | | |
|---|---|---|
| tagtccatac tgagtgtcat caacaatcca gactgaagtc ttctatttta atctcaatcc | 60 | |
| ccttttctga tttgccaccc atgcctcttc aggctgaaaa caatctcttg gttccctaaa | 120 | |
| gcactttctt ctgactgctg tgattcagtg aaccttgccc tttgctttct attacttgtg | 180 | |
| catttgcctc acctgacaat gttttaaatc gcctttgtat tccttagct gctcaataa | 239 | |

<210> SEQ ID NO 167
<211> LENGTH: 477
<212> TYPE: DNA
<213> ORGANISM: Homo sapiens
<220> FEATURE:
<221> NAME/KEY: misc_feature
<222> LOCATION: (1)..(477)
<223> OTHER INFORMATION: AffymetrixID: 201887_at

<400> SEQUENCE: 167

| | | |
|---|---|---|
| ctgggaagca aaacccatgc ctccccctag ccatttttac tgttatccta tttagatggc | 60 | |
| catgaagagg atgctgtgaa attcccaaca aacattgatg ctgacagtca tgcagtctgg | 120 | |
| gagtggggaa gtgatctttt gttcccatcc tcttcttta gcagtaaaat agctgaggga | 180 | |
| aaagggaggg aaaaggaagt tatgggaata cctgtggtgg ttgtgatccc taggtcttgg | 240 | |
| gagctcttgg aggtgtctgt atcagtggat ttcccatccc ctgtgggaaa ttagtaggct | 300 | |
| catttactgt tttaggtcta gcctatgtgg attttttcct aacatacca agcaaaccca | 360 | |
| gtgtcaggat ggtaattctt attctttcgt tcagttaagt ttttccctc atctgggcac | 420 | |
| tgaagggata tgtgaaacaa tgttaacatt tttggtagtc ttcaaccagg gattgtt | 477 | |

<210> SEQ ID NO 168
<211> LENGTH: 444
<212> TYPE: DNA
<213> ORGANISM: Homo sapiens
<220> FEATURE:
<221> NAME/KEY: misc_feature
<222> LOCATION: (1)..(444)
<223> OTHER INFORMATION: AffymetrixID: 211582_x_at

<400> SEQUENCE: 168

| | | |
|---|---|---|
| agcccacctg ctggatgagg aacttgaggc aagtcaccag cccctgatca tttcgcctaa | 60 | |
| aagagcaagg actagagttc ctgacctcca ggccagtccc tgatccctga cctaatgtta | 120 | |
| tcgcggaatg atgatatatg tatctacggg ggctggggc tgggcgggct cctgcttctg | 180 | |
| gcagtggtcc ttctgtccgc ctgcctgtgt tggctgcatc gaagagcacc ttctgtcctg | 240 | |

```
gtcccaggcc cagggctcct cagagcagga actccactat gcatctctgc agaggctgcc    300
agtgcccagc agtgagggac ctgacctcag gggcagagac aagagaggca ccaaggagga    360
tccaagagct gactatgcct gcattgctga gaacaaaccc acctgagcac cccagacacc    420
ttcctcaacc caggcgggtg gaca                                          444

<210> SEQ ID NO 169
<211> LENGTH: 490
<212> TYPE: DNA
<213> ORGANISM: Homo sapiens
<220> FEATURE:
<221> NAME/KEY: misc_feature
<222> LOCATION: (1)..(490)
<223> OTHER INFORMATION: AffymetrixID: 219030_at

<400> SEQUENCE: 169
agttaacaca tcagctggac ctatttcccg aatgcagggt aacccttctg ttatttaaag     60
atgtaaaaaa tgcgggagac ttgagaagaa aggccatgga aggcaccatc gatggatcac    120
tgataaatcc tacagtgatt gttgatccat ttcagatact tgtggcagca aacaaagcag    180
ttcacctcta caaactggga aaaatgaaga caagaactct atctactgaa attattttca    240
acctttcccc aaataacaat atttcagagg ctttgaaaaa atttggtatc tcagcaaatg    300
acacttcaat tctaattgtt tacattgaag agggagaaaa acaaataaat caagaatacc    360
taatatctca gtagaaggt catcaggttt ctctgaaaaa tcttcctgaa ataatgaata    420
ttacagaagt caaaaagata tataaactct cttcacaaga agaaagtatc gggacattat    480
tggatgctat                                                          490

<210> SEQ ID NO 170
<211> LENGTH: 412
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (1)..(412)
<223> OTHER INFORMATION: AffymetrixID: 212706_at

<400> SEQUENCE: 170
agatatttag gtgacttaca gcaaccaatn gcaacanaac aaaatgttaa gaaatgatct     60
ttntatgagg caatnggaaa tttgaacact gatcaactat aggatgattg gaattattaa    120
tttttaaagg tgtgataaga tactgcactt ggctgggcac agtggcacat gcctgtaatc    180
ccagctactt ggcaggctga ggtgggagaa tcgcttgagc tcaggagttc gagaccagcc    240
tgggcaacgt ggcgaaatcc ccgtctttac aaaacaaac aaacaaacaa aaagatatt     300 gcagttgtgt tgtaagcgtc cttatctttc agagctacat agtggaatgt ttatggaata    360
tttaggataa atgatatagg catttgggat ttgctgcaaa atgacccaga gg           412
```

<210> SEQ ID NO 171
<211> LENGTH: 419
<212> TYPE: DNA
<213> ORGANISM: Homo sapiens
<220> FEATURE:
<221> NAME/KEY: misc_feature
<222> LOCATION: (1)..(419)
<223> OTHER INFORMATION: AffymetrixID: 202902_s_at

<400> SEQUENCE: 171
caaaatatcg tgctgccaca tgttcaaagt acactgaact tccttatggg agagaagatg      60
tcctgaaaga agctgtggcc aataaaggcc cagtgtctgt tggtgtagat gcgcgtcatc     120
cttctttctt cctctacaga agtggtgtct actatgaacc atcctgtact cagaatgtga     180
atcatggtgt acttgtggtt ggctatggtg atcttaatgg gaaagaatac tggcttgtga     240
aaaacagctg gggccacaac tttggtgaag aaggatatat tcggatggca agaaataaag     300
gaaatcattg tgggattgct agctttccct cttacccaga aatctagagg atctctcctt     360
tttataacaa atcaagaaat atgaagcact ttctcttaac ttaattttc ctgctgtat      419

<210> SEQ ID NO 172
<211> LENGTH: 452
<212> TYPE: DNA
<213> ORGANISM: Homo sapiens
<220> FEATURE:
<221> NAME/KEY: misc_feature
<222> LOCATION: (1)..(452)
<223> OTHER INFORMATION: AffymetrixID: 200663_at

<400> SEQUENCE: 172
tgtcttatga tcacgtttgc catctttctg tctcttatca tgttggtgga ggtggccgca      60
gccattgctg gctatgtgtt tagagataag gtgatgtcag agtttaataa caacttccgg     120
cagcagatgg agaattaccc gaaaaacaac cacactgctt cgatcctgga caggatgcag     180
gcagatttta agtgctgtgg ggctgctaac tacacagatt gggagaaaat cccttccatg     240
tcgaagaacc gagtccccga ctcctgctgc attaatgtta ctgtgggctg tgggattaat     300
ttcaacgaga aggcgatcca taaggagggc tgtgtggaga agattggggg ctggctgagg     360
aaaaatgtgc tggtggtagc tgcagcagcc cttggaattg cttttgtcga ggttttggga     420
attgtctttg cctgctgcct cgtgaagagt at                                   452

<210> SEQ ID NO 173
<211> LENGTH: 517
<212> TYPE: DNA
<213> ORGANISM: Homo sapiens
<220> FEATURE:
<221> NAME/KEY: misc_feature
<222> LOCATION: (1)..(517)
<223> OTHER INFORMATION: AffymetrixID: 202138_x_at

<400> SEQUENCE: 173
cagaataaaa aacagccccg ccaagactat cagctgggat tcactttaat ttggaagaat      60
gtgccgaaga cgcagatgaa attcagcatc cagacgatgt gccccatcga aggcgaaggg     120
aacattgcac gtttcttgtt ctctctgttt ggccagaagc ataatgctgt caacgcaacc     180
cttatagata gctgggtaga tattgcgatt tttcagttaa agagggaag cagtaaagaa     240 aaagccgctg ttttccgctc catgaactct gctcttggga agagcccttg gctcgctggg     300
aatgaactca ccgtagcaga cgtggtgctg gtctgtac tccagcagat cggaggctgc     360
agtgtgacag tgccagccaa tgtgcagagg tggatgaggt cttgtgaaaa cctggctcct     420

```
tttaacacgg ccctcaagct ccttaagtga attgccgtaa ctgattttaa agggtttaga      480
ttttaagaat ggtgctcttt catgcctatt atcagta                              517

<210> SEQ ID NO 174
<211> LENGTH: 506
<212> TYPE: DNA
<213> ORGANISM: Homo sapiens
<220> FEATURE:
<221> NAME/KEY: misc_feature
<222> LOCATION: (1)..(506)
<223> OTHER INFORMATION: AffymetrixID:  200851_s_at

<400> SEQUENCE: 174
gttgaaggcc tcgcttagtt gtactggatt ctcagggagc cctctgtggc cttttgcttt       60
gcgtgctgtt tcccttgtac cagagggcgg caccgtggaa attctgtttt ccctgtagca      120
tattgtgttg gattgcatta ctggcagaga aaggacaagg tgccattcaa gtcctagggt      180
gggcttccag ctgccttaat agaagtactc aagtcttttg ggtagtgagc tggaaagcct      240
acaggaaaag aggggtacct gttttcattt gaaactttg  attcatggaa cctttaaaac      300
taatctcaga aaaattttg  gtgcccatgc agctgtagtt gttcactgct ttcctggatg      360
gatgggactc ttatgtcata acttctgtta ctcctttggc ccatagctaa ggtcatcctt      420
ccccacaggg gtggctttgg gattggatga tacagctttt gcttctgtgt agtatacctg      480
tacatacttg tttcaggcag cctttc                                          506

<210> SEQ ID NO 175
<211> LENGTH: 558
<212> TYPE: DNA
<213> ORGANISM: Homo sapiens
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (1)..(558)
<223> OTHER INFORMATION: AffymetrixID:  201109_s_at

<400> SEQUENCE: 175
tcatgatgct gactggcgtt agctgattaa cccatgtaaa taggcactta aatagaagca       60
ggaaagggag acaaagactg gcttctggac ttcctccctg atccccaccc ttactcatca      120
cctngcagtg gccagaatta gggaatcaga atcaaaccag tgtaaggcag tgctggctgc      180
cattgcctgg tcacattgaa attggtggct tcattctaga tgtagcttgt gcagatgtag      240
caggaaaata ggaaaaccta ccatctcagt gagcaccagc tgcctcccaa aggaggggca      300
gccgtgctta tattttatg  gttacaatgg cacaaaatta ttatcaacct aactaaaaca      360
ttcctttcct ctttttcct  gaattatcat ggagttttct aattctctct tttggaatgt      420 angattttt  ttaaatgctt tacgatgtaa aatatttatt ttttacttat tctgaagat       480 ctggctgaag gattattcat ggaacaggaa gaagcgtaaa gactatccat gtcatctttg      540
ttgagagtct tcgtgact                                                   558

<210> SEQ ID NO 176
<211> LENGTH: 502
<212> TYPE: DNA
<213> ORGANISM: Homo sapiens
```

```
<220> FEATURE:
<221> NAME/KEY: misc_feature
<222> LOCATION: (1)..(502)
<223> OTHER INFORMATION: AffymetrixID: 202531_at

<400> SEQUENCE: 176
acaggagtca gtgtctggct ttttcctctg agcccagctg cctggagagg gtctcgctgt      60
cactggctgg ctcctagggg aacagaccag tgaccccaga aaagcataac accaatccca     120
gggctggctc tgcactaagc gaaaattgca ctaaatgaat ctcgttccaa agaactaccc     180
cttttcagct gagccctggg gactgttcca aagccagtga atgtgaagga aactcccctc     240
cttcggggca atgctccctc agcctcagag gagctctacc ctgctccctg ctttggctga     300
ggggcttggg aaaaaaactt ggcacttttt cgtgtggatc ttgccacatt tctgatcaga     360
ggtgtacact aacatttccc ccgagctctt ggcctttgca tttatttata cagtgccttg     420
ctcggggccc accaccccct caagcccag cagccctcaa caggcccagg gagggaagtg      480
tgagcgcctt ggtatgactt aa                                              502

<210> SEQ ID NO 177
<211> LENGTH: 513
<212> TYPE: DNA
<213> ORGANISM: Homo sapiens
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (1)..(513)
<223> OTHER INFORMATION: AffymetrixID: 216274_s_at

<400> SEQUENCE: 177
ggaatgattg tctcatcggc actaatgatc tggaaggggt taatggtaat aactggaagt      60
gaaagtccga ttgtagtggt gctcagtggc agcatggaac ctgcatttca tagaggagat     120
cttctctttc taacaaatcg agttgaagat cccatacgag tgggagaaat tgttgttttc     180
aggatagaag gaagagagat tcctatagtt caccgagtct tgaagattca tgaaaagcaa     240
aatgggcata tcaagttttt gaccaaagga gataataatg cggttgatga ccgaggcctc     300
tataaacaag gacaacattg gctagagaaa aaagatgttg tggggagagc caggggattt     360
gttccttata ttggaatngt gacgatcctc atgaatgact atcctaaatt tangtatgca     420
gttctctttt tgctgggttt attcgtgctg gtncatcgtg agtaagaagc ctgccttgct     480
gttcctggga agatgccata gttttcgtta ctg                                  513

<210> SEQ ID NO 178
<211> LENGTH: 338
<212> TYPE: DNA
<213> ORGANISM: Homo sapiens
<220> FEATURE:
<221> NAME/KEY: misc_feature
<222> LOCATION: (1)..(338)
<223> OTHER INFORMATION: AffymetrixID: 200041_s_at

<400> SEQUENCE: 178
agaggctttc tcggtatcag cagtttaaag attttcaacg acgaattctt gtggctacca      60
```

-continued

```
acctatttgg ccgaggcatg gacatcgagc gggtgaacat tgcttttaat tatgacatgc    120
ctgaggattc tgacacctac ctgcatcggg tggccagagc aggccggttt ggcaccaagg    180
gcttggctat cacatttgtg tccgatgaga atgatgccaa gatcctcaat gatgtgcagg    240
atcgctttga ggtcaatatt agtgagctgc ctgatgagat agacatctcc tcctacattg    300
aacagacacg gtagaagact cgcccatttt ggaatgtg                            338
```

<210> SEQ ID NO 179
<211> LENGTH: 498
<212> TYPE: DNA
<213> ORGANISM: Homo sapiens
<220> FEATURE:
<221> NAME/KEY: misc_feature
<222> LOCATION: (1)..(498)
<223> OTHER INFORMATION: AffymetrixID: 200052_s_at

<400> SEQUENCE: 179

```
ggacatggtc tgctatacag ctcagactct cgtccgaatc ctctcacatg gtggctttag    60
gaagatcctt ggccaggagg gtgatgccag ctatcttgct tctgaaatat ctacctggga   120
tggagtgata gtaacaccct cagaaaaggc ttatgagaag ccaccagaga agaaggaagg   180
agaggaagaa gaggagaata cagaaagaac cacctcaagg agaggaagaa gaaagcatgg   240
aaactcagga gtgacattcc cttcactcct tttcctaccc aagggaaaga ctggagccta   300
agctgcctgc tactggcttt acatggtgac agacattccg tggataggaa gatagcagga   360
gaaagtaact ccatagagtg tcattccact ggttgatatt ggcttagctg ccagtctccc   420
atttgtgacc tatgccatcc atctataatg gaggatacca acatttcttc ctaatattct   480
ataatctcca actcctga                                                  498
```

<210> SEQ ID NO 180
<211> LENGTH: 478
<212> TYPE: DNA
<213> ORGANISM: Homo sapiens
<220> FEATURE:
<221> NAME/KEY: misc_feature
<222> LOCATION: (1)..(478)
<223> OTHER INFORMATION: AffymetrixID: 200064_at

<400> SEQUENCE: 180

```
aatagacttg tgtcttcacc ttgctgcatt gtgaccagca cctacggctg gacagccaat    60
atggagcgga tcatgaaagc ccaggcactt cgggacaact ccaccatggg ctatatgatg   120
gccaaaaagc acctggagat caaccctgac cacccattg tggagacgct gcggcagaag   180
gctgaggccg acaagaatga taaggcagtt aaggacctgg tggtgctgct gtttgaaacc   240
gccctgctat cttctggctt ttcccttgag gatccccaga cccactccaa ccgcatctat   300
cgcatgatca gctaggtct aggtattgat gaagatgaag tggcagcaga ggaacccaat   360
gctgcagttc ctgatgagat cccccctctc gagggcgatg aggatgcgtc tcgcatggaa   420
gaagtcgatt aggttaggag ttcatagttg gaaaacttgt gcccttgtat agtgtccc     478
```

<210> SEQ ID NO 181
<211> LENGTH: 508
<212> TYPE: DNA
<213> ORGANISM: Homo sapiens
<220> FEATURE:
<221> NAME/KEY: misc_feature
<222> LOCATION: (1)..(508)
<223> OTHER INFORMATION: AffymetrixID: 200079_s_at

<400> SEQUENCE: 181
agctgccaga aacgaacctc tttgaaactg aagaaactcg caaaattctt gatgatatct 60
gtgtggcaaa agctgttgaa tgccctccac ctcggaccac agccaggctc cttgacaagc 120
ttgttgggga gttcctggaa gtgacttgca tcaatcctac attcatctgt gatcacccac 180
agataatgag ccctttggct aaatggcacc gctctaaaga gggtctgact gagcgctttg 240
agctgtttgt catgaagaaa gagatatgca atgcgtatac tgagctgaat gatcccatgc 300
ggcagcggca gctttttgaa gaacaggcca aggccaaggc tgcaggtgat gatgaggcca 360
tgttcataga tgaaaacttc tgtactgccc tggaatatgg gctgcccccc acagctggct 420
ggggcatggg cattgatcga gtcgccatgt ttctcacgga ctccaacaac atcaaggaag 480
tacttctgtt tcctgccatg aaacccga 508

<210> SEQ ID NO 182
<211> LENGTH: 393
<212> TYPE: DNA
<213> ORGANISM: Homo sapiens
<220> FEATURE:
<221> NAME/KEY: misc_feature
<222> LOCATION: (1)..(393)
<223> OTHER INFORMATION: AffymetrixID: 200629_at

<400> SEQUENCE: 182
tccagtttac tgaactccag accatgcatg tagtccactc cagaaatcat gctcgcttcc 60
cttggcacac cagtgttctc ctgccaaatg accctagacc ctctgtcctg cagagtcagg 120
gtggcttttc ccctgactgt gtccgatgcc aaggagtcct ggcctccgca gatgcttcat 180
tttgaccctt ggctgcagtg gaagtcagca cagagcagtg ccctggctgt gtcctggacg 240
ggtggactta gctagggaga aagtcgaggc agcagccctc gaggccctca cagatgtcta 300
ggcaggcctc atttcatcac gcagcatgtg caggcctgga agagcaaagc caaatctcag 360
ggaagtcctt ggttgatgta tctgggtctc ctc 393

<210> SEQ ID NO 183
<211> LENGTH: 439
<212> TYPE: DNA
<213> ORGANISM: Homo sapiens
<220> FEATURE:
<221> NAME/KEY: misc_feature
<222> LOCATION: (1)..(439)
<223> OTHER INFORMATION: AffymetrixID: 200634_at

<400> SEQUENCE: 183
gaaaacgttc gtcaacatca cgccagctga ggtgggtgtc ctggttggca aagaccggtc 60
aagtttttac gtgaatgggc tgacacttgg gggccagaaa tgttcggtga tccgggactc 120
actgctgcag gatggggaat ttagcatgga tcttcgtacc aagagcaccg gtggggcccc 180
caccttcaat gtcactgtca ccaagactga caagacgcta gtcctgctga tgggcaaaga 240
aggtgtccac ggtggtttga tcaacaagaa atgttatgaa atggcctccc accttcggcg 300
ttcccagtac tgacctcgtc tgtcccttcc ccttcaccgc tccccacagc tttgcacccc 360
tttcctcccc atacacacac aaaccatttt attttttggg ccattacccc ataccccta 420
ttgctgccaa aaccacatg 439

<210> SEQ ID NO 184
<211> LENGTH: 541
<212> TYPE: DNA
<213> ORGANISM: Homo sapiens
<220> FEATURE:
<221> NAME/KEY: misc_feature
<222> LOCATION: (1)..(541)
<223> OTHER INFORMATION: AffymetrixID: 200802_at

<400> SEQUENCE: 184

```
taattgcacg gattaccagg ctcgccggct tcgaatccga tatgggcaaa ccaagaagat      60
gatggacaag gtggagtttg tccatatgct caatgctacc atgtgcgcca ctacccgtac     120
catctgcgcc atcctggaga actaccagac agagaagggc atcactgtgc ctgagaaatt     180
gaaggagttc atgccgccag gactgcaaga actgatcccc tttgtgaagc ctgcgcccat     240
tgagcaggag ccatcaaaga gcagaagaa gcaacatgag ggcagcaaaa agaaagcagc     300
agcaagagac gtcacccctag aaaacaggct gcagaacatg gaggtcaccg atgcttgaac     360
attcctgcct ccctatttgc caggctttca tttctgtctg ctgagatctc agagcctgcc     420
caacagcagg gaagccaagc acccattcat ccccctgccc ccatctgact gcgtagctga     480
gaggggaaca gtgccatgta ccacacagat gttcctgtct cctcgcatgg gcatagggac     540
c                                                                    541
```

<210> SEQ ID NO 185
<211> LENGTH: 456
<212> TYPE: DNA
<213> ORGANISM: Homo sapiens
<220> FEATURE:
<221> NAME/KEY: misc_feature
<222> LOCATION: (1)..(456)
<223> OTHER INFORMATION: AffymetrixID: 200860_s_at

<400> SEQUENCE: 185

```
acttcagttg caccatgctg tacctttttg cagaggccaa tacggaagcc atccaagaac      60
agatcacaag agttctcttg gaacggttga ttgtaaatag gccacatcct tggggtcttc     120
ttattacctt cattgagctg attaaaaacc cagcgtttaa gttctggaac catgaatttg     180
tacactgtgc cccagaaatc gaaaagttat ccagtcggt cgcacagtgc tgcatgggac     240
agaagcaggc ccagcaagta atggaaggga caggtgccag ttagacgaaa ctgcatctct     300
gttgtacgtg tcagtctaga ggtctcactg caccgagttc ataaactgac tgaagaatcc     360
tttcagctct tcctgacttt cccagccctt tggtttgtgg gtatctgccc caactactgt     420
tgggatcagc ctcctgtctt atgtgggcac gttcca                              456
```

<210> SEQ ID NO 186
<211> LENGTH: 506
<212> TYPE: DNA
<213> ORGANISM: Homo sapiens
<220> FEATURE:
<221> NAME/KEY: misc_feature
<222> LOCATION: (1)..(506)
<223> OTHER INFORMATION: AffymetrixID: 200983_x_at

<400> SEQUENCE: 186

```
aggagttgag acctacttca cagtagttct gtggacaatc acaatgggaa tccaaggagg      60
gtctgtcctg ttcgggctgc tgctcgtcct ggctgtcttc tgccattcag gtcatagcct     120
gcagtgctac aactgtccta acccaactgc tgactgcaaa acagccgtca attgttcatc     180
tgattttgat gcgtgtctca ttaccaaagc tgggttacaa gtgtataaca agtgttggaa     240
gtttgagcat tgcaatttca cgacgtcac aacccgcttc agggaaaatg agctaacgta     300
ctactgctgc aagaaggacc tgtgtaactt taacgaacag cttgaaaatg gtgggacatc     360
cttatcagag aaaacagttc ttctgctggt gactccattt ctggcagcag cctggagcct     420
tcatcccctaa gtcaacacca ggagagcttc tcccaaactc ccgttcctg cgtagtccgc     480
```

-continued tttctcttgc tgccacattc taaagg        506

<210> SEQ ID NO 187
<211> LENGTH: 375
<212> TYPE: DNA
<213> ORGANISM: Homo sapiens
<220> FEATURE:
<221> NAME/KEY: misc_feature
<222> LOCATION: (1)..(375)
<223> OTHER INFORMATION: AffymetrixID: 200991_s_at

<400> SEQUENCE: 187
tgccacccgg gagtctatgg tcaaactctc aagtaagctg agtgccgtga gcttgcgggg        60
aattggcagt cccagcacag atgccagtgc cagtgatgtc cacggcaatt tcgccttcga       120
gggcattgga gatgaggatc tgtaatctcc actgcttgga tgtctgccct ctaccccaga       180
ggaatttaca gaaacttgcc ctgtgcctgt gtccccatg ctaggggcgg aggggtcttt       240
tccttcttct ttcctaccta ccccttttct cttggccagg ggcctcgtat cctacctttc       300
cttgtcccct gggctggctg cacagaggat tgccccttct cttttcagag ctggccctcg       360
atgccaaatt agcat                                                       375

<210> SEQ ID NO 188
<211> LENGTH: 312
<212> TYPE: DNA
<213> ORGANISM: Homo sapiens
<220> FEATURE:
<221> NAME/KEY: misc_feature
<222> LOCATION: (1)..(312)
<223> OTHER INFORMATION: AffymetrixID: 201112_s_at

<400> SEQUENCE: 188
agatctgtgc ggttggcata accaacttac taacagaatg tcccccaatg atggacactg        60
agtataccaa actgtggact ccattattac agtctttgat tggtcttttt gagttacccg       120
aagatgatac cattcctgat gaggaacatt ttattgacat agaagataca ccaggatatc       180
agactgcctt ctcacagttg gcatttgctg gaaaaaaga gcatgatcct gtaggtcaaa       240
tggtgaataa ccccaaaatt cacctggcac agtcacttca catgttgtct accgcctgtc       300
caggaagggt tc                                                          312

<210> SEQ ID NO 189
<211> LENGTH: 338
<212> TYPE: DNA
<213> ORGANISM: Homo sapiens
<220> FEATURE:
<221> NAME/KEY: misc_feature
<222> LOCATION: (1)..(338)
<223> OTHER INFORMATION: AffymetrixID: 201214_s_at

<400> SEQUENCE: 189
agagctgcaa gagttctgga tgaacgacaa tctccttgag agctggagcg acctcgacga        60
gctgaaggga gccaggagcc tggagacagt gtacctggag cggaacccct tgcagaagga       120
cccccagtac cggcggaagg tcatgctcgc cctcccctcc gtgcggcaga tcgatgccac       180
gttcgtcagg ttctgagtcc ttcttggctc ctcatgtggt ccctctcctc ggaagaactg       240
cccagccacg ggttttttaac ccacctgttg ctcctgaggt cgtcactata tcaacagtca       300
caaacccaat ggcaataaag gcactgacga tagctggc                               338

<210> SEQ ID NO 190
<211> LENGTH: 385

```
<212> TYPE: DNA
<213> ORGANISM: Homo sapiens
<220> FEATURE:
<221> NAME/KEY: misc_feature
<222> LOCATION: (1)..(385)
<223> OTHER INFORMATION: AffymetrixID: 201241_at

<400> SEQUENCE: 190
aggatgggtc tggcaatttc cctggtggca acagaaaaag aaaaggtttg gtaccatgta      60
tgtagcagcc gtggaaaagg gtgttataac acaagactca aggaagatgg aggctgtacc     120
atatggtaca acgagatgca gttactatct gagatagaag aacacctgaa ctgtaccatt     180
tctcaggttg agccggatat aaaggtacca gtggatgaat tgatgggaa agttacctac      240 ggtcagaaaa gggctgctgg tggtggaagc tataaaggcc atgtggatat tttggcacct     300
actgttcaag agttggctgc ccttgaaaag gaggcgcaga catctttcct gcatcttggc     360
taccttccta accagctgtt cagaa                                            385

<210> SEQ ID NO 191
<211> LENGTH: 371
<212> TYPE: DNA
<213> ORGANISM: Homo sapiens
<220> FEATURE:
<221> NAME/KEY: misc_feature
<222> LOCATION: (1)..(371)
<223> OTHER INFORMATION: AffymetrixID: 201263_at

<400> SEQUENCE: 191
gatctggatc caggctgtac attgaataaa aagattcgaa atgcacagtt agcacagtat      60
aacttcattt tagttgttgg tgaaaaagag aaaatcactg gcactgttaa tatccgcaca     120
agagacaata aggtccacgg ggaacgcacc atttctgaaa ctatcgagcg gctacagcag     180
ctcaaagagt tccgcagcaa acaggcagaa gaagaatttt aatgaaaaaa ttacccagat     240
tggctccatg gaaaaggagg aacagcgttt ccgtaaaatt gactttgtac tcgaaaacgt     300
caatttatat tgaacttgga ggaggagttt ggcaaagtct gaaataggtc aacctgcagg     360
cgtaactatt t                                                           371

<210> SEQ ID NO 192
<211> LENGTH: 492
<212> TYPE: DNA
<213> ORGANISM: Homo sapiens
<220> FEATURE:
<221> NAME/KEY: misc_feature
<222> LOCATION: (1)..(492)
<223> OTHER INFORMATION: AffymetrixID: 201386_s_at

<400> SEQUENCE: 192
ggagatcatc tgacactgct gaacgtctac catgcttta aacaaaatca tgaatcggtt       60
cagtggtgtt atgacaactt cattaactac aggtccctga tgtccgcaga caatgtacgc     120
cagcagctat ctcgaattat ggacagattt aatttgcctc gtcgaagtac tgactttaca     180
agcagggact attatattaa tataagaaaa gctttggtta ctgggtattt tatgcaggtg     240
gcacatttag aacgaacagg gcattactta actgtgaaag ataaccaggt ggttcagttg     300
catccctcta ctgttcttga ccacaaacct gaatgggtgc tttataatga gtttgttcta     360
acaacaaaga attacatccg gacatgtaca gatatcaagc cagaatggtt ggtgaaaatt     420 gccccctcaat attatgacat gagcaatttc ccacagtgtg aagcaaagag acagttggac     480
cgcatcattg cc                                                          492
```

<210> SEQ ID NO 193
<211> LENGTH: 408
<212> TYPE: DNA
<213> ORGANISM: Homo sapiens
<220> FEATURE:
<221> NAME/KEY: misc_feature
<222> LOCATION: (1)..(408)
<223> OTHER INFORMATION: AffymetrixID: 201417_at

<400> SEQUENCE: 193

| | | | | | |
|---|---|---|---|---|---|
| gtaaaccaca | tctttttgc | acttttttta | taagcaaaaa | cgtgccgttt | aaaccactgg | 60 |
| atctatctaa | atgccgattt | gagttcgcga | cactatgtac | tgcgttttc | attcttgtat | 120 |
| ttgactattt | aatcctttct | acttgtcgct | aaatataatt | gttttagtct | tatggcatga | 180 |
| tgatagcata | tgtgttcagg | tttatagctg | ttgtgtttaa | aaattgaaaa | aagtggaaaa | 240 |
| catctttgta | catttaagtc | tgtattataa | taagcaaaaa | gattgtgtgt | atgtatgttt | 300 |
| aatataacat | gacaggcact | aggacgtctg | cctttttaag | gcagttccgt | taagggtttt | 360 |
| tgttttaaa | cttttttttg | ccatccatcc | tgtgcaatat | gccgtgta | | 408 |

<210> SEQ ID NO 194
<211> LENGTH: 422
<212> TYPE: DNA
<213> ORGANISM: Homo sapiens
<220> FEATURE:
<221> NAME/KEY: misc_feature
<222> LOCATION: (1)..(422)
<223> OTHER INFORMATION: AffymetrixID: 201576_s_at

<400> SEQUENCE: 194

| | | | | | |
|---|---|---|---|---|---|
| aatggcttta | accttggccg | ctattggcca | gcccggggcc | ctcagttgac | cttgtttgtg | 60 |
| ccccagcaca | tcctgatgac | ctcggcccca | aacaccatca | ccgtgctgga | actggagtgg | 120 |
| gcaccctgca | gcagtgatga | tccagaacta | tgtgctgtga | cgttcgtgga | caggccagtt | 180 |
| attggctcat | ctgtgaccta | cgatcatccc | tccaaacctg | ttgaaaaaag | actcatgccc | 240 |
| ccacccccgc | aaaaaaacaa | agattcatgg | ctggaccatg | tatgatgatg | aaagcctgtg | 300 |
| tctttgaggg | attctacccct | gaacatacct | cacagatcct | ccctgtcatg | ccacatttca | 360 |
| ctgattggaa | tgtggaaatg | gaaaaggaat | ttaggatgtg | cattttcacc | tgaggtttcc | 420 |
| ct | | | | | | 422 |

<210> SEQ ID NO 195
<211> LENGTH: 551
<212> TYPE: DNA
<213> ORGANISM: Homo sapiens
<220> FEATURE:
<221> NAME/KEY: misc_feature
<222> LOCATION: (1)..(551)
<223> OTHER INFORMATION: AffymetrixID: 201872_s_at

<400> SEQUENCE: 195

| | | | | | |
|---|---|---|---|---|---|
| gagatccaaa | caactatagg | ccacgaataa | acaaacttaa | ttcaattaag | gatgtagaac | 60 |
| aaaagaagag | tggaaactac | tttttcttgg | atgattagac | tgactctgag | aatattgata | 120 |
| agccatttat | taaaaggagt | atttactaga | attttttgtc | atataaaact | tgaatcagga | 180 |
| ttttatgccc | cacatactct | ggaacttgaa | gtataatata | cttaatataa | cataaaaagc | 240 |
| cagttgggtt | ctaaattgta | gttgaaacac | agaaaatgcc | acttttctgt | tcctgaagag | 300 |
| gctcttttgt | gcataatatt | ctaaaatgaa | gacatttcaa | gctatacaaa | ttacttccaa | 360 |
| gttttcatga | tgtatgggaa | gatttcagt | aggtgtatta | tattcacggt | accaaatgct | 420 |
| gaccagtgtt | gctccatttt | ttaaatcttg | aaaagggttt | ctgtacttac | ctggtttgcc | 480 | aagtatgcca gtgtaatgaa actgcccttA ttttaaaagc cagtcaaaga ttccactgat    540 tgacatttga t                                                        551

```
<210> SEQ ID NO 196
<211> LENGTH: 519
<212> TYPE: DNA
<213> ORGANISM: Homo sapiens
<220> FEATURE:
<221> NAME/KEY: misc_feature
<222> LOCATION: (1)..(519)
<223> OTHER INFORMATION: AffymetrixID:  201892_s_at
```

<400> SEQUENCE: 196
tgtcagagta tgcacggcgc tttggtgttc cggtcattgc tgatggagga atccaaaatg     60
tgggtcatat tgcgaaagcc ttggcccttg gggcctccac agtcatgatg ggctctctcc    120
tggctgccac cactgaggcc cctggtgaat acttcttttc cgatgggatc cggctaaaga    180
aatatcgcgg tatgggttct ctcgatgcca tggacaagca cctcagcagc cagaacagat    240
atttcagtga agctgacaaa atcaaagtgg cccagggagt gtctggtgct gtgcaggaca    300
aagggtcaat ccacaaattt gtcccttacc tgattgctgg catccaacac tcatgccagg    360
acattggtgc caagagcttg acccaagtcc gagccatgat gtactctggg gagcttaagt    420
ttgagaagag aacgtcctca gcccaggtgg aaggtggcgt ccatagcctc cattcgtatg    480
agaagcggct tttctgaaaa gggatccagc acacctcct                          519

```
<210> SEQ ID NO 197
<211> LENGTH: 283
<212> TYPE: DNA
<213> ORGANISM: Homo sapiens
<220> FEATURE:
<221> NAME/KEY: misc_feature
<222> LOCATION: (1)..(283)
<223> OTHER INFORMATION: AffymetrixID:  202174_s_at
```

<400> SEQUENCE: 197
caacctttaa atagtgctgc ccataaggag tcacctccta ctgttgattc aactcaacag     60
cctaaccctt tgccgttacg tttacctgaa atggaaccct tagtgcctag agtcaaagaa    120
gttaaatctg ctcaggaaac tcctgaaagc tctctggctg gaagtcctga tactgaatct    180
ccagtgttag tgaatgacta tgaagcagaa tctggtaata aagtcaaaaa gtctgatgaa    240
gaagattttg taaaagttga agatttacca ctgaaactga caa                      283

```
<210> SEQ ID NO 198
<211> LENGTH: 522
<212> TYPE: DNA
<213> ORGANISM: Homo sapiens
<220> FEATURE:
<221> NAME/KEY: misc_feature
<222> LOCATION: (1)..(522)
<223> OTHER INFORMATION: AffymetrixID:  202176_at
```

<400> SEQUENCE: 198
ggtgatcacg aaactcgctg gcatggagga ggaagacttg gcgttttcga caaaagaaga     60
gcaacagcag ctcttacaga aagtcctggc agccactgac ctggatgccg aggaggaggt    120
ggtggctggg gaatttggct ccagatccag ccaggcatct cggcgctttg gcaccatgag    180
ttctatgtct ggggccgacg acactgtgta catggagtac cactcatcgc ggagcaaggc    240
gcccagcaaa catgtacacc cgctcttcaa gcgctttagg aaatgatgct taggcagggt    300
acttcgttca agaccggcgc ttggcaccct tgttggaaag ggattttcag cataacattt    360

```
tccttccacc tctttgacct tccctccagc gttggccaaa ttgtgctgag gaagatgcat      420
caagggcttg gctgtgcctt cataggtcat ctagggtttt ataaaggagg aggagacaat      480
attttttcaa acttttgggg gagtggggtc atttctgtat at                         522
```

<210> SEQ ID NO 199
<211> LENGTH: 423
<212> TYPE: DNA
<213> ORGANISM: Homo sapiens
<220> FEATURE:
<221> NAME/KEY: misc_feature
<222> LOCATION: (1)..(423)
<223> OTHER INFORMATION: AffymetrixID: 202220_at

<400> SEQUENCE: 199

```
tgatccaaag ctggcacctt caggcacatt ggtctcatag ccattactgt ttttattgcc       60
cttctaagat cctgtcttca gctgggtcag agaaaacttc ttgactaaaa ctggtcagaa      120
ctcatcacag aaatgaaata cagtggtctc tctctcccag aactggttgc agctaaaaca      180
gagagatctg actgctggct ataggatttt ggacttaatg actgaaattg caaattgtcc      240
tttttcttgg cattacagat tttgccaaaa taacttttg tatcaaatat tgatgtgtga       300
aagtgaagga gctagtctgc tgaaccagga atagtttgag atattgaact gtcattttg       360 cacatttgaa tactttgcag gctggctttg tataaactta cctctggtt tcctatatgt      420 tgt                                                                   423
```

<210> SEQ ID NO 200
<211> LENGTH: 344
<212> TYPE: DNA
<213> ORGANISM: Homo sapiens
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (108)..(113)
<223> OTHER INFORMATION: n is a, c, g, or t
<220> FEATURE:
<221> NAME/KEY: misc_feature
<222> LOCATION: (1)..(344)
<223> OTHER INFORMATION: AffymetrixID: 202225_at

<400> SEQUENCE: 200

```
gatactgtaa agtccacaca cacattaaat cttgttttcc tgaaagtatg gcatcaaaaa       60
tacttgtaga aaaaccttgt cacaactgat ttgaatgttc ctattntnnn nnnctttgac      120
tttgatattg gcttgtaatg tctcttttca tcatatgtaa tatcagtgga acaggcagcg      180
ctactcaagt cctaaggatt cctcagtgat cagtgatcca gggccgttca tgaaccactg      240
ggctggattt gactgttgag tgtggcagtt aatgcccctc aagaaatcaa aggatgtctt      300
ataagtgtct tccaaaaaaa agcaaatgct gaaatcctat ggc                       344
```

<210> SEQ ID NO 201
<211> LENGTH: 371
<212> TYPE: DNA
<213> ORGANISM: Homo sapiens
<220> FEATURE:
<221> NAME/KEY: misc_feature
<222> LOCATION: (1)..(371)
<223> OTHER INFORMATION: AffymetrixID: 202464_s_at

<400> SEQUENCE: 201

```
tattctgtcc tgagaccacg ggcaaagctc ttccattttg agagagaaga aaaactgttt       60
```

```
ggaaccacac caatgatatt tttctttgta atacttgaaa tttattttt tattattttg      120 atagcagatg tgctatttat ttatttaata tatgtataag gagtcctaaa caatagaaag      180
ctgtagaagc tgtagagata ggcttcagtt gttaattggt ttggagcctc ctatgtgtga      240
cttatgactc tctgtgttct gtgtatttgt ctgaattaat gacctgggat ataaagctat      300
gctagctttc aaacaggaga tgccttcaga aagctttgta tattttgcag ttgccagacc      360
aataaaatac c                                                          371
```

<210> SEQ ID NO 202
<211> LENGTH: 445
<212> TYPE: DNA
<213> ORGANISM: Homo sapiens
<220> FEATURE:
<221> NAME/KEY: misc_feature
<222> LOCATION: (1)..(445)
<223> OTHER INFORMATION: AffymetrixID: 202545_at

<400> SEQUENCE: 202

```
atcgccctg agatcctaca gggcctgaag tacacattct ctgtggactg gtggtctttc       60
ggggtccttc tgtacgagat gctcattggc cagtccccct tccatggtga tgatgaggat      120
gaactcttcg agtccatccg tgtggacacg ccacattatc cccgctggat caccaaggag      180
tccaaggaca tcctggagaa gctctttgaa agggaaccaa ccaagaggct gggaatgacg      240
ggaaacatca aaatccaccc cttcttcaag accataaact ggactctgct ggaaaagcgg      300
aggttggagc cacccttcag gcccaaagtg aagtcaccca gagactacag taactttgac      360
caggagttcc tgaacgagaa ggcgcgcctc tcctacagcg acaagaacct catcgactcc      420
atggaccagt ctgcattcgc tggct                                           445
```

<210> SEQ ID NO 203
<211> LENGTH: 482
<212> TYPE: DNA
<213> ORGANISM: Homo sapiens
<220> FEATURE:
<221> NAME/KEY: misc_feature
<222> LOCATION: (1)..(482)
<223> OTHER INFORMATION: AffymetrixID: 202838_at

<400> SEQUENCE: 203

```
agaaagaggc gctgctcact gttttcctgc ttcagttttt ctcttatagt accatcacta       60
taatcaacga acttctcttc tccacccaga gatggctttt ccaacacatt ttaattaaag      120
gaactgagta cattaccctg atgtctaaat ggaccaaaga tctgagatcc attgtgatta      180
tatctgtatc aggtcagcag aagaaggaac tgagcagttg aactctgagt tcatcaattc      240
taatatttgg aaattatcta caatggaatc ttccctctgt tctctgataa cctacttgct      300
tactcaatgc ctttaagcca agtcaccctg ttgcctatgg gaggaggtgg aaggatttgg      360
caagctcaac cacatgctat ttagttagca tcagttgtca ccaacagtct ttctgcaaag      420
ggcaggagag ctttggggga aaggaaaagg cttaccaggc tgctatggtc aactcttcag      480
aa                                                                    482
```

<210> SEQ ID NO 204
<211> LENGTH: 386
<212> TYPE: DNA
<213> ORGANISM: Homo sapiens
<220> FEATURE:
<221> NAME/KEY: misc_feature
<222> LOCATION: (1)..(386)
<223> OTHER INFORMATION: AffymetrixID: 202896_s_at

<400> SEQUENCE: 204

```
ccaccaccca actggggcta gagtggggaa gatttcccct ttagatcaaa ctgcccttc      60 catggaaaag ctggaaaaaa actctggaac ccatatccag gcttggtgag gttgctgcca    120
acagtcctgg cctcccccat ccctaggcaa agagccatga gtcctggagg aggagaggac    180
ccctcccaaa ggactggaag caaaaccctc tgcttccttg ggtccctcca agactccctg    240
gggcccaact gtgttgctcc acccggaccc atctctccct tctagacctg agcttgcccc    300
tccagctagc actaagcaac atctcgctgt aagcgcctgt aaattactgt gaaatgtgaa    360
acgtgcaatc ttgaaactga ggtgtt                                         386
```

<210> SEQ ID NO 205
<211> LENGTH: 486
<212> TYPE: DNA
<213> ORGANISM: Homo sapiens
<220> FEATURE:
<221> NAME/KEY: misc_feature
<222> LOCATION: (1)..(486)
<223> OTHER INFORMATION: AffymetrixID: 202950_at

<400> SEQUENCE: 205

```
taacatgtta gttgtcattt ggcatgagtg tgcattccag taattcttaa ttgatatttg     60
attaattcca tacctttgat taaaacatgc tagttcaaaa taagactgct cagtttccaa    120
gggttttcaa gcctacttac ctttataaag gttctctagt ctctgattag ccatgactgt    180
attggacttt gaacattttc tgaactaaaa acctctattc taaactaatc tcatttggat    240
gtgtaagtct tttgtaaagg caagaataaa taatatccag gacaatttat tagttttctc    300 agtatttttcc caaatattag aatatttact tcattattgg ttggctgcca atgaccccat    360
atgttctgtg agaatagtag ctttatcttt gatataatac atagtctcca aataggtaat    420
acttcgcaat tgattagatt ttcagagtag atttagagtt atctgttttt ctggtgaggg    480
tcaaat                                                               486
```

<210> SEQ ID NO 206
<211> LENGTH: 466
<212> TYPE: DNA
<213> ORGANISM: Homo sapiens
<220> FEATURE:
<221> NAME/KEY: misc_feature
<222> LOCATION: (1)..(466)
<223> OTHER INFORMATION: AffymetrixID: 203037_s_at

<400> SEQUENCE: 206

```
agtagtgcct gtggtttagc ccaccaatct tgatgactaa agtagctga tgcattgtgc      60 atatgatgct tgagatggtt tttgcaaaag cagaaatcgc tgcaaggtaa tcacaataga    120
taaaagtggt attttaaacc tttgaaataa atggatgtaa ctgtaccttg gtacagcttt    180
tcacttgttt agttttaaa cgttagtata atctgaataa ataaaatgtt gccaaattca    240
atgtagaaag aatgtgacaa cacaccttgg gtagttctgc ttgtgttttt gcatattgta    300
aaagcagtgt cacagctaaa aagaaagaaa tcgtttctaa cagtaaatta ttgtgcttta    360
gttgctagtt tgtactgaga gttgacctct ccctgtgcag ttttttgttc taaacttgta    420
taaataacaa ttgtgtaatg tgtctcccte ctacattgta acaatt                   466
```

<210> SEQ ID NO 207
<211> LENGTH: 497
<212> TYPE: DNA
<213> ORGANISM: Homo sapiens

```
<220> FEATURE:
<221> NAME/KEY: misc_feature
<222> LOCATION: (1)..(497)
<223> OTHER INFORMATION: AffymetrixID: 203155_at

<400> SEQUENCE: 207
gtcttcgtgg atacccatga tcttcgcttc ccctgggtgg ccttctttgc cagcaaaaga      60
atccgggctg ggacagaact tacttgggac tacaactacg aggtgggcag tgtggaaggc     120
aaggagctac tctgttgctg tggggccatt gaatgcagag gacgtcttct ttagaggaca     180
gccttcttcc caaccttct tgaactgtcg tttcctcagg aactgggtct tcctgattgt      240
tgaaccctga cccgaagtct ctgggctagc tactcccccc agctcctagt tgatagaaat     300
gggggttctg gaccagatga tcccttccaa tgtggtgcta gcaggcagga tcccttctcc     360
acctccaaag gccctaaagg gtggggagag atcaccactc taacctcggc ctgacatccc     420
tcccatccca tatttgtcca agtgttcctg cttctaacag actttgttct tagaatggag     480
cctgtgtatc tactatc                                                    497

<210> SEQ ID NO 208
<211> LENGTH: 478
<212> TYPE: DNA
<213> ORGANISM: Homo sapiens
<220> FEATURE:
<221> NAME/KEY: misc_feature
<222> LOCATION: (1)..(478)
<223> OTHER INFORMATION: AffymetrixID: 203371_s_at

<400> SEQUENCE: 208
ctttcctgcc gtgagaaact cgaggtgacc aacctccgtt tccggttggc tccggttgca      60
gagttgagtg tcctgagagg tcagattgct gtcagacatg gcccatgaac atggacatga     120
gcatggacat cataaaatgg aacttccaga ttatagacaa tggaagatag aagggacacc     180
attagaaact atccagaaga agctggctgc aaaaaggcta aggatccat ggggccgcaa      240 tgaagcttgg agatacatgg gtggctttgc aaagagtgtt tccttttctg atgtattctt     300
taaaggattc aaatggggat ttgctgcatt tgtggtagct gtaggagctg aatattacct     360
ggagtccctg aataaagata agaagcatca ctgaagataa tacctggaag catcatagtg     420
gtttcttaac tctccaaaat aagatttctt ctctgtagcc tacttgtctg gtttatcc       478

<210> SEQ ID NO 209
<211> LENGTH: 510
<212> TYPE: DNA
<213> ORGANISM: Homo sapiens
<220> FEATURE:
<221> NAME/KEY: misc_feature
<222> LOCATION: (1)..(510)
<223> OTHER INFORMATION: AffymetrixID: 203821_at

<400> SEQUENCE: 209
gagccactct atgagttgga cttcagtctt gcctaggcga ttttgtctac catttgtgtt      60
ttgaaagccc aaggtgctga tgtcaaagtg taacagatat cagtgtctcc ccgtgtcctc     120
tccctgccaa gtctcagaag aggttgggct tccatgcctg tagcttcct ggtccctcac      180 ccccatggcc ccaggccaca gcgtgggaac tcactttccc ttgtgtcaag acatttctct     240
aactcctgcc attcttctgg tgctactcca tgcagggtc agtgcagcag aggacagtct      300
ggagaaggta ttagcaaagc aaaaggctga gaaggaacag gaacattgg agctgactgt      360 tcttggtaac tgattacctg ccaattgcta ccgagaaggt tggaggtggg gaaggctttg     420
tataatccca cccacctcac caaaacgatg aaggtatgct gtcatggtcc tttctggaag     480
```
tttctggtgc catttctgaa ctgttacaac                                      510

<210> SEQ ID NO 210
<211> LENGTH: 419
<212> TYPE: DNA
<213> ORGANISM: Homo sapiens
<220> FEATURE:
<221> NAME/KEY: misc_feature
<222> LOCATION: (1)..(419)
<223> OTHER INFORMATION: AffymetrixID:  203966_s_at

<400> SEQUENCE: 210
gatgcaacag atatatagcc ctttcaagtc atgttgtgtt tggacttggg gttggaacag      60
ggagagcagc agccatgtca gctacacgct caaatgtgca gatgattatg gaaaataacc     120
tcaaaatctt acaaagctga acatccaagg agttattgaa aactatctta aatgttcttg     180 gtagggagt tggcattgtt gataaagcca gtcccttcat ttaactgtct ttcaggatgt     240
tccttcgttg tttccatgag tattgcaggt aataatacag tgtgttccat aagaatctca     300
atcttggggc taaatgcctt gtttctttgc acctcttttc aagtccttac atttaattac     360
taattgataa gcagcagctt cctacatata gtaggaaact gccacatttt tgctatcat     419

<210> SEQ ID NO 211
<211> LENGTH: 356
<212> TYPE: DNA
<213> ORGANISM: Homo sapiens
<220> FEATURE:
<221> NAME/KEY: misc_feature
<222> LOCATION: (1)..(356)
<223> OTHER INFORMATION: AffymetrixID:  204192_at

<400> SEQUENCE: 211
tacccgcagg actggttcca agtcctcatc ctgagaggta acgggtcgga ggcgcaccgc      60
gtgccctgct cctgctacaa cttgtcggcg accaacgact ccacaatcct agataaggtg     120
atcttgcccc agctcagcag gcttggacac ctggcgcggt ccagacacag tgcagacatc     180
tgcgctgtcc ctgcagagag ccacatctac cgcgagggct gcgcgcaggg cctccagaag     240
tggctgcaca acaaccttat ttccatagtg ggcatttgcc tgggcgtcgg cctactcgag     300
ctcgggttca tgacgctctc gatattcctg tgcagaaacc tggaccacgt ctacaa        356

<210> SEQ ID NO 212
<211> LENGTH: 507
<212> TYPE: DNA
<213> ORGANISM: Homo sapiens
<220> FEATURE:
<221> NAME/KEY: misc_feature
<222> LOCATION: (1)..(507)
<223> OTHER INFORMATION: AffymetrixID:  204419_x_at

<400> SEQUENCE: 212
acactcgctt ctggaacgtc tgaggttatc aataagctcc tagtccagac gccatgggtc      60
atttcacaga ggaggacaag gctactatca caagcctgtg gggcaaggtg aatgtggaag     120
atgctggagg agaaaccctg ggaaggctcc tggttgtcta cccatggacc cagaggttct     180
ttgacagctt tggcaacctg tcctctgcct ctgccatcat gggcaacccc aaagtcaagg     240
cacatggcaa gaaggtgctg acttccttgg gagatgccaa aaagcacctg atgatctca     300 agggcacctt tgcccagctg agtgaactgc actgtgacaa gctgcatgtg gatcctgaga     360
acttcaagct cctgggaaat gtgctggtga ccgtttggc aatccatttc ggcaaagaat     420
tcacccctga ggtgcaggct tcctggcaga agatggtgac tggagtggcc agtgccctgt     480

```
cctccagata ccactgagct cactgcc                                          507
```

<210> SEQ ID NO 213
<211> LENGTH: 463
<212> TYPE: DNA
<213> ORGANISM: Homo sapiens
<220> FEATURE:
<221> NAME/KEY: misc_feature
<222> LOCATION: (1)..(463)
<223> OTHER INFORMATION: AffymetrixID: 204566_at

<400> SEQUENCE: 213

```
gccacttgtc ttgaaaactg tgcaactttt taaagtaaat tattaagcag actggaaaag     60
tgatgtattt tcatagtgac ctgtgtttca cttaatgttt cttagagcca agtgtcttt    120
aaacattatt ttttatttct gatttcataa ttcagaacta aattttttcat agaagtgttg  180
agccatgcta cagttagtct tgtcccaatt aaaatactat gcagtatctc ttacatcagt   240
agcatttttc taaaaccta gtcatcagat atgcttacta aatcttcagc atagaaggaa    300
gtgtgtttgc ctaaaacaat ctaaaacaat tcccttcttt ttcatcccag accaatggca   360
ttattaggtc ttaaagtagt tactcccttc tcgtgtttgc ttaaaatatg tgaagtttc    420
cttgctattt caataacaga tggtgctgct aattcccaac att                     463
```

<210> SEQ ID NO 214
<211> LENGTH: 304
<212> TYPE: DNA
<213> ORGANISM: Homo sapiens
<220> FEATURE:
<221> NAME/KEY: misc_feature
<222> LOCATION: (1)..(304)
<223> OTHER INFORMATION: AffymetrixID: 204689_at

<400> SEQUENCE: 214

```
cttttctgta atctgtttat ctcccactta atgaaaggc aaagggtac cccaaatcca      60
gaggtgccta catttcaggc agccttggag tatttaaaa ggaaaacatt ctttactttt    120
atatgacatt cttatactgc tgtctcaaat ccttttcat ttcagagctc ttgtctcaga    180
gatgtgtgtt cttttgtca gagatatggt tgatgagaat cttaaatgct tgttttgcac   240
tatcacttag tacctgtttg accaaggtgt taagggatag tacctcccat cagcagagaa   300
actg                                                                304
```

<210> SEQ ID NO 215
<211> LENGTH: 524
<212> TYPE: DNA
<213> ORGANISM: Homo sapiens
<220> FEATURE:
<221> NAME/KEY: misc_feature
<222> LOCATION: (1)..(524)
<223> OTHER INFORMATION: AffymetrixID: 205249_at

<400> SEQUENCE: 215

```
ggaacgtagc aatatctgct ccttttcgag ttgtttgaga aatgtaggct attttttcag    60
tgtatatcca ctcagatttt gtgtatttt gatgtaccca cactgttctc taaattctga   120
atctttggga aaaatgtaa agcatttatg atctcagagg ttaacttatt taaggggat    180
gtacatattc tctgaaacta ggatgcatgc aattgtgttg gaagtgtcct tggtcgcctt   240
gtgtgatgta gacaaatgtt acaaggctgc atgtaaatgg gttgccttat tatggagaaa   300
aaaatcactc cctgagttta gtatggctgt atatttatgc ctattaatat ttggaatttt   360
ttttagaaag tatatttttg tatgctttgt tttgtgactt aaaagtgtta cctttgtagt   420
```

```
caaatttcag ataagaatgt acataatgtt accggagctg atttgtttgg tcattagctc      480
ttaatagttg tgaaaaaata aatctattct aacgcaaaac cact                      524

<210> SEQ ID NO 216
<211> LENGTH: 307
<212> TYPE: DNA
<213> ORGANISM: Homo sapiens
<220> FEATURE:
<221> NAME/KEY: misc_feature
<222> LOCATION: (1)..(307)
<223> OTHER INFORMATION: AffymetrixID:  205552_s_at

<400> SEQUENCE: 216
gctcctgacg gtctatgctt gggagcgagg gagcatgaaa acacatttca acacagccca       60
gggatttcgg acggtcttgg aattagtcat aaactaccag caactctgca tctactggac      120
aaagtattat gactttaaaa accccattat tgaaaagtac ctgagaaggc agctcacgaa      180
acccacgcct gtgatcctgg acccggcgga ccctacagga aacttgggtg gtggagaccc      240
aaagcgttgg aggcagctgg cacaagaggc tgaggcctgg ctgaattacc catgctttaa      300
gaattgg                                                               307

<210> SEQ ID NO 217
<211> LENGTH: 525
<212> TYPE: DNA
<213> ORGANISM: Homo sapiens
<220> FEATURE:
<221> NAME/KEY: misc_feature
<222> LOCATION: (1)..(525)
<223> OTHER INFORMATION: AffymetrixID:  206115_at

<400> SEQUENCE: 217
ctcgctcctt ctggtatatg catgtcactg catgataatt gagttttcct ttgttttaat       60
aaaactgttc tcagacatta agctaaacta agagaaaaat aactttgttg ccaaaaggtt      120
gtgctatcca gatttttat atgtctgcat gtttaaaaaa aaaaagcaa caaagaaaa       180 tgcactctaa cttatgtgaa ctgagagaaa aaaatcaggt tttaaacagg aaaacctatg      240
gggaatgata ttttttgaaa gacttttgta taaagttgag tacttagaaa aaagacaaac      300
cagatgtaat atattttgtg gatgttttta tttcttggat ttatagtacc ttatactaag      360
gttaaaaaaa tatgcttgat attgtgaaaa ggtgaaattc ttcaccaaca tttcatttgc      420
tcctttgtca tattgtaatg ccaatataat atagttaatg aaaacagcat ttttaaaaac      480
cgaaatattg aaatggtgta atgttgtacc atttgcactg tgagc                     525

<210> SEQ ID NO 218
<211> LENGTH: 509
<212> TYPE: DNA
<213> ORGANISM: Homo sapiens
<220> FEATURE:
<221> NAME/KEY: misc_feature
<222> LOCATION: (1)..(509)
<223> OTHER INFORMATION: AffymetrixID:  206584_at

<400> SEQUENCE: 218
tgatgattag ttactgatcc tctttgcatt tgtaaagctt tggagatatt gaatcatgtt       60
accatttctg ttttttttcca ccctgttttc ttccatattt actgaagctc agaagcagta     120
ttgggtctgc aactcatccg atgcaagtat ttcatacacc tactgtgata aaatgcaata      180
cccaatttca attaatgtta acccctgtat agaattgaaa ggatccaaag gattattgca      240
cattttctac attccaagga gagatttaaa gcaattatat ttcaatctct ataaactgt       300
```

```
caacaccatg aatcttccaa agcgcaaaga agttatttgc cgaggatctg atgacgatta    360 ctcttttgc agagctctga agggagagac tgtgaataca acaatatcat tctccttcaa    420
gggaataaaa ttttctaagg gaaaatacaa atgtgttgtt gaagctattt ctgggagccc    480
agaagaaatg ctcttttgct tggagtttg                                      509

<210> SEQ ID NO 219
<211> LENGTH: 431
<212> TYPE: DNA
<213> ORGANISM: Homo sapiens
<220> FEATURE:
<221> NAME/KEY: misc_feature
<222> LOCATION: (1)..(431)
<223> OTHER INFORMATION: AffymetrixID: 206877_at

<400> SEQUENCE: 219
gaaaagccgt tcaccaaatc gaccagcttc agcgagagca gcgacacctg aagaggcagc    60
tggagaagct gggcattgag aggatccgga tggacagcat cggctccacc gtctcctcgg    120
agcgctccga ctccgacagg gaagaaatcg acgttgacgt ggagagcacg gactatctca    180
caggtgatct ggactggagc agcagcagtg tgagcgactc tgacgagcgg ggcagcatgc    240
agagcctcgg cagtgatgag ggctattcca gcaccagcat caagagaata aagctgcagg    300
acagtcacaa ggcgtgtctt ggtctctaag agagtgggca ctgcggctgt ctccttgaag    360
gttctccctg ttggttctga ttaggtaacg tattggacct gcccacaact cccttgcacg    420
taaacttcag t                                                          431

<210> SEQ ID NO 220
<211> LENGTH: 377
<212> TYPE: DNA
<213> ORGANISM: Homo sapiens
<220> FEATURE:
<221> NAME/KEY: misc_feature
<222> LOCATION: (1)..(377)
<223> OTHER INFORMATION: AffymetrixID: 207170_s_at

<400> SEQUENCE: 220
aaaacagcac tcctttggct ggagcacttg tgtccgtgca tgtacttggg tgtttccctc    60
catcctttct gatatgacca aaaatcaagt tgttttgttt tttgtcacct tcactggcat    120
gggctaacca cttcttttc aaaccctctg aacacctttt tctgatgggt aacttgcagg    180
aatattctat tggaaaagat aacaggaagt acaagtgctt cttgacccct tcctcaatgt    240
ttctagcctt cactctccat tgtctttct gggctgtatt acagccctct gtggatcttc    300
aactctgctg cctccactgt gatgcagcag tccaactgta actgacagtg gctgccttct    360
ctgggccatg gatcaca                                                    377

<210> SEQ ID NO 221
<211> LENGTH: 518
<212> TYPE: DNA
<213> ORGANISM: Homo sapiens
<220> FEATURE:
<221> NAME/KEY: misc_feature
<222> LOCATION: (1)..(518)
<223> OTHER INFORMATION: AffymetrixID: 208631_s_at

<400> SEQUENCE: 221
ccagaactgc tgacacagat ggtgtccaag ggcttcctag gtcgtaaatc tgggaagggc    60
ttttacatct atcaggaggg tgtgaagagg aaggatttga attctgacat ggatagtatt    120
ttagcgagtc tgaagctgcc tcctaagtct gaagtctcat cagacgaaga catccagttc    180
```

```
cgcctggtga caagatttgt gaatgaggca gtcatgtgcc tgcaagaggg gatcttggcc      240
acacctgcag agggagacat cggagccgtc tttgggcttg gcttcccgcc ttgtctggga      300 gggccttttcc gctttgtgga tctgtatggc gcccagaaga tagtggaccg gctcaagaaa    360
tatgaagctg cctatggaaa acagttcacc ccatgccagc tgctagctga ccatgctaac     420
agccctaaca agaagttcta ccagtgagca ggcctcatgc ctcgctcagt cagtgcacta     480
accccagctg ccggcagtgc tggttctcca acagagtg                             518
```

```
<210> SEQ ID NO 222
<211> LENGTH: 168
<212> TYPE: DNA
<213> ORGANISM: Homo sapiens
<220> FEATURE:
<221> NAME/KEY: misc_feature
<222> LOCATION: (1)..(168)
<223> OTHER INFORMATION: AffymetrixID: 208691_at

<400> SEQUENCE: 222
gagttctgtc atgattcact attctagaac ttgcatgacc tttactgtgt tagctctttg      60
aatgttcttg aaattttaga ctttctttgt aaacaaataa tatgtcctta tcattgtata     120
aaagctgtta tgtgcaacag tgtggagatt ccttgtctga tttaataa                  168
```

```
<210> SEQ ID NO 223
<211> LENGTH: 555
<212> TYPE: DNA
<213> ORGANISM: Homo sapiens
<220> FEATURE:
<221> NAME/KEY: misc_feature
<222> LOCATION: (1)..(555)
<223> OTHER INFORMATION: AffymetrixID: 208868_s_at

<400> SEQUENCE: 223
acatctagaa acattacacc acacacaccg tcatcacatt ttcacatgct caattgatat      60
tttttgctgc ttcctcggcc cagggagaaa gcatgtcagg acagagctgt tggattggct    120
ttgatagagg aatggggatg atgtaagttt acagtattcc tggggtttaa ttgttgtgca    180
gtttcataga tgggtcagga ggtggacaag ttggggccag agatgatggc agtccagcag    240
caactccctg tgctcccttc tctttgggca gagattctat ttttgacatt tgcacaagac    300
aggtagggaa aggggacttg tggtagtgga ccatacctgg ggaccaaaag agacccactg    360
taattgatgc attgtggccc ctgatcttcc ctgtctcaca cttcttttct cccatcccgg    420
ttgcaatctc actcagacat cacagtacca ccccagggggt ggcagtagac aacaacccag   480
aaatttagac agggatctct tacctttgga aaatagggggt taggcatgaa ggtggttgtg   540
attaagaaga tggtt                                                      555
```

```
<210> SEQ ID NO 224
<211> LENGTH: 456
<212> TYPE: DNA
<213> ORGANISM: Homo sapiens
<220> FEATURE:
<221> NAME/KEY: misc_feature
<222> LOCATION: (1)..(456)
<223> OTHER INFORMATION: AffymetrixID: 208869_s_at

<400> SEQUENCE: 224
gactaaaacc actcttagca tctcctctag tattttccat gtatcaggac agaggtgtct      60
tatgtaggga gggggcaagt atgaagtaag gtaattatat actactctca ttcaggattc    120
ttgctcccat gctgctgtcc cttcaggctc acatgcacag gaatgctaca tgatggccag    180
```

```
ctgcttccct ccttggttat catccactgc agctgctagt tagaaaggtt tggagggatg    240
acttttagta aatcatgggg attttattga tttattttca cttttgggat tttgtggggt    300
gggagtgggg agcaggaatt gcactcagac atgacatttc aattcatctc tgctaatgaa    360
aagggttctt tctcttgggg gaaatgtgtg tgtcagttct gtcagctgca agttcttgta    420
taatgaagtc aatgccatca ggccaaggaa ataaaa                              456

<210> SEQ ID NO 225
<211> LENGTH: 298
<212> TYPE: DNA
<213> ORGANISM: Homo sapiens
<220> FEATURE:
<221> NAME/KEY: misc_feature
<222> LOCATION: (1)..(298)
<223> OTHER INFORMATION: AffymetrixID:  208942_s_at

<400> SEQUENCE: 225
caacatggcg aacgcagga gacacaagaa gcggatccag gaagttggtg aaccatctaa      60
agaagagaag gctgtggcca agtatcttcg attcaactgt ccaacaaagt ccaccaatat    120
gatgggtcac cggttgatt attttattgc ttcaaaagca gtggactgtc ttttggattc    180
aaagtgggca aaggccaaga aaggagagga agctttatttt acaaccaggg agtctgtggt    240
tgactactgc aacaggcttt taaagaagca gttttttcac cgagccctaa aagtaatg     298

<210> SEQ ID NO 226
<211> LENGTH: 454
<212> TYPE: DNA
<213> ORGANISM: Homo sapiens
<220> FEATURE:
<221> NAME/KEY: misc_feature
<222> LOCATION: (1)..(454)
<223> OTHER INFORMATION: AffymetrixID:  209092_s_at

<400> SEQUENCE: 226
aaatccaatc atgagtccag gtagagaacg cctgctgtaa tctacactgt tgctgggact     60
gcgcattctg tatataactg tgttggatga gtgacagatg attgtccaga ctaggacagc    120
ggcatgaaca tgactttggt tgggattgcg gatagttagg gttacctctg aatcgtgtag    180
cttttatgag agcagctgtg caagtgaatc cacattaatg ccttgtcgtg gtgccattcc    240
cagcgcctga cgatacgctc ttctattgtc ttattctggc aggttttgac gttttaaatt    300
ttttaaagaa attttattcc ttggaccaaa aggtttggtt aaccacccce ctcttacttg    360 cttcacattt ttgagtgtcc agaggaaaca gaaaggaatg agtgtgtgac gttgctgcac    420
gcctgactct gtgcgagctt ctttctgtgt atat                                454

<210> SEQ ID NO 227
<211> LENGTH: 465
<212> TYPE: DNA
<213> ORGANISM: Homo sapiens
<220> FEATURE:
<221> NAME/KEY: misc_feature
<222> LOCATION: (1)..(465)
<223> OTHER INFORMATION: AffymetrixID:  209193_at

<400> SEQUENCE: 227
gattgtagtg gatctaattt ttcagaaatt ttgcctttaa gttatttac ctgttttgt       60 ttcttgtttt gaaagatgcg cattctaacc tggaggtcaa tgttatgtat ttatttattt    120
atttatttgg ttcccttcct attccaagct tccatagctg ctgccctagt tttctttcct    180
cctttcctcc tctgacttgg ggacctttg ggggagggct gcgacgcttg ctctgttttgt    240
```

```
ggggtgacgg gactcaggcg ggacagtgct gcagctccct ggcttctgtg gggcccctca    300
cctacttacc caggtgggtc ccggctctgt gggtgatggg gagggggcatt gctgactgtg   360 tatataggat aattatgaaa agcagttctg gatggtgtgc cttccagatc ctctctgggg   420
ctgtgttttg agcagcaggt agcctggctg gtttttatctg agtga                 465

<210> SEQ ID NO 228
<211> LENGTH: 447
<212> TYPE: DNA
<213> ORGANISM: Homo sapiens
<220> FEATURE:
<221> NAME/KEY: misc_feature
<222> LOCATION: (1)..(447)
<223> OTHER INFORMATION: AffymetrixID:  209200_at

<400> SEQUENCE: 228
ggagcaatcc aagccacata tcttctacat caaatttttc catttttggtt attttcataa    60 tctggtattg cattttgcct tccctgttca tacctcaaat tgattcatac ctcagtttaa   120
ttcagagagg tcagttaagt gacggattct gttgtggttt gaatgcagta ccagtgttct   180
cttcgagcaa agtagacctg ggtcactgta ggcataggac ttggattgct tcagatggtt   240
tgctgtatca tttttcttct ttttcttttc ctggggactt gtttccatta aatgagagta   300
attaaaatcg cttgtaaatg agggcataca agcatttgca acaaatattc aaatagaggc   360
tcacagcggc ataagctgga ctttgtcgcc actagatgac aagatgttat aactaagtta   420
aaccacatct gtgtatctca agggact                                      447

<210> SEQ ID NO 229
<211> LENGTH: 337
<212> TYPE: DNA
<213> ORGANISM: Homo sapiens
<220> FEATURE:
<221> NAME/KEY: misc_feature
<222> LOCATION: (1)..(337)
<223> OTHER INFORMATION: AffymetrixID:  209861_s_at

<400> SEQUENCE: 229
aagtaaatac ttgatggctc tgaagaatct gtgtgacttg ggcattgtag atccatatcc    60
accattatgt gacattaaag gatcatatac agcgcaattt gaacatacca tcctgttgcg   120
tccaacatgt aaagaagttg tcagcagagg agatgactat taaacttagt ccaaagccac   180
ctcaacacct ttattttctg agctttgttg gaaaacatga taccagaatt aatttgccac   240
atgttgtctg ttttaacagt ggacccatgt aatacttttta tccatgttta aaaagaagga   300
atttggacaa aggcaaaccg tctaatgtaa ttaacca                            337

<210> SEQ ID NO 230
<211> LENGTH: 196
<212> TYPE: DNA
<213> ORGANISM: Homo sapiens
<220> FEATURE:
<221> NAME/KEY: misc_feature
<222> LOCATION: (1)..(196)
<223> OTHER INFORMATION: AffymetrixID:  209967_s_at

<400> SEQUENCE: 230
ttcctaaaaa tgcttcactg tacgtagtta agtcgtagct ataacttcaa attttttaaa    60
agggacaaac tgtaaaaaat gtgtgtattc ttaaaatgca atatttgtaa ggcttgttcc   120
aatgccacat acttgcagct cccattctat gtgtcatcaa tagtgtccta tgcaataaat   180
tatttgcagg tcttta                                                  196
```

<210> SEQ ID NO 231
<211> LENGTH: 535
<212> TYPE: DNA
<213> ORGANISM: Homo sapiens
<220> FEATURE:
<221> NAME/KEY: misc_feature
<222> LOCATION: (1)..(535)
<223> OTHER INFORMATION: AffymetrixID: 210027_s_at

<400> SEQUENCE: 231

| | | | | | |
|---|---|---|---|---|---|
| tgggatgaag | cctttcgcaa | gttcctgaag | ggcctggctt | cccgaaagcc | ccttgtgctg | 60 |
| tgtggagacc | tcaatgtggc | acatgaagaa | attgaccttc | gcaaccccaa | ggggaacaaa | 120 |
| aagaatgctg | gcttcacgcc | acaagagcgc | caaggcttcg | gggaattact | gcaggctgtg | 180 |
| ccactggctg | acagctttag | gcacctctac | cccaacacac | cctatgccta | cacctttttgg | 240 |
| acttatatga | tgaatgctcg | atccaagaat | gttggttggc | gccttgatta | cttttttgttg | 300 |
| tcccactctc | tgttacctgc | attgtgtgac | agcaagatcc | gttccaaggc | cctcgcgagt | 360 |
| gatcactgtc | ctatcaccct | atacctagca | ctgtgacacc | accctaaat | cactttgagc | 420 |
| ctgggaaata | agccccctca | actaccattc | cttcttaaa | cactcttcag | agaaatctgc | 480 |
| attctatttc | tcatgtataa | aacgaggaat | cctccaacca | ggctcctgtg | ataga | 535 |

<210> SEQ ID NO 232
<211> LENGTH: 358
<212> TYPE: DNA
<213> ORGANISM: Homo sapiens
<220> FEATURE:
<221> NAME/KEY: misc_feature
<222> LOCATION: (1)..(358)
<223> OTHER INFORMATION: AffymetrixID: 210053_at

<400> SEQUENCE: 232

| | | | | | |
|---|---|---|---|---|---|
| aacgtagtta | ctgtatggca | ctcaaaaact | atgttaaatg | atccactaac | ttttttttttc | 60 |
| ttggcccatg | attaatggaa | tgtatgtaac | taggtagggt | tccttcttcta | gatctagagg | 120 |
| aagtacagcc | acccactgac | atctgaattt | atatacctgt | tgagttttga | gtgcacccaa | 180 |
| acactcgata | aaccaggtga | agaaatttag | cttccatgtt | ctacttcagc | taaaacagct | 240 |
| acatacaacc | tagtacactt | gaagtcagac | agacatttca | gttgcttacc | tccagtactg | 300 |
| agccttgctt | tgggaaacta | aaagatttag | accaagtcac | tgccagtttt | tgcctttg | 358 |

<210> SEQ ID NO 233
<211> LENGTH: 391
<212> TYPE: DNA
<213> ORGANISM: Homo sapiens
<220> FEATURE:
<221> NAME/KEY: misc_feature
<222> LOCATION: (1)..(391)
<223> OTHER INFORMATION: AffymetrixID: 210172_at

<400> SEQUENCE: 233

| | | | | | |
|---|---|---|---|---|---|
| ggtaaatata | cgttctgcat | ccaaatgcac | tttgagattg | ttacgattta | ttctgagcaa | 60 |
| gatctgcatt | ttttgaaagt | ttgagattgt | agttatcttt | tttgagatga | gatactttca | 120 |
| cgactttggt | atcatctgtc | agttttttgcc | cagtgagttc | tgcatttgca | gctccttgtt | 180 |
| ttggtctgtt | cgtaactgca | gtgttctcca | tgagtatcag | gaaggtaggg | tttcacttag | 240 |
| gagtaagaac | agtccccagt | ccagcagcca | cccttttcag | ctgctgttca | ttgccagttg | 300 |
| atgaggtgag | tgtcatctgc | ctctctggac | aggccccagt | ggagaacacc | gcaggtactg | 360 |
| taaaccaagt | acttttcaca | gcgtggcctt | t | | | 391 |

<210> SEQ ID NO 234
<211> LENGTH: 164
<212> TYPE: DNA
<213> ORGANISM: Homo sapiens
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (1)..(164)
<223> OTHER INFORMATION: AffymetrixID: 210766_s_at

<400> SEQUENCE: 234

| | | |
|---|---|---|
| ggttccatca atggtgagca ccagcctgaa tgcagaagcg ctccagtatc tccaagggta | 60 |
| ccttcaggca gccagtgtga cactgcttta aactgcattt ttctnaatgg gctaaaccca | 120 |
| gatggttttcc taggaaatca caggcttctg agcacagctg catt | 164 |

<210> SEQ ID NO 235
<211> LENGTH: 381
<212> TYPE: DNA
<213> ORGANISM: Homo sapiens
<220> FEATURE:
<221> NAME/KEY: misc_feature
<222> LOCATION: (1)..(381)
<223> OTHER INFORMATION: AffymetrixID: 210949_s_at

<400> SEQUENCE: 235

| | | |
|---|---|---|
| acaaagtccg caccatgctg gttaggaaga tccaggaaga gtcactgagg acctacctct | 60 |
| tcacctacag cagtgtctat gactccatca gcatggagac gctgtcagac atgtttgagc | 120 |
| tggatctgcc cactgtgcac tccatcatca gcaaaatgat cattaatgag gagctgatgg | 180 |
| cctccctgga ccagccaaca cagacagtgg tgatgcaccg cactgagccc actgcccagc | 240 |
| agaacctggc tctgcagctg gccgagaagc tgggcagcct ggtggagaac aacgaacggg | 300 |
| tgtttgacca caagcagggc acctacgggg gctacttccg agaccagaag gacggctacc | 360 |
| gcaaaaacga gggctacatg c | 381 |

<210> SEQ ID NO 236
<211> LENGTH: 545
<212> TYPE: DNA
<213> ORGANISM: Homo sapiens
<220> FEATURE:
<221> NAME/KEY: misc_feature
<222> LOCATION: (1)..(545)
<223> OTHER INFORMATION: AffymetrixID: 211458_s_at

<400> SEQUENCE: 236

| | | |
|---|---|---|
| aaatagcatt aaactggaat tgacagagtg agttgagcat ctctgtctaa cctgctcttt | 60 |
| ctctctggtg ctcctcatct caccectacc ttggaattta ataagcttca ggcatttcca | 120 |
| attgcagact aaaaccactt ctaccatctc ctctagtatt ttccatgtat caggacagag | 180 |
| atgtcttatg tagggaaggg gcaggtatga agtgaggtag attatctata cctctcactc | 240 |
| attcaggatt ctcgctccca tgctgctgtc ccttcattct cacactcaca ggaatgctat | 300 |
| gtgatggcca gctgcttccc ttcttggtta tccactgcag ctgctagtta gaaaggtttg | 360 |
| cagggatgac ttttagtaaa tcatgggat tttattgatt tattatcact tataggattt | 420 |
| tgtggggtgg gagtggggag caggaattgc actcagacat gacatttcaa ttcatctctg | 480 |
| caaatgaaaa gggttcttcc tcttggggga aatctgtgtg tcagttctgt cagctgcaag | 540 |
| ttctt | 545 |

<210> SEQ ID NO 237
<211> LENGTH: 311
<212> TYPE: DNA
<213> ORGANISM: Homo sapiens
<220> FEATURE:
<221> NAME/KEY: misc_feature
<222> LOCATION: (1)..(311)
<223> OTHER INFORMATION: AffymetrixID: 211546_x_at

<400> SEQUENCE: 237

```
gggagttgtg gctgctgctg agaaaaccaa acagggtgtg gcagaagcag caggaaagac      60
aaaagagggt gttctctatg tagtggctga gaagaccaaa gagcaagtga caaatgttgg     120
aggagcagtg gtgacgggtg tgacagcagt agcccagaag acagtggagg gagcagggag     180
cattgcagca gccactggct ttgtcaaaaa ggaccagttg ggcaagaatg aagaaggagc     240
cccacaggaa ggaattctgg aagatatgcc tgtggatcct gacaatgagg cttatgaaat     300
gccttctgag g                                                          311
```

<210> SEQ ID NO 238
<211> LENGTH: 482
<212> TYPE: DNA
<213> ORGANISM: Homo sapiens
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (1)..(482)
<223> OTHER INFORMATION: AffymetrixID: 212199_at

<400> SEQUENCE: 238

```
attttgctgt tacctttgtg acctgattgt tttttggaac acgtcaagac gtgggatcag      60
aatcttccaa ctttagaggt gcaatggaag acactacgct acttggttga gcctggtgaa     120
gaatgtatta atgagactgc tttgcataaa actgggaaga aagagaagac agttggagat     180
ggaagatggt tttgtatata ttttggaact ttagttcctc tgtgagacga aagaggagag     240
ctatgttttg tgtcacattg tctgatatat attgtgtaac ctgtcaggtg agttgattta     300
gacaacatag ctgacctttt atgacaaggc agtttgaata gggactattg taatacctc     360
acacattata ggggcancag agaatggcat ggaagagaca gtctacagag agctttaaga     420
ggccggagaa aggaaaagac attatcaggg cctggaaagt ctcttccagt tcatcagggt     480
ag                                                                    482
```

<210> SEQ ID NO 239
<211> LENGTH: 419
<212> TYPE: DNA
<213> ORGANISM: Homo sapiens
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (1)..(419)
<223> OTHER INFORMATION: AffymetrixID: 212224_at

<400> SEQUENCE: 239

```
acagtgttct ctaatgttac agatgagatg cgcattgcca agaggagat ttttggacca       60
gtgcagcaaa tcatgaagtt taatctttta gatgacgtga tcaaaagagc aaacaatact     120
ttctatggct tatcagcagg agtgtttacc aaagacattg ataaagccat aacaatctcc     180
```

```
tctgctctgc aggcaggaac agtgtgggtg aattgctatg gcgtggtaag tgcccagtgc    240 cccctttggnt gggattcaag atgtctggaa atggaagaga actgggagag tacggtttcc    300
atgaatatac agaggtcaaa acagtcacag tgaaaatctc tcagaagaac tcataaagaa    360
aatacaagag tggagagaag ctcttcaata gctaagcatc tccttacagt cactaatat     419
```

<210> SEQ ID NO 240
<211> LENGTH: 438
<212> TYPE: DNA
<213> ORGANISM: Homo sapiens
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (1)..(438)
<223> OTHER INFORMATION: AffymetrixID: 212388_at

<400> SEQUENCE: 240

```
gtgacagtta tgacaggctt accttggaag agttgtcatt tttactgcca attttttgga    60
tgaagatgtt tttataaacc tttcaaaatg gtctgcaaac agagcaggaa ttgcacaatt    120
aactcaataa tgctgtgtgt tctcaagaag ctcccttagt gaggccgatc ttaagatggc    180
cgattctgcc cgttgaaggc atncctggga aagaaaacaa gcatcccagc gggcatctca    240
ccacgacttc tcctggagtc ctcacacggt cactgacaac tacagtcagt tttaggaact    300
agagtgccgt atcatcagac ttaccctgtc ctgccccacc ttccctgcta acatcgaggt    360
gtgtgcagtt accttctgag cttggaacaa gcagactgga attttcctct gctacctctt    420
gtgtataaaa tcttgttt                                                  438
```

<210> SEQ ID NO 241
<211> LENGTH: 546
<212> TYPE: DNA
<213> ORGANISM: Homo sapiens
<220> FEATURE:
<221> NAME/KEY: misc_feature
<222> LOCATION: (1)..(546)
<223> OTHER INFORMATION: AffymetrixID: 212591_at

<400> SEQUENCE: 241

```
ggcccagatt gcagatggat ttcgtattag agttgatctc gcatctgaga cctcatctag    60
agacaagaga tcggtttttg tggggaatct cccttataaa gttgaagaat ctgccattga    120
gaagcacttt ctggactgtg gaagtatcat ggccgtgagg attgtgagag acaaaatgac    180
aggcatcggc aaagggtttg gctatgtgct ctttgagaat acagattctg ttcatcttgc    240
tctgaaatta ataattctg aactcatggg gagaaaactc agagtcatgc gttctgttaa     300
taaagaaaaa tttaaacaac aaaattcaaa tccacgattg aagaatgtca gtaaacctaa    360
gcagggactt aattttactt ccaaaactgc agaaggacat cctaaaagct tatttattgg    420
agaaaaagct gttctcctta aaacgaagaa gaaggacag aagaaaagtg gacgccctaa     480
gaaacagaga aaacagaaat aacaaccagg aactgctttt tcttttcctg ctgagtactg    540
ctaata                                                               546
```

<210> SEQ ID NO 242
<211> LENGTH: 560
<212> TYPE: DNA
<213> ORGANISM: Homo sapiens
<220> FEATURE:
<221> NAME/KEY: misc_feature

```
<222> LOCATION: (49)..(49)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (1)..(560)
<223> OTHER INFORMATION: AffymetrixID:  212696_s_at

<400> SEQUENCE: 242
ctgaaggagt gtccctcctc tatgtgaaaa gaaaattgtt ttattcttnc attctgactt      60
tttaancngt tnggctcact tnccagttag tttgaatgaa ataataatt  ttctacttgg    120 nagttgaaga gggcagaatc cgcagctctc atcattgtga tgtgtagcat gtctgccctc    180
tgactggaca tcattgccat taactttctt ctgggcatca cggcaatgtc acgatgccca    240
gacttggagc aaggcaacct tggagtcagt ccactcataa aatatggtaa cacccatttt    300
aaaatttaag ttttgtcctt aaagacaact tcagtggtta attataaaag ttgtgttact    360
tcgtcctaaa ttaaattgat agaaagattt aaaaatgtgt tttgtttcta ctattcagaa    420
actgcgaact agggaaaggt tggtatgaaa aaatgtcttt cctttttca  atgtacatag    480 ttcaactctt tctttgttac atttaaacta tatccatgga tatcagtctg ctttggactc    540
ctctgctagt gttacagatg                                                560

<210> SEQ ID NO 243
<211> LENGTH: 516
<212> TYPE: DNA
<213> ORGANISM: Homo sapiens
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (1)..(516)
<223> OTHER INFORMATION: AffymetrixID:  212709_at

<400> SEQUENCE: 243
tgcaaattaa gactcacctt cactttccaa aatagctgag ggttgtnggc ttgttgtagc      60
tgaccaccaa aagcagtcac tgcaaatctt ttaattcttc cctatcacct tttgtatttt    120
aatgcaatta ttttggtcca gaactgacct gtattttctg tattgtacac aaaagctaat    180
aattttgtgt acttttttatt tattttggag gttttatatg atcttcaatt gagtattaaa    240
taatttgcct agattaagcc taaaatgatg accagctaat taagaagat  attttgaatc    300 tggttctgag ctaaagttga gtaaattctt agctaagaaa aaattggaaa tccatcatct    360
atattagcaa cagattctca gagtaaattg ttaacttcta tgatttatga taatcaagct    420
ggacttgatc atacaagtta gtctcataat gtattggacc aaaatgtaaa cttcattggt    480
```
cagatttaga agcattcatg ctcacaagtt ttggga 516

<210> SEQ ID NO 244
<211> LENGTH: 428
<212> TYPE: DNA
<213> ORGANISM: Homo sapiens
<220> FEATURE:
<221> NAME/KEY: misc_feature
<222> LOCATION: (1)..(428)
<223> OTHER INFORMATION: AffymetrixID: 212714_at

<400> SEQUENCE: 244
aactttaggc ttttgggcat atgctagtct gagcttccga aaagatacat atatgtttcc       60
cttttcatta gctgaatgag gatattttaa gaagttgaaa gagaatttat tttcaagttg      120
tgagtaaatc ctcctttgaa attcacctga ttattagata acttaaagtt tatttttaaa      180
agctgacaac ttttatgaa tcttcgagtt gacagttcct aaaagcgtaa ctcagatatt       240
aatgggctgt gtattaaatg gttttatttt cagttttgca gcacagaaca ctgttgaaat      300
atccatatca acttgatttt tttaacctaa ttcaggtgtc ctttgcatct cttaaatgtt      360
gggggtgggg gtcagagcca gttatccggc ttctgttttg tcgattgctt agatttgttc      420
ctgttgtc                                                              428

<210> SEQ ID NO 245
<211> LENGTH: 489
<212> TYPE: DNA
<213> ORGANISM: Homo sapiens
<220> FEATURE:
<221> NAME/KEY: misc_feature
<222> LOCATION: (1)..(489)
<223> OTHER INFORMATION: AffymetrixID: 212893_at

<400> SEQUENCE: 245
aattgtcctt aattaccaac agtgaagcac tacaggaggc aactgtggca ttgcttcctt       60
aaccagctca tggtgtgtga atgttataaa attgtcactc agatatattt tttaaatgta      120
atgttatata agatgatcat gtgatgtgta caaactatgg tgaaaagtgc cagtggtagt      180
aactgtgtaa agtttctaat tcacaacatt aattccttta aaatacacag ccttctgcct      240
ctgtatttgg agttgtcagt acaactcatc aaagaaaact gcctaatata aaaatcatat      300
atatggtaat aatttccctc ttttgtagtc tgcacaagat ccataaaaga ttgtattttt      360
attactattt aaacaagtga ttaaatttag tctgcacagt gagcaagggt tcacatgcat      420
tcttttatac tgctggattt tgttgtgcat catttaaaac attttgtatg tttcttctta      480
tctgtgtat                                                             489

<210> SEQ ID NO 246
<211> LENGTH: 417
<212> TYPE: DNA
<213> ORGANISM: Homo sapiens
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (1)..(417)
<223> OTHER INFORMATION: AffymetrixID: 212989_at

<400> SEQUENCE: 246
gtcagagcct gttcacatat tgtgatcagg tagcaatgac atgtaccact taaattattt       60
tatcgtcgat ttggtagttc natttaact actcaatgaa aacagccatg aatatctttt      120

```
cttaaagaga gttttgaaaa tgatcactta cctaaaactt gaaagctatg aattagttat    180
ccatactctc atgacaattt tgttggtgaa caacaaaaaa gagatctatt tctttaaaag    240
atatttgtgc agaaactgca tgtaactcta agttttactc ctaacataca tatgtttggg    300
gaagtattct attctatact tgccaatgtg gagaacaaaa tagtttttta agaatgaaga    360
agtatatata tccattctgt attttacgtg cagcagaatt atcttccgta ggatttt       417
```

<210> SEQ ID NO 247
<211> LENGTH: 448
<212> TYPE: DNA
<213> ORGANISM: Homo sapiens
<220> FEATURE:
<221> NAME/KEY: misc_feature
<222> LOCATION: (1)..(448)
<223> OTHER INFORMATION: AffymetrixID: 213410_at

<400> SEQUENCE: 247

```
gacaaattac ggttgagttc tgtggcttct tcacttgaag tgctaacatc agaatcaaac     60
ttaaagcttc cactatttat gtctttgaga agtatgtagt acctcggtat taacagacct    120
gctgtgatgc agttacactt tcacgtattt ttgaagtatg tcaagctaca cgggtctaag    180
atatgattat tttggataaa atgttacttt ggtcaagaga acttttatcc agatgacatt    240
acaggttcaa gtgggttaag gagacctcct gtacatctac agtgtttcct tttaaattgt    300
ccagaaaaaa ggtgtgttct tcataagctt cagtgcagga tttttcaaag acgagctgtt    360
gtgcaatttg ctgtatttaa tgcatgttct gaaaggattc acttttgact ttatatgaca    420
gttgatcaag aacaggtact acccctttt                                      448
```

<210> SEQ ID NO 248
<211> LENGTH: 234
<212> TYPE: DNA
<213> ORGANISM: Homo sapiens
<220> FEATURE:
<221> NAME/KEY: misc_feature
<222> LOCATION: (81)..(82)
<223> OTHER INFORMATION: n is a, c, g, or t
<220> FEATURE:
<221> NAME/KEY: misc_feature
<222> LOCATION: (1)..(234)
<223> OTHER INFORMATION: AffymetrixID: 213515_x_at

<400> SEQUENCE: 248

```
ggatgatctc aagggcacct ttgcccagct gagtgaactg cactgtgaca agctgcatgt     60
ggatcctgag aacttcaagc nncctgggaa atgtgctggt gaccgttttg gcaatccatt    120
tcggcaaaga attcacccct gaggtgcagg cttcctggca gaagatggtg actggagtgg    180
ccagtgccct gtcctccaga taccactgag ctcactgccc atgatgcaga gctt          234
```

<210> SEQ ID NO 249
<211> LENGTH: 407
<212> TYPE: DNA
<213> ORGANISM: Homo sapiens
<220> FEATURE:
<221> NAME/KEY: misc_feature
<222> LOCATION: (1)..(407)
<223> OTHER INFORMATION: AffymetrixID: 213528_at

<400> SEQUENCE: 249

```
aactgcattc aagggagggt ccaaagaaat tcactttcaa gattataaca gtatggtgat     60
tgatgaagta accttaccta atgtagtagc taactccact ttggaagatg aagaaaatga    120
tgtaaatgag ccagatgtga aaagatgcag gaaaccaaaa gtaacacaac tatataaatg    180
```

```
ccgattttttt  tctggtgagt  ggtctgagtt  ttgtaagctt  gtactaagta  gtgaaaaact    240
ttttgtaaaa  tatgatctca  ttctcacctc  agaaaccatt  tacaacccag  attattatag    300
taatttgcac  cagactttcc  ttagactgtt  aagtaaaaat  ggacgtgtac  ttttggccag    360
caaagcacat  tattttggtg  taggtggagg  tgttcatctc  tttcaga                   407
```

<210> SEQ ID NO 250
<211> LENGTH: 406
<212> TYPE: DNA
<213> ORGANISM: Homo sapiens
<220> FEATURE:
<221> NAME/KEY: misc_feature
<222> LOCATION: (1)..(406)
<223> OTHER INFORMATION: AffymetrixID: 213604_at

<400> SEQUENCE: 250

```
gcaatgtcag  tatccatttt  ggcacataaa  gattttgat   gagccctgtt  tgcatagagc    60
cagatgtttt  cccctccccc  aagagtatct  acatcaggga  tgtgacttgg  tgcgaagagt    120
caggggaaag  aggaaaaacc  caatttctaa  atgacctcct  tgcccagctt  actaaaatgg    180
ctgcagagca  gacacaggat  gaatttgaac  ctgacacagg  atgaatttga  acctttggtc    240
tcatttatgg  aaaaacttgt  gcaatttttt  ttctgtgcta  cactacatac  aaatcaccaa    300
attacaaatt  accctttgt   gatccttggt  gtactgagca  gtttctttgg  ggcttttct    360 ttctgggaag  cgggagggaa  aggagcaagg  tgtcatcctg  ctcttc                    406
```

<210> SEQ ID NO 251
<211> LENGTH: 466
<212> TYPE: DNA
<213> ORGANISM: Homo sapiens
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (1)..(466)
<223> OTHER INFORMATION: AffymetrixID: 213619_at

<400> SEQUENCE: 251

```
aatcaaggcc  tcagaatttc  atacaaacac  caagaccaaa  atcctaagta  ttggtattgc    60
gtctcaaatt  ttcccatta   acttnaaaaa  aaaaaaagc   ttaaacttac  gtgccttaca   120
ggttattaaa  tgaaactaga  attaacaaac  atgccaaaat  gtttcacttt  taatagtaga   180
cacagctcct  atattgtttt  acaaaaaaat  aaaagcatgt  ctttcaacat  gcatccaaaa   240
cagtgttcaa  tttaacgtgg  caagggcaa   catttaacat  aattcaactg  cttttaccta   300
aatacgctta  ctgcttaagt  acatcctata  actaacttga  gaaaagctgg  aacttaagtt   360
taacagttat  agtttactca  gcttcactgt  tacatcctag  atgagtattg  tattcaaaaa   420
tactgggcct  taagtcttca  taacaatcct  gatttccact  tagagt                   466
```

<210> SEQ ID NO 252
<211> LENGTH: 474
<212> TYPE: DNA
<213> ORGANISM: Homo sapiens
<220> FEATURE:
<221> NAME/KEY: misc_feature
<222> LOCATION: (1)..(474)
<223> OTHER INFORMATION: AffymetrixID: 213655_at

<400> SEQUENCE: 252

```
cttcaacgct  aacctgcttc  agtgggagag  taaagtaggc  aagaatgagc  agccacggat    60
```

```
tgttgaactg ttaccagcac catgcttttc agcaacattt cagcggagtt ggaaacattt      120
tttacagcaa aaccattaca acgaagtccc tccccaaacc acctttaacc atctcaagct      180
aacacccaat tacttgcaaa cactggtata aaacacagtt taaacaatta gaaaatgaa       240 aactgatacc acttatgcct ctatagtgtg attaacctct ctcttagatg cttgcatcac      300
ctataagtct aatggctttc aaatgtaatt tccatttgct aatggtgatc ttgccacatc      360
tggcacggag acgacacagt aatgctgaaa aagcctctat gtagtcctgt tagtgtctta      420
aagaacctaa aagctgggac cagtaaaatc cacagaaatt cactcttgcc ttta            474
```

<210> SEQ ID NO 253
<211> LENGTH: 302
<212> TYPE: DNA
<213> ORGANISM: Homo sapiens
<220> FEATURE:
<221> NAME/KEY: misc_feature
<222> LOCATION: (1)..(302)
<223> OTHER INFORMATION: AffymetrixID: 213743_at

<400> SEQUENCE: 253

```
ttgtgtgagc tattcaaact cttcaacccc tgaacagggt attaagcttc caaaataatg      60
atggggataa atatggaaat ccttttaag ttgtatttcc attaaacaaa aacccttata      120
attcatacta tcatgaattt gctttatcca tctcatttgc ataacagttc atctgtctgg     180
tcccattagg ctctaccaaa gaaagactct gatgagtgga cattattact gtgactcttg     240
taagtagcca taaataaacc aaaatagtat caaatttagg tatgaaattc cacatgtgca     300
aa                                                                     302
```

<210> SEQ ID NO 254
<211> LENGTH: 549
<212> TYPE: DNA
<213> ORGANISM: Homo sapiens
<220> FEATURE:
<221> NAME/KEY: misc_feature
<222> LOCATION: (1)..(549)
<223> OTHER INFORMATION: AffymetrixID: 213788_s_at

<400> SEQUENCE: 254

```
gtttcagtca tttccggact aactgtgaca acgcgtgagc agggagcacc gtgcgagtct      60
ccgggaggga atcctcctgg ggcccagaga ctcctccacc cctggggagg gcagacaggc     120 tcggagggc ctggccaggc cactggaggc tggcagggag caggcatgtc cacccgcaag     180
cctgggaggc taactctggc attcctggcc ggagccgcca tgctcattgg tgggccagtt    240
tgggacatcc ccgtactcaa agaccatatg gcagcctctg ggaaaacaaa accaaaacat    300
caccttctat taaactctgt atattattat tttttacaat agaaagttaa aaatcaagac    360
ttagatttac tatacatttt ttctctcaga ttacaaagtt tatattatat aactggggtt    420
ccctaaattg atttctttta aaacagtctt aaagagacca gaagtgaata caaaagaact    480
aaacaaaata aaaaattaga atgtgctgta gctgaaagct gtctatacct gtaagcctcc    540
aagtttcat                                                            549
```

<210> SEQ ID NO 255
<211> LENGTH: 576
<212> TYPE: DNA
<213> ORGANISM: Homo sapiens
<220> FEATURE:
<221> NAME/KEY: misc_feature
<222> LOCATION: (99)..(99)
<223> OTHER INFORMATION: n is a, c, g, or t

```
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (1)..(576)
<223> OTHER INFORMATION: AffymetrixID:   213872_at

<400> SEQUENCE: 255
aaactggtca gctagagatt cttttttctt tctaagctga gcacgtagtc tgttcagagc      60
ttgtttcttc cgggagtttg ggtcccccat tttgaaatnc nggtggtact aaagcctttg     120
gaaattgtca ctaaactatg ggcacttttt cttaagactc aagtacaaca gaaacaagtc     180 atttttttc ctgctaatat gattgattag cgaaaatcac gactataacc caaaaactgc      240
accttctgtc aatattagca gactgtcata ttacagggtc aagaaacaaa agctgctgtc     300
cagtcatgtt tggacaataa cgtttggggt cagacgggaa aaagggagga agaaaggaa      360 agaaagagga gaaataact aactttctgg aaaacacatt tggcttaact gccaaaataa      420
aggctttgcg gagaaatgaa aagcctataa tcaggattta ggtgtgcaat aaaacacagc     480
tgacaccaga ccaatcccta aaatccatcc ggatttccc cccttttag aaagggatt       540 aaggaacagg gaggggaag tgtgatcctt gctttc                                576

<210> SEQ ID NO 256
<211> LENGTH: 380
<212> TYPE: DNA
<213> ORGANISM: Homo sapiens
<220> FEATURE:
<221> NAME/KEY: misc_feature
<222> LOCATION: (1)..(380)
<223> OTHER INFORMATION: AffymetrixID:   213979_s_at

<400> SEQUENCE: 256
aaatggttac agtcacaaac atgattttaa ccaaaatatt gctagcctac cacatcagca      60
ggacggcact ggtgcaggcg gggacgctgc caccctccac gtccccagga cagacgtcga     120
tgggcagcgg gcacgctggg caccgcccaa gcttttcctt ttggagctgc ttcgtgatgc     180
cgtcttcatt tggaacaagg ggggttcat gccaaaatta ggaaaaacag cctttgtttt     240
gtttttctaa attattctaa aaataagaca agcaggtaga aaaaacaatg cactgtgtgg     300
cataaaaaga aaaacgggaa ggattcattg tcctgagaag tttgccaact gcctcattct     360
ggggcacgtt ccaacataca                                                  380

<210> SEQ ID NO 257
<211> LENGTH: 371
<212> TYPE: DNA
<213> ORGANISM: Homo sapiens
<220> FEATURE:
<221> NAME/KEY: misc_feature
<222> LOCATION: (1)..(371)
<223> OTHER INFORMATION: AffymetrixID:   214257_s_at

<400> SEQUENCE: 257
attataacct gggcctgcct tgttctcat gaagccaggg gcctctccat atcctatact       60
tgctcttacg ctaataacaa accaaatgct gcaaaataaa agtaataatg acccaaacta     120
atttaagtct tttgtttaag gagtaaatga gagaaacatt ttagcttctt aatcaaggag     180
tgctataatt tcaaggcatc ttaatataat tcacttaccc taaagcaatt gtgcaataag     240
caaattataa aaggaaaaca acaaaggtta actttctaca ggggccaata gacaagatct     300
gtggagcaca gcaattaacc ttcacatact ggagtcttgt ttaaaaggcc atcaaaaact     360
```
cagattactg a                                                          371

<210> SEQ ID NO 258
<211> LENGTH: 244
<212> TYPE: DNA
<213> ORGANISM: Homo sapiens
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (164)..(169)
<223> OTHER INFORMATION: n is a, c, g, or t
<220> FEATURE:
<221> NAME/KEY: misc_feature
<222> LOCATION: (171)..(172)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (180)..(181)
<223> OTHER INFORMATION: n is a, c, g, or t
<220> FEATURE:
<221> NAME/KEY: misc_feature
<222> LOCATION: (1)..(244)
<223> OTHER INFORMATION: AffymetrixID:  214414_x_at

<400> SEQUENCE: 258
tcaacttcaa gctcctaagc cactgcctgc tggtgaccct ggccgcccac ctccccgccg    60
agttcaaccc ctgnggtgca cgcctccctg ganaagttcc tggcttctgt gagcaccgtg   120
ctgacctcca ataccgttta agctggagcc tcggtagccg ttcnnnnnnc nngctnggcn   180
ntccaacggg ccctcctccc ctccttgcac cggcccttcc tggtctttga ataaagtctg   240
agtg                                                                244

<210> SEQ ID NO 259
<211> LENGTH: 519
<212> TYPE: DNA
<213> ORGANISM: Homo sapiens
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (1)..(519)
<223> OTHER INFORMATION: AffymetrixID:  214696_at

<400> SEQUENCE: 259
gagtatacat cggtgcaggc ttcctggatg acagttgggt gatatgtgtc atgtggccta    60
aaagcctcca tgtcatttga cctacgaatt ctatctttgg gaatttatcc taagaaanta   120

```
cttanggatt tanttngtga taagatgttc atcccagcat tgcaatggag aaaaatggga      180
agcaatggtt tggttgggaa tttattcctt ttctgctgta acgaaagttt gcaataggggg    240 attgcttaag taaattattg tatctccatc cagatggtgg agtaccgcgc agacattaaa     300
agtcatgtaa aagaacatct gactgaaaga aaaatgctcc ttgaatatta aaaggttgta    360
aaaatagtgc atgttatgtg atttcaattt tgtttttttaa aatatgggtg tatgcttgta   420
tacgtagagc agataaaaaa gacggaaggc atactaaaaa atgttgagtg gttatctttg   480
tatggtggaa caaagtcact gtaattttca tctttggtt                          519
```

<210> SEQ ID NO 260
<211> LENGTH: 399
<212> TYPE: DNA
<213> ORGANISM: Homo sapiens
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (1)..(399)
<223> OTHER INFORMATION: AffymetrixID: 214933_at

<400> SEQUENCE: 260

```
aatctttcct ttccctgatg aagacagctg gtggccgagt gcggnaanga agccagaagg    60
aaccagaatc ccagngccct acacccacca ccagacacac tcacacccac acacgttctc   120
agacacacac aagagtgctt gccggttata ccaaacccta ctattactgc ctgcagaaat   180
caatttaaaa aataataat aacaataaac aatttaaaa aggacaaaaa aattaatgat    240
tgagaaaaga ggcattttttt tctgacattt ggtcctgctt gaaacaacaa agaagaaga  300 aaaacccacc atcaccaccg attcctttgc ttctttttttc ctttttttcct accttgtttg   360 aaaaccgtgg gcttgggact gtgaattatt gcatgacat                          399
```

<210> SEQ ID NO 261
<211> LENGTH: 202
<212> TYPE: DNA
<213> ORGANISM: Homo sapiens
<220> FEATURE:
<221> NAME/KEY: misc_feature
<222> LOCATION: (1)..(202)
<223> OTHER INFORMATION: AffymetrixID: 215043_s_at

<400> SEQUENCE: 261

```
cagtctttcc cagggaactc cgatgaagtg ttccaacaaa atgagcgagt gaaccaagaa    60
gaggatgaca ttagatccag gagatacaac agaggagata atctccagga tgcctgtgaa   120
gaaagatccc tggatcccag gatgattata ggacaagttg ttcataatcc agcaggccag   180
aagacttcca gggaaactca tt                                           202
```

<210> SEQ ID NO 262
<211> LENGTH: 501
<212> TYPE: DNA
<213> ORGANISM: Homo sapiens
<220> FEATURE:
<221> NAME/KEY: misc_feature

```
<222> LOCATION: (37)..(37)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (1)..(501)
<223> OTHER INFORMATION: AffymetrixID: 215933_s_at

<400> SEQUENCE: 262
ggacagttcc tgtgatcaga ggcaagattt gcccagngaa cagaataaag gtgcttcttt      60
ggatagctct caatgttcgc cctccctgc ctcccaggaa gaccttgaat cagagatttc      120
agaggattct gatcaggaag tggacattga gggcgataaa agctatttta atgctggatg    180
atgaccactg gcattggcat gttcagaaaa ctggatttag gaataatgtt ttgctacaga    240
aaatcttcat agaagaactg gaaggctata taagaaaggg aatcaattct ctggtattct    300
ggaaacctaa aaatatttgg tgcactgctc aattaacaaa cctacatgga gaccttaatt    360
ttgacttaac aaatagttta tgtactgctc ttaggttgtt ttgataaagt gacattatag    420
tgattaaatt ctttccnctt taaaaaaaca gntagtggtt ttcactattt ataaatagga    480
ccttcttgaa cgactttct g                                                501

<210> SEQ ID NO 263
<211> LENGTH: 502
<212> TYPE: DNA
<213> ORGANISM: Homo sapiens
<220> FEATURE:
<221> NAME/KEY: misc_feature
<222> LOCATION: (1)..(502)
<223> OTHER INFORMATION: AffymetrixID: 216199_s_at

<400> SEQUENCE: 263
ctggagtctg gggtgtgttg tcatagagat ggtgactggc aaggtttgca cagatgaaga      60
atgaagccta gtagaatatg gacttggaaa attctcttaa tcactactgt atgtaatatt    120
tacataaaga ctgtgctgag aagcagtata agccttttta accttccaag actgaagact    180
gcacaggtga caagcgtcac ttctcctgct gctcctgttt gtctgatgtg gcaaaaggcc    240
ctctggaggg ctggtggcca cgaggttaaa gaagctgcat gttaagtgcc attactactg    300
tacacggacc atcgcctctg tctcctccgt gtctcgcgcg actgagaacc gtgacatcag    360
cgtagtgttt tgacctttct aggttcaaaa gaagttgtag tgttatcagg cgtcccatac    420 cttgtttta atctcctgtt tgttgagtgc actgactgtg aaacctttac cttttttgtt    480
gttgttggca agctgcaggt tt                                              502

<210> SEQ ID NO 264
<211> LENGTH: 158
<212> TYPE: DNA
<213> ORGANISM: Homo sapiens
<220> FEATURE:
<221> NAME/KEY: misc_feature
<222> LOCATION: (1)..(158)
<223> OTHER INFORMATION: AffymetrixID: 216202_s_at

<400> SEQUENCE: 264
gttcacaaag agttttggtg cttctggagg atatattgga ggcaagaagg agctgataga      60
ctacctgcga acacattctc atagtgcagt gtatgccacg tcattgtcac ctcctgtagt    120
```

```
ggagcagatc atcacctcca tgaagtgcat catggggc                                  158
```

<210> SEQ ID NO 265
<211> LENGTH: 490
<212> TYPE: DNA
<213> ORGANISM: Homo sapiens
<220> FEATURE:
<221> NAME/KEY: misc_feature
<222> LOCATION: (1)..(490)
<223> OTHER INFORMATION: AffymetrixID: 216996_s_at

<400> SEQUENCE: 265

```
gctgcatact ttggatactt gtctaaaact tgatgatact gtctatctga gggacatagc           60
cttgtcactc ccacagctgc cgcgggagct gccatcgtca catacaaatg caaaggtggc          120
agaggtgctg agcagccttc tgggaggtga aggacacttc tcaaaggatg tgcacttgcc          180
acacaattat catattgatt ttgaaatcag aatggacact aacaggaatc aagtgctacc          240
actttctgat gtgatacaac ttctgctaca gatattcaaa gagtagctgt gctatgtgtt          300
tccagatctg cttattgttt gggttcaagc cacccagag gattccttgc tatgaaaatg           360
cggcatttga atgcaatggg ttttcatgtg atcttggtca ataactggga gatggacaaa          420
ctagagatgg aagatgcagt cacattttg aagactaaaa tctattcagt agaagctctt          480
cctgttgctg                                                                 490
```

<210> SEQ ID NO 266
<211> LENGTH: 374
<212> TYPE: DNA
<213> ORGANISM: Homo sapiens
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (1)..(374)
<223> OTHER INFORMATION: AffymetrixID: 217554_at

<400> SEQUENCE: 266

```
aatgctcacc aaattcacag gaaagaagtg cctaggtgat catttactgc tatttactgc           60
ttcctggtat ggagcaaaat tgccctctgg taggtaacta catttctaat tagtatgaaa          120
ggttctacta ttttcctttc ttttgcttat ttccccttaa gcacaatttg cagaccctac          180
ttctatttaa ctgatcatac cctttttaaat gccttgtcat cattttttcat agttcctgca         240 tcctagaaaa aataaaaaat catttaaaat attccttggt gtctagaaaa gaaaatttct          300
ctaacaatag agatnatcat tttgctttct cacttaagct gatctgaatg atgatttggt          360
actgccttta tgag                                                            374
```

<210> SEQ ID NO 267
<211> LENGTH: 462
<212> TYPE: DNA
<213> ORGANISM: Homo sapiens
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (203)..(204)
<223> OTHER INFORMATION: n is a, c, g, or t
<220> FEATURE:
<221> NAME/KEY: misc_feature
<222> LOCATION: (286)..(286)
<223> OTHER INFORMATION: n is a, c, g, or t
<220> FEATURE:
<221> NAME/KEY: misc_feature
<222> LOCATION: (1)..(462)
<223> OTHER INFORMATION: AffymetrixID: 217682_at

<400> SEQUENCE: 267

| | | | | | |
|---|---|---|---|---|---|
| cacgaggtca | atttatggtt | atcaaatagg | ttttttttt | tttttttgag | actgagtgtc | 60 |
| gctctatagc | ccaggctgga | gtgtagtgct | cactgcgact | tccgcctcct | gggttcaant | 120 |
| gattctcgtg | cctcagtctc | ccgagtagct | gggattgtag | gcgcctgcca | ccacgcccag | 180 |
| ctaattttg | tatttgtagt | agnnatgggg | tttcatcatg | ttggcgaagc | tggtcttgaa | 240 |
| cacctgacct | caagtgatct | gccttagcct | cactgcttgc | ccctangtgg | tgggattgca | 300 |
| ggtgtgagcc | actgtgctgg | cctcaaatag | tttttatcaa | agctacttca | attagtggtt | 360 |
| agcaaggctt | aaagactaat | tcagtgcttt | attttgacac | ttgttcgcaa | catgttgctt | 420 |
| tttttcctgt | gtcctatggg | acctagtcat | ctgtatgtta | ga | | 462 |

<210> SEQ ID NO 268
<211> LENGTH: 482
<212> TYPE: DNA
<213> ORGANISM: Homo sapiens
<220> FEATURE:
<221> NAME/KEY: misc_feature
<222> LOCATION: (1)..(482)
<223> OTHER INFORMATION: AffymetrixID: 217840_at

<400> SEQUENCE: 268

| | | | | | |
|---|---|---|---|---|---|
| gccatccagc | acgtcatcaa | ttatgacatg | ccagaggaga | ttgagaacta | tgtacaccgg | 60 |
| attggccgca | ccgggcgctc | gggaaacaca | ggcatcgcca | ctaccttcat | caacaaagcg | 120 |
| tgtgatgagt | cagtgctgat | ggacctcaaa | gcgctgctgc | tagaagccaa | gcagaaggtg | 180 |
| ccgcccgtgc | tgcaggtgct | gcattgcggg | gatgagtcca | tgctggacat | tggaggagag | 240 |
| cgcggctgtg | ccttctgcgg | gggcctgggt | catcggatca | ctgactgccc | caaactcgag | 300 |
| gctatgcaga | ccaagcaggt | cagcaacatc | ggtcgcaagg | actacctggc | ccacagctcc | 360 |
| atggacttct | gagccgacag | tcttcccttc | tctccaagag | gcctcagtcc | ccaagactgc | 420 |
| caccagtcta | cacatacagc | agcccctgg | acagaatcag | catttcagct | cagctggcct | 480 |
| gg | | | | | | 482 |

<210> SEQ ID NO 269
<211> LENGTH: 492
<212> TYPE: DNA
<213> ORGANISM: Homo sapiens
<220> FEATURE:
<221> NAME/KEY: misc_feature
<222> LOCATION: (1)..(492)
<223> OTHER INFORMATION: AffymetrixID: 218229_s_at

<400> SEQUENCE: 269

| | | | | | |
|---|---|---|---|---|---|
| gacctcacag | acaaagccat | tgctagaaat | gtcattccaa | tgatcagatc | tggaaacagg | 60 |
| ctgccataac | cacttttcct | tcttgtagac | tcagctcacc | tgtatattta | aactgttctt | 120 |
| ggcatcttga | aacacctatt | tctactcagg | tactcattgt | cctgttactg | attcacctt | 180 |
| ctgatccttt | tcaaccagtt | ttcccccaag | gggggaaatt | ttacttaacc | tctagtattt | 240 |
| gaacaactca | atatttgaat | tgttgcccca | tttgctttta | cctgtactgt | attccttggtc | 300 |
| atctcaaatg | gcgtctaaac | ccagctactt | tgcattccag | aagtttccat | tccctccaat | 360 |
| tccacctaat | ttttcatctg | tcctagttac | tggctcttc | ttcatgtctt | atttctcttg | 420 |
| ctttgggagc | ttaaaagatt | ttacaagacc | taatttggg | ttccttcctt | ggagccatag | 480 | ttaccctgcc aa                                                      492

<210> SEQ ID NO 270
<211> LENGTH: 177
<212> TYPE: DNA
<213> ORGANISM: Homo sapiens
<220> FEATURE:
<221> NAME/KEY: misc_feature
<222> LOCATION: (1)..(177)
<223> OTHER INFORMATION: AffymetrixID: 218356_at

<400> SEQUENCE: 270
ctgaaatttc catctgggga ttaacttctg tctttctggt gaacaatata gcaattcacg    60
cattcttcaa gcagcaaaag ttcccggaac aattagggaa gacgtatggt ctgaatttat   120
ccaggcagtg ggtctgcttt ggttttttgct ggaaatttat atcagtgtct gggctcc     177

<210> SEQ ID NO 271
<211> LENGTH: 453
<212> TYPE: DNA
<213> ORGANISM: Homo sapiens
<220> FEATURE:
<221> NAME/KEY: misc_feature
<222> LOCATION: (1)..(453)
<223> OTHER INFORMATION: AffymetrixID: 218432_at

<400> SEQUENCE: 271
gaaactatgt gactcattct gtgaaaagac ttcttgcagt tgtgagttat ttagaaatga    60
tcaaaatttg taattaggct aatccattta gtgattccta atattttgta ctcacagaga   120
actaattgac taaacaactt gaacgctagt ggtttgtcct tagacaatct gtctttgaat   180
ttaaagtctt tatcgctaag accttgactt taaattttc atcactacaa ccttgaattt    240
aatttcaggt cttcaacatg atgaccttgg atttaattta aagtcttcaa cactatgcgc   300
tttatcatat tattcacaga tgcatttttg aaatgtagta tgtaaaagta tgtaacgtgc   360
tgtttattaa caaaagattg ttcacaacat ctcatgtagt ttaaatttgt aaatactgct   420
tctgttttgt ttctccttta tacacttgac tgt                               453

<210> SEQ ID NO 272
<211> LENGTH: 557
<212> TYPE: DNA
<213> ORGANISM: Homo sapiens
<220> FEATURE:
<221> NAME/KEY: misc_feature
<222> LOCATION: (1)..(557)
<223> OTHER INFORMATION: AffymetrixID: 218589_at

<400> SEQUENCE: 272
gggtaacaat gcctcagaag cctgctttga aaattttcca gaagccacat ggaaaacata    60
tctctcaagg attgtaattt tcatcgaaat agtgggattt tttattcctc taattttaaa   120
tgtaacttgt tctagtatgg tgctaaaaac tttaaccaaa ccagttacat taagtagaag   180
caaaataaac aaaactaagg ttttaaaaat gattttgta catttgatca tattctgttt    240
ctgttttgtt ccttacaata tcaatcttat tttatattct cttgtgagaa cacaaacatt   300
tgttaattgc tcagtagtgg cagcagtaag gacaatgtac ccaatcactc tctgtattgc   360
tgtttccaac tgttgttttg acccctatagt ttactacttt acatcggaca caattcagaa  420
ttcaataaaa atgaaaaact ggtctgtcag gagaagtgac ttcagattct ctgaagttca   480
tggtgcagag aattttattc agcataacct acagaccta aaaagtaaga tatttgacaa    540
tgaatctgct gcctgaa                                                 557

<210> SEQ ID NO 273
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: AffymetrixID: 218604_at

<400> SEQUENCE: 273

| | | | | | |
|---|---|---|---|---|---|
| tttgttttat | tgtatgcgtt | gggtttgcag | catgaacttg | cacagataat | gcacgttttc | 60
| tggttaagta | aacatgatgc | acactattct | gtaacagaaa | gccctattgt | gccttacctg | 120
| tgtgcttttg | tgggcacctt | gtttatgaag | aataaaaaat | gatttgttat | ctgaagagaa | 180
| taaattttaa | attctcagtt | tatgtctcag | atgctaacgt | gtgaaaatat | aaatatatat | 240
| aatatataaa | gtaaccagtc | ttcctgtatt | ttatgtgcat | catagtgatt | tatctgagct | 300
| tagtgacccc | catcttgtaa | cctgttgcaa | gagtgaatgt | aaaaaatagt | tgtggcattt | 360
| taaaaggtcg | cctttgatgc | agatgcatct | ttttcttgct | tctaaaacat | atttcatgta | 420
| aacattgtac | atttattatt | gtaatatata | ctattatgca | gcttatttta | cctgaaactg | 480
| ttaagccgac | caagatccct | | | | 500

<210> SEQ ID NO 274
<211> LENGTH: 558
<212> TYPE: DNA
<213> ORGANISM: Homo sapiens
<220> FEATURE:
<221> NAME/KEY: misc_feature
<222> LOCATION: (1)..(558)
<223> OTHER INFORMATION: AffymetrixID: 218689_at

<400> SEQUENCE: 274

| | | | | | |
|---|---|---|---|---|---|
| cctgggtgtt | ccacagctga | tagtgattgc | cttgaataaa | ttcaagggca | atttattcat | 60
| ttttactagg | gagatagacc | tttacagcaa | tcaagatatt | tttgtccata | tccaggttag | 120
| ctggtaagag | gattttttg | gagaaaaaaa | atgatattta | gaaagttaat | ttctaattcc | 180
| ggaatggaat | aaaaacaata | tgagtagtgt | aatcttgtag | aaaaagagtt | gtataatctt | 240
| gtagaatttc | tcattctgtg | gtacaaccca | ggggtaaact | attattccag | tagtcagtac | 300
| acttttctag | ataaatcttg | agtgaaaacc | agcaatttct | ttttccttgt | ggtctgattc | 360
| cttttttctaa | tccatgaagg | ccatcttgta | gattacattt | atcattaatg | caagaataaa | 420
| gacaattcct | cctgtcagtt | gcgtgaattt | tttttaagaa | acacccagt | gaagagttct | 480
| accatagcaa | ggcctaatgt | tagctttagc | tttagaaaat | aacagtttgt | gaacttactt | 540
| ccctatattt | gcagctgt | | | | 558

<210> SEQ ID NO 275
<211> LENGTH: 385
<212> TYPE: DNA
<213> ORGANISM: Homo sapiens
<220> FEATURE:
<221> NAME/KEY: misc_feature
<222> LOCATION: (1)..(385)
<223> OTHER INFORMATION: AffymetrixID: 218889_at

<400> SEQUENCE: 275

| | | | | | |
|---|---|---|---|---|---|
| gcttgtattc | aggttcattg | gcttttgctg | gatgatccac | ctaaagaagt | tacctaattt | 60
| ggccttttaa | aaaaggtgtt | agtgtttatt | atagctactt | tcaaggaaag | tttgaatatg | 120
| attctagtct | ctaaagttct | tcacgttttc | tgacattccc | tggagggtga | ctggggaaga | 180

```
attgctccag ggtagaagaa ccaggcccaa gactttacca ttctgatcta gagacaaagg    240
atactcaatg aggagctttt ttcccctctt ggaacaggta aaatgctttt tcttattaat    300
ataattataa aacagtattt tatgtaacag ctattcccat attctaggag tggcctaaga    360
aatgcgtgtt tcagtgacta gatta                                          385
```

```
<210> SEQ ID NO 276
<211> LENGTH: 554
<212> TYPE: DNA
<213> ORGANISM: Homo sapiens
<220> FEATURE:
<221> NAME/KEY: misc_feature
<222> LOCATION: (1)..(554)
<223> OTHER INFORMATION: AffymetrixID:  218973_at

<400> SEQUENCE: 276
ctgcaagtga aacctcagcg cctgatggca gctatgtaca catgtgacat catggccact     60
ggtgatgttc tcggtcgagt ctatgctgtc ttgtcaaaga gagaaggtcg ggtacttcaa    120
gaagaaatga aagaagggac agacatgttc atcatcaagg ctgtgctgcc tgttgctgaa    180
agctttggtt ttgctgatga aatcaggaag aggacaagtg gcctggccag cccacaacta    240
gtattcagcc attgggagat cattcccagt gaccccttct gggtgccaac tactgaggag    300
gaatacttgc actttgggga aaggctgac tctgagaacc aagcccggaa gtacatgaac    360
gcagtacgaa agcggaaggg gctttatgtg aagaaaaga ttgtggagca tgcagaaaag    420
cagaggacac tcagcaaaaa taagtagcta cctactactg gtggattctt ttccttatag    480
tgaatttaaa agtatcatca agggtttaat attgggaaaa tttctttttg ccacattatc    540
tctgtttatt cact                                                      554
```

```
<210> SEQ ID NO 277
<211> LENGTH: 262
<212> TYPE: DNA
<213> ORGANISM: Homo sapiens
<220> FEATURE:
<221> NAME/KEY: misc_feature
<222> LOCATION: (1)..(262)
<223> OTHER INFORMATION: AffymetrixID:  219069_at

<400> SEQUENCE: 277
gaatattgta tactgcatcc cctaccacaa tttacacaat cctgtggata gtcctacctc     60
accctggtca acctacatga tccttaagct aatggcgaat cacgatgacc ttgtagacat    120
gcacacaact ataccttgt ccaacagatc ataatatatc tgctatccaa ctggttttac     180
ctgcctaatc ctactgattt gggcactgct tgtatagtct ctcaagttca caggaaatgt    240
tgattttcta aggtcctcat tt                                             262
```

```
<210> SEQ ID NO 278
<211> LENGTH: 490
<212> TYPE: DNA
<213> ORGANISM: Homo sapiens
<220> FEATURE:
<221> NAME/KEY: misc_feature
<222> LOCATION: (1)..(490)
<223> OTHER INFORMATION: AffymetrixID:  219093_at

<400> SEQUENCE: 278
tagagaccca tgtcatctta acctaaaggg aaatcttatt gcgttatcat aaaattgatg     60
atatcttagg gtcagaattg ccctttttt tattttgaat gggaagctct cactaaaaca    120
atcctgagat ttcttaattt catggttctt taaatattat aaacacagag tcaacataga    180
```

```
atgaaattgt atttgttaaa atacacacat tggaggacaa gagcagatga ctacttttcg    240
aagtaatgct gctccttcct aaaagtctgt tttcaatcct ggtaatatta ggggcactgc    300
ggcacctaag aagccttaaa tgagagctaa tccaatttag agagcgatgg tgtcagcatt    360
tcggtctgca tatctgtgtg tccgtatctg cgtttgtgtg cgtgtacgtg tgccctgtg    420 tgtgggccca gttttcaggc atgtagaata agcatggagt catattgagg aggactcact    480
tcttgaagat                                                           490
```

<210> SEQ ID NO 279
<211> LENGTH: 442
<212> TYPE: DNA
<213> ORGANISM: Homo sapiens
<220> FEATURE:
<221> NAME/KEY: misc_feature
<222> LOCATION: (1)..(442)
<223> OTHER INFORMATION: AffymetrixID: 219099_at

<400> SEQUENCE: 279

```
aatggactga ctgaaactcg ctaaggttaa atctgcatca aaatctaacc aatttgagcc     60
tctgaaggga gtgccattgg ctttatttac ttctctcctc tgctagtcct gatttggaaa    120
cagttaaaag ccaatttta gctccagtgg aaccatagcc acataaaact ttaatggaca     180
accatataga attaacttat tttgtccaag tacagttggc attttccaga ataattttac    240
caccctgcta gatgtcatct ctggattgca catggatgat gaaggaactc agcattgaaa    300
gttgggggat tagtaacctt gttacaacgg tttcttttc attttagcct atttttaatgg    360 ctattggtaa gatactgtat gttttagta tctcatccag tgcttagaag aaagaatggt    420
ttataattcc cagtacatgt tt                                             442
```

<210> SEQ ID NO 280
<211> LENGTH: 454
<212> TYPE: DNA
<213> ORGANISM: Homo sapiens
<220> FEATURE:
<221> NAME/KEY: misc_feature
<222> LOCATION: (1)..(454)
<223> OTHER INFORMATION: AffymetrixID: 219176_at

<400> SEQUENCE: 280

```
caacaggagg catctccatt tactatgatg agaaaggaag gaagtttgtt aacatcctga     60
tgtgcttttg gtatctaacc agtgccaaca tccccagtga aacttaaga ggagccagtg     120 tattccaggt taagttgggg aatcagaatg tggaaactaa acaacttctt agtgcaagct    180
atgagtttca gagggagttc acacaaggag taaagcctga ctggaccatt gcacggattg    240
aacactcaaa attattagaa taattttctt ggaaaaatca gcttatggac tttagcagtt    300
gctgtgaaaa actaaggaag aaaaattttg gggtcatttg atcttcactt aatctaagtc    360
tgtgaattac ttttatatta ttttgaaata ctccttgcag tatattggca tgatacagta    420
aaagcatttt ccacagattg ttatcacctt cttt                                454
```

<210> SEQ ID NO 281
<211> LENGTH: 517
<212> TYPE: DNA
<213> ORGANISM: Homo sapiens
<220> FEATURE:
<221> NAME/KEY: misc_feature
<222> LOCATION: (1)..(517)
<223> OTHER INFORMATION: AffymetrixID: 219243_at

<400> SEQUENCE: 281

```
tcttctagat tctctctatg ttggcagata atctccccttt gtagcttcca ctcacttatt      60
cttgcattca gagtcacaat gatcatctta cccatgtggt ttttgagaaa gaaagatcaa     120
ttctttgttt gcagtgggta atcttagaga tggagatgat tgtagaatta ttcctagatg     180
agtgtcaatt tatttaattc cattgtcata taaggagtca aattgtttct tatcatttgt     240
tcattgaaga acagagacct gtctggaaaa tcgatctcta caaattcaat taaataatga     300
tccccaaatg ctgaaaaagt gaaatacagc aattcaacag ataatagagc aatgtttagt     360
atattcagct gtatctgtag aaactctttg acgaacctca atttaaccaa tttgatgaat     420
acccagttct cttcttttct agagaaagat agttgcaacc tcacctccct cactcaacac     480
tttgaatact tattgtttgg caggtcatcc acacact                              517
```

<210> SEQ ID NO 282
<211> LENGTH: 501
<212> TYPE: DNA
<213> ORGANISM: Homo sapiens
<220> FEATURE:
<221> NAME/KEY: misc_feature
<222> LOCATION: (1)..(501)
<223> OTHER INFORMATION: AffymetrixID: 219363_s_at

<400> SEQUENCE: 282

```
tggtcagaaa agcaccattt ttgctgaact tttcagtgga aagactggat aaccagattg      60 gatttttttca gaaggaactg gaacttagtg tgaagaagac tagagatctg gtagttcgtc    120
tcccaaggct gctaactgga agtctggaac ccgtgaagga aaatatgaag gtttatcgtc     180
ttgaacttgg tttttaaacat aacgaaattc aacatatgat caccagaatc ccaaagatgt    240
taactgcaaa taaaatgaaa cttaccgaga cgtttgattt tgtgcacaat gtgatgagca     300
ttccccacca catcattgtc aagttcccac aggtatttaa tacaaggctg tttaaggtca     360
aagaaagaca cttgtttctt acctatttag gaagagcaca gtatgatcca gcaaaaccta     420
actacatctc tttggacaaa ctagtatcta ttcctgatga aatattttgt gaagagattg     480
ccaaagcatc agtacaggac t                                               501
```

<210> SEQ ID NO 283
<211> LENGTH: 467
<212> TYPE: DNA
<213> ORGANISM: Homo sapiens
<220> FEATURE:
<221> NAME/KEY: misc_feature
<222> LOCATION: (1)..(467)
<223> OTHER INFORMATION: AffymetrixID: 219434_at

<400> SEQUENCE: 283

```
ccatgatcat ggtttactgc gcgtccgaat ggtcaacctt caagtggaag attctggact      60
gtatcagtgt gtgatctacc agcctcccaa ggagcctcac atgctgttcg atcgcatccg     120
cttggtggtg accaagggtt tttcagggac ccctggctcc aatgagaatt ctacccagaa     180
tgtgtataag attcctccta ccaccactaa ggccttgtgc ccactctata ccagccccag     240
aactgtgacc caagctccac ccaagtcaac tgccgatgtc tccactcctg actctgaaat     300
caaccttaca aatgtgacag atatcatcag ggttccggtg ttcaacattg tcattctcct     360
ggctggtgga ttcctgagta gagcctggt cttctctgtc ctgtttgctg tcacgctgag     420
gtcatttgta cccctaggccc acgaacccac gagaatgtcc tctgact                  467
```

<210> SEQ ID NO 284
<211> LENGTH: 354

<212> TYPE: DNA
<213> ORGANISM: Homo sapiens
<220> FEATURE:
<221> NAME/KEY: misc_feature
<222> LOCATION: (1)..(354)
<223> OTHER INFORMATION: AffymetrixID: 221485_at

<400> SEQUENCE: 284

```
aatgtgacct tgtgcatata ttggtagctg aaaatcttca aggctactga tgggtggccc      60
cttaatcttg tctttgattg ctgtgtgcag ggaaaggtgt ccccgtttgt tcatgctgtt     120
ttgggggtg gggggtatt tgcaagaata ctcattttga cataataggt cctcttgtca      180
gagatcctct accacagaca ttaatagctg agcaggagcc acatggattg attgtatcca     240
ctcaccattg acgatggcat tgagcgtagc tagcttattt ccatcactac gtgtttttga     300
gcttgctctt acgttttaag aggtgccagg ggtacatttt tgcactgaaa tcta          354
```

<210> SEQ ID NO 285
<211> LENGTH: 465
<212> TYPE: DNA
<213> ORGANISM: Homo sapiens
<220> FEATURE:
<221> NAME/KEY: misc_feature
<222> LOCATION: (1)..(465)
<223> OTHER INFORMATION: AffymetrixID: 221652_s_at

<400> SEQUENCE: 285

```
ggccagtgtc gttattatcc ttgtggagaa tagaatcaat actgccaatt ccagaaaaca      60
tcaggaattt gctggacgtt tgaactctgt taataacaga gctgaactat atcaacatct     120
taaagaggaa aatgggatgg agacaacaga aaatggaaaa gccagccggc agtgaagagt     180
gacttgaaga actaaattta gcatattgca aaaatatttt gtgcggaatt cgatataagt     240
acttttacag caagatggta tagttatgtt gcctggactg gttttttacat ttttaaaata    300
tttcagctgt cattttttgta ctaattataa aattggcaca taattcaaaa atatacattt    360
gagatgattt gtcctcccaa attatacaag tttatttat ggtataaagt gttctctctg     420
gaaatgtttt taaaaaaatt cttaggcttc tctttgcgaa ataaa                    465
```

<210> SEQ ID NO 286
<211> LENGTH: 392
<212> TYPE: DNA
<213> ORGANISM: Homo sapiens
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (93)..(95)
<223> OTHER INFORMATION: n is a, c, g, or t
<220> FEATURE:
<221> NAME/KEY: misc_feature
<222> LOCATION: (97)..(98)
<223> OTHER INFORMATION: n is a, c, g, or t
<220> FEATURE:
<221> NAME/KEY: misc_feature
<222> LOCATION: (101)..(103)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (109)..(110)
<223> OTHER INFORMATION: n is a, c, g, or t
<220> FEATURE:
<221> NAME/KEY: misc_feature

```
<222> LOCATION: (112)..(118)
<223> OTHER INFORMATION: n is a, c, g, or t
<220> FEATURE:
<221> NAME/KEY: misc_feature
<222> LOCATION: (1)..(392)
<223> OTHER INFORMATION: AffymetrixID:  221755_at

<400> SEQUENCE: 286
ggagcctcat ggagtcaggt gccaacaagc tgcaggagga ggtgctgatc caggagtggt      60
tcaccctggt caacaagaag nacgctctca tcnnnannca nnnccngcnn cnnnnnnnca     120
tggaggagca ggacttggag cgaaggttcg agctgctgag ccgcgagctg cgggccatgc    180
tggccatcga agactggcag aaaacgtccg ctcagcagca ccgagagcag ctcctactgg    240
aggagctggt gtcgctggtg aaccagcgcg atgagctagt ccgggacctg gaccacaagg    300
agcggatcgc cctggaggag gacgagcgcc tggagcgcgg cctggaacag cggcgccgca    360
agctgagccg gcagttgagc cggcgggagc gc                                   392

<210> SEQ ID NO 287
<211> LENGTH: 488
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (1)..(488)
<223> OTHER INFORMATION: AffymetrixID:  221970_s_at

<400> SEQUENCE: 287
gcgaaaatgc tactatgact cttcctggaa tacacccacc taccttgaac cagattatgg      60
attggatatg tctacttctg gatgcgaatt ttactgttgt ngtaatgatg ccagaagcaa     120
agaggctact gataaatctt tacaagcttg taaaatctca gatatctgtt tattctgagc    180
tcaacaagat tgaagtaagt tttcgggagc tacagaaatt aaatcaagaa aagaataata    240
gaggattata ttcaattgaa gtgctggagc tcttctgata ttatcaattc tccttcatag    300
acattttata aagctctttt atgtgaactc ttgcttcatc caggcaagaa cggtgttttg    360
tttgcgacca tctcagtgtc aagagaaacg tgtcagtgag tacctggacc atcacttaac    420
tgatgctccg gggtaggact gcaggtttca catgaacctg ttntaggctg tggacattgg    480
tgtggaga                                                              488

<210> SEQ ID NO 288
<211> LENGTH: 462
<212> TYPE: DNA
<213> ORGANISM: Homo sapiens
<220> FEATURE:
<221> NAME/KEY: misc_feature
<222> LOCATION: (1)..(462)
<223> OTHER INFORMATION: AffymetrixID:  222127_s_at

<400> SEQUENCE: 288
ctcgctgtta tcctggatct ggtgttacaa tggaattcac tattcaggac attctggatt      60
attgttccag cattgcacag tcccactaaa ccttgtgaaa gaagaaaaga taactgaatg     120
aagcatttga gtataacaga cactatacca aaataccaag caactgtttt gagaacccag    180
acttaaaatt ttatgtatta ttaaatgtta gataaatggg tagtaccata ctacaaatat    240
```

```
ttaaatgcaa aattaccaac ctatatagca gttttatttg ccctataggt tgcatactaa    300
cttaagcatt catgtcacca taaaatgcct ttagcatttc tcaatgactg gatgggaaat    360
tttcctttat tgcctagctg cttgtgtttg agtggttgtc ctatgagcaa tgcatttgga    420
gttcttcagc tttcactact tctctgttgc ttgctaatca tg                      462

<210> SEQ ID NO 289
<211> LENGTH: 535
<212> TYPE: DNA
<213> ORGANISM: Homo sapiens
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (171)..(465)
<223> OTHER INFORMATION: n is a, c, g, or t
<220> FEATURE:
<221> NAME/KEY: misc_feature
<222> LOCATION: (1)..(535)
<223> OTHER INFORMATION: AffymetrixID:  36711_at

<400> SEQUENCE: 289
ttgcacggat ctaagttatt ctccccagcc agagcccgng ctnnctgctc ccngggaaaa     60
gntggcgtan tggncctgag ctgggnttta tattttatat ctgcaaataa atnacatttt    120
atcntanatt tagggaaagc cngagagnaa caacaaaaaa tgtttaagcc nnnnnnnnnn    180
nnnnnnnnnn nnnnnnnnnn nnnnnnnnnn nnnnnnnnnn nnnnnnnnnn nnnnnnnnnn    240
```

```
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnntattg cccggctcct    480
agaatttatt tatttcctga cttacagcaa gcgagttatc gtcttctgta ttttg         535
```

<210> SEQ ID NO 290
<211> LENGTH: 494
<212> TYPE: DNA
<213> ORGANISM: Homo sapiens
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (184)..(184)
<223> OTHER INFORMATION: n is a, c, g, or t
<220> FEATURE:
<221> NAME/KEY: misc_feature
<222> LOCATION: (237)..(262)
<223> OTHER INFORMATION: n is a, c, g, or t
<220> FEATURE:
<221> NAME/KEY: misc_feature
<222> LOCATION: (447)..(464)
<223> OTHER INFORMATION: n is a, c, g, or t
<220> FEATURE:
<221> NAME/KEY: misc_feature
<222> LOCATION: (1)..(494)
<223> OTHER INFORMATION: AffymetrixID: 38037_at

<400> SEQUENCE: 290

```
ccactctatg agttggactt cagtcttgcc taggcgattt tgtctaccat ttgtgttttg     60
aaagcccaag gtgctgatgt caaagtgtaa cagatatcag tgtctccccg tgtcctctcc    120
ctgncaagtc tcagaagagg ttgggcttcc atgcctgtag ctttcctggt ccctcacccc    180
catngcccca ggcccacagc gtgggaactc actttcccct gtgtcaagac atttctnnnn    240
nnnnnnnnnn nnnnnnnnnn nnactccatg caggggtcag tgcagcagag gacagtctgg    300
agaaggtatt agcaaagcaa aaggctgaga aggaacaggg aacattggag ctgactgttc    360
ttggtaactg attacctgcc aattgctacc gagaaggttg gaggtgggga aggctttgta    420
taatcccacc cacctcacca aaacgannnn nnnnnnnnnn nnnngtcctt tctggaagtt    480
tctggtgcca tttc                                                     494
```

<210> SEQ ID NO 291
<211> LENGTH: 258
<212> TYPE: DNA
<213> ORGANISM: E. coli
<220> FEATURE:
<221> NAME/KEY: misc_feature
<222> LOCATION: (1)..(258)
<223> OTHER INFORMATION: AffymetrixID: AFFX-BioB-M_at

<400> SEQUENCE: 291

```
gccggagttt tacggcaata tcatcaccac acgcacttat caggaacgcc tcgatacgct     60
ggaaaaagtg cgcgatgccg ggatcaaagt ctgttctggc ggcattgtgg gcttaggcga    120
aacggtaaaa gatcgcgccg gattattgct gcaactggca aacctgccga cgccgccgga    180
aagcgtgcca atcaacatgc tggtgaaggt gaaaggcacg ccgcttgccg ataacgatga    240
tgtcgatgcc tttgattt                                                 258
```

```
<210> SEQ ID NO 292
<211> LENGTH: 276
<212> TYPE: DNA
<213> ORGANISM: E. coli
<220> FEATURE:
<221> NAME/KEY: misc_feature
<222> LOCATION: (1)..(276)
<223> OTHER INFORMATION: AffymetrixID:  AFFX-r2-Ec-bioC-3_at

<400> SEQUENCE: 292
cgctggtgca gggatcgtta cccgaacgtc atcaggcgtg gcaggcggtg gacgagcgtc      60
cgcatgctaa tcgcttttta ccgccagatg aaatcgaaca gtcgctgaac ggcgtgcatt     120
atcaacatca tattcagccc atcacgctgt ggtttgatga tgcgctcagt gccatgcgtt     180
cgctgaaagg catcggtgcc acgcatcttc atgaagggcg cgacccgcga atattaacgc     240
gttcgcagtt gcagcgattg caactggcct ggccgc                              276

<210> SEQ ID NO 293
<211> LENGTH: 462
<212> TYPE: DNA
<213> ORGANISM: Homo sapiens
<220> FEATURE:
<221> NAME/KEY: misc_feature
<222> LOCATION: (1)..(462)
<223> OTHER INFORMATION: AffymetrixID:  204018_x_at

<400> SEQUENCE: 293
ggtccccaca gactcagaga gaacccacca tggtgctgtc tcctgccgac aagaccaacg      60
tcaaggccgc ctggggtaag gtcggcgcgc acgctggcga gtatggtgcg gaggccctgg     120
agaggatgtt cctgtccttc cccaccacca agacctactt cccgcacttc gacctgagcc     180
acggctctgc ccaggttaag ggccacggca agaaggtggc cgacgccctg accaacgccg     240
tggcgcacgt ggacgacatg cccaacgcgc tgtccgccct gagcgacctg cacgcgcaca     300
agcttcgggt ggacccggtc aacttcaagc tcctaagcca ctgcctgctg gtgaccctgg     360
ccgcccacct ccccgccgag ttcacccctg cggtgcacgc ctccctggac aagttcctgg     420
cttctgtgag caccgtgctg acctccaaat accgttaagc tg                       462

<210> SEQ ID NO 294
<211> LENGTH: 323
<212> TYPE: DNA
<213> ORGANISM: Homo sapiens
<220> FEATURE:
<221> NAME/KEY: misc_feature
<222> LOCATION: (1)..(323)
<223> OTHER INFORMATION: AffymetrixID:  222043_at

<400> SEQUENCE: 294
tcgactctgc tgctcatggg aagaacagaa ttgctcctgc atgcaactaa ttcaataaaa      60
ctgtcttgtg agctgatcgc ttggagggtc ctctttttat gttgagttgc tgcttcccgg     120
catgccttca tttttgctatg gggggcaggc aggggggatg gaaaataagt agaaacaaaa     180
aagcagtggc taagatggta tagggactgt cataccagtg aagaataaaa gggtgaagaa     240
taaaagggat atgatgacaa ggttgatcca cttcaagaat tgcttgcttt caggaagaga     300
gatgtgtttc aacaagccaa cta                                            323

<210> SEQ ID NO 295
<211> LENGTH: 540
<212> TYPE: DNA
<213> ORGANISM: Homo sapiens
<220> FEATURE:
<221> NAME/KEY: misc_feature
```

<222> LOCATION: (1)..(540)
<223> OTHER INFORMATION: AffymetrixID: 206026_s_at

<400> SEQUENCE: 295

```
tacaagtact acttctactg gaaataaaaa cttttttagct ggaagattta gccacttata        60
aaaaaaaaaa aggatgatca aaacacacag tgtttatgtt ggaatctttt ggaactcctt       120
tgatctcact gttattatta acatttattt attattttc taaatgtgaa agaaatacat        180
aatttaggga aaattggaaa atataggaaa ctttaaacga gaaatgaaa cctctcataa        240
tcccactgca tagaaataac aagcgttaac attttcatat tttttctttt cagtcatttt      300
tgtatttgtg gtatatgtat atatgtacct atatgtattt gcatttgaaa ttttggaatc      360
ctgctctatg tacagttttg tattatactt tttaaatctt gaactttatg aacattttct      420
gaaatcattg attattctac aaaaacatga ttttaaacag ctgtaaaata ttctatgata      480
tgaatgtttt atgcattatt taagcctgtc tctattgttg gaatttcagg tcattttcat      540
```

<210> SEQ ID NO 296
<211> LENGTH: 101
<212> TYPE: DNA
<213> ORGANISM: Homo sapiens
<220> FEATURE:
<221> NAME/KEY: misc_feature
<222> LOCATION: (1)..(101)
<223> OTHER INFORMATION: AffymetrixID: 208894_at

<400> SEQUENCE: 296

```
cgatcaccaa tgtacctcca gaggtaactg tgctcacgaa cagccctgtg gaactgagag        60
agcccaacgt cctcatctgt ttcatagaca agttcacccc a                          101
```

<210> SEQ ID NO 297
<211> LENGTH: 491
<212> TYPE: DNA
<213> ORGANISM: Homo sapiens
<220> FEATURE:
<221> NAME/KEY: misc_feature
<222> LOCATION: (1)..(491)
<223> OTHER INFORMATION: AffymetrixID: 222150_s_at

<400> SEQUENCE: 297

```
taatcttgct cattaacctt actcctttga gaattcttta acaatattta aaattggtaa        60
caaaaatagt ttagccataa ttgtttagcc atgtgagttt caggttggta cacgttcaga      120
cagaactgct gtatcacatt ccaattttga atagccagtg agcaatcaag tgtagagaaa      180
tgataaatgg cctaagaagg catacagtgg cataaacgat gctcttccta gtagcttaat      240
aggccacaag ctagtttctg ttgccctctg aaataaaata tgctttaaaa atgtagggac      300
cagtgcttag aaaagcaaaa actaggtgtg tcattgaaat aataggcata aaaattaaat      360
gttacataag acccctattt ggaaaaaggg tccttttaaa aactgaattt gtactaaatc      420
agatttgcca tgtccagtac agaataattt gtacttagta tttgcagcag ggtttgtctt      480
tgtgaattca g                                                           491
```

<210> SEQ ID NO 298
<211> LENGTH: 485
<212> TYPE: DNA
<213> ORGANISM: Homo sapiens
<220> FEATURE:
<221> NAME/KEY: misc_feature
<222> LOCATION: (1)..(485)
<223> OTHER INFORMATION: AffymetrixID: 207113_s_at

<400> SEQUENCE: 298

-continued

```
ccagaactca ctggggccta cagctttgat ccctgacatc tggaatctgg agaccaggga        60
gcctttggtt ctggccagaa tgctgcagga cttgagaaga cctcacctag aaattgacac       120
aagtggacct taggccttcc tctctccaga tgtttccaga cttccttgag acacggagcc       180
cagccctccc catggagcca gctccctcta tttatgtttg cacttgtgat tatttattat       240
ttatttatta tttatttatt tacagatgaa tgtatttatt tgggagaccg gggtatcctg       300
ggggacccaa tgtaggagct gccttggctc agacatgttt tccgtgaaaa cggaggctga       360
acaataggct gttcccatgt agcccccctgg cctctgtgcc ttcttttgat tatgttttt       420 aaaatattat ctgattaagt tgtctaaaca atgctgattt ggtgaccaac tgtcactcat       480
tgctg                                                                   485
```

<210> SEQ ID NO 299
<211> LENGTH: 491
<212> TYPE: DNA
<213> ORGANISM: Homo sapiens
<220> FEATURE:
<221> NAME/KEY: misc_feature
<222> LOCATION: (1)..(491)
<223> OTHER INFORMATION: AffymetrixID: 205067_at

<400> SEQUENCE: 299

```
agctgtaccc agagagtcct gtgctgaatg tggactcaat ccctagggct ggcagaaagg        60
gaacagaaag gttttttgagt acggctatag cctggactttt cctgttgtct acaccaatgc       120
ccaactgcct gccttagggt agtgctaaga ggatctcctg tccatcagcc aggacagtca       180
gctctctcct ttcagggcca atccccagcc cttttgttga gccaggcctc tctcacctct       240
cctactcact taaagcccgc ctgacagaaa ccacggccac atttggttct aagaaacct       300 ctgtcattcg ctcccacatt ctgatgagca accgcttccc tatttattta tttatttgtt       360
tgtttgtttt attcattggt ctaatttatt caaggggggc aagaagtagc agtgtctgta       420
aaagagccta gtttttaata gctatggaat caattcaatt tggactggtg tgctctcttt       480
aaatcaagtc c                                                            491
```

<210> SEQ ID NO 300
<211> LENGTH: 356
<212> TYPE: DNA
<213> ORGANISM: Homo sapiens
<220> FEATURE:
<221> NAME/KEY: misc_feature
<222> LOCATION: (1)..(356)
<223> OTHER INFORMATION: AffymetrixID: 201290_at

<400> SEQUENCE: 300

```
gaacacacgt gttggtgctt ctgggtagca ctggtttgca ttagtttatg tttccatgcc        60
agagtttgtg tgggcgggcg catgtgcacc acagagtgca ctcgagggga cttttcagtca      120 caggatttca taattgtcat tgtcacactt tcaaattttt gtacatcagt gaatttttt       180 atattaaaag gttgagccaa aaagccccca gtgtttgtat tttgaagcca agcttcactt      240
ctaaagtgcc tacagagact tgtaaatgaa aatgcagctc tgcacgagtt tgaaaccgtc      300
atacctcctt ctattaggaa tggcatatac tgaggtggtc gtaagtctta acttct          356
```

<210> SEQ ID NO 301
<211> LENGTH: 4666
<212> TYPE: DNA
<213> ORGANISM: Homo sapiens
<220> FEATURE:
<221> NAME/KEY: misc_feature -continued
<222> LOCATION: (1)..(4666)
<223> OTHER INFORMATION: CD11c full-length n.t.

<400> SEQUENCE: 301

| | | | | | |
|---|---|---|---|---|---|
| agtaccttgg | tccagctctt | cctgcaacgg | cccaggagct | cagagctcca | catctgacct | 60 |
| tctagtcatg | accaggacca | gggcagcact | cctcctgttc | acagccttag | caacttctct | 120 |
| aggtttcaac | ttggacacag | aggagctgac | agccttccgt | gtggacacgc | ctgggtttgg | 180 |
| agacagcgtg | gtccagtatg | ccaactcctg | ggtggtggtt | ggagccccc | aaaagataac | 240 |
| agctgccaac | caaacgggtg | gcctctacca | gtgtggctac | agcactggtg | cctgtgagcc | 300 |
| catcggcctg | caggtgcccc | cggaggccgt | gaacatgtcc | ctgggcctgt | ccctggcgtc | 360 |
| taccaccagc | ccttcccagc | tgctggcctg | cggccccacc | gtgcaccacg | agtgcgggag | 420 |
| gaacatgtac | ctcaccggac | tctgcttcct | cctgggcccc | acccagctca | cccagaggct | 480 |
| cccggtgtcc | aggcaggagt | gcccaagaca | ggagcaggac | attgtgttcc | tgatcgatgg | 540 |
| ctcaggcagc | atctcctccc | gcaactttgc | cacgatgatg | aacttcgtga | gagctgtgat | 600 |
| aagccagttc | cagagaccca | gcacccagtt | ttccctgatg | cagttctcca | acaaattcca | 660 |
| aacacacttc | actttcgagg | aattcaggcg | cagctcaaac | cccctcagcc | tgttggcttc | 720 |
| tgttcaccag | ctgcaagggt | ttacatacac | ggccaccgcc | atccaaaatg | tcgtgcaccg | 780 |
| attgttccat | gcctcatatg | ggcccgtag | ggatgccgcc | aaaattctca | ttgtcatcac | 840 |
| tgatgggaag | aaagaaggcg | acagcctgga | ttataaggat | gtcatcccca | tggctgatgc | 900 |
| agcaggcatc | atccgctatg | caattggggt | tggattagct | tttcaaaaca | gaaattcttg | 960 |
| gaaagaatta | aatgacattg | catcgaagcc | ctcccaggaa | cacatattta | agtggagga | 1020 |
| ctttgatgct | ctgaaagata | ttcaaaacca | actgaaggag | aagatctttg | ccattgaggg | 1080 |
| tacggagacc | acaagcagta | gctccttcga | attggagatg | gcacaggagg | gcttcagcgc | 1140 |
| tgtgttcaca | cctgatggcc | ccgttctggg | ggctgtgggg | agcttcacct | ggtctggagg | 1200 |
| tgccttcctg | tacccccaa | atatgagccc | taccttcatc | aacatgtctc | aggagaatgt | 1260 |
| ggacatgagg | gactcttacc | tgggttactc | caccgagctg | ccctctgga | aaggggtgca | 1320 |
| gagcctggtc | ctgggggccc | ccgctacca | gcacaccggg | aaggctgtca | tcttcaccca | 1380 |
| ggtgtccagg | caatggagga | tgaaggccga | agtcacgggg | actcagatcg | gctcctactt | 1440 |
| cggggcctcc | ctctgctccg | tggacgtaga | cagcgacggc | agcaccgacc | tggtcctcat | 1500 |
| cggggccccc | cattactacg | agcagacccg | agggggccag | gtgtctgtgt | gtcccttgcc | 1560 |
| caggggtgg | agaaggtggt | ggtgtgatgc | tgttctctac | ggggagcagg | gccaccctg | 1620 |
| gggtcgcttt | ggggcggctc | tgacagtgct | ggggatgtg | aatggggaca | agctgacaga | 1680 |
| cgtggtcatc | ggggcccag | gagaggagga | gaaccggggt | gctgtctacc | tgtttcacgg | 1740 |
| agtcttggga | cccagcatca | gcccctccca | cagccagcgg | atcgcgggct | cccagctctc | 1800 |
| ctccaggctg | cagtattttg | gcaggcact | gagcgggggt | caagacctca | cccaggatgg | 1860 |
| actggtggac | ctggctgtgg | gggccggggg | ccaggtgctc | ctgctcagga | ccagacctgt | 1920 |
| gctctgggtg | ggggtgagca | tgcagttcat | acctgccgag | atccccaggt | ctgcgtttga | 1980 |
| gtgtcgggag | caggtggtct | ctgagcagac | cctggtacag | tccaacatct | gcctttacat | 2040 |
| tgacaaacgt | tctaagaacc | tgcttgggag | ccgtgacctc | caaagctctg | tgaccttgga | 2100 |
| cctggcccctc | gaccctggcc | gcctgagtcc | ccgtgccacc | ttccaggaaa | caaagaaccg | 2160 |
| gagtctgagc | cgagtccgag | tcctcgggct | gaaggcacac | tgtgaaaact | tcaacctgct | 2220 |
| gctcccgagc | tgcgtggagg | actctgtgac | ccccattacc | ttgcgtctga | acttcacgct | 2280 |

```
ggtgggcaag cccctccttg ccttcagaaa cctgcggcct atgctggccg ccgatgctca    2340
gagatacttc acggcctccc tacccttgta gaagaactgt ggagccgacc atatctgcca    2400
ggacaatctc ggcatctcct tcagcttccc aggcttgaag tccctgctgg tggggagtaa    2460
cctggagctg aacgcagaag tgatggtgtg aatgacggg gaagactcct acggaaccac     2520
catcaccttc tcccacccg caggactgtc ctaccgctac gtggcagagg gccagaaaca     2580
agggcagctg cgttccctgc acctgacatg tgacagcgcc ccagttggga gccagggcac    2640
ctggagcacc agctgcagaa tcaaccacct catcttccgt ggcggcgccc agatcacctt    2700
cttggctacc tttgacgtct cccccaaggc tgtcctggga gaccggctgc ttctgacagc    2760
caatgtgagc agtgagaaca acactcccag gaccagcaag accaccttcc agctggagct    2820
cccggtgaag tatgctgtct acactgtggt tagcagccac gaacaattca ccaaatacct    2880
caacttctca gagtctgagg agaaggaaag ccatgtggcc atgcacagat accaggtcaa    2940
taacctggga cagagggacc tgcctgtcag catcaacttc tgggtgcctg tggagctgaa    3000
ccaggaggct gtgtggatgg atgtggaggt ctcccacccc cagaacccat cccttcggtg    3060
ctcctcagag aaaatcgcac ccccagcatc tgacttcctg gcgcacattc agaagaatcc    3120
cgtgctggac tgctccattg ctggctgcct gcggttccgc tgtgacgtcc cctccttcag    3180
cgtccaggag gagctggatt tcaccctgaa gggcaacctc agctttggct gggtccgcca    3240
gatattgcag aagaaggtgt cggtcgtgag tgtggctgaa attacgttcg acacatccgt    3300
gtactcccag cttccaggac aggaggcatt tatgagagct cagacgacaa cggtgctgga    3360
gaagtacaag gtccacaacc ccaccccct catcgtaggc agctccattg ggggtctgtt    3420
gctgctggca ctcatcacag cggtactgta caaagttggc ttcttcaagc gtcagtacaa    3480
ggaaatgatg gaggaggcaa atggacaaat tgccccagaa aacgggacac agaccccag    3540 cccgcccagt gagaaatgat ccctctttg ccttggactt cttctccccc gcagttttc     3600 cccacttact taccctcacc tgtcaggcct gacggggagg aaccactgca ccaccgagag    3660
aggctgggat gggcctgctt cctgtctttg ggagaaaacg tcttgcttgg aaggggcct    3720 ttgtcttgtc aaggttccaa ctggaaaccc ttaggacagg gtccctgctg tgttcccaa    3780 aggacttgac ttgcaatttc tacctagaaa tacatggaca ataccccag gcctcagtct    3840 cccttctccc atgaggcacg aatgatcttt cttctttc tttttttt tttttcttt       3900 cttttttttt tttttgagac ggagtctcgc tctgtcaccc aggctggagt gcaatggcgt    3960
gatctcggct cactgcaacc tccgcctccc gggttcaagt aattctgctg tctcagcctc    4020
ctgagtagct gggactacag gcacacgcca cctcgcccgg cccgatcttt ctaaaataca    4080
gttctgaata tgctgctcat ccccacctgt cttcaacagc tccccattac cctcaggaca    4140
atgtctgaac tctccagctt cgcgtgagaa gtccccttcc atcccagagg gtgggcttca    4200
gggcgcacag catgagaggc tctgtgcccc catcaccctc gtttccagtg aattagtgtc    4260
atgtcagcat cagctcaggg cttcatcgtg gggctctcag ttccgatttc ccaggctgaa    4320
ttgggagtga gatgcctgca tgctgggttc tgcacagctg gcctcccgcg ttgggcaaca    4380
ttgctggctg gaagggagga gcgccctcta gggagggaca tggccccggt gcggctgcag    4440
ctcacccagc cccaggggca gaagagaccc aaccacttct attttttgag gctatgaata    4500
tagtacctga aaaatgccaa agacatgatt attttttttaa aaagcgtact ttaaatgttt    4560
gtgttaataa attaaaacat gcacaaaag atgcatctac cgctcttggg aaatatgtca    4620
aaggtctaaa aataaaaaag ccttctgtga aaaaaaaaa aaaaaa                   4666
```

<210> SEQ ID NO 302
<211> LENGTH: 1163
<212> TYPE: PRT
<213> ORGANISM: Homo sapiens
<220> FEATURE:
<221> NAME/KEY: misc_feature
<222> LOCATION: (1)..(1163)
<223> OTHER INFORMATION: CD11c full-length a.a.

<400> SEQUENCE: 302

```
Met Thr Arg Thr Arg Ala Ala Leu Leu Leu Phe Thr Ala Leu Ala Thr
1               5                   10                  15

Ser Leu Gly Phe Asn Leu Asp Thr Glu Glu Leu Thr Ala Phe Arg Val
            20                  25                  30

Asp Ser Ala Gly Phe Gly Asp Ser Val Val Gln Tyr Ala Asn Ser Trp
        35                  40                  45

Val Val Val Gly Ala Pro Gln Lys Ile Thr Ala Ala Asn Gln Thr Gly
50                  55                  60

Gly Leu Tyr Gln Cys Gly Tyr Ser Thr Gly Ala Cys Glu Pro Ile Gly
65                  70                  75                  80

Leu Gln Val Pro Pro Glu Ala Val Asn Met Ser Leu Gly Leu Ser Leu
                85                  90                  95

Ala Ser Thr Thr Ser Pro Ser Gln Leu Leu Ala Cys Gly Pro Thr Val
            100                 105                 110

His His Glu Cys Gly Arg Asn Met Tyr Leu Thr Gly Leu Cys Phe Leu
        115                 120                 125

Leu Gly Pro Thr Gln Leu Thr Gln Arg Leu Pro Val Ser Arg Gln Glu
130                 135                 140

Cys Pro Arg Gln Glu Gln Asp Ile Val Phe Leu Ile Asp Gly Ser Gly
145                 150                 155                 160

Ser Ile Ser Ser Arg Asn Phe Ala Thr Met Met Asn Phe Val Arg Ala
                165                 170                 175

Val Ile Ser Gln Phe Gln Arg Pro Ser Thr Gln Phe Ser Leu Met Gln
            180                 185                 190

Phe Ser Asn Lys Phe Gln Thr His Phe Thr Phe Glu Glu Phe Arg Arg
        195                 200                 205

Ser Ser Asn Pro Leu Ser Leu Leu Ala Ser Val His Gln Leu Gln Gly
210                 215                 220

Phe Thr Tyr Thr Ala Thr Ala Ile Gln Asn Val Val His Arg Leu Phe
225                 230                 235                 240

His Ala Ser Tyr Gly Ala Arg Arg Asp Ala Ala Lys Ile Leu Ile Val
                245                 250                 255

Ile Thr Asp Gly Lys Lys Glu Gly Asp Ser Leu Asp Tyr Lys Asp Val
            260                 265                 270

Ile Pro Met Ala Asp Ala Ala Gly Ile Ile Arg Tyr Ala Ile Gly Val
        275                 280                 285

Gly Leu Ala Phe Gln Asn Arg Asn Ser Trp Lys Glu Leu Asn Asp Ile
290                 295                 300

Ala Ser Lys Pro Ser Gln Glu His Ile Phe Lys Val Glu Asp Phe Asp
305                 310                 315                 320

Ala Leu Lys Asp Ile Gln Asn Gln Leu Lys Glu Lys Ile Phe Ala Ile
                325                 330                 335

Glu Gly Thr Glu Thr Thr Ser Ser Ser Ser Phe Glu Leu Glu Met Ala
            340                 345                 350

Gln Glu Gly Phe Ser Ala Val Phe Thr Pro Asp Gly Pro Val Leu Gly
```

```
                355                 360                 365
Ala Val Gly Ser Phe Thr Trp Ser Gly Gly Ala Phe Leu Tyr Pro Pro
        370                 375                 380

Asn Met Ser Pro Thr Phe Ile Asn Met Ser Gln Glu Asn Val Asp Met
385                 390                 395                 400

Arg Asp Ser Tyr Leu Gly Tyr Ser Thr Glu Leu Ala Leu Trp Lys Gly
                405                 410                 415

Val Gln Ser Leu Val Leu Gly Ala Pro Arg Tyr Gln His Thr Gly Lys
            420                 425                 430

Ala Val Ile Phe Thr Gln Val Ser Arg Gln Trp Arg Met Lys Ala Glu
            435                 440                 445

Val Thr Gly Thr Gln Ile Gly Ser Tyr Phe Gly Ala Ser Leu Cys Ser
            450                 455                 460

Val Asp Val Asp Ser Asp Gly Ser Thr Asp Leu Val Leu Ile Gly Ala
465                 470                 475                 480

Pro His Tyr Tyr Glu Gln Thr Arg Gly Gly Gln Val Ser Val Cys Pro
                485                 490                 495

Leu Pro Arg Gly Trp Arg Arg Trp Cys Asp Ala Val Leu Tyr Gly
            500                 505                 510

Glu Gln Gly His Pro Trp Gly Arg Phe Gly Ala Ala Leu Thr Val Leu
            515                 520                 525

Gly Asp Val Asn Gly Asp Lys Leu Thr Asp Val Val Ile Gly Ala Pro
            530                 535                 540

Gly Glu Glu Glu Asn Arg Gly Ala Val Tyr Leu Phe His Gly Val Leu
545                 550                 555                 560

Gly Pro Ser Ile Ser Pro Ser His Ser Gln Arg Ile Ala Gly Ser Gln
                565                 570                 575

Leu Ser Ser Arg Leu Gln Tyr Phe Gly Gln Ala Leu Ser Gly Gly Gln
            580                 585                 590

Asp Leu Thr Gln Asp Gly Leu Val Asp Leu Ala Val Gly Ala Arg Gly
            595                 600                 605

Gln Val Leu Leu Leu Arg Thr Arg Pro Val Leu Trp Val Gly Val Ser
            610                 615                 620

Met Gln Phe Ile Pro Ala Glu Ile Pro Arg Ser Ala Phe Glu Cys Arg
625                 630                 635                 640

Glu Gln Val Val Ser Glu Gln Thr Leu Val Gln Ser Asn Ile Cys Leu
                645                 650                 655

Tyr Ile Asp Lys Arg Ser Lys Asn Leu Leu Gly Ser Arg Asp Leu Gln
            660                 665                 670

Ser Ser Val Thr Leu Asp Leu Ala Leu Asp Pro Gly Arg Leu Ser Pro
            675                 680                 685

Arg Ala Thr Phe Gln Glu Thr Lys Asn Arg Ser Leu Ser Arg Val Arg
            690                 695                 700

Val Leu Gly Leu Lys Ala His Cys Glu Asn Phe Asn Leu Leu Leu Pro
705                 710                 715                 720

Ser Cys Val Glu Asp Ser Val Thr Pro Ile Thr Leu Arg Leu Asn Phe
                725                 730                 735

Thr Leu Val Gly Lys Pro Leu Leu Ala Phe Arg Asn Leu Arg Pro Met
            740                 745                 750

Leu Ala Ala Asp Ala Gln Arg Tyr Phe Thr Ala Ser Leu Pro Phe Glu
            755                 760                 765

Lys Asn Cys Gly Ala Asp His Ile Cys Gln Asp Asn Leu Gly Ile Ser
            770                 775                 780
```

-continued

```
Phe Ser Phe Pro Gly Leu Lys Ser Leu Leu Val Gly Ser Asn Leu Glu
785                 790                 795                 800

Leu Asn Ala Glu Val Met Val Trp Asn Asp Gly Glu Asp Ser Tyr Gly
            805                 810                 815

Thr Thr Ile Thr Phe Ser His Pro Ala Gly Leu Ser Tyr Arg Tyr Val
        820                 825                 830

Ala Glu Gly Gln Lys Gln Gly Gln Leu Arg Ser Leu His Leu Thr Cys
    835                 840                 845

Asp Ser Ala Pro Val Gly Ser Gln Gly Thr Trp Ser Thr Ser Cys Arg
850                 855                 860

Ile Asn His Leu Ile Phe Arg Gly Gly Ala Gln Ile Thr Phe Leu Ala
865                 870                 875                 880

Thr Phe Asp Val Ser Pro Lys Ala Val Leu Gly Asp Arg Leu Leu Leu
            885                 890                 895

Thr Ala Asn Val Ser Ser Glu Asn Asn Thr Pro Arg Thr Ser Lys Thr
        900                 905                 910

Thr Phe Gln Leu Glu Leu Pro Val Lys Tyr Ala Val Tyr Thr Val Val
    915                 920                 925

Ser Ser His Glu Gln Phe Thr Lys Tyr Leu Asn Phe Ser Glu Ser Glu
930                 935                 940

Glu Lys Glu Ser His Val Ala Met His Arg Tyr Gln Val Asn Asn Leu
945                 950                 955                 960

Gly Gln Arg Asp Leu Pro Val Ser Ile Asn Phe Trp Val Pro Val Glu
            965                 970                 975

Leu Asn Gln Glu Ala Val Trp Met Asp Val Glu Val Ser His Pro Gln
        980                 985                 990

Asn Pro Ser Leu Arg Cys Ser Ser  Glu Lys Ile Ala Pro  Pro Ala Ser
    995                 1000                1005

Asp Phe Leu Ala His Ile Gln  Lys Asn Pro Val Leu  Asp Cys Ser
    1010                1015                1020

Ile Ala Gly Cys Leu Arg Phe  Arg Cys Asp Val Pro  Ser Phe Ser
    1025                1030                1035

Val Gln Glu Glu Leu Asp Phe  Thr Leu Lys Gly Asn  Leu Ser Phe
    1040                1045                1050

Gly Trp Val Arg Gln Ile Leu  Gln Lys Lys Val Ser  Val Val Ser
    1055                1060                1065

Val Ala Glu Ile Thr Phe Asp  Thr Ser Val Tyr Ser  Gln Leu Pro
    1070                1075                1080

Gly Gln Glu Ala Phe Met Arg  Ala Gln Thr Thr Thr  Val Leu Glu
    1085                1090                1095

Lys Tyr Lys Val His Asn Pro  Thr Pro Leu Ile Val  Gly Ser Ser
    1100                1105                1110

Ile Gly Gly Leu Leu Leu Leu  Ala Leu Ile Thr Ala  Val Leu Tyr
    1115                1120                1125

Lys Val Gly Phe Phe Lys Arg  Gln Tyr Lys Glu Met  Met Glu Glu
    1130                1135                1140

Ala Asn Gly Gln Ile Ala Pro  Glu Asn Gly Thr Gln  Thr Pro Ser
    1145                1150                1155

Pro Pro Ser Glu Lys
    1160

<210> SEQ ID NO 303
<211> LENGTH: 107
<212> TYPE: PRT
<213> ORGANISM: Homo sapiens
```

```
<220> FEATURE:
<221> NAME/KEY: misc_feature
<222> LOCATION: (1)..(107)
<223> OTHER INFORMATION: Adalimumab VL

<400> SEQUENCE: 303

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 304
<211> LENGTH: 121
<212> TYPE: PRT
<213> ORGANISM: Homo sapiens
<220> FEATURE:
<221> NAME/KEY: misc_feature
<222> LOCATION: (1)..(121)
<223> OTHER INFORMATION: Adalimumab VH

<400> SEQUENCE: 304

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 305
<211> LENGTH: 9
<212> TYPE: PRT
<213> ORGANISM: Artificial Sequence
<220> FEATURE:
<223> OTHER INFORMATION: Synthetic consensus motif for adalimumab VL
      CDR3
<220> FEATURE:
<221> NAME/KEY: misc_feature
<222> LOCATION: (9)..(9)
<223> OTHER INFORMATION: Xaa is Thr or Ala

<400> SEQUENCE: 305

Gln Arg Tyr Asn Arg Ala Pro Tyr Xaa
```

```
1               5

<210> SEQ ID NO 306
<211> LENGTH: 12
<212> TYPE: PRT
<213> ORGANISM: Artificial Sequence
<220> FEATURE:
<223> OTHER INFORMATION: Synthetic consensus motif for adalimumab VH
      CDR3
<220> FEATURE:
<221> NAME/KEY: misc_feature
<222> LOCATION: (12)..(12)
<223> OTHER INFORMATION: Xaa is Tyr or Asn

<400> SEQUENCE: 306

Val Ser Tyr Leu Ser Thr Ala Ser Ser Leu Asp Xaa
1               5                   10

<210> SEQ ID NO 307
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Adalimumab VL CDR2

<400> SEQUENCE: 307

Ala Ala Ser Thr Leu Gln Ser
1               5

<210> SEQ ID NO 308
<211> LENGTH: 17
<212> TYPE: PRT
<213> ORGANISM: Homo sapiens
<220> FEATURE:
<221> NAME/KEY: misc_feature
<222> LOCATION: (1)..(17)
<223> OTHER INFORMATION: Adalimumab VH CDR2

<400> SEQUENCE: 308

Ala Ile Thr Trp Asn Ser Gly His Ile Asp Tyr Ala Asp Ser Val Glu
1               5                   10                  15

Gly

<210> SEQ ID NO 309
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Adalimumab VL CDR1

<400> SEQUENCE: 309

Arg Ala Ser Gln Gly Ile Arg Asn Tyr Leu Ala
1               5                   10

<210> SEQ ID NO 310
<211> LENGTH: 5
<212> TYPE: PRT
<213> ORGANISM: Homo sapiens
<220> FEATURE:
<221> NAME/KEY: misc_feature
```

-continued

```
<222> LOCATION: (1)..(5)
<223> OTHER INFORMATION: Adalimumab VH CDR1

<400> SEQUENCE: 310

Asp Tyr Ala Met His
1               5
```